US011813319B2

(12) United States Patent
Gladue et al.

(10) Patent No.: US 11,813,319 B2
(45) **Date of Patent: *Nov. 14, 2023**

(54) DEVELOPMENT OF A NOVEL LIVE ATTENUATED AFRICAN SWINE FEVER VACCINE BASED IN THE DELETION OF GENE I177L

(71) Applicant: The United States of America, as represented by the Secretary of Agriculture, Washington, DC (US)

(72) Inventors: Douglas P. Gladue, Guilford, CT (US); Manuel V. Borca, Westbrook, CT (US)

(73) Assignee: The United States of America, as represented by The Secretary of Agriculture, Washington, DC (US)

(*) Notice: Subject to any disclaimer, the term of this patent is extended or adjusted under 35 U.S.C. 154(b) by 102 days.

This patent is subject to a terminal disclaimer.

(21) Appl. No.: 17/223,252

(22) Filed: Apr. 6, 2021

(65) Prior Publication Data

US 2021/0244809 A1 Aug. 12, 2021

Related U.S. Application Data

(63) Continuation of application No. 16/580,058, filed on Sep. 24, 2019, now Pat. No. 11,007,263.

(51) Int. Cl.

| | |
|---|---|
| ***A61K 39/12*** | (2006.01) |
| ***A61P 31/20*** | (2006.01) |
| *A61K 39/00* | (2006.01) |

(52) U.S. Cl.

CPC .............. *A61K 39/12* (2013.01); *A61P 31/20* (2018.01); *A61K 2039/5254* (2013.01)

(58) Field of Classification Search

None

See application file for complete search history.

(56) References Cited

U.S. PATENT DOCUMENTS

| | | | | |
|---|---|---|---|---|
| 9,474,797 | B1 | 10/2016 | Borca et al. | |
| 9,808,520 | B1 | 11/2017 | Borca et al. | |
| 11,007,263 | B2 * | 5/2021 | Gladue | A61P 31/20 |
| 2016/0130562 | A1 | 5/2016 | Borca et al. | |

FOREIGN PATENT DOCUMENTS

| | | | |
|---|---|---|---|
| WO | 2015091322 | A1 | 6/2015 |

OTHER PUBLICATIONS

Alignment of instant SEQ ID No. 1 with 17130814 SEQ ID No. 1; Dec. 2020.*

Gaudreault et al. (Frontiers in Veterinary Science. May 2020; 7 (Article 215): 1-17.

(Continued)

*Primary Examiner* — Shanon A. Foley

(74) *Attorney, Agent, or Firm* — John D. Fado; Mark D. McNemar

(57) ABSTRACT

Provided herein are details on the construction of a recombinant African Swine Fever Virus (ASFV) live attenuated vaccine for prevention of ASF caused by various strains of ASFV, such as the highly virulent Georgia 2007 isolate ("ASFV-G"). An exemplary vaccine comprises the ASFV-GΔI1771 modified virus, a recombinant ASFV-G modified by deleting a portion of the I177L ORF rendering the I177L gene nonfunctional.

9 Claims, 6 Drawing Sheets

Specification includes a Sequence Listing.

(56) References Cited

OTHER PUBLICATIONS

Xiong et al. ("Rapid phylogenetic analysis of African swine fever virus from metagenomic sequences." bioRxiv (2019): 756726.
Olesen et al. (Journal ofVirological Methods. 2018; 261: 14-16.
Cackett, Gwenny, et al. ("Temporal Transcriptome and Promoter Architecture of the African Swine Fever Virus." BioRxiv (2019): 847343).
Borca, Manuel V. et al. "Development of a highly effective African swine fever virus vaccine by deletion of the 177L gene results in sterile immunity against the current epidemic Eurasia strain", Journal of Virology, Jan. 22, ?020, vol. 94, issue 7, pp. 1-15.
Krug, Peter W. et al., "The progressive adaptation of a georgian isolate of the African swine fever virus to vero cells leads to a gradual attenuation or virulence in swine corresponding to major modifications of the viral genome", Journal of Virology, 2015, vol. 89, No. 4. pp. 2324-2332.
PCT/ISA/220, PCT International Search Report, dated Jul. 8, 2020.

* cited by examiner

Red arrow = p72mCherry Cassette

DEVELOPMENT OF A NOVEL LIVE ATTENUATED AFRICAN SWINE FEVER VACCINE BASED IN THE DELETION OF GENE I177L

CROSS-REFERENCE TO RELATED APPLICATIONS

This application is a continuation of U.S. patent application Ser. No. 16/580,058, filed on Sep. 24, 2019, the contents of which are hereby incorporated by reference herein in their entirety.

BACKGROUND OF THE INVENTION

Field of Invention

The present disclosure provides details on the construction of a recombinant African Swine Fever Virus (ASFV) live attenuated vaccine for prevention of ASF caused by various strains of ASFV, such as the highly virulent Georgia 2007 isolate ("ASFV-G"). An exemplary vaccine comprises the ASFV-GΔI1771 modified virus, a recombinant ASFV-G modified by deleting a portion of the I177L ORF rendering the I177L gene nonfunctional.

Background

African Swine Fever (ASF) is a contagious viral disease of swine. The causative agent, ASF virus (ASFV), is a large enveloped virus containing a double-stranded DNA genome of approximately 190 kilobase pairs. ASFV shares aspects of genome structure and replication strategy with other large double-stranded DNA viruses, including the Poxviridae, Iridoviridae and Phycodnaviridae (Costard et al, Phil. Trans. Royal Soc. B, (2009) 364:2683-96). ASFV infections in domestic pigs are often fatal and are characterized by fever, hemorrhages, ataxia and severe depression. However, the course of infection varies, ranging from highly lethal to sub-clinical, depending on the host characteristics and the particular virus strain (Tulman et al, Curr. Top. Microbial. Immunol. (2009) 328:43-87).

Currently, the disease is endemic in more than twenty sub-Saharan African countries. In Europe, ASF is still endemic on the island of Sardinia (Italy) and new outbreaks have been declared in the Caucasus region since 2007, affecting Georgia, Armenia, Azerbaijan and Russia. Outbreaks have been recently reported in Ukraine, Belarus, Lithuania, Latvia and Poland, affecting both wild boar and swine farms. In 2018-2019 ASF spread into China, Mongolia, Vietnam, Cambodia and North Korea, in both wild boar and domestic swine farms. In 2019 ASF has also spread to wild boar populations in Belgium, where ASF is currently only affecting a small containment area in the country. Recent ASF outbreaks pose the risk of further dissemination into neighboring countries. The parental epidemic virus ASFV Georgia 2007/1, is a highly virulent isolate belonging to the genotype II (Chapman et al, Emerging Infect. Dis. (2011) 17:599-605), and is responsible for all the current outbreaks in Asia and Europe, with outbreak viruses having 90% or greater similarity to the parental strain.

Currently, there is no commercial vaccine available for ASF and disease outbreaks are controlled by animal quarantine and slaughter. Attempts to vaccinate animals using infected cell extracts, supernatants of infected pig peripheral blood leukocytes, purified and inactivated virions, infected glutaraldehyde-fixed macrophages, or detergent-treated infected alveolar macrophages failed to induce protective immunity (Coggins, L., Prag. Med. Viral. (1974) 18:48-63; Forman et al, Arch. Viral., (1982) 74:91-100; Kihm et al, (1987) In: *African Swine Fever*, Becker, Y. (ed), Martinus Nijhoff, Boston, pp 127-44; Mebus, C. A., Adv. Virus Res., (1988) 35:251-69). Homologous protective immunity does develop in pigs surviving viral infection. Pigs surviving acute infection with moderately virulent or attenuated variants of ASFV develop long-term resistance to homologous, but rarely to heterologous, virus challenge (Hamdy and Dardiri, *Am. J. Vet. Res.* (1984) 45:711-14; Ruiz-Gonzalvo et al, (1981) In: *FAO/CEC Expert Consultation in ASF Research*, Wilkinson, P. J. (ed), Rome, pp 206-16). Herein, we report the development of a recombinant vaccine in which a portion of the I177L gene has been deleted from the ASFV-G genome. Vaccination of pigs with this virus protected swine from developing ASF. Because there are not ASFV vaccines currently available, the development of any vaccine that may induce protection against the lethal presentation of the disease is of great interest.

SUMMARY OF THE INVENTION

The present disclosure provides a genetically modified virus, wherein the virus comprises a viral genome at least 99% identical to SEQ ID NO: 2. In a particular embodiment, the viral genome comprises SEQ ID NO:2.

Also provided herein is vaccine composition against African Swine Fever Virus (ASFV), comprising a genetically modified virus comprising a viral genome at least 99% identical to SEQ ID NO: 2. In some embodiments, the ASFV strain is the ASFV-Georgia 2007 isolate.

Further provided herein is a method for the protection of swine against ASFV, comprising administering to a swine a live attenuated vaccine comprising a genetically modified virus, wherein the virus comprises a viral genome at least 99% identical to SEQ ID NO: 2 in an amount effective to protect the swine from clinical ASFV disease. In some embodiments, the ASFV is ASFV-G. In particular embodiments, the amount effective to protect the swine from clinical ASFV disease is a vaccine comprising $10^2$-$10^6$ $HAD_{50}$ of the genetically modified virus.

An additional embodiment provided herein is a recombinant ASFV mutant virus, comprising a synthetic mutation in the I177L open reading frame or in a regulatory element controlling expression of the I177L protein, resulting in a non-functional genomic I177L gene. In particular embodiments, the synthetic mutation is a deletion mutation resulting the deletion of one or more nucleotides between positions 174471 and 175004 of SEQ ID NO:1. In other embodiments, the synthetic mutation is a frameshift mutation, insertion mutation, nonsense mutation of one or more nucleotides between positions 174471 and 175004 of SEQ ID NO:1. In some embodiments, the mutant ASFV is an ASFV-Georgia isolate. In specific embodiments, the mutant ASFV comprises a genome at least 95% identical to, or at least 99% identical to SEQ ID NO: 2.

Further provided herein is a vaccine composition against ASFV-G, comprising a recombinant ASFV mutant virus, comprising a synthetic mutation in the I177L open reading frame or in a regulatory element controlling expression of the I177L protein, resulting in a non-functional genomic I177L gene.

Also provided herein is a method for the protection of swine against ASFV, comprising administering to a swine a live attenuated vaccine comprising a recombinant ASFV mutant virus, comprising a synthetic mutation in the I177L open reading frame or in a regulatory element controlling expression of the I177L protein, resulting in a non-functional genomic I177L gene in an amount effective to protect said swine from clinical ASFV disease. In particular embodiments, the ASFV is ASFV-G. In some embodiments, the amount effective to protect the swine from clinical ASFV disease is a vaccine comprising $10^2$-$10^6$ $HAD_{50}$ of the genetically modified virus.

INCORPORATION BY REFERENCE

All publications, patents and patent applications mentioned in this specification are herein incorporated by reference to the same extent as if each individual publication, patent or patent application was specifically and individually indicated to be incorporated by reference.

BRIEF DESCRIPTION OF THE DRAWINGS

The novel features of the invention are set forth with particularity in the claims. Features and advantages of the present invention are referred to in the following detailed description, and the accompanying drawings of which:

DETAILED DESCRIPTION OF THE INVENTION

Figure 1:
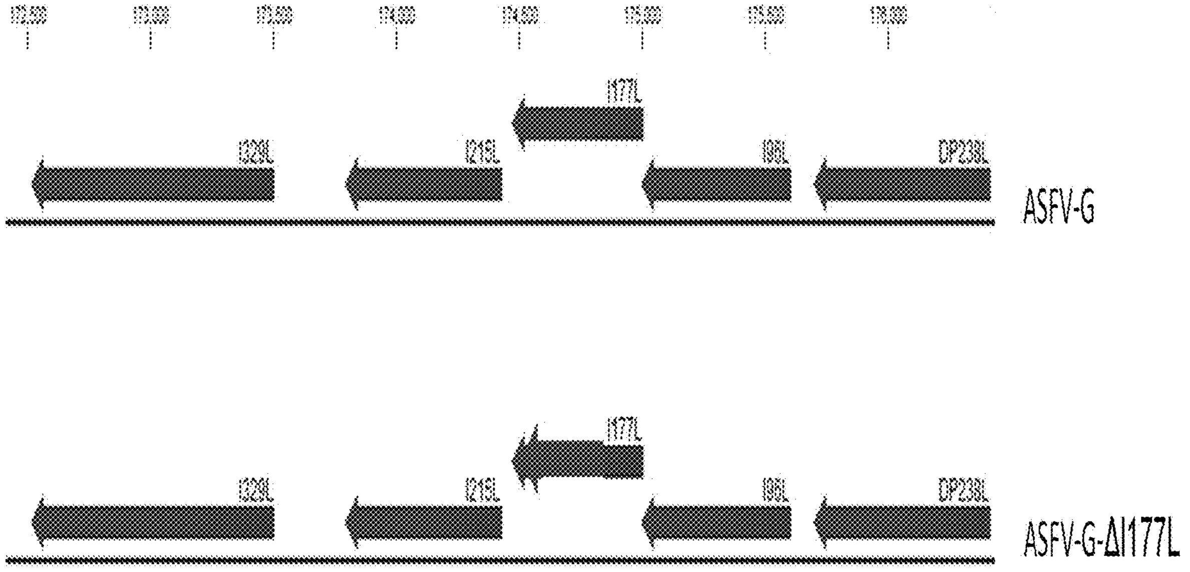
FIG. 1 provides a graphic representation of the cassette used to create the ASFV-G ΔI177L recombinant mutant virus.

African swine fever virus (ASFV) is the etiological agent of a contagious and often lethal viral disease of domestic pigs that has significant economic consequences for the swine industry. The control of African Swine Fever (ASF) has been hampered by the unavailability of vaccines. Experimental vaccines have been previously reported that were derived from naturally occurring, cell culture-adapted, or genetically modified live attenuated ASFV. However, none of these vaccines have been developed for commercial use. Here we report the discovery that deletion of a previously uncharacterized gene, I177L, from the highly virulent ASFV isolate Georgia isolate (ASFV-G) produces its complete attenuation in swine. Animals inoculated with the virus lacking a functional I177L gene—such as the specific ASFV-G-ΔI177L mutant described herein—administered intramuscularly (IM) remain clinically normal during a 28-day observational period. Importantly, ASFV-G-ΔI177L infected animals were protected when challenged with the virulent parental strain ASFV-G.

Preferred embodiments of the present invention are shown and described herein. It will be obvious to those skilled in the art that such embodiments are provided by way of example only. Numerous variations, changes, and substitutions will occur to those skilled in the art without departing from the invention. Various alternatives to the embodiments of the invention described herein may be employed in practicing the invention. It is intended that the included claims define the scope of the invention and that methods and structures within the scope of these claims and their equivalents are covered thereby.

Technical and scientific terms used herein have the meanings commonly understood by one of ordinary skill in the art to which the instant invention pertains, unless otherwise defined. Reference is made herein to various materials and methodologies known to those of skill in the art. Standard reference works setting forth the general principles of recombinant DNA technology include Sambrook et al., "Molecular Cloning: A Laboratory Manual", 2d ed., Cold Spring Harbor Laboratory Press, Plainview, N.Y., 1989; Kaufman et al., eds., "Handbook of Molecular and Cellular Methods in Biology and Medicine", CRC Press, Boca Raton, 1995; and McPherson, ed., "Directed Mutagenesis: A Practical Approach", IRL Press, Oxford, 1991.

Any suitable materials and/or methods known to those of skill can be utilized in carrying out the instant invention. Materials and/or methods for practicing the instant invention are described. Materials, reagents and the like to which reference is made in the following description and examples are obtainable from commercial sources, unless otherwise noted. This invention teaches methods and describes tools for producing genetically altered strains of ASFV.

As used in the specification and claims, use of the singular "a", "an", and "the" include plural references unless the context clearly dictates otherwise.

The terms isolated, purified, or biologically pure as used herein, refer to material that is substantially or essentially free from components that normally accompany the referenced material in its native state.

The term "about" is defined as plus or minus ten percent of a recited value. For example, about 1.0 g means 0.9 g to 1.1 g and all values within that range, whether specifically stated or not.

The term "a nucleic acid consisting essentially of", and grammatical variations thereof, means nucleic acids that differ from a reference nucleic acid sequence by 20 or fewer nucleic acid residues and also perform the function of the reference nucleic acid sequence. Such variants include sequences which are shorter or longer than the reference nucleic acid sequence, have different residues at particular positions, or a combination thereof.

The term "adjuvant" means a substance or vehicle that non-specifically enhances the immune response to an antigen. Adjuvants can include a suspension of minerals (alum, aluminum hydroxide, or phosphate) on which antigen is adsorbed; or water-in-oil emulsion in which antigen solution is emulsified in mineral oil (for example, Freund's incomplete adjuvant), sometimes with the inclusion of killed mycobacteria (Freund's complete adjuvant) to further enhance antigenicity. Immunostimulatory oligonucleotides can also be used as adjuvants (for example, see U.S. Pat. Nos. 6,194,388; 6,207,646; 6,214,806; 6,218,371; 6,239,116; 6,339,068; 6,406,705; and 6,429,199). Adjuvants also include biological molecules, such as costimulatory molecules.

The term "administer"/"administration" means any method of providing a subject with a substance, such as a therapeutic agent by any effective route. Exemplary routes of administration include, but are not limited to, injection (such as subcutaneous, intramuscular, intradermal, intraperitoneal, and intravenous), oral, intraductal, sublingual, rectal, transdermal, intranasal, vaginal and inhalation routes.

The terms "coding sequence" and "coding region" as used herein refer to nucleotide sequences and nucleic acid sequences, including both RNA and DNA, that encode genetic information for the synthesis of an RNA, a protein, or any portion of an RNA or protein.

The term "effective amount" of a composition provided herein refers to the amount of the composition capable of performing the specified function for which an effective amount is expressed. The exact amount required can vary from composition to composition and from function to function, depending on recognized variables such as the compositions and processes involved. An effective amount can be delivered in one or more applications. Thus, it is not possible to specify an exact amount, however, an appropriate "effective amount" can be determined by the skilled artisan via routine experimentation.

The terms "I177L", "ASFV I177L", and "genomic I177L" are synonyms and refer to the gene defined herein as SEQ ID NO: 3, or any version of SEQ ID NO: 3 with base substitutions that result in a protein with a sequence identical to SEQ ID NO: 4). These terms, in the appropriate context, can also refer to modified versions of these SEQ ID NOs, such as those comprising deletions, insertions, and other recombinant modifications. ASFV-G open reading frame I177L encodes a 177 amino acid protein (SEQ ID NO: 4) and is positioned on the reverse strand between nucleotide positions 174471 and 175004 of SEQ ID NO:1.

In the context of the present invention, the term "non-functional genomic I177L" refers to a modified I177L gene, located in the genome of an ASFV, wherein such modification of the ASFV I177L gene results in no ASFV I177L gene product at all or a biologically non-functional ASFV I177L gene product as compared to an unmodified functional ASFV I177L gene. Such modifications can include, but are not limited to, full or partial deletion of the coding sequence, disruption of the open reading frame (e.g., by insertion of a shift mutation or insertion of a nonsense codon), modification of upstream or downstream regulatory elements, and/or any other currently known or conceivable method of inactivating or knocking-out functional expression of such ASFV Il 17L gene.

The term "immunize" means to render a subject protected from an infectious disease, such as by vaccination.

For the purpose of this invention, the "sequence identity" of two related nucleotide or amino acid sequences, expressed as a percentage, refers to the number of positions in the two optimally aligned sequences which have identical residues (×100) divided by the number of positions compared. A gap, i.e., a position in an alignment where a residue is present in one sequence but not in the other is regarded as a position with non-identical residues. The alignment of the two sequences is performed by the Needleman and Wunsch algorithm (Needleman and Wunsch, J Mol Biol, (1970) 48:3, 443-53). A computer-assisted sequence alignment can be conveniently performed using a standard software program such as GAP which is part of the Wisconsin Package Version 10.1 (Genetics Computer Group, Madison, Wisconsin, USA) using the default scoring matrix with a gap creation penalty of 50 and a gap extension penalty of 3.

The phrase "high percent identical" or "high percent identity", and grammatical variations thereof in the context of two polynucleotides or polypeptides, refers to two or more sequences or sub-sequences that have at least about 80%, identity, at least about 81%, 82%, 83%, 84%, 85%, 86%, 87%, 88%, 89%, 90%, 91%, 92%, 93%, 94%, 95%, 96%, 97%, 98%, 99%, or 100% nucleotide or amino acid identity, when compared and aligned for maximum correspondence, as measured using a sequence comparison algorithm or by visual inspection. In one exemplary embodiment, the sequences are high percent identical over the entire length of the polynucleotide or polypeptide sequences.

The term "swine" can generally refer to any member of the Suidae family and includes domesticated and wild pigs, hogs and boars.

A "vaccine" is herein defined as a biological agent capable of providing a protective response in an animal to which it has been delivered but not capable of causing a serious disease. Administration of the vaccine results in immunity from the disease. Thus, the vaccine stimulates antibody production or cellular immunity against the disease-causing pathogen (e.g., ASFV). Immunity is herein defined as the induction of significantly higher levels of protection against lethality and clinical symptoms following vaccination in a swine population, as compared to the non-vaccinated group. In particular, the vaccine according to the invention protects most of the vaccinated animals against the development of clinical symptoms and lethality of the disease. The vaccine of the present disclosure is typically a genetically engineered (recombinant) mutant virus vaccine.

In the context of the present disclosure, the term "non-deficient in its replication" refers to a non-naturally occurring recombinant ASFV which is able to replicate in vitro and/or in vivo and/or is capable of producing viral progeny although such replication and/or viral progeny production may also occur at reduced levels compared to the unmodified parent strain. Therefore, it can be the case that such ASFV is non deficient in its replication in vitro, e.g. in a cell culture, although in vivo in a mammal such ASFV is at least partially impaired in its replication, e.g. resulting in a replication and/or viral progeny production below detection limits.

As used herein, the term "minimal dose" or "minimal effective dose" refers to a dose that demonstrates the absence of, or minimal presence of, toxicity to the recipient, but still results in producing a desired result (e.g., protective immunity).

Viruses/Vaccines

Provided herein is a novel mutant ASFV-G ΔI177L virus (SEQ ID NO: 2), resulting from the recombinant deletion of a portion of the I177L gene (SEQ ID NO: 3) of the parental ASFV-G genome (SEQ ID NO: 1). The genomic nucleotide sequence of a specific recombinant mutant ASFV-G ΔI177L (SEQ ID NO: 2) is described herein and differs from the genomic nucleotide sequence encoding the parental ASFV-G (SEQ ID NO: 1). The ASFV-G I177L-encoded protein of 177 amino acids (SEQ ID NO: 4) differs from the predicted mutant Il77L protein encoded by the mutant nucleotide sequence of ASFV-G ΔIl77L. The I177L protein (SEQ ID NO: 6) from ASFV-GΔI177L is predicted to lack amino acids 112 through 150 of the wild-type I177L protein. Because the p72Mcherry Cassette is inserted in this position (see Examples section), it is not believed that the remaining coding region after this insertion is transcribed, resulting in no functional I177L protein being produced during viral infection.

The exemplary mutant strain (ASFV-G ΔI177L (SEQ ID NO: 2)) is representative of the genus of recombinant vaccines in which the ASFV I177L gene is non-functional, which includes, without limitation, deletion mutants, nonsense mutants, insertional mutants, frameshift mutants and other mutants resulting in non-expression of the I177L protein, or expression of a non-functional I177L protein. Other recombinant viruses envisioned include mutants in regulatory elements resulting in non-expression or non-translation of the I177L protein.

Modifications intended to preclude functional expression of a target protein (e.g., I177L) or reduced expression or reduced activity of a target protein can involve mutations of the DNA or gene encoding the target protein, including deletion of all or a portion of a target gene, including but not limited to the open reading frame of a target locus, transcriptional regulators such as promoters of a target locus, and any other regulatory nucleic acid sequences positioned 5' or 3' from the open reading frame, insertion of premature stop codons in the open reading frame, and insertions or deletions that shift the reading frame leading to premature termination of translation. Such deletional mutations can be achieved using any technique known to those of skill in the art. Reduced levels of the target protein or reduced activity of the target protein may also be achieved with point mutations or insertions in the DNA or gene encoding the target protein. Mutational, insertional, and deletional variants of the disclosed nucleotide sequences and genes can be readily prepared by methods which are well known to those skilled in the art. Techniques used to achieve reduced levels and/or reduced activity of the target protein may include CRISPR/Cas, TALEN, and Zn-finger nuclease. It is well within the skill of a person trained in this art to make mutational, insertional, and deletional mutations which are equivalent in function to the specific ones disclosed herein.

The approaches described herein that were used to create a deletion mutant of I117L in ASFV-G can be used in different isolates of ASFV (such as isolates circulating in Asia, Europe or Africa), where a functional I117L is present. Such approaches can be varied by methodologies known in the art, such as using different selection markers that can select recombinant virus by purification such as, but not limited to, fluorescent proteins, enzymes such as beta-glucuronidase or beta-galactosidase that can be used with chromogenic substrates, and drug selection makers. Such approaches can also be used to create any mutation to the ORF of I177L as well as to regulatory elements controlling the expression and translation of the I177L gene that results in a non-functional I177L protein.

Mutants of I177L (and related strain-specific alleles) in other ASFV strains and genotypes is also encompassed by the present disclosure. ASFV strains comprising synthetic mutations in nucleic acid sequences that exhibit at least 80%, 81%, 82%, 83%, 84%, 85%, 86%, 87%, 88%, 89%, 90%, 91%, 92%, 93%, 94%, 95%, 96%, 97%, 98%, or 99% identity to SEQ ID NO: 3 are encompassed in the instant invention. ASFV strains comprising entire genomes with 95%, 96%, 97%, 98%, 99% or higher identity to SEQ ID NO: 2 are also encompassed in the instant invention.

The present disclosure further contemplates the combination of a non-functional I177L gene with other recombinant mutations. As such, it is not only wild-type viruses that can be modified as disclosed herein, but also strains containing non-naturally occurring mutations in other genes or genomic regions (see, e.g., U.S. Pat. No. 9,814,771).

The present disclosure provides that such rationally-designed, live, attenuated ASFV-G ΔI177L can be incorporated into immunogenic compositions to produce a vaccine effective to protect an animal, such as a pig, from clinical ASF disease when challenged with ASFV-G. Thus, one object of the invention is to provide a method for protecting an animal against ASFV-G by administering an effective amount of rationally designed live attenuated ASFV-G ΔI177L vaccine. In another embodiment, the present disclosure provides a method for eliciting a protective immune response in an animal, preferably of the family Suidae (e.g., domestic pigs (*Sus scrofa domesticus*), wild pigs (*Sus scrofa scrofa*), warthogs (*Potamochoerus porcus*), bushpigs (*Potamochoerus larvatus*), giant forest hogs (*Hylochoerus meinertzhageni*) as well as feral pigs), Such methods will typically comprise administering to such animal the one or more ASFV immunogenic compositions and vaccines described herein.

An additional object of the present disclosure is to provide a method for distinguishing animals infected with a wild-type ASFV from animals vaccinated with a recombinant virus described herein. Such methodologies for differentiating infected from vaccinated animals (DIVA) can be accomplished by serological tests that detect the difference between wild-type I177L protein and a mutant I177L protein. Alternately, such methodologies can include genetic screening approaches such as PCR amplification and detection of different products based. Typically, such approaches utilize one or more primer sets that flank the site of a mutation and expand the same region, resulting in products of different lengths or sequences.

The immunogenic composition(s) of the invention herein, regardless of other components included, comprise a recombinant ASFV with a non-functional I177L gene/protein. I177L proteins of the present invention can comprise the entirety of SEQ ID NO: 4 and proteins with 90%, 91%, 92%, 93%, 94%, 95%, 96%, 97%, 98%, 99%, or higher identity to the protein of SEQ ID NO: 4.

The immunogenically effective amounts of immunogenic compositions disclosed herein can vary based upon multiple parameters. In general, however, effective amounts per dosage unit for intramuscular application can be about $10^2$ 50% hemadsorption dose ("$HAD_{50}$") to $10^6$ $HAD_{50}$. One, two, or more dosage units can be utilized in practicing the methodologies of the present invention. A dosage unit can readily be modified to fit a desired volume or mass by one of skill in the art. Regardless of the dosage unit parameters, immunogenic compositions disclosed herein can be administered in an amount effective to produce an immune response.

Dosage levels of active ingredients in vaccines disclosed herein, can be varied by one of skill in the art to achieve a desired result in a subject or per application. As such, a selected dosage level can depend upon a variety of factors including, but not limited to, formulation, combination with other treatments, severity of a pre-existing condition, and the presence or absence of adjuvants. In preferred embodiments, a minimal dose of an immunogenic composition is administered. Determination of a minimal dose is well within the capabilities of one skilled in the art.

Vaccines of the present invention can be prepared by conventional methods used for commercially available live attenuated ASFV vaccines. In a specific embodiment, a susceptible substrate is inoculated with a ASFV-G ΔI177L mutant and propagated until the virus has replicated to a desired titer after which ASFV-G ΔI177L-containing material is harvested. Following this, the harvested material can be formulated into a vaccine preparation with immunogenic properties. Every substrate which is able to support the replication of the recombinant viruses provided herein can be used in the present invention, including primary cultures of swine peripheral blood macrophages or blood from infected swine.

Formulations and Administration

A vaccine provided herein comprises one of the recombinant viruses as defined above in a live form, and a pharmaceutically acceptable carrier or diluent customarily used for such compositions. Carriers include stabilizers, preservatives and buffers. Suitable stabilizers include, for example, SPGA (sucrose, phosphate, glutamate and albumin), carbohydrates (sorbitol, mannitol, starch, sucrose, dextran, glutamate, and glucose), proteins (dried milk, serum, albumin, casein), or degradation products thereof. Suitable buffers include, for example alkali metal phosphates. Preservatives that can be utilized, include, but are not limited to, thimerosal, merthiolate and gentamicin. Diluents include water, aqueous buffers (e.g., buffered saline), alcohols and polyols (e.g., glycerol).

In some instances, vaccines of the present invention also contain or comprise one or more adjuvants, which includes any material included in the immunogenic composition formulation that enhances an immune response in the recipient that is induced by the immunogenic composition. In some instances, such adjuvants can include proteins other components included with the recombinant virus. Other adjuvants can be included as an extra component of the immunogenic compositions, and include such categories as aluminum salts (alum), oil emulsions, saponins, immune-stimulating complexes (ISCOMs), liposomes, microparticles, nonionic block copolymers, derivatized polysaccharides, cytokines, and a wide variety of bacterial derivatives. Any relevant adjuvant known in the art can be utilized in practicing the inventions disclosed herein. Factors influencing the selection of an adjuvant include animal species, specific pathogen, antigen, route of immunization, and type of immunity needed and can be readily determined by one of skill in the art.

Immunogenic compositions of the present disclosure can also comprise carriers in addition to the recombinant virus. Carriers utilized in practicing the immunogenic compositions provided herein can be any known in the art and can be liquid, solid, semi-solid, or gel. The type of formulation can be modified depending on the route of administration of the antigen. Preferably, carriers are non-toxic to the recipient. One of skill in the art is readily able to choose such carriers for application to recipient animals such as poultry.

The present disclosure provides immunogenic compositions for introducing a recombinant ASFV lacking a functional I177L gene/protein in a composition containing, at a minimum, the recombinant virus, into targets (e.g., swine). Thus, the compositions provided herein can be utilized to induce immunity or resistance to ASFV disease.

Vaccines provided herein may be administered by intramuscular, subcutaneous, intranasal or injection in an amount which is effective to protect the animal against challenge by a virulent strain of ASFV. The vaccine may be administered orally, through direct oral inoculation, dosed in drinking water, or though bait delivery systems. The effective amount of recombinant virus may vary according to parameters considered by those skilled in the art. Effective amounts can be experimentally determined as necessary by those of skill in the art by following any known method or the guidance provided in the Examples herein.

Having generally described this invention, the same will be better understood by reference to certain specific examples, which are included herein to further illustrate the invention and are not intended to limit the scope of the invention as defined by the claims.

EXAMPLES

Example 1

Cell Culture and Viruses.

Primary swine macrophage cell cultures were prepared from defibrinated swine blood as previously described (Zsak et al, J. Virol., (1998) 72:1028-35). Briefly, heparin-treated swine blood was incubated at 37° C. for 1 hour to allow sedimentation of the erythrocyte fraction. Mononuclear leukocytes were separated by flotation over a Ficoll-Paque (Pharmacia, Piscataway, N.J.) density gradient (specific gravity, 1.079). The monocyte/macrophage cell fraction was cultured in plastic Primaria (Falcon; Becton Dickinson Labware, Franklin Lakes, N.J.) tissue culture flasks containing macrophage media, composed of RPMI 1640 Medium (Life Technologies, Grand Island, NY) with 30% L929 supernatant and 20% fetal bovine serum (HI-FBS, Thermo Scientific, Waltham, MA) for 48 hours at 37° C. under 5% CO2. Adherent cells were detached from the plastic by using 10 mM EDTA in phosphate buffered saline (PBS) and were then reseeded into Primaria T25, 6- or 96-well dishes at a density of $5\times10^6$ cells per ml for use in assays 24 hours later.

Virus titration was performed on primary swine macrophage cell cultures in 96-well plates. Virus dilutions and cultures were performed using macrophage medium. Presence of virus was assessed by hemadsorption (HA) and virus titers were calculated by the Reed and Muench method (Amer. J. Hygiene, (1938) 27:493-497).

ASFV Georgia (ASFV-G) utilized for this study was a field isolate kindly provided by Dr. Nino Vepkhvadze, from the Laboratory of the Ministry of Agriculture (LMA) in Tbilisi, Republic of Georgia.

Example 2

Construction of a Recombinant ASFV-G ΔI177L

Recombinant ASFVs were generated by sequential homologous recombination between the parental ASFV genome and recombination transfer vectors in infection and transfection procedures using swine macrophage cell cultures (Neilan et al, Virol., (2004) 319:337-42; Zsak et al, supra). Recombinant transfer vector (p72GUSΔI177L) containing flanking genomic regions including portions of I177L mapping to the left (1 kbp) and right (1 kbp) of the gene and a reporter gene cassette containing the mCherry gene with the ASFV p72 late gene promoter, p72mCherry was used. This construction created a 112-nucleotide deletion in the I177L ORF (amino acid residues 112 to 150) (FIG. 1). Recombinant transfer vector p72mCherryΔI177L was obtained by DNA synthesis (Epoch Biosciences, Bothwell, WA, USA). Macrophage cell cultures were infected with ASFV-G and transfected with p72mCherryΔI177L. Recombinant viruses representing independent primary plaques were purified to homogeneity by successive rounds of plaque assay purification. The recombinant virus was obtained after 14 successive plaque purification events on monolayers of primary swine macrophage cell cultures.

Example 3

Full Genome Sequence Analysis of ASFV-G ΔI177L Relative to Parental ASFV-G.

To evaluate the accuracy of the genetic modification and the integrity of the genome of the recombinant virus, full genome sequences of ASFV-G ΔI177L and parental ASFV-G were obtained using Next Generation Sequencing (NGS) and compared. As a first step, a full-length genome comparison between the parental ASFV-G laboratory strain used to construct the ASFV-G ΔI177L mutant virus and the original ASFV Georgia 2007/1 (Chapman et al, Emerg. Infect. Dis., (2001) 17:599-605; GenBank accession FR682468) was performed. ASFV DNA was obtained from the cytoplasm of infected cells using the Trizol method (Life Technologies, Grand Island, NY, USA). DNA concentration was determined using the Qubit® dsDNA HS assay kit (Life Technologies) and read on a Qubit® 2 Flourometer (Life Technologies). In Brief, the viral DNA was sheared using enzymatic reactions assessed for the distribution of size fragmentation, then ligation of identifying barcodes using an adapter sequence were added to the DNA fragments. Using a Pippin Prep™ (Sage Science, Beverly, MA) the required size range of the library was collected, and normalized. We then used this DNA library for NGS sequencing using the NextSeq (Illumnia, San Diego, CA) following the manufactures protocol. Sequence analysis was performed using CLC Genomics Workbench software (CLCBio, Waltham, MA).

The following differences were observed between these two viruses (nucleotide positions are provided based on ASFV Georgia 2007/1, GenBank accession FR682468?): (i) three nucleotide insertions, T at position 433, an A at position 441 in a non-coding segment of the genome, and a A at position 174954 in the I177L gene, which causes I177L to merge with ORF ASFV_G_ACD_01760, this additional nucleotide allows ORF I117L to resemble a similar full length gene as other isolates, as with the additional A, there is not an early stop codon and out of frame mutation as described in the reference genome; (ii) two nucleotide deletions, T at position 1602 and T at position 1603 in the MGF 360-1L gene ORF resulting in a frameshift; (iii) a nucleotide deletion, T at position 1620 in the MGF 360-1L gene ORF resulting in a frameshift; (iv) a nucleotide mutation, A to G at position 97391 resulting in a silent mutation in ORF B438L; (v) a nucleotide mutation, C to G at position 166192 resulting in a residue substitution (Ala to Pro) at residue position 85 in ORF E199L; and (vi) a nucleotide insertion, at position 183303, a non-coding segment of the genome.

To determine if the recombinant virus acquired additional genetic changes from the parent strain, a full-length genome comparison between ASFV-G ΔI177L and the parental ASFV-G was performed. The DNA sequence assemblies of ASFV-G ΔI177L and ASFV-G revealed a deletion of 112 nucleotides in I177L gene corresponding with the introduced modification. The consensus sequence of the ASFV-G ΔI1771 genome showed an insertion of 3944 nucleotides in I177L gene corresponding to the p72-mcherry cassette sequence introduced to generate a 112-nucleotide deletion in the targeted gene. Besides the insertion of the cassette, no additional differences were observed between ASFV-G ΔI1771 and ASFV-G genomes. In summary, ASFV-G ΔI1771 virus did not accumulate any significant mutations during the process of homologous recombination and plaque purification.

Example 4

Assessment of ASFV-G ΔI177L Virulence in Swine.

Animal experiments were performed under biosafety level 3 conditions in the animal facilities at PIADC following a protocol approved by the Institutional Animal Care and Use Committee.

ASFV-G ΔI177L was assessed for its virulence phenotype relative to the virulent parental ASFV-G virus using 80-90-pound commercial breed swine. Five pigs were inoculated intramuscularly (IM) either with $10^2$, $10^4$, $10^6$ $HAD_{50}$ of ASFV-G ΔI177L or with $10^2$ $HAD_{50}$ of ASFV-G virus. Clinical signs (anorexia, depression, fever, purple skin discoloration, staggering gait, diarrhea and cough) and changes in body temperature were recorded daily throughout the experiment. In protection experiments animals were IM inoculated with $10^2$, $10^4$, $10^6$ $HAD_{50}$ of ASFV-G ΔI177L and 28 days lager IM challenged with $10^2$ $HAD_{50}$ of the parental virulent ASFV-Georgia 2007 strain. Presence of clinical signs associated with the disease was assessed as described earlier.

All pigs inoculated via IM with $10^4$ $HAD_{50}$ of ASFV-G exhibited increased body temperature (>$10^{4}$° F.) by 3 to 4 days post-infection. Pigs presented clinical signs associated with the disease including anorexia, depression, purple skin discoloration, staggering gait and diarrhea (Table 1). Signs of the disease aggravated progressively over time and animals either died or were euthanized in extremis by days 7 or 9 post-infection. Conversely, animals inoculated via IM with either $10^2$, $10^4$, or $10^6$ $HAD_{50}$ of ASFV-G ΔI177L did not present any signs of clinical disease during the entire observation period (21 days). Therefore, deletion of I177L gene produced a complete attenuation of the parental virulent ASFV-G. All animals in the Mock vaccinated group were euthanized due to humanitarian reasons following the corresponding IACUC protocol.

TABLE 1

Swine survival and fever response following infection with $10^2$ $HAD_{50}$ doses of ASFV-G-ΔI177L or parental ASFV-G.

| Virus | No. of survivors/ total | Mean time to death (days ± SD) | Fever: No. of days to onset (days ± SD | Fever: Duration No. of days (days ± SD) | Fever: Maximum daily temp (° F. ± SD) |
|---|---|---|---|---|---|
| ASFV-G | 0/5 | 4.8 (0.84) | 4.8 (0.84) | 0.8 (0.84) | 105.2 (0.6) |
| ASFV-G-ΔI177L $10^2$ $HAD_{50}$ | 5/5 | — | — | — | 102.9 (0.5) |
| ASFV-G-ΔI177L $10^4$ $HAD_{50}$ | 5/5 | — | — | — | 102.8 (0.57) |
| ASFV-G-ΔI177L $10^6$ $HAD_{50}$ | 5/5 | — | — | — | 102.8 (0.49) |

Figure 3:
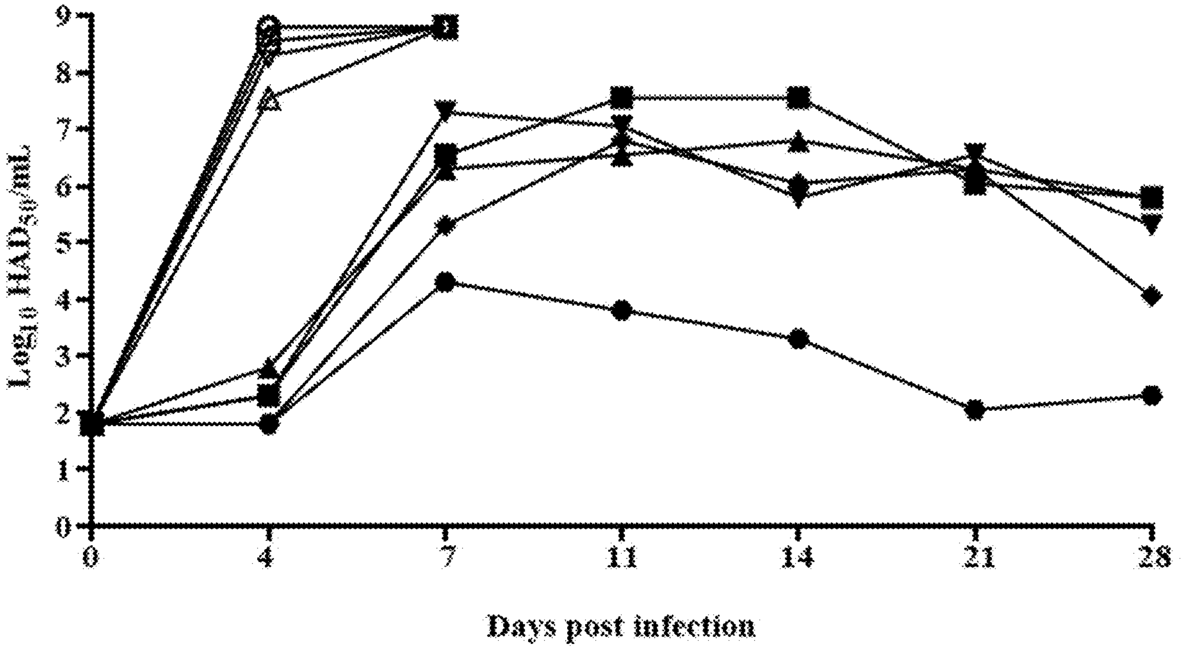
FIG. 3 provides graphic representation of viremia titers detected in pigs IM inoculated with either $10^2$ $HAD_{50}$ of ASFV-G-ΔI177L or $10^2$ $HAD_{50}$ of ASFV-G. Each curve represents values from individual animals in each of the group. Sensitivity of virus detection: ≥$\log_{10}$ 1.8 $\log_{10}$ $TCID_{50}$/ml.

Animals infected with ASFV-G presented with expected high homogenous titers ($10^{7.5}$-$10^{8.5}$ $HAD_{50}$/ml) on day 4 pi, increasing (around $10^{8.5}$ $HAD_{50}$/ml) by day 7 pi when all animals were euthanized. Conversely, ASFV-G-ΔI177L revealed a different pattern with low viremia ($10^{1.8}$-$10^{2.3}$ $HAD_{50}$/ml) at day 4 pi, reaching peak values ($10^{3.8}$-$10^{7.5}$ $HAD_{50}$/ml) by day 11 pi and then decreasing titers ($10^{2.3}$-$10^4$ $HAD_{50}$/ml) until day 28 pi (FIG. 3). It should be noted that one of the five animals inoculated with ASFV-G-ΔI177L showed a remarkably lower viremia (1,000- to 10,000-fold lower depending on the time point considered) than the average viremia values of the other animals in the group. Therefore, deletion of the I177L gene produced complete attenuation of the parental highly virulent ASFV-G virus when inoculated at a low dose, with the infected animals presenting long viremias with relatively low values.

Example 5

Protective Effect of ASFV-G ΔI177L Against Challenge with Parental ASFV-G.

Because pigs inoculated via IM with $10^2$ $HAD_{50}$-$10^6$ $HAD_{50}$ of ASFV-G ΔI177L survived the infection without signs of the disease, groups of animals (n=5) inoculated with $10^2$ $HAD_{50}$-$10^6$ $HAD_{50}$ of ASFV-G ΔI177L were challenged via IM with $10^2$ $HAD_{50}$ of parental ASFV-G at day 28 post-inoculation (homologous challenge). Five naive animals that were challenged using the same route and dose served as a non-inoculated/challenged control group. All animals were IM vaccinated with $10^2$ $HAD_{50}$ of ASFV-G ΔI177L and challenged IM 28 days later with $10^2$ $HAD_{50}$ of ASFV-G virus. All animals in the Mock vaccinated group were euthanized due to humanitarian reasons following the corresponding IACUC protocol. All animals in the ASFV-G ΔI177L vaccinated group remain clinically normal during the observational period of 21 days after the challenge.

The five ASFV-G ΔI177L-inoculated and challenged animals remained completely asymptomatic during all the observational period (21 days) (Table 2). All the animals in the mock inoculated/challenged control group developed disease with a clinical course similar to that observed in animals inoculated with $10^2$ $HAD_{50}$ of ASFV-G (see above). Therefore, ASFV-G ΔI177L is able to induce protection against the presentation of clinical disease when challenged with the highly virulent parental virus.

TABLE 2

Swine survival and fever response in animals challenged with ASFV-G virus at 28 days post-ASFV-G-ΔI177L infection.

| Virus | No. of survivors/ total | Mean time to death (days ± SD) | Fever: No. of days to onset (days ± SD | Fever: Duration No. of days (days ± SD) | Fever: Maximum daily temp (° F. ± SD) |
|---|---|---|---|---|---|
| Mock | 0/5 | 5.6 (0.55) [(1)] | 4.2 (0.84) | 1.4 (0.88) | 105.6 (0.78) |
| ASFV-G-ΔI177L $10^2$ $HAD_{50}$ | 10/10 | — | — | — | 102.7 (0.68) |
| ASFV-G-ΔI177L $10^4$ $HAD_{50}$ | 5/5 | — | — | — | 102.9 (0.37) |
| ASFV-G-ΔI177L $10^6$ $HAD_{50}$ | 5/5 | — | — | — | 103 (0.43) |

Figure 5:
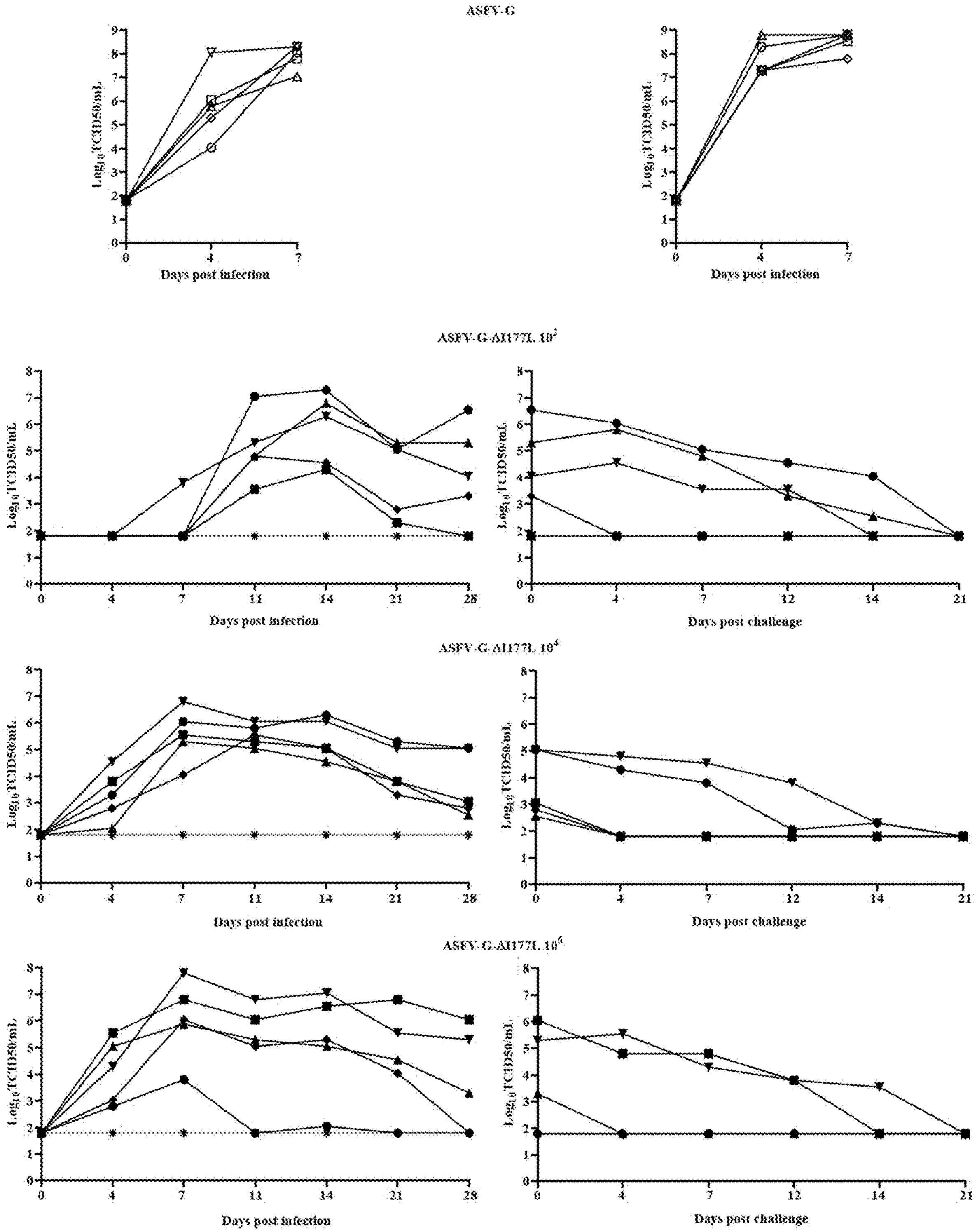
FIG. 5 provides graphic representation of viremia titers detected in pigs IM inoculated with either $10^2$, $10^4$, or $10^6$ $HAD_{50}$ of ASFV-G-ΔI177L or $10^2$ $HAD_{50}$ of ASFV-G. Viremia after the challenge with $10^2$ $HAD_{50}$ of ASFV-G Each curve represents values from individual animals in each of the group. Sensitivity of virus detection: ≥$\log_{10}$ 1.8 $TCID_{50}$/ml.

Analysis of viremia in animals infected with ASFV-G presented with expected high titers ($10^{7.3}$-$10^{8.3}$$HAD_{50}$/ml) on day 4 pi, increasing (averaging $10^{8.5}$ $HAD_{50}$/ml) by day 7 pi when all animals were euthanized. After challenge, none of the ASFV-G-ΔI177L-infected animals had viremias with values higher than those present at challenge and viremia values decreased progressively until the end of the experimental period (21 days after challenge) when, importantly, no circulating virus could be detected in blood from any of these animals (FIG. 5).

In summary, here we present evidence that deletion of the I177L gene drastically alters virulence of ASFV-G producing a completely attenuated virus named ASFV-G ΔI177L. Animals immunized with ASFV-G ΔI177L were protected against challenge with the virulent parental ASFV-G.

Example 6

The Ability of ASFV-G-I117L to Grow in Swine Macrophages

Figure 2:
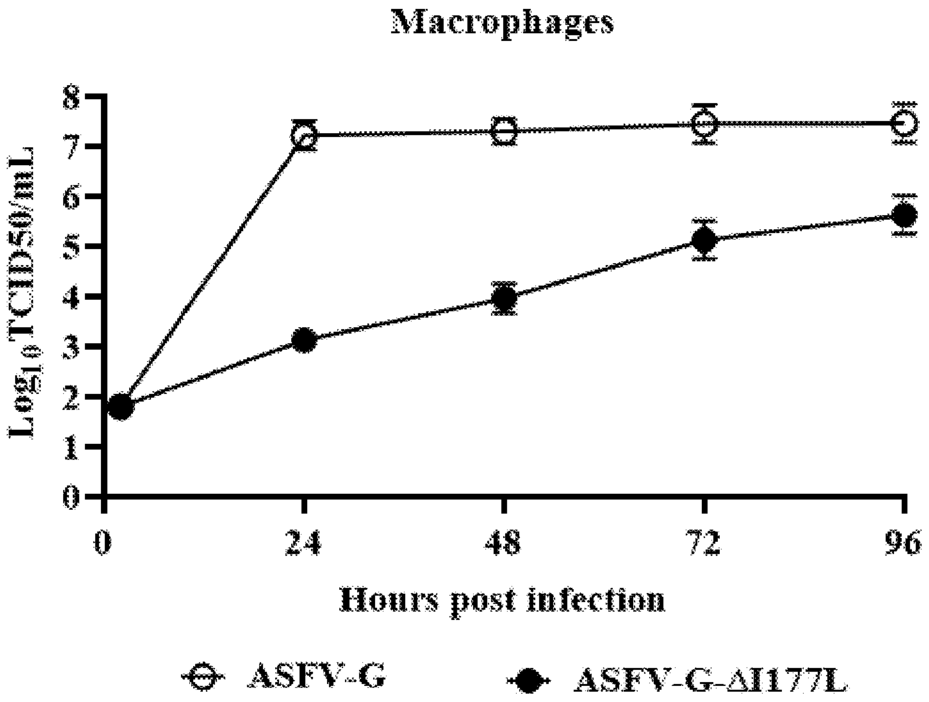
FIG. 2 provides graphic representation of in vitro growth characteristics of ASFV-G-ΔI177L and parental ASFV-G. Primary swine macrophage cell cultures were infected (MOI=0.01) with each of the viruses and virus yield titrated at the indicated times post-infection. Data represent means from three independent experiments. Sensitivity of virus detection: ≥1.8 $\log_{10}$ $HAD_{50}$/ml.

In vitro growth characteristics of ASFV-G-ΔI177L were evaluated in primary swine macrophage cell cultures, the primary cell targeted by ASFV during infection in swine and compared relative to parental ASFV-G in multistep growth curves (FIG. 2). Cell cultures were infected at a MOI of 0.01 and samples were collected at 2, 24, 48, 72 and 96-hours post-infection (hpi). Results demonstrated that ASFV-G-ΔI177L displayed a growth kinetic significantly decreased when compared to parental ASFV-G. ASFV-G-ΔI177L yields are approximately 100 to 1,000-fold lower than those of ASFV-G depending on the time point considered.

Therefore, deletion of the I177L gene significantly decreased the ability of ASFV-G-ΔI177L, relative to the parental ASFV-G isolate, to replicate in vitro in primary swine macrophage cell cultures.

Example 7

ASFV-G-ΔI117L Infected Animals do not Shed Vaccine Virus

Figure 4:
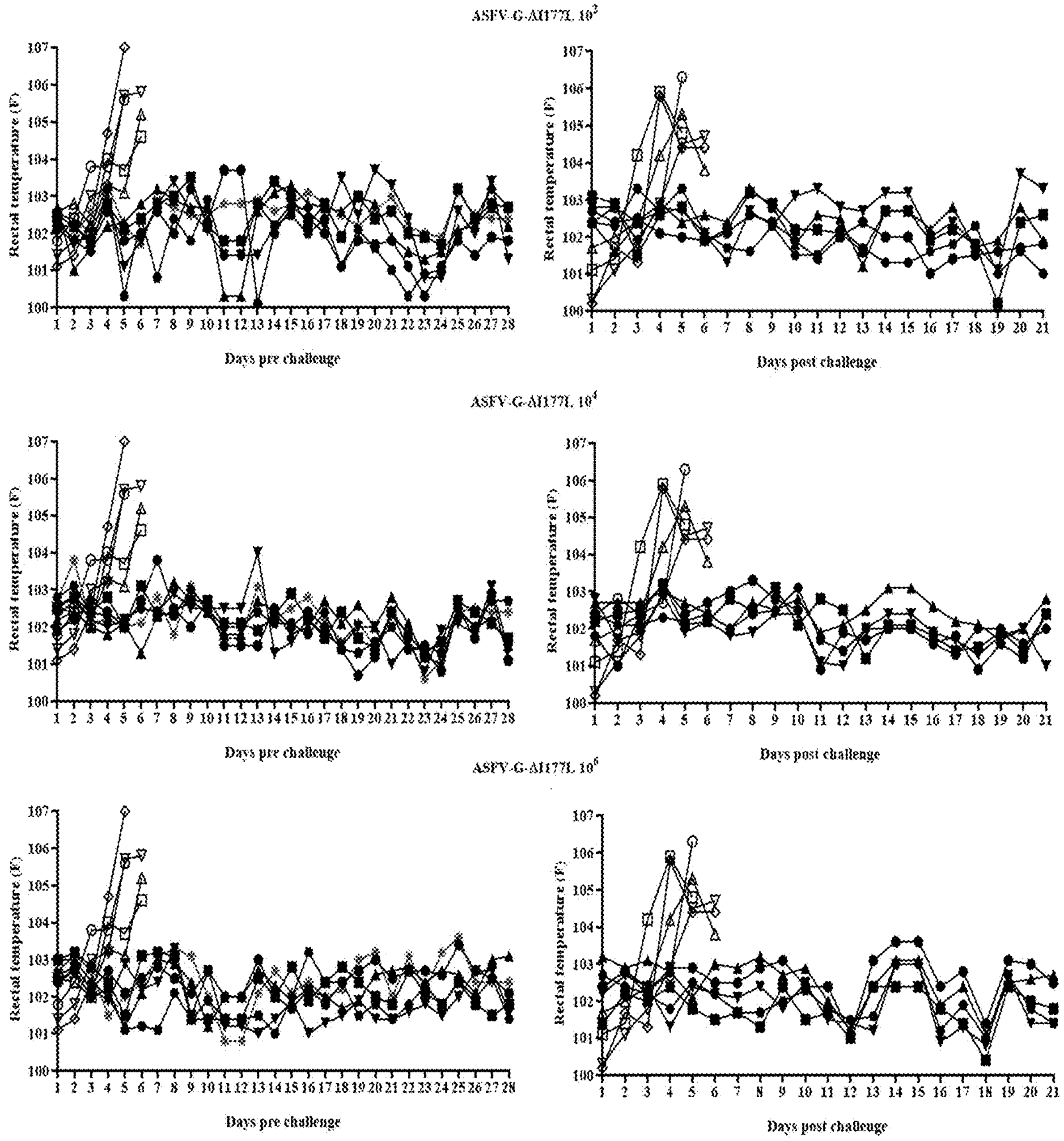
FIG. 4 provides graphic representation of kinetics of body temperature values in pigs IM inoculated with either $10^2$, $10^4$, or $10^6$ $HAD_{50}$ of ASFV-G-ΔI177L (filled symbols), mock inoculated (sentinels, showed in red) or $10^2$ $HAD_{50}$ of ASFV-G (empty symbols) (panels on the left) and after the challenge with $10^2$ $HAD_{50}$ of ASFV-G (panels on the right). Each curve represents individual animal's values in each of the group.

In the above example where different groups of five pig were infected IM with either $10^2$, $10^4$, or $10^6$ $HAD_{50}$ of ASFV-G-ΔI177L, a mock infected animal was cohabitating in each of the groups as sentinel to detect the potential virus shedding from the infected animals. All sentinel animals remained clinically normal (FIG. 4). No virus was detected in any of the samples obtained from sentinel animals (all sampled blood time points as well as tonsil and spleen samples obtained at 28 days pi), indicating that ASFV-G-ΔI177L infected animals are not able to shed enough virus to infect naive pigs for 28 days, a relatively long period of time of cohabitation.

In summary, a non-vaccinated animal that comingled with vaccinated animals for 28 days did not present any clinical symptoms and all sampled blood, tonsil and spleen samples were negative for vaccine virus, indicating that the vaccine virus was unable to shed to a non-vaccinated animal.

Example 8

Host Antibody Response in Animals Infected with ASFV-G-ΔI177L

Figure 6:
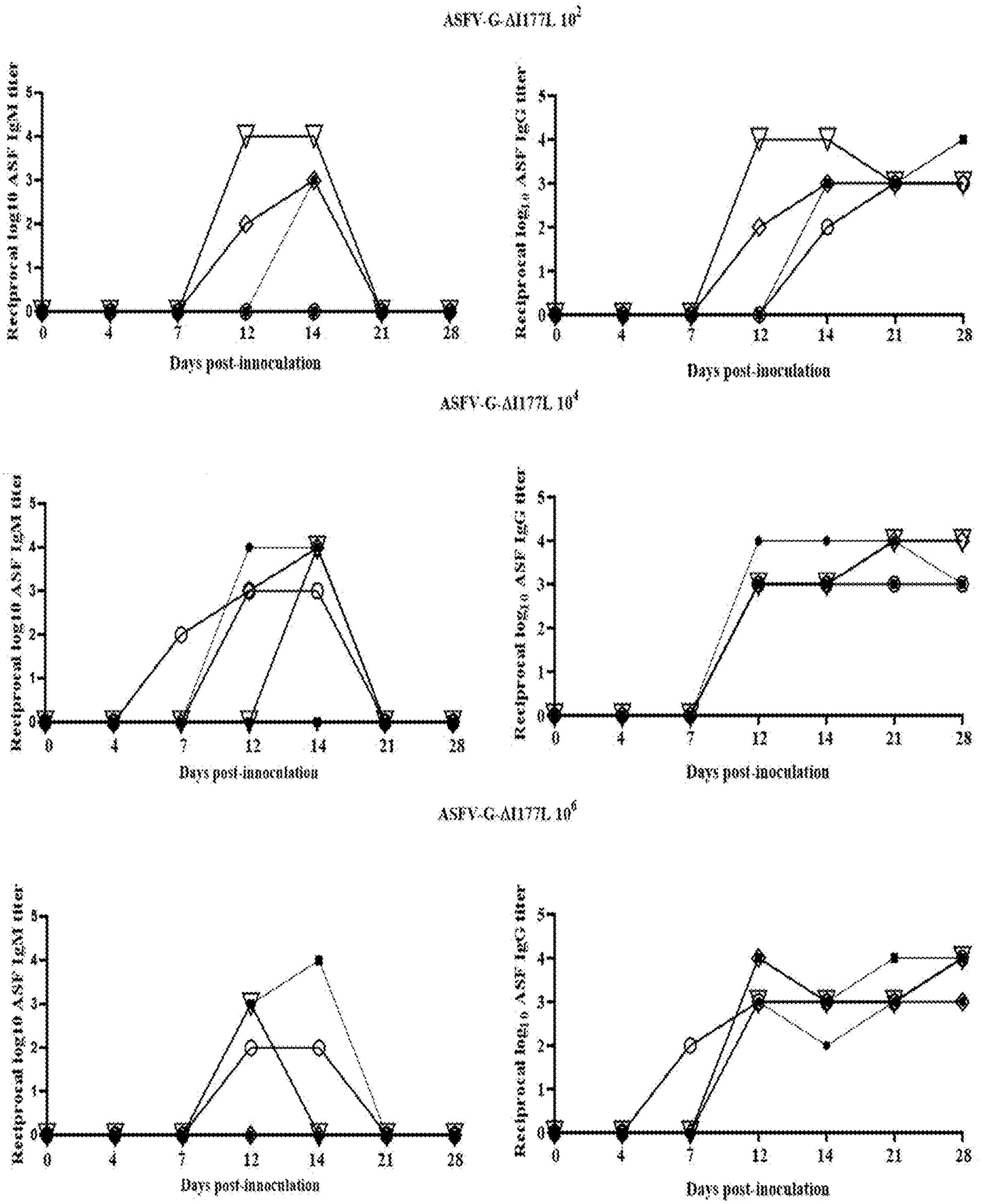
FIG. 6 provides graphic representation of anti-ASFV antibody (IgM mediated shown in panels in the left column, and IgG mediated shown in panels in the right column) titers detected by ELISA in pigs IM inoculated with either $10^2$, $10^4$, or $10^6$ $HAD_{50}$ of ASFV-G-ΔI177L. Antibody response mediated by IgM Each curve represents values from individual animals in each of the group.

All animals infected with ASFV-G-ΔI177L, regardless the dose of virus received possessed similar high titers of circulating anti-ASFV antibodies (FIG. 6). Antibody response, mediated by IgM and IgG isotypes, starts being detected in all three groups by day 12 pi. By day 14 pi response mediated by both antibody isotypes reached maximum levels in all groups. IgM mediated antibody response disappeared in all animals by day 21 pi, while IgG mediated response stay high with minimal fluctuation until day 28 pi without significant differences between animals in the three groups inoculated with ASFV-G-ΔI177L. Therefore, there is a close correlation between presence of anti-ASFV antibodies at the moment of the challenge and protection. It should be mentioned that no antibodies were detected in any serum sample obtained from the sentinel animals with the exception of the one sample at 28 days after infection with ASFV-in the group receiving $10^6$ $HAD_{50}$ of G-ΔI177L where low antibody titer was observed (FIG. 6).

Example 9

Induction of Sterile Immunity

Using an I177L specific real time PCR to specifically detect only challenge virus (which allows the detection of approximately 10 $HAD_{50}$) all blood samples tested negative for the presence of challenge virus. Furthermore, tonsils and spleen samples were obtained from all animals at the end of the observational period (21 days post challenge) and tested for the presence of virus by virus isolation in swine macrophage cultures. Most of the animals in each group showed presence of infectious virus either in tonsils or spleen (data not shown). All positive samples were then assessed using the I177L specific real time PCR detecting the presence of the challenge virus in only one spleen belonging to one of the animals initially infected with $10^2$ $HAD_{50}$/ml of ASFV-G-ΔI177L. These results suggest that replication of challenge virus was absent in all infected animals receiving $10^4$ $HAD_{50}$/ml or higher and most of the animals receiving a $10^2$ $HAD_{50}$/ml of ASFV-G-ΔI177L.

In summary, sterile immunity (immunity that doesn't allow the replication of challenge virus) was achieved partially in animals vaccinated with $10^2$ $HAD_{50}$/ml of ASFV-G-ΔI177L and was fully achieved at a dose of $10^4$ $HAD_{50}$/ml or $10^6$ $HAD_{50}$/ml of ASFV-G-ΔI177L.

While the invention has been described with reference to details of the illustrated embodiments, these details are not intended to limit the scope of the invention as defined in the appended claims.

The embodiments of the disclosure in which exclusive property or privilege is claimed is defined as follows:

1. A recombinant ASFV mutant virus, comprising a synthetic mutation in the I177L open reading frame or in a regulatory element controlling the expression of the I177L protein, resulting in a non-functional genomic I177L gene.

2. The recombinant virus of claim 1, wherein the synthetic mutation is a deletion mutation resulting the deletion of one or more nucleotides between positions 174471 and 175004 of SEQ ID NO:1.

3. The recombinant virus of claim 1, wherein the synthetic mutation is a frameshift mutation, insertion mutation, nonsense mutation of one or more nucleotides between positions 174471 and 175004 of SEQ ID NO:1.

4. The recombinant virus of claim 1, wherein the mutant ASFV is an ASFV-Georgia isolate.

5. The recombinant virus of claim 1, wherein the mutant ASFV comprises a genome at least 95% identical to SEQ ID NO: 2.

6. A vaccine composition against ASFV-G, comprising the recombinant virus of claim 1.

7. A method for the protection of swine against ASFV, comprising administering to a swine a live attenuated vaccine comprising the recombinant virus of claim 1 in an amount effective to protect said swine from clinical ASFV disease.

8. The method of claim 7, wherein the ASFV is ASFV-G.

9. The method of claim 7, wherein the amount effective to protect said swine from clinical ASFV disease is a vaccine comprising $10^2$-$10^6$ $HAD_{50}$ of the genetically modified virus of claim 1.

* * * * *

SEQUENCE LISTING

```
<160> NUMBER OF SEQ ID NOS: 6

<210> SEQ ID NO 1
<211> LENGTH: 189346
<212> TYPE: DNA
<213> ORGANISM: African swine fever virus

<400> SEQUENCE: 1

gaatatacca tattattgct attgccatca atgagaatgc cacgtaggca taggtcatcc      60

tatggccgga ccaatccatg gctgcactta aaaatatcaa aaaagtttaa gttttgggcc     120

ggcgttaaaa tttaaacctt ttctggttga tctttagcca tgtatagctg cgatgtttgg     180

tgccttatct acatgctatt ggcattcctg atattcgcac taaagtgcta tgttacaacc     240

gtcttatgcg tgatttttat ccaccttatt ggccgaaggg ccgccttgta tttcctgtta     300

ggtggtttgg ccgtattcta ctggtggcaa gcagctatca ataaaattta atggctctca     360

cttaagatcc ttgctgtaag cgggcgttta catactttga tcaagaaaaa aaattatttt     420
```

-continued

```
tggacccccc cccatgtttt atcaaaaatc atataataaa gtggcgacaa tcaacatatt    480
aatcaaccac agcattttat gatgtgttaa tcaacatata ccatattaat caaccacagc    540
attttatgat gcgtcaatca acatattatt acggagagcg tcaatcaata taatattgag    600
aacagcgact tgataccgtg tatggtggtg gcggcggcat gttgtttgta acagcatttt    660
tcatcattcg aagcttacaa aagatatgta taagatagca tattaatgtt attaacagta    720
atatcaataa ggcgtagcta tagatcttca ctttggtaga ccaataatcc atggttgcgc    780
ttaaaaatac caaaaaaaac attaagtttt ggagggtaag attggttttt caccattggt    840
aaagattatt attctaaatg tttaccccat agatgtgaaa caatgattct tcatatatta    900
acatattttt tgacttatac ttttcttcat ctagtaaggc gttaattttt tccggatctg    960
tcgtttttat tgataaaaga gaagagtctg gactgtaatt tttaaataat aagatattta   1020
ttaatatcca attattcgtt tggctcgcta tttccatgct ctcttcgaaa gcatcagctc   1080
ctaaatctat acaaaggaat aagttacctt cacaaaaatt cattaccgag gtaatcattg   1140
cccgattaat gtcagccccc aacataaaac aataatatat agttgtataa ttacaatcat   1200
acatacaggc caactgcatc atttcatcaa tgtctatatt tgtcttctct ttgttataaa   1260
tttcatgaag gtcaaagacg ttgttataag caaccccaca tattaaccgc caatctttaa   1320
aatgactata tcgttgataa aaatattgga tggcttcagt aagcttatat agtatcgcca   1380
tactatacca atacctagtt agcatttcgt tgaatgaaat attatccaat gtaaagttaa   1440
ttgataatgt atctagttca ccaaaaattc ttaatttcag ttgagcatta tttaggaaaa   1500
ggggattatc agataataat tcatggcata gaataatatt actgctagtt ttaacatact   1560
gtacattata aaatatttct aaaattttat tttcactcaa agctttcctc gcacctaact   1620
ttggcatagg tcctggtgca ctccatattg acagtaacca acccaaagct gatgtctgca   1680
ccccattcgg taaacagctc tattaaacca tgattgtttt cctgtacagc cttcattaat   1740
gcaacattta atgttaaacc atgtttaaaa cttgctgttt ttattaatat ttgttcatct   1800
atacaagtat gataaatcgt aattggggct tcatgccacc acaaaccaca acgctctaaa   1860
atacaataat catcttttaa cacaggctgt gtagctagta ctttttttagt aagtgcttgt   1920
aaagtagatg gcatcttcta tctgcaaaat aattatttcc gaaaaaaaaa tcaaattaaa   1980
atactaaatt ctattttttt ttttaataaa gcctgtaaat tatataataa atctcgccca   2040
ccgtattatt tccggacaca actttttata cctcattata tttttagatc tatagttttt   2100
taacaaggca ttaatttttt ctggatctgt cgtttttaaa gataaaagag agacgtttga   2160
actataataa tctttaaatg ataatatttc tactaatata tcatgattct tttgttttgc   2220
taattctaag ctctcttcga aagcattagc tcctaaatct atacaaaaga acaagttatt   2280
catataaaag ttttttaccg aggtaaccat tgcccgattg atgtcagccc ccaatacaaa   2340
acaatagtaa atggttaaaa aattgctatc tctcatacag gccagatata tcatttcatc   2400
aatattcata tcaacctttt ttatatgata catttcatga agatcagaca cgttattaaa   2460
agaaagccca catattagcc gccaatcttt aaaatgacta tatcgttgat aaaaatattg   2520
gatggcttca gtaagcttac atagtatcgc tatactatac caatatctag ttagcatttc   2580
gttgaatgtt atttcattca atataaagtt gatcgatatc ttctctagaa aacaacaaat   2640
tattactttt aattcctcta tattctggaa aaggggatta ttagataaca atttatggca   2700
taaaataata ttactactag ttttaatacg atgtatttta taaaatattt gtacaatatc   2760
```

-continued

```
catttcattc aaaatttttg cgcctaactc ccggcagaaa ttccaagtat gctccgtatt   2820
gacagtgact aagctagagt tgatgtctgc accccattca gtaaacaact ctattagatc   2880
atagttgttt tcctgcacag ttttcattaa tgcgagattt aactctaaac catctttaaa   2940
aattgctgat tttatcatca attgattatc ctcattagta gaaagcataa ttggagctcc   3000
atgccaccac aaaccacaat atttcaaaat aaagtagtgt tctttagata tgtgctgtgt   3060
ggccagtatt tttttagcaa gagcctgcag agaaattgga gtagacatat ttttttttgc   3120
aaaatggttt aagtttttca agaatacaga ttggataaat taggttgttg acttagttac   3180
aggaggtatt aaatattatg tagacataaa aatgagatcc tccaaaaaaa taaacaacaa   3240
aaaaaatatg tttaatatta aaatgacaat ttctacattg cttattgctc ttattatact   3300
acttattatt attttagtag tgtttttata ctataagaaa caacaaccac cgaaaaaggt   3360
ctgtaaagta gataaagatt gtggtagtgg agagcattgt gttcgtggat catgtagctc   3420
attgagctgc ttagatgccg taaaaatgga caaacgaaat attaagatag attctaagat   3480
ttcctcatgc gaattcactc ccaattttta ccgttttacg gatactgctg ctgatgagca   3540
gcaagaattt ggaaaaacac ggcatcctat aaaaataact ccatctccaa gtgaatccca   3600
tagcccccaa gaggtgtgtg aaaaatattg ttcatgggga accgatgact gtacaggttg   3660
ggaatatgtt ggtgatgaaa aggagggaac atgttatgta tataataatc cacatcaccc   3720
ggttcttaaa tatggtaagg atcacatcat agccttacct agaaatcata aacatgcata   3780
aataaataca ttaggctcat cgtatctttt taaaatccat aaatattcgt ttgatatatg   3840
ctgaaatttt tataaaaaaa ataactattt cctataaatc atctagaaat agtcctcgtt   3900
ttgatcggtt tatatcttat aatattgtgc atcgatgcac aactgctttt tttggtcctt   3960
ctggaacatc attatatttt ctttcattaa tataccattc agatgtaaac gttgaataat   4020
ttttatggca acaatctacc attgaattat atttagtaac atctaataca tcgtttgttt   4080
tatcaggctc agctctataa tcttgataat ttttgttatc agcttctaaa gctccatcat   4140
tatttttcaa agaagtatcc ataattatgt ttggtaaaaa tactttaagt tttaatgtga   4200
tatttaaaat ggttgttata taaatttacc gcttacaggt aatctttatt cagtgtcata   4260
aactatactt ttgatgattc agtattttgt gaatcagtac atttattatc attaatattt   4320
ttaggctgtt tttccaatgt tttattgttg caatgagcct gctcctcctt tgacgaggaa   4380
gtgtctgttg gagtcatctg tttaggaaga gtatcatcca tatctattat gaagaaaata   4440
tataaatatt gatatacaat caaaaatatt tttgatcacg tctttgttat ctatcgatat   4500
tgttgataac gtcttgaata acctacatca ttttttttaca taaaaaaata gatataattt   4560
ttattatatc tcaattattt taaagataat tatcaataca gcaaatatca taagctaaca   4620
tatttttcga ataatagttt tttagtaaag tattaatctt ttcaggattg gtttcttttg   4680
ataataagat aggattcgct ttataaattt ttaaagataa tatattcaca atgatagaat   4740
aaccgtatat atctgctaat gtcttactgt gttcaataac attagcccct aaatccatac   4800
aaaagaacat attttcaata caaaagtttt ttaccgagat taacattgct cgattagcgt   4860
tggctcccaa tgcaaaacag tagtaaatgg tcaaaaaatt attatcgcgc atacaggcca   4920
gctccatcat tttattaata ctcatatgaa ttttcgttgt gttacatatt tcatgaaggt   4980
caaacacatt gttgaaagaa agtgcacaaa ttaatcgcca ttcatcaaaa tgcctgtatt   5040
cttgacaaaa atattgaata gcttctttaa gattatattt taccgctatg ccataccaat   5100
atttggttag catctcacta aatgagatct catttaacat agaatttgtt gttaaatcct   5160
```

```
tcaactccca ataaatgatc atccttaaat ccaccatgtt tacattttgt aaaaaagggt   5220
tattagaaaa taattcatga cacaaaatga cattactact tgttatttta cactttgttt   5280
caaagaaaaa tcgtaaaatt tcacttgtct caagctcttc tttagctccc aattttcggc   5340
ataggtttcg agtatgctcg ttattaataa aaagtaaccc ataattaata tttgcacccc   5400
attcagtaaa caacatgatt agatcatcat tgttttcctt aactgccaat accaatgcag   5460
tattaagcct tataccctct ttaaagcata atgtccttat cattatttga ttatcatcat   5520
ctatatacat tgagatagga gcttcatgcc accataaacc ataacgctct aaaatataat   5580
aatcatcttt agatacgtgt tgcgtggcca atgccctttt agcaagtgct tgtaaagtcg   5640
atggctgcat gtttattctg ttaaaaaaaa tcaaattatc gggtaaacat aaggatcaac   5700
ccgtagttaa tatttgcagt agtatttttt aacaatgaat tataataaaa aaataattca   5760
ttactatcta ttataaaacc catctttaac tttaaagaag aactagatca tctttttttt   5820
gttgtgtcag aacttcttca atttattacc cacattttat ctaaaaaaat aaaaactaca   5880
tcatatcttg tttcttcatc aaattatcat accatttata gggtgtaggt tgggaacatt   5940
ccatcatgtg gtaatcaggg tatttatata ttttttgata gtaacatcta tttggcagat   6000
gtattgtcca acaatcatgt ctaataaaat cattttcacc tatgggggaa tcatcttaaa   6060
aaccttattc ctacagattc cattttgaca gtcccagcaa aagtcacaat attttccatg   6120
agtacaccaa tgttcaagct ctctttcggg aggaatgctg ccaattttat gtttttttagc   6180
ttctaactct ctgtacaaca tcagttggga aagcagaaag aagattacca ggagaaccat   6240
taaatatata atagtctgca aactacgttt gcgaatgtaa tttgcaacta aaacacaacc   6300
cacaaggtaa aatccataag ttaataactt ttgccatttt cgtatgacag cctcgtgcca   6360
ttcatggttg tgttgtgggc attctgttcg gtaaacttca tgaggcttta tagaagttac   6420
atagtaggta cagaattcat tgtgacgaaa aacactgcag ttagctatgt agtcattttc   6480
aagaatggga gaatggtttt caaagacctt attcttacag atgccatctt gacagtccca   6540
acagaaccta caatgatttg cataggtgca ccagtattca agctcctttt caggaggggt   6600
tcttgttaga tccaggagct ctagctcata tgtataaaga agagttggaa tggatagtaa   6660
agtaaatatt tgcagaccaa gcatggctac ttgtgaacaa gtggctgctc gtcaacaaat   6720
agctgtttat cagcaaatag ctgtttatca gcaacaacta attatcagca aatgctgctt   6780
gtgggtaagc caataaatag gccataccct tgaaaggaga attcagtttg ataaaaaaaa   6840
taacgagttt tctaataacc cggtcaagca tttaataaat gaatagcatc acacgtctgc   6900
atcgtgcatt ctgcctggaa aatgggccca tctctaatat atttacactg acggtgaatc   6960
atacagtgtt ccatgggata gctatgctcc tgtacaggag gcatatcttt tagaacttta   7020
ttcttacaaa gaccatcttg acaagcccag caaaaccgac aatttttcac atattgacac   7080
cagtatctaa gctcctcttc caggggattg tcggtcgaaa acccctgtag actagctagg   7140
ccagctagca gcaagccgag gtaactaaag aacctcattg tagtgttata ttacgaaaaa   7200
acatgttaaa atttggaaaa aaaagccctt tttatagatc tggaaaaaaa ttttcacaaa   7260
tctaattaaa agccttacag atcatccttt tcataaattt tcattaacaa ttggtggggg   7320
cggttgtgag gtactggatc agaacaatcc ataacatggt aatgtccatt tccttcacca   7380
tatgtacact ggttatacca gcgagaaacc tcacaagatg tcaaataact gttctcaaca   7440
atcaatggca tgctcttatt caccttgttc ttgcaaattc catgtgcaca ttcccagcaa   7500
```

-continued

```
aacttgcagt tttccatgta agtacaccag tatccaagtt cttcttgtgg aggattatcc   7560
gttgaacgaa gatgccctcc tgcctgagta ggtagtccta agacctgatt ggccagcagg   7620
ccaagaattt ccaagaagat caccaacatt gctacggctg gctgaacagc tggcagatag   7680
ctagctaatt agcaaaccaa gtgactcgcc ctctctactc ttaatatgag aatttaagat   7740
tcggtccggc tttttttccca tgttttacag ggaaaaggta tttttagcct atgaatgtac  7800
atggttccgc acattaaaaa aaataaaaga aattatttaa tattggctgt tattttcttt   7860
caactagcaa caagccaggt aactaaagaa cttcattgta gttttatatt acggaaaagg   7920
ttaaattttg gacaaaaaaa tcatatctaa ttaaaaatcc tcacagatct ttcttttcat   7980
aaattttcat taacaattgg taggggcggt tgtgaggtac tggatcagaa caatccataa   8040
catggtaatg cccatttcct tcaccatatg tacactggtt ataccagcga gaaacctcac   8100
atgttgtcaa gtagctgttt tcaataatca atggcatgct attattcacc ttgttcttgc   8160
aaattccatg tgcacattcc cagcaaaact tgcacctttc catgtaagtg caccagtatc   8220
caagttcttc ttgtggagga ttatccgttg aacgaagatg ccctcctgcc tgagtaggta   8280
gtcctacgac ctgattggcc agcaggccaa gaattcccaa gaagactacc aacattgcta   8340
cggctggctg aacagctggc agatagctag ctaattagca aaccaagtga ctcaccctct   8400
ctactcttaa tatgagaatt taagatccgg tccgacattt ttccgatatt ttacaagaaa   8460
aagatatttt tagctacaaa tacacttcat atatccctaa aaaaacaaaa atttatttaa   8520
ttttaactat tattttcttt ccactctctc tttaagattt tgtaaggatt ccagggcttt   8580
ggttcagaac aggccattac atggtgaatc ccctgtccta gatcatacat acatttattt   8640
agccagcggg aaactataca tgattgcaca tactcatttt caagaattgt tgtattctcc   8700
aatttgccct cacaaaggcc attttgacaa ttccagcaaa acttgcagtt ttctgtataa   8760
gtgcaccagt attcaagttc ttcttgtgga ggattatccg ttggatgaag ttgtccagct   8820
ggttgattag gtagccctaa gacctggttg caattcatgg tatggtagat acccttatct   8880
aaatcataca tacatttatc cagccaacgg gaaaccagac atgatttcac atactcattc   8940
ttgtaaatta ctgacccatc tattttgttt atacaagtgc cgtcttggca gtcccagcaa   9000
aattggcaac tttccatgta ggcacaccag tattcgagtt cttcctctgg aggctcctct   9060
gttggacgaa gttgtccaac gagctgactt gaaacctggc tggccagaag gccaagaatt   9120
cccaagaaga tcaccaacat tgctacggct ggctgaacag ctgactgaat agctagccaa   9180
ttagcaatcc actgtacttt tcataagatc atttaagatt cggtcggcat tttttcaata   9240
gtttgctagg aaaaaatttt taattttata gattcacact acttcattct catgcttagg   9300
aaaaaaacaa actaaatctt acaatgtatc tggatctaat gagaagctag aattcatctt   9360
ttttcaaatc ctttctggga tgttcattct ttttccactc cttccttgca attttataag   9420
gattccaggg ctttgggtca gaacagttca tgctatggta aatgtgctcc tccacatcat   9480
atctacatag gtcaccccag cgggaaacct cacaatattt tacatagtca ttctcaataa   9540
tacttgtgga gttgtttccc caaaccctgc tggtacaaat cccatcttca caatcccagc   9600
agaaccgaca gctttccaca taagtgcacc agtatccaag ttcattctct gggggttcaa   9660
atgttagagg aagatgtcca cctacccgag tagaagtgga ggatgaaacc aggttgctac   9720
tggccagcag gccaataatt cccaggataa tcaccagcat tgtgctcaac cagcaacggc   9780
tagcaacgac tagcaactga ctagcaatag ctagaaatgg ctagcaatca gtagtagcta   9840
acgctctact ctttataaga aaatttaaaa ttcgatcaga ttttttttaga attgagaatg   9900
```

agtaaaacgc ttatattctt tttctagcta gaaaaaataa gctagtttaa gataggattt 9960
cccttactaa cggtttaatt tttagcaaag gtataggtaa aatacacttg tacttagctg 10020
caaaaaaata agcttatggc gtataagccg ccataagttt atttaattaa aatgttaaac 10080
tctgtgataa gactggaatc ttaggcaggt ttgatgtgga gaacagcatg aaatacaaga 10140
gtgcctgtta cacgaataag ttctctcaaa ccggggatgg tcatactcac atctatgaaa 10200
tcctggtcta ggagattcat ttgatgcatg atggccgcac ccacacttat gagacactga 10260
agaactaaag ggtttaattt tgatctgaat ggtactatat aggatgatgg caatccatat 10320
caagattaga gcaatcaaaa tcacctcctc aagaagcatg atgtagcctt aaatcttaga 10380
ctgctttaaa ccttaggccc tcactatctt taatgaagga gtttaaattt tgatcccttt 10440
ttcaagaccc atttagaaga aaaaataaag tttatatcaa tctaattcat aagtcatctc 10500
tttcataaat cttcatgtat tctctatgtg gataagtatg ggatgttgga tttgcgcagt 10560
ccatttgatg atctgtatgg tttttgggtc cttcataata actacatata ccattccagc 10620
gggaaaccgt gcaatttata atccagtcat tttgatgaat aactggccaa tctgtttgaa 10680
tcctgtttcg gcagataccg tggacgcatt cccagcaaaa gtcacattgg tttgcgtaag 10740
tgcaccaata aactagctca tgttcaggag gataacgggt tggtagtaaa tcttctaatt 10800
tacgtatagg agcggcttga aggacaacca cccccagtag tactagaatc agtaccttta 10860
tagtggccac cctacactag acctctaagt tgaagacaaa gaactaaaat ttagagccgt 10920
ttaattacta ctaataatta tattttttat tgtctacaat aggattctat taaaaaataa 10980
tgatttttac caagaaatat ttttataaaa aattaatata ttttgtaata aactttattt 11040
ccaatgactg ttaaaataag gaaactatcc ttagttagtc gaggaagatg gttaggttat 11100
ttcgcaatcc gataaaatgt ttattttatc gtaggtctcg taaaatccag gaaaaaaaat 11160
tacggaagag tttaaaaaag ctaaattttt accaccctcc agaagattgt tgtcaaatat 11220
atcgtttgct agaaaatgtt cctggaggaa cttactttat tacagaaaat atgacgaatg 11280
atttaattat ggtcgtaaag gattcggtgg ataaaaaaat taaaagcatt aaattatatc 11340
ttcatggaag ttatattaag attcatcagc actattatat taatatttat atgtatctta 11400
tgagatatac ccaaatttat aaatatccct taatttgttt taacaaatat tataacatct 11460
aagtaaatat tcttggaatg gattttctta tagaatggtt acaggatatg tcagcgacag 11520
gcttaataac aaatttgtta atattttttt gttaaataaa tgaacaggcc accatttaat 11580
attacccgtt gcaaaataag aaaaaaaaac aaacttatag ttacaaatca tcttgattaa 11640
tcacatgtcg ttttaactca atgaaccatt ctaaatcttt gggttgtgaa caattcatgt 11700
tatgttgata gtgtatccta aagtgagctt catacataca ccggtcatgc caccgggaaa 11760
ctgtacaatt aacaatataa tcattttgcg taataatagg gtggtcacta aacactttat 11820
ttttacacat tccatcttta caggtccagc agaagtcaca gtgttttgca taggtgcacc 11880
agaacttgag atccctttca ggaggcctac gcatttgcat cggattatct gtggaaagag 11940
gtaggttcat tattatgttc gtcatcaaaa ttcctaaaag aacatagaag ccaagaaaga 12000
taagcagtct tgtagcggct tgcattcgca ttcgtgagta ttgtttgcga acatagctta 12060
tgagagcaat ggtagctatc atacaaagac aagtatgttt gatattctca gtgtcaatga 12120
ccctatcctc ctttatttgc attaactcat caaaccaatc ataatatgtg ggatttgtac 12180
agctcatgat gtgaaagcgg cgtatcctag agtctgtaaa gtagctacat ctttcattat 12240

-continued

```
agcgagaaac cctacatatt tgtatgtaat catttttttt gatgagaggg tgtttttcaa  12300
aaaccttatt tttacaaacc ccgtgtcgac aattccagca gaagtcacac gattttgcat  12360
aggtgcacca atactcaagc tctctctttg gaggtctccg ggtcattggt aactctcctg  12420
ttcctggaaa agattggctt tgaatgaccg gctgcatgac cgccagtacc aaaaggaaca  12480
caatcacctt catggctgca acttataagt tgcaacttat gggttgcaat actgcaacgt  12540
ataggttgca ccttatagat cgcgactcaa aaggtatgaa aaccttaccc tcaatacaga  12600
atttaagttt taatcctgat aatgtatctg tttatgaaaa aaaatttttt ttactcatgt  12660
atgaattctt atacgaatca taatatgtag gctgagaata ataattcata tacggtgttg  12720
cgggctcaat aaaaatttg ttaccacaaa aaataaatgc tggattttta agatatatat  12780
ctattaatga ctaaaccctt tatacgctgt aggctgaaaa caatccatat aatgaatata  12840
cggtgatttg ggtttaataa aatacataca acggtcaaaa tagcgggcaa tactacattg  12900
actaatataa tcattttgtt taataagagg catatcatcc cacactttat ttttacaaat  12960
accgttccta cattcccagc agaaatcaca gtgttttcca tacgtgcacc agtattcaag  13020
ctctcttata ggaggcgtat aagtccttgg taaattttgt ttcatataaa agatggaaag  13080
gggtcgattt aaacccggct gagatagcca aatcaaaata cataaaagag caagtagttt  13140
catagtggta tttagatgta aatttttata gtatgcaaat acaatgtaac ctacaaatac  13200
aatactaaat acaaggtaaa aacaacaatg tcttataatg attggccaat aatcaccccc  13260
ccccccccca tttttccatg aatatttcat ttcctgtata gggtctagga tgtgaacact  13320
ccatgttatg atgattaggc attttaactg atatttcata aaaacacccc caggaattgc  13380
gattaactat acagtttaca atcgaattca tcgaattaga ctcatttgtt atcttatttt  13440
tacaaatgcc attttgacaa tcccagcaga agtcacaatt ctttacatac gtacaccaat  13500
atggaagctc ctccttagga ggatgctggg ttcttggtaa ttctggtaat tcatgtgcaa  13560
gaatgaggac tgagtagccc aacaaaagtc ctagaacctt catgttgtgt ccaaatggca  13620
cctgtcattt taaaaaagat ttaaattttg ctaccgcaaa aaaaatccag tatgtatttt  13680
tttaatacat ataattattg aagtcttata agataaagcc gagaacacta tattttgtat  13740
agatgatgta tccggtattc aaactctctt ataagtacat gtaggaaatg gtcaattatt  13800
caagattggc tgagataaca acaaaaccaa aatactcaaa agcataagta atttcatggt  13860
tgtactcagt cgtagatttt tgcagatcgc aaatgcaacg caaccagcaa atacaaagct  13920
aaatacaagg taaaaacaat aataccttat aatgattggc caattcttat ccctccattt  13980
ttccatgaac atttcatgtt cataaagtct aggatacgaa caacatttca tgctatgatg  14040
attaggtatt ttaagtgata tttcataaaa acaccacggg gttgttggtg attgataggt  14100
aagaataagg atggttgaat aacctagtaa aagtcctaga aaaaccttca tattgcgttc  14160
ataccacaga tgttatttaa aaaaaatata aattttacag tatgtgatat acacatacca  14220
caaaaatgtt cttatattaa ctaaaatatg tgggcagaga gcaattcata taatgaatat  14280
atggtatttt aggctcaata aagtacatac aacgatcaat aaaacgggta atactacatt  14340
tactgatgta atcattttga acaataagag gcatatcatc caaaacctta tttttacaaa  14400
taccattctt acaatcccag cagaaatcac agtgttttcc atacgtacac caatattcaa  14460
gttctctcat aggaggcgta taggtccttg gtaaaatttg tttcgtataa aagatggaaa  14520
ggggtcgatt taaaactggc tgtgctaacc aaaccaaaat actcaaaaga acgaaaagtt  14580
tcatggttgt actcagacgc agattcttac aaagcgcaca tacaaagcag cctgtatatg  14640
```

-continued caataccaat gatgaaatag agacagtatt gctttataga taattgttga tggtcacccc 14700
cccccccccc ccatgtttgc atgaatattt catttcctgt atagggtcta ggatgtaaac 14760
attccatgct aaagtgatta ggcattttag atgaaatttc atataaacag gattgagtct 14820
tggaatcacg gaaaactcta cagtttacaa tagaatgatt ggagtcaatg aaacgagatt 14880
ccgttatctt atttttgcaa atgccatctt gacagtccca acagaaatcg cattgtggta 14940
catacgtaca ccaatatgaa agctcactct tgggaggatg ctgggttctt ggtaagtctg 15000
gtaattcatg tgcgagaatg aggactgagt agcccaacaa aagtcccaga agaaccttca 15060
tgttgcgtct aaatgacacc tgcacttaca aaaaaaaatt taaattttga atataacaca 15120
aaaaaaccac cttaaaattt cttatattat ttcttggatc tgccccgacg tcatacaatg 15180
tattaaaatt atagaccaat catctttttg tatataggct aatcatcttt atatatagat 15240
tttagatgtt tgcttgttgt atcaacttaa ctgctagcga agaaaatgga taaaaacttt 15300
ctgtattttt ataggttgaa atcattttat gcacatcgct aggatctaat attttatttt 15360
gaagaaccga atgtgggctt aaaatttttt tcttagaaaa aagtagaatc ataatattgc 15420
tatgtttttg tttaatgatt tcttgtatct tttttgtata cgggttggca cccaaaccta 15480
tacaaaaata tacattactc aaataactac cttctataca taatcttttt tccccacgta 15540
ttttcctatt tatttcccta tttatggaat taaaggatat caatctctct aaggcacggt 15600
caaggtctgc gcctaaggca aaacaataat atatacctaa tttattccca gggcgtgcac 15660
aggcaagaaa catcatgacg tttagcccta aacgtatatt ttcctgaaaa tacgcatgat 15720
gaacttcatc aatattacct aagtatatgg ccgtttgtaa acgccaaaga tctaaatgag 15780
gaaatttttt actaagataa tgaataggtt ttgtgagatt aaaatctatg gcgaacttat 15840
accaaaattt taatacaagt gtatttctcg tcatttcttc ttctttttca tctaaatata 15900
agataaaacg attgtaaaca aagtctatca ataggtgaaa atcattgcta ttaaagctgt 15960
cgagaatcaa aatattgtca taataaattt cgatcgccag taaaaccttt tttcgtttga 16020
cgagataaac aaacatatta tacaacccta catctaaaaa ttctggattg gctcctagtt 16080
ggatacacag gtctttagtc tgcttcgttt tggcacacat gatgccaaaa ttaatatcag 16140
caccccataa aacaaataac ttgattagat cagtctggtt ttccttcaca gcttttacta 16200
aggctctgtc aagctcatag ctgtcgacat cagagcatga catagagcca ccggttacca 16260
ttttacattg cttacaaaaa cctatgggtc cgttttccca ccatagtcca agctgttgta 16320
gaataaaaat atcatcctca tgataatttg aaaaagcctt ggtttctatc aagacttttt 16380
ttgtaagaac ctgtaaagag ttcatcgtat tattatgaat aacaggagta aacgtaatca 16440
attataaaag tgattttttc gaaaaaaact ttagatggtt gaaaatgata atgtacatgt 16500
tcatacaaaa aatagatgca gtgatgtcta aaatcaaaat ttaattttct atgtaaaaag 16560
tacagactta cttatttggg ttaaattgtt tattttaaac tttaattaac cgtttgagtt 16620
agcgatgttt gatttatctt ccatactcat ccgggggggg ggggtcctta tagctctgac 16680
attattgtgg attattgaat ataatgaata cttcatagat gctaaacatt ttaatagtag 16740
ttctgaggct taattgtact ctataaattt ataaaaactt tttgatcaaa atttaatttc 16800
ttataaaaag agtacagacg tcgcttgttt aagcttcatc atgtttcatt cattactttc 16860
tacaattacg ggggggggga gtcccctcat agctttagta ttgctatggt ttactaatta 16920
ttatgtagaa tttatagaag catatgtacc tgaaagtata cctactctat aaaattaaat 16980

```
aatttcagta tatttttttt atgaatagaa cggaaatgat ataaaaataa tttaatattg  17040
caaaaaaaat tcataatgtt ggtatgtatt ataaacataa tagcatgtgt aatttataaa  17100
ctgactcctc tatataatta ttagatgagg taccaaccta cttatgatat gccgatgata  17160
gatattgtat actataaaac aaaattattt taaatgtatt catggataca ttataacatt  17220
tttaccgcaa attgtctctc agcgaagaaa atgaatgaaa cgtttctgta tattcatagg  17280
ttgaaattat tttacgcact tcactaggtt ctaatatttt cttatgaagt attgaatggg  17340
ggcttaaaag tcctttctta aaaagaagtt tcatcataac attcttttct tgtctaagaa  17400
gagtttcttg tatttttttt gtataaggat tggcacccaa acttatacaa aaatgtacat  17460
tactccaaat accataattt gaaaagaaag ttatttccct atttacttca tgattaatga  17520
aacctatcaa cgtctctaag gccgtattga tatttgcgcc taaggcaaaa caatagtata  17580
tacccaattt attttgaggg tacatacaag caagcgacat catgtcattt ggatctaaac  17640
gtatattttc ctgaaaatat gcatgatgga tttcatcaac attacctaag tatacagccg  17700
tttttaaacg ccaataatct aggtgaggaa atttcttact aagaaaacga ataggtttta  17760
taagattaaa ctctatggcg atcttaaacc aaaattttaa tacatatgta tttttatca  17820
ttttttcttt ttcatctaaa tttaagataa aacgattgta aataaagtct atcaacacgt  17880
aaaaatcatg gctatcaaaa ctgtcgagaa tcgaaatatt gtcataataa atatctatag  17940
ctaataagac cttttgttgt ttaattagat caacaaacat attatacaac cctacatcta  18000
aaaattttgg atcagctcct agttgaatac acagaacttt cgtcctttcc gtcttggcac  18060
atatgatgcc ataattaatg ttggcacccc ataaaacaaa taacttgatt agatcagtct  18120
ggtttttctt cacagccctc accaaggctc tgtcaagctc atagctgtca acatcagaac  18180
atgacataga gccactggtt accattttac attgtttaca aaaacctatg ggtccgtttt  18240
cccaccataa tccaagctgc tgtaaaataa aaatatcatc ctcatgataa tttgaaaaag  18300
ccttgttttc tatcaagact ttttttgtaa gaacctgtaa agaattcatc gtattatcat  18360
gaatgaaagc agtaaatgta atcaattata aaattgactt attgaagaga aatgttaaat  18420
gagtgaaatc ggtgtttatg atgatgtaca tgatcatacg aagaaacacg ttcactggtg  18480
tccatgatca aaatttaatg ttttacgtaa aaagtacaga tgttaactgt ttagtttaaa  18540
cataaattta acctttagtt taaaccctag ttaatgatgt ttaatatttc ttctatactc  18600
attcagggaa gtgtaatgat tctaatactg ttgttatgga ttattaatga aaactttaca  18660
gatgctggag ggaataattt taatcatact gttttaatgt agctatataa gctttcatca  18720
aaatttaatt tttttataa aaatacacga attaaactaa agtctaaact ttagtttgac  18780
tatttgagtt aatgatgctt aacttatctt ccatgcttat caaggggggg tcctaatagt  18840
tttgatacta ttgttgtgga ttgttgaata taataaatac tttatagatg ctgaaatgtt  18900
tgaaaataat agtacatcaa tgttgtaagt ttgatcaaaa tttaatttct cataaaaaag  18960
gtacacatca acattgctca tttaagtttc atgatgtttg attcattact tcctacaatt  19020
actggggggg ggggggggtc tttaatagct ttagcattgt tatggtttgc tgactattat  19080
gtagaattca tagaagcacg tttagatagt aatatcactg cagtgtagat tatgaaatac  19140
atactaaact aatttcagta tatttttttt gttcatataa gttaaggtac aaaaatgatt  19200
aaacattgca aaaaaagaaa atcacaatgc tattatacat agtgatcata gtggcttgta  19260
tcatttctaa actagttcca aatgaatatt gggcaataca tctatttttt atcattatga  19320
tttttatggt atatatgtat gaaaagttag atatacatca aaaatctcag ttctggaatt  19380
```

```
ataccatgtc aggcttatct ggacataacg tacaggtaac atgtaagtgt tactaaatac  19440
tatgaagtat ctattttttt tgttgtaaaa aaaagaactt gatagtattt tttaaaaaat  19500
aaaataatta attgtacgtc aacttcctta ttttattctt taaaaataac tcgtaagtat  19560
tatttatcta tttttgaaa aaatagatgt aatcggtttc atcatttagg tgtgtatttc  19620
tttttagcat ctatcaagaa ttcattgttt agtgatatga aaacaatgaa tgatcattat  19680
cttctattta acaaccacct aaataaatga acgtcttttt catcttaact gattaccaaa  19740
agttattttg cgaaaaggca tacatatgat caatatcaga cctacaatga atatttccat  19800
aatatccctt tattgtaata attctatttt tgcattccga tatctcatca tctgtgctat  19860
tatatgtttc cataactgtt tcatcatcaa acataaatcc tgttaaatag gcaaaagact  19920
ttaatcccgg atagattttt accattttcc tgagagccgt gtatagcttg taataaatgg  19980
ccaaaaatat gcaataaagc gtagaaagag agtaattttt ggcataaaag attttgaagg  20040
tttgatgaat ggctaaatcg catataatat aagatacgat tttaaagcgc acctgttcac  20100
gcagatttgt tgaaaaattc gtggaaagat ttaacaaata aaaggttatt aatagttgct  20160
catcattccc cttatacgac atcgtcagac gctctaatat tttactacta ggcacatctg  20220
ccacatgttg aacatttaaa gcctgttctt cttctgtgtt acggcaaaag agccgtgcgt  20280
attcaggtga agctccccag gataacaacg tccttgctac ggctaaattt tttttgacga  20340
tgacttttat cagaaataag tctttatttt tgcattgatc actatgcgaa tttgtatagt  20400
tgacgccgtt gcattgagta cattgatata atgttttaca attccagcgt agccctaaat  20460
ggtataaaag aactgtattt tcgacataag catgctgatt aacgatgttt ttgagacaac  20520
acgtcgttaa ggacaccata ttgtctccaa tttgttagat aaaagtcttt actaaaaaaa  20580
tagattttta gttttaacaa tcgagatttt attatttgga tgcatcatca aaaagattta  20640
taagtataag aggttgtata agaaaaaaat gatgttatac tatttatgtt aaaatttaat  20700
ttatcatata aaaagtacag atttaatcag ttggttaaac tatttagtta attaaactaa  20760
atagtttaac catttagtca gactacttgg ttagcaatgt ttgagctttc ttccattctt  20820
atccgggggg gggggtccta atcgttctaa tactattgtg gatagttgaa tataatgaag  20880
actttataga tgctataatg atgaattcta gtatgcctgt ataaaataat taaccttttt  20940
gatcaaaatt taattttttt ataaaaagct acagagtagt gttttattaa acgtggctta  21000
tttaaaagtt acacaatgtt aaaatctcta cttactttaa ttctttgtgg ggttttatta  21060
actttatcca tattatggct tactacttac catgtagaac ttatagaggc aatagatgat  21120
ttctacgact gaaatataga atagtccatt ttctatttgt aaaataatga tttatattct  21180
ttcctaaaaa tgatacttta tatggtttga aaacaaatat taacaacttg attttttttt  21240
ctataaataa actataaatg aaaatagtaa aactcataga gtcttataag tgaacatctt  21300
cataatgtta ctcaaacgtt ggactattaa aaaatattcc gtgtgcatta ttgcttttaa  21360
tcagtatgat tactttatac gaagccgcta ttaaaacgct tatcacacac cgaaaacaaa  21420
ttttaaaaca ccccgatagc cgtgaaattt tactagcttt ggggttgtac tgggataaaa  21480
ctcatattct tgttaaatgt cgtgaatgtg ggaatatgag tcttaccgga aaacacagta  21540
caaaatgtat taacattaat tgtctactta ttcttgccat aaaaaaaaga ataagcgtat  21600
tgttgatacc ttgataggaa tgggcgcgga tgtaacatat atacatcttt taaagaataa  21660
gataaaactg tcatacaacc agctgtctat gcttaaaagc aactcgcaga tttcattgaa  21720
```

-continued

```
ggagcttcat gctatatgct atcttttata tggtcggctt cccaaaaaaa ttaaacaagg  21780
gatgcgactg tgtaaaacaa tggcgggact atgtggtgaa cttttatgtg catttttagc  21840
tccgtaaatg ataatatgta tttaaaacaa acagatatta ccaaaatata ttctatgtac  21900
ataatatctg ggaaattatt ttttttctc atacccttaa atataaaaat attgggtttc  21960
ttcactaaac tttagaggta aaaatttttc tttgttttgc accatcatgt atgggtttag  22020
gctgtcccag ggattgttta tttgaatatt tcctaaatag gaacacaacg ccatgatcat  22080
atatctttca ttctggtaag ctttttgata catcttcaaa gatgccgtac ctccgagtgt  22140
gtaacagcaa acaaacgtcc gtacttttcc atgggtcgca gcccattcca ttccgtagct  22200
cagcatcttt tgctgtattt ttttattcgc tttataaaaa aagtttttca tccattccac  22260
gttctcataa aaacaggcac ttaaaaagag cactaggggt agtgtagtct tattatagaa  22320
tgtaggaatg tatgttttag ttattttttt caacgcgtgt tccatactat gttttaccgc  22380
cataaaaata caaaaccaat accaactttt tctataaaag gttttgctgt acacatataa  22440
acgagcaaaa tatatttcaa actctatatt ctttttataa aaaaactcga gacagtcgtt  22500
tatgttacga ctttttctaa atacctcaaa aacagtaatt aattcactgt cgctgtggaa  22560
atgttcgtaa gctaactgtt taatgtcttt aggggtcaat tctttttttg ggagcagtgg  22620
tttgagattc ggcaaaggtc gtctaaagta gtgagcgaac ttttcattcg ctccccaaca  22680
caaaagccga taagccagca tgtagttatc acgttttacc gcgtaaataa gcaaatagtt  22740
tatattgata catgtaccat gttgctgccc gtttggacat atgttgccgc attctgaaca  22800
cttatgaatg agatcatagt tcttacaaca taaccccaaa cgggttagta cttctttgtc  22860
acgttttaaa aactcgacat gattctttaa tgttaatgct ttgagcgcaa tgttaaataa  22920
actctgcatt ttattaaaat gaggttagta tcatgtttta gtataaaatt tagcggctgt  22980
ttacataatg ctaaataaac ttaacgttcc tactaaacca aaaaaaatca aattgactaa  23040
gtcatagaga atttgacgat gttggtaggt aatttttaa catggtatat atttttttag  23100
ggtcggttat attaggtaat aaaagaggac gtgccgttaa agtattttgc ttaagatcct  23160
ttagatcctt acaaaaatat agattgttcg tctgatgatg ccactgtgtt gcagtgatgg  23220
cttgatcaat atcacctccc aagacaaaac agtagtatat cgttaaaaag ttgtaatctt  23280
tcatacaagc caactgcatc attttatcga tgtccatatg aacgatcttt tgctcgtata  23340
tttcatgaag gtcaaataca ttgttgaagt aaatggcgca catgagtcgc cacatactaa  23400
ggtgcccata tgtttgatag aaaaaggaga tagctctttt aagcttatat tttactgcta  23460
tggcatagca gtatttaacg aatacgttca tgggtacatt atctaagata taaaatatga  23520
aaaactttaa ctctcgatga atctcttccc ccatttcctg tacatttaga gcttccaaca  23580
taggattttt atcaaatatt tcatgacata aaataatgtt attgctcgtt ttatgacgca  23640
ttaaaccggt gaaaatttcc ttattattta aactatcttt agctcctaac tttcgacaca  23700
gctcctgagt ttgttccgtc ctagcacagg tcagcccata ataaatgttt gctccccact  23760
cggtgaacag ccttattacg tcatagttat tttcttttat ggccatgatt aatgccacat  23820
caagatgaag aagttccccc ttaaaggggg ttgagcttaa aataacgtaa ttacagtagt  23880
gacataagct aatgggcttg ttttgccacc ataagccaca atattttaaa atataatgat  23940
actcctcagg cacgctctgt ttggccacag cctttttggc cagggtttgc aaggagagca  24000
tgataacttc ttgaaaaaaa aactcaaatt aagttcctac ttttttaaaa tattagtatg  24060
gacagatcta ccatcatatg aaggaattct ttcatcgtta aacactgaag agataatact  24120
```

-continued

```
ttcatcgtat agagaatatc atgtcaatcc atatattgaa tgttatatat cattaaaccc  24180
atcattaata tagtgtttat gtgctatgga caggtttttt gaatgataat cttttaacat  24240
acgttttata acttcgggat cagtttcttt taaagataaa gaatcattca tgttataaca  24300
atttaatgat aacatgctgg caatgaacga gttgtctttt tgatgcgcta gagtctttcc  24360
ctcctcaaag gcattggcgc ctaagtctat acaaaagaat atgtttccga tattatagaa  24420
ctgaatagaa tgaaacatgg cctgattgat atcagcccct aagacgacgc aacagtaata  24480
aatcgttaaa tagttatagt tcttgcgaca ggcccacttt agcatttcat tcatgtctat  24540
gcgaatcctc tccttttcgt acacttcgtg aagttcaaac acattattgt aaaaaagggc  24600
gcacataagc cgccaccgat gtagatgagc atatctctga taaaaatagc aaatcgcctc  24660
cttaaggtta cattctattg ccatcgcgta ccaatattta gtaaacatct cgcttaatat  24720
atcggtttct accattaatc cctccagttg ttcataaatc attcccttta cttcaaaacg  24780
atttatggta tctaaaatgg gattattaga aaatacctca tggcagaaaa tgatgttact  24840
gctagttaga tcacgtttca atgtgtaaaa aaatcgtaaa atttcctggt catttaactg  24900
ttctttggca cctagctgcc tgcacaggtc tcgggtgtgc tccgtgttga cagaaagcaa  24960
accgtagttg atgtttgcac cccactcggt gaacaattct attagatcgt gattgttttc  25020
ctccacagct ttcaccaagg ccgcgttaag atttgtgccg ttcttaaaat acggcgtcca  25080
tattttcttt tgatgataca tgatagggcc attatgccac catagaccgc agcacttcaa  25140
aaaatgagga tggcatttgg ccggatactg gctggccagc acctttttgg tgagagtctg  25200
cagagagagg accatatttc ttttttttga aaaaatcaaa ttaaaaaaat catgcttgtt  25260
tagcatacat gtaatattgt tataattacg ttataattac gttataatta cgttataact  25320
atattataac aatggtataa caatggtata acaatgttat aacaatgtta taacgatgta  25380
tcattgatgt catcattcaa ctaggccaac atacttttta atttatagtt ttttaataga  25440
tgatatattt tgttaggatc tgcttctttt aacgttaata gcgaggagtc tgcactataa  25500
atgtctaatg ataaatgatg agatatcaaa tagtaattcc gttgctctgc tagggccttt  25560
gcctcttcaa aggcgtcggc tcccagatct atacaaaaga acaagttatc catattataa  25620
aatcgtacgc aggcaagcat agctgaatta atattagctc ctaagagaaa acaataaatat  25680
atggttaaaa aattgttatc ttttgtgcag gccatccgca tcatttcatc cacgtccatg  25740
cggatctttt ccttttcata caaattatgt aggtcaaaca gcttattaaa acaaagagca  25800
cagattaacc accacgtatt tagatactta aaatgttggt aaacataaga aatggcctcc  25860
ctaagattat cctgcaatgc cactataaaa cagtatatcg ttaacatatc accatccgac  25920
atattactta atatgtcggt gtcttctact aacctttttca acttccaata tatggatgac  25980
cttatttccc ttataatgac ataggctgga aagggattat cattaaaaag tttaagacat  26040
aagataatat tactgctagt agtgccaggg tgtattaatt taaagaacat gtgcataatc  26100
ttctttttat ccacgcggta cttggctcct aattcccagc aaaattctcg aacaggcggc  26160
gtattggcgc aaattaaccc atagttgatg tctgcgcccc attctgtaaa cagttttatt  26220
aactgatagt tgttttcctt tgtagccaac attagtgccg tattaaggtc caagccgtct  26280
gcaaagcttg gcagctttat cagcatatgt ttgcaatcaa gggaaattgg ggccttatac  26340
caccatagtc cgcagcgttc taagataaca tggtactcaa tagatacttg ctgtctggct  26400
agtacctttt tggcgaagga ttgtaaggaa ggaaacatcc tgtttctttt tttttaaaaa  26460
```

-continued

```
tcaattatct ttgttcataa tcaagaaaaa tccccatatt tattgagtga taatttttta  26520
acatgcaatt tatttttca gggtccgtaa cgatcgacaa cagagaaata accggattgt  26580
aatgctttaa tgataaggca tgggctatca gataattttc cttttgttct gccaaagctt  26640
tgccctcctc aaaggcatcg gcacccaggt ctatacaaaa gaacaggttt ccaagattat  26700
agttttgtat ggaaacaagc atggcttgat tgatgttggc tcccatgata aaacagtagt  26760
aaatggccga atagctataa tcttggatgc aggctatgtg catcatttca tcaatatcca  26820
tgcggaccct ttctatttcg tacagctcgt gaaggtcgaa cacgttgttg taaaaaaggg  26880
cgcacatgag ccgccaccta tgtagacgcg ggtatttctg gtaaaagtag cggatagcat  26940
ctttgaggtc atagtccacc gctatcgcgt accagtattt ggttaaaaca gtgctaaagc  27000
tatcatcatg gtccagcatg aaggttatct ccatgagccc tcttaactcc cacatgattt  27060
ccccctcag atccagatta tctataatcc ttaaattggg gttattggaa aacacctcgt  27120
ggcaaaagat aatattgcta ctggttttat cgcgcgttgt atcaaagaaa atttttaaaa  27180
tatactctct ttctaaatat tctttggctc ccagctcttt gcacagatca cgggtatttt  27240
ccgtgagagc acaaatcatt ccatagttaa tatctgcacc ccattcagta aacagcttta  27300
tcaagtcatg attattctcc ttcacggctt tcatcagtcc tatgtttaac tcgatacctt  27360
gactaaaaca ggttgacctt ataaataatt tattgcgtcg aatatgaagc ataatggggc  27420
cattatgcca ccacaggcca caacacttca ggacatgata ttgatctacc ggtatacact  27480
gcccggccag tactttcttc gtgagggatt gcagggaagg caacatgcct ttccatcctt  27540
tgacggaaat caaattatct actaataact atcagtgttt atattaagta tttagatatt  27600
atcccgggct ggatacgtag tatcgctatt cacatgtact tccaactcta gccggagcct  27660
gcagggtcat ttatttttaa tattgattct tttttgtatt taatcattta gagaaggtca  27720
tcataggagc cagatgttct ctctccagaa cttatgtcga aaaacattac ctaaccgtaa  27780
acttcctgaa tttttgacg aatatatatt acaactgctg ggattatact gggaaaacca  27840
tggaactatt caacgagcag gaaacaactg tgtgcttata cagcaacata ccctcattcc  27900
cgtaaatgaa gccctgagaa cagcagcatc tgaagaaaat tatgagatcg tgagcctttt  27960
attagcgtgg gaggggaacc tttactatgc tattataggg gctctagagg gcaaccgcca  28020
cgacttaatt cgtaaatatg atgaccaaat caaggaccat catgaaattc tgccattcat  28080
tgacgatcca gtcatatttc acaaatgcca tatcatgcgg caatgctttt ttgattgtat  28140
tttatatcaa gctgtaaaat atagtaagtt tcgcgttctt ctttacttta aacatagatt  28200
agaggatgat ttgcccttca ctcatttact tattgaaaag gcatgtaaag atcataatta  28260
tgaagttatt aaatggatat atgaaaacct acatatctac aatatgatag ataccttga  28320
atgtgctatt gcccataagg atctacatct atattgtttg ggtatagat ttatatataa  28380
cagaatcgta cccgataagt atcatcattt agatattcgc atgctttcaa gcctacaact  28440
cctacataag gtggcagcca aaggatactt agattttatc ctagaaacct taaagtatga  28500
tcataataaa gataatataa atattattct aacacaagct gcaacctata accatagaaa  28560
aattttaatc tatttcattc ctcaatcaac ccacgcacag atagaacaat gtttactagt  28620
ggcgataaaa gcaaaatctt ccaggaaaac cttgaactta ctactgtctc acctaaacct  28680
ttccatcaac ctcatcaaaa aaataagcca ttatgttgcc acttacaatt caacaaatat  28740
aataggcatt ctgagtatgc ggcggaaaaa gaagatatat ttagatatca tattgacaaa  28800
atttgtaaaa aaagctattt ttaataagtt tgtcgttcga tgtatggata cattttctat  28860
```

-continued

```
aaacccggaa agaatcctta aaatagccgc gcgaataaat aggatgatgt tagtgaaaaa  28920
aatatctgaa catgtttgga aaaatcatgc ggttagactt aaatacctta aacatgcggt  28980
acacacgatg aagcataaag atgggaaaaa tagactcatg aactttatct atgatcgctg  29040
ttattaccat atgcaagggg aagaaatctt tagcctcgca agattttatg caatccatca  29100
tgcaccaaag ttgtttgacg ttttttatga ttgttgtatc ctagatacga tacgattcaa  29160
aagccttctt ttagattgtt cacatatcat aggtaaaaac gctcatgatg ctaccaatat  29220
caacatcgtg aacaagtata tcggcaacct gtttgttatg ggagttctta gcaaaaaaga  29280
aatcttacag gactatccat ccatttattc taaacaatac atgccttagt ttattttttt  29340
tgcggccgaa acattattct taccctagaa aacgcttata gtcatcttaa atcataggta  29400
aggaagatca tcatattttt tgaaacgtaa ttttttaacg catgatctat gatttcaggg  29460
tccgtgcttt taggcaacgg ggtggtggcc ggactataaa tctttaggga taaaatgttc  29520
tttataagct catacccttc ccctaaagct gtagtaccct cttcgaaaac atcagccccc  29580
agatctatac aaaagaacat gttttctata ttatagtact gtattgagct aagcatggct  29640
tgattgatgt tggcgcccag gacatagcag tagtacatgg ttgaaaggtt gtggtctttg  29700
atgcaggcga tccgcatcat ctcttctatg tccatatgga tcttgtcctt ttcatacgcc  29760
tcatgaaggt caaacacatt attaaaacaa agagcacatg ttaaccgcca cgtattcagg  29820
tgtgtatatt tttggtaaaa atactgtatg gcctctttca ggttatagcg tatggctata  29880
gcgtaccagt atttgagtag taatgtactg agcgaaaact cattatttag cagatcggtt  29940
tttactatta actcccttaa ctcccagaaa atttctatcc tcatttttat attatttact  30000
ttttgtaata tcggattgtt ggaaaacacc tcatggcata aaataatgtt actactagtt  30060
ttatgaaact ttagatctat aaaaatttgt aaaatttctt cttcattcaa ggtttccttg  30120
gcacctagct ctcgacagag gtcccaggtg tgctccgtgt tgacagatac cagcccgtag  30180
ttgatgtccg ccccccactc tgcaaacagt tttataaggt tgtagttgtt ttcccttaca  30240
gccttcacta acgccgtatt taggtttaag ccctctttaa tacctgctga ttttatgagc  30300
cttaggttat gatcaaacgt gatcggagca tcatgccacc ataggtcata acactttaaa  30360
agataatgtt ggttcgtggg cacgcattgt ccagccaaca cctttttggt cagagattgc  30420
agggaaggca acatgtctct tcatctttta aaaaaaaatc aaattaatta gccgaataaa  30480
tttttctttc gagggctttt taaaagagct ctttaagagc tctttaagag ctttttaaga  30540
gattaaaaaa ttattcttgc tggcattctg ccaagtatgc ggcattccta tcatctatag  30600
tatattatga gaatattccc aaatgatgga taagtttttt gatttataat cttttaataa  30660
actgcttatt tcttcggggt cctttaagtt tagtggcaag gaagcatctg agctgtaaat  30720
atccaaagcc aaactatggc tcagaaaatt ataacctttt tgttccgcta tggcacgacc  30780
ctcttcaaag gcattaccac ccaaatctat acagaaaaat atattaccga tgttataata  30840
ttgtactgaa gtaagcatag cttggttgat gttgcccccc agcgcgtaac agtaatatat  30900
tgttaatgga ttgttatcct tggtagaagc cagacatatc atgtcatgga cgtctatttg  30960
gatgttttcc ttgtggtaca tctcatgaag ctcatatatt ttgttataat acaggagaca  31020
ttttaatcgc cattcattaa gatccgtata tttctcatct agaaaacaaa tggcgtcctt  31080
acaatcgtat tgtactgctt tggcgtacca atacttcact agtaaaccat ttaactcgtc  31140
cgtttctttt atttctatga gcccccatag tcttttataa attaagcccc ttaattgtat  31200
```

```
aacaaatttg ttttctaaaa taggattatt cataaaaatt tcatggcaca aaataatact  31260
gccgctggtt ttattgtgca ttatcctggt aaaaatacgg aaaatatcgt tgtcctctag  31320
agtttctttg gcgcctagct gtctacacaa ctctcggatg tgcttcgtat tgatagaaag  31380
caaaccatag ttgatatttg cgccccactc tgtaaagagc tttatcagac tatagttgtt  31440
ttccttaaca gctattatta atgccacacg aaggtctata tcttctccta aaaatcctga  31500
ttttatttgt attcggccac gatccataca aagcttgaga ggagcatcat gccaccatag  31560
gccacaatat ttcaaaatgc agtgttcatc tattgacaaa cactggctgg ctatcgtctt  31620
tttgacgagg gtctgcagag agagcggcaa cgacatgttt ctttttcacc aaaaaaaatc  31680
aaatgttctc gtctttaaag gttaattcat gttcttaaaa tgttcatttc atgatagtga  31740
ttaataatat ggtttaataa cgctagaagg cttgtttata agacagtcat aagcagtcta  31800
taagacagtc tataagcagt ctataagaca gtctatgact tagtctataa ctataatttc  31860
tggatgggct gtaagatact cttcggctcg tttcagattt tttgaagtat atgtctttag  31920
catatcatat atttcctggg gttcggttac atctaatacc aaggtcacat cacggctgaa  31980
aagctgcttt actaagaaaa tgttgctcaa gttatacata taagctttgt gcgcaatgag  32040
ttgtgcccta tcaaaatcgg cagcccccaa atcaatacag aaaaacatgt ttaaagtatt  32100
attgttatag atagaaagat tcatgccata atcgagacta gcccccaacc tatgacagta  32160
ataaatggcc gcgtaatttt tttcccgcaa gcaagcaaat ttcatcatca gattagggct  32220
gatgcaaatc tctttttcac gacacaactc gtgtatgtca aaaatgttat taaaataaag  32280
gctacaagct acccgccaat agaggtgatt tttatgcctt ttatagaaat agtgaatagc  32340
ctttgtaaaa ttatgtcgta atgccagggc aaaccaaaac tttgttaata ggtggtgcgc  32400
cgtatccccc gtcaacggaa tgtttgaaca ggtgtacgta actgtgtcta aagtggttct  32460
agttacggtt tccaagagtg gattatgaca aaacatgtca taacccagca gaactcctgc  32520
acaggatttt agcctggcca cttcttttaa aatttccaga agacggggtt cggatacagg  32580
cgttaagcct cccagttccg cacacagccg ctttagatac acggcaggaa cacgtataag  32640
cccatattca ggatttgcgc cccaatccac aaataaacgt ataagttcaa gattatcgct  32700
cttcacggcc tttactagcg ccgcttcgag acaaagatca tcctcagaaa aacactgtaa  32760
atgtttatac gaaaaaactt gcttacaatt gttacatagg tgaataggac ctaaatccca  32820
ccacaaacca aaacgctgca acgtataatc atagtcactt gaaagataat tgcatgccac  32880
aacttttttg gccaacgttt gtaaagacaa catactaagt ttaaaacatc ttaaatctaa  32940
gctagctaac tttcaagaaa accctctatc cctaagaata tatcttataa ctagacttat  33000
agcagtaaaa atcaactttg gttattcttt ttaatataaa acgtctaatt acttgcaaag  33060
gactataaag cccattttcc tcagctagaa tttttatttt ttaatgaagt agggggatat  33120
gttttccctt caagaccttt gccgaaagca tctttttatt cttcccgatg tttttggcga  33180
gcatgtacta caacgattag gactgtattg gagatgtcac ggctcccttc aacgcatagg  33240
agacgaccac atactcatac gacgggatct catcctttcc accaacgagg ccttaagaat  33300
ggcgggagag gaaggaaaca atgaagtagt aaagctcttg ttactgtgga agggaaatct  33360
tcattacgcc gtcataggag ccttgcaggg tgatcaatat gacctgatcc ataagtatga  33420
aaaccaaatc ggcgactttc attttatctt accattgatt caagacgcga atacgtttga  33480
aaaatgccac gctttagaac gtttttgtgg tgtttcatgt ctgctaaaac atgctacaaa  33540
atacaacatg ctccctattc tccaaaaata ccaagaagag ctgtctatga gagcgtatct  33600
```

-continued

```
tcacgaaacc ctatttgaac tagcatgcct atggcagagg tatgatgtcc ttaaatggat  33660
agagcaaacc atacatgttt acgacctaaa gattatgttt aatattgcca tctccaagag  33720
ggatctgact atgtactcct taggatatat tttcctttt gatagaggga acaccgaagc  33780
tacgttgcta acgcaacatc tcaagaagac agcggccaaa gggctcctcc actttgtgct  33840
agaaacgtta aaatacggcg gcaacataga taccgtcctg acccaagccg taaagtacaa  33900
tcatagaaaa cttttagatt attttctgcg tcaactacct cgtaaacata ttgaaaaact  33960
tttgttgctg gccgtgcagg aaaaggcttc taaaaaaaca ttgaacttac tgttgtcaca  34020
tttaaactac tccgtgaaac gcatcaaaaa actaccgcgc tatgtgatag agtacgagtc  34080
caccttggtg ataaagattt tattaaaaaa aagagtgaac ctgatagatg ccatgttgga  34140
aaagatggta agatattttt ctgcgacgaa agtgaggacg atcatggatg agctttcgat  34200
tagtccggaa agagtcatta agatggctat acagaaaatg agaacggata tcgtaatcca  34260
tacttcttat gtttgggagg atgatctaga acgtcttact cgtcttaaaa atatggtata  34320
caccataaag tacgaacatg ggaaaaaaat gttaattaaa gtcatgcacg gcatatacaa  34380
aaacttatta tacggcgaaa gggaaaaagt catgttttat ttagccaagc tctatgttgc  34440
tcaaaacgcg gccacccaat tcagagacat ttgtaaggac tgttacaaac tggatgtggc  34500
acggtttaaa ccgcggttta agcaactaat attagactgt ttagaaatta ttactaaaaa  34560
atcttgctat agtatcctgg aaatcttaga aaaacatatt atttccctgt ttactatgaa  34620
agttatgact gaagaagaaa aaaacctatg tttagaaata ttatataaag taattcatta  34680
taaaacaata caatgttaaa attcaataga tatccatcat taatattgat tatattttcg  34740
aatattatct tctatggtgc aagataatca tctagcgcgt gaaacatgtc ctcttctctt  34800
caggaacttt gtcgaaaaaa gctgcctgac tgcatacttc cagagttttt tgacgactat  34860
gtattgcaac tgttaggact gcactggcaa gatcatggtt cccttcagcg tatcgagaag  34920
aaccagatac ttgttcaaca ggaacccatc catatcaatg aagcactcaa agtagcagca  34980
tcggaaggga actatgaaat cgtagagctg ttgttgtcat gggaggcaga tccccgctac  35040
gccgtcgtag gagccctaga aagcaaatac tatgacctgg tttacaaata ctatgaccaa  35100
gttaaagact gccatgatat cttgccgctg attcaaaatc cggaaacatt cgaaagatgt  35160
catgagttaa acagcacctg ttcactgaaa tgcttattca agcatgctgt gataaatgac  35220
atgctgccga ttcttcaaaa atatacagac tatctggata ggtgggagta ttgcagccag  35280
atgctgttcg aactggcatg tagtaaaaaa aaatatgaga tggttgtgtg gatagaggga  35340
gttctaggcg tcggcaaagt tacatctctt ttcaccattg cgattagcaa cagagaccta  35400
cagctgtatt ctctgggcta ctcaattatc cttgagaatt tgtactcctg tggacaggac  35460
cccaagtttt tactaaatca tttcctgcga gacgtttcaa taaaagggct tctacccttt  35520
gtaatcaaaa ccatagaata tggtggaagc aaggagatag ccataactct ggctaaaaaa  35580
tatcagcata aacatatttt gaaatacttc gaaacctggg aaagctaggt tcagtatggt  35640
gtactcacta ttgtagtgaa tcgtatcctg taaattttgt aaaaaagctt aaacttttga  35700
ccacatcata ttgttttaga aatctcaaac cagtgaacaa cagtcttatc atacattaaa  35760
attccagtaa aatttatatt ttttttggta aacaaatgtt ttctcttcaa gacatctgtc  35820
ggaaacatct ttttcaactt cctgacgctt ttgatgaata tatattacaa gcgctaggac  35880
tatactggga aaaacacgga tctcttcaac gaataagaaa ggacgctgtg tttgtacagc  35940
```

-continued

```
gaaacatcgt cctttctacc aatgaggccc tgagaatcgc agcctcagag ggaaacgaaa  36000
gggtaataaa acttctgtta tcatgggagg gaaattttca ttatgtgatc ataggagctc  36060
tagagggtga ccaatatgac ctaattcata agtatgatag tcaaattaaa gactaccaca  36120
tgattttatc attgatccaa aatgcaaata cctttgaaaa gtgtcatcag ttatccaata  36180
gtaatatgtg gtgtcttata cagaatgcta taaaatataa tatgctccct attctccaaa  36240
aacacagaaa tattctgaca catgagggag agaatcagga attgtttgag atggcatgtg  36300
aggaacagaa atatgacata gttttatgga taggacaaac cctaatgtta aatgagccgg  36360
agtttatttt tgatatcgcc ttcgaacgga tagatttttc tttattaaca atgggttata  36420
gccttctttt tgataacaag atgagtagta tagacattca tgatcaagaa gatcttactt  36480
cattaccaac agaacacctc gaaaaagcag ccactaaggg atgtttcttc tttatgctag  36540
aaactttaaa acatggtgga aatgtaaata tggcagtctt atctaaagct gttgagtata  36600
atcatagaaa aattttagac cattttattc ggcggcaaaa atgtttatca cgtgaagaga  36660
ttgaaaacct attattaacc gccataacca attgtgcatc cataaaaacg ttaaacttac  36720
tcttgtctta cctaaactat tccgtaaaaa atatcattgg aaaaatagta caacatgtca  36780
taaaagatgg tgattatacc atcatattac ttttaaaaaa aaagaaaata aacctagtgg  36840
aacctgtttt aacaggtttt atagattatt actatagcta ttgttttata aaacatttta  36900
tccaagagtt tgctattcgt ccggaaaaac tgattaaaat ggccgcgcga aaaggtaaac  36960
taaatatgat tatcgaattc cttaacgaaa aatatgttca taaagatgat cttggaacta  37020
tatttaaata tctcaaaacc ctagtatgta ccatgaaaca taaaaaagga aaagagacat  37080
taattgttct tattcataaa atatatcaag atattcatct ggagactaaa gaaaaattta  37140
aattattaag attttatgtc atgcatgatg caactatcca atttctatct atgtgcaaag  37200
actgttttaa tttagccggt tttaaaccat ttgttttaga atgtttggat attgctatta  37260
aaaaaaatta ccctgatatg atacaatata tagaaattct atcgaaatct gagtaaaatt  37320
tatttttttg atcagagtaa gaaaatgttc tccctccagg agatctgtcg aaagaacatc  37380
tactttctac ctgactggct cggtgagcat gtgattcagc gactaggtct gtactgggaa  37440
aaacatggtt ctcttcagcg aatcggagac aactatgtac ttatacaaca ggacctcatc  37500
atccccatca atgaagccct aagaatggca ggggaggagg ggaatgatga ggtggtacaa  37560
ctcctattac tatgggaggg aaacattcat tatgccatca taggagcttt ggagagtgac  37620
cattatagcc taatacgtaa gctctatgac caaatcgaag actgtcacga catccttccc  37680
ttgattcaag acccaaaact ctttgaaaaa tgccatgaat tagataaatc ttgtaacatt  37740
ttatgtctcg tattacacgc cgtaaaaaac gatatgcttt gcattcttca agagtataaa  37800
atgcatctaa gtggagagga tattcaagtg gtgtttgaaa cagcatgccg ttcacaaaaa  37860
aacgatattg tgtcatggat gggacaaaat attgcaatat acaaccccga agttattttt  37920
gatattgcct ttgataagat gaatgtgtcc ttattatcta tagggtatac gcttcttttc  37980
aatcatcata taaataatac gaacgaaaat attaattctt tattgacaca acatcttgaa  38040
tgggctgccg gcatgggcct tcttcatttt atgctggaaa ctttaaagta tggcggggat  38100
gtaacgataa tagtcttgtc tgaggccgta aaatatgacc acagaaagat tttagattat  38160
tttctccgtc gaaaaaactt gtaccaagaa gatcttgaag aactattatt gttggcgata  38220
cgtgcagatt gttctaaaaa gaccttaaac ttgttattat cttacttaaa ctattccata  38280
aacaatatcc gtaaaaaaat attacaatgt gtaaaagaat atgaaacgac cgttattata  38340
```

-continued

```
aaaattttac ggaaaagaaa gataaatctg atagagccca ttttggcaga ctttatagga  38400
tatcatagct atacctatat ggtagatttt atgcgtgagt tttccatcca tccggaaaaa  38460
atgatcaaaa tggctgcacg agaatcgagg gaggacttga tcataaaatt ttccaaaaaa  38520
gtttgcaaag agcctaaaga tagacttcac tatctcaaaa gcttagtgta tactatgcga  38580
cataaagaag gcaaacaact gttaatttat acaatccata acttatacaa agcttgtcat  38640
ctagagagta aagaaatgtt taatttggca cgattttatg cacggcataa tgcagtgatc  38700
cagttcaaat cgatttgcca cgatctctcc aagctcaata ttaatatcaa aaacttgttg  38760
ttagaatgtt taggtattgc tattaaaaaa aattactttc aacttatcaa aacaatagaa  38820
acggatatgc gttatgagta acatttttag atgagggaag attctaccaa actaactaag  38880
acctttcgct agaatgtatc ttattgttaa tatagatgag atatgtcatt gtgaaaaaat  38940
agattaggta ggttgtgaaa aacagattaa acttaaaatt atgtgtatta tgtaaaattt  39000
tagaaataaa aatttatttt ttttattgag ggtacggaaa atgttctccc tacaggacct  39060
ctgtcggaag aacattttct tccttccaaa tgattttagc aagcataccc tacaatggct  39120
gggattatat tggaaagagc atggatccgt ccatcgagca gaaaaagaca gcataatgat  39180
acagaatgaa ttggttcttt ctatcaatga tgctttacag cttgcaggag aggaggggga  39240
cacagatgta gtacagctct tgttattatg ggagggaaat ctgcattatg ccatcatagg  39300
agccttgaag actgaaaaat ataacctaat atgtgagtat catagccaaa ttcaggactg  39360
gcatattctc ctacccatga ttcaagatcc agaaacattc gaaaaatgtc atgatttaag  39420
ccttggatgt gactttattt gccttctcca acatgctgta aaatacaaca tgctttctat  39480
tcttgtcaaa tataaggagg atctactaaa tgcaaggatt aggcatcgta tccaatccct  39540
gtttgttttg gcatgcgaaa atcggagaat tgaaattatt gattggatag gccaaaatct  39600
gccaattcct gaacctgatg ccatttttag cattgctgtt gctacaagag atttagaact  39660
gttttcctta gggtacaaga ttatttttga ttacatgcaa agacagggaa tcattcaatt  39720
aaccaatgga gttcgcatgg ttgtgctaaa tcgtcacatt agcatggcaa tagataatgg  39780
tcttttacct tttgttctgg aaactttaaa acatggtggg aatatacata gagccttatc  39840
ttatgcagta acacacaata gaagaaaaat tctggattat cttattcgcc agaaaaatat  39900
agcccctaat acaattgaaa gacttttata tctggccgtg aaaaatcaat cttccaggaa  39960
aactttgaac ttgttgctat cttacataaa ttacaaggtg aaaaatgtta aaaagctggt  40020
agagcatgta gtaaatgaga aatccactct tgtgttaaaa attttattag aaaaaaagga  40080
aaatctagtg gatgctgttt taacaagact tgtaaaacat tctacatatt tccaggtgag  40140
agaatttatc caggagtttt ccatcagccc agaaaaattc attaaaatag ctgtgcggga  40200
aaagaaaaat gtgttaatcg aggctatttc tgaagatatt tgggaaaatc ccacagaaag  40260
aattacttat ctcaaacaga tagtgcacac cataaaatat gaaagtggaa ggcgattttt  40320
ggtagacatc attcacagca tttaccaaag ttactcacta aaacacgaag atattcttaa  40380
actggcaaca ttttatgtca aacacaatgc aatcacccat tttaaagacc tctgcaaata  40440
tctttggctg aacagaggaa cagaaagtaa gaaactgttt ttagagtgtt tagaaattgc  40500
tgatgagaag gagtttcctg atattaaaag tattgtgagt gaatatatta actacttgtt  40560
tactgcagga gctattacca aggaagaaat catgcaagcc tatgatgctt tagagtagcc  40620
atgtattaac attctgaaag tagaataaaa tatactatat actaaaaacc aaattagcca  40680
```

-continued

```
tttttaacta tcttcttctt aaaaactctg gataaaaatt tatttttttt aatttgggta  40740
gggaaaatgt tctcccttca ggacctctgt cggaagaaca ccttcttcct tccaagtgat  40800
tttagcaagc ataccctgca tttgctgggg ttatactgga aggggcatgg atctatccaa  40860
aggataaaga atgatggtgt gcttatagag catgatctta ctctttccat caatgaagcc  40920
ttaattcttg caggagaaga gggaaacaat gaagtagtaa agctcttgtt actatgggaa  40980
ggaaatcttc attatgccat cataggagct ttgaggactg agaactataa cctagtatgt  41040
gagtaccata gtcaaattca ggactggcat gttctcctcc ctttgattca agatccagaa  41100
acattcgaaa aatgtcatga tttaagcctt gaatgtgatc tttcatgcct tctccaacat  41160
gctgtaaaat ataacatgct ttcgattctt gttaaatata aagaggatct actaaatgta  41220
ctatttaggc aacaaattca aggactattt attttagcat gtgaaaatcg gaagcttgag  41280
attcttacgt ggatgggtca aaatctgcca attcctgatc ctgagcctat ttttagcatt  41340
gctgttgtca caaaagattt agaaatgttt tccttagggt acaagattgt tttgaatac  41400
atggaaaacc aaggacttca tttaacccag gtagttcgta tggttatgct aaatcatcac  41460
tttggcatgg taataaataa aggactttta ccctttgtgc tggaaatttt aaattatggt  41520
gggaatgtaa atagagcctt atcttatgct gtcacacaaa ataaaagaaa gatttagac  41580
catgttgttc gccaaaagaa tataccccat aaaaccattg aaagaatgtt gcatctggct  41640
gtaaaaaagc atgctcccag gaaaactctg aacttgttac tatcttacat aaattacaag  41700
gtgaaaaatg ttaaaaagtt gttagaacat gtagtgaaat acaactctac tcttgtgata  41760
agactcttgt tagaaaaaaa gaaaaacctg ctggatgcta ctttgacaag atatgtcaaa  41820
gattctacat actttcaggt gaaagaattt atgcaagact tctccatcag cccagaaaaa  41880
ttcattaaaa tagctgtgcg ggaaaagaga aatgtgttga tcaagggtat ttctgaagat  41940
atttgggaaa atcccgcgga aagaatcagg aatcttaagc agatagtgtg taccataaaa  42000
tatgaaagtg gaagacaatt cctgataaat atcattcaca ccatttacca gagttattct  42060
ttgaaacctg aagaaattct taaattggca acattttatg tcaaacacaa tgcaaccacc  42120
cattttaaag atctctgcaa atatctttgg ctgaacagaa gaacagaaag taagaaactg  42180
tttttagagt gcttggaaat tgctgataag aaggagtttc ctgatattaa aagtattgtg  42240
agtgaataca ttaactattt gtttactgca ggagctatta ccaaggaaga aatcatgcaa  42300
gcctatgctt tggagtatgc catgtattaa atttctgaat cagtaagcaa tagatagatt  42360
ttagaatatg ctgtattaag ttagtttctg aataagtaat taatagatag attttagttt  42420
atgtaaaaat gttaacattt gttcataagt tttagatacc attttagagt tacttttta  42480
gatattacta ttttagccat tattatctta aataatcact attttagata ggtccccgta  42540
ttaaaaacca aattaaccat tatctatgtt tttaataata ctttttaaaa accctccata  42600
aaaatttatt tttttcata aaagtagaga aaatgttctc cctacaggat ctctgtcgga  42660
agaacctttt tcttccactt gagcccttag gcaagcatgt ggttcaacgg ctgggattat  42720
actgggaagg ccatggttca gttaaacgag tgggtgattg ctttatatgt gtagaccaga  42780
tttggatgct atcaatccat aaggctatac aaattgcagc ctcggaagga aatgagaaca  42840
ttgtcaagct tttcttacta tggaagggga gtctacaata tgccatcata ggagccttag  42900
agggcaggca atatgatctg attcaaaaat attacaacca aattggggac tgccatcaga  42960
ttctaccact gattcaagat ccagaaattt acgaaagatg tcatgaatta aatgttacat  43020
gtacctttca atgcttattt caacatgcta taagagataa catgctgccc attttccaaa  43080
```

```
aatatggaga agatctgaat ggaaacagga gaatggttca acttctgtat gagatggcat  43140
gccgattaca aaattatgat atcatcaaat ggataggatc taacctgcat gtttataact  43200
tggaagccat ttttagcatt gcttttgtta gaaaggattt aactttgtat tctttaggct  43260
acatgcttct tctgggtaga atgagtactg aagatagaaa ctttatctca atcataacac  43320
gccatcttga atacgcatca aaaaagggac tttttgactt tgtactagaa tctttgaaat  43380
atggaggtca agtggataca gtgttgtttc aggctgtaaa atacaaccat aggaaaattt  43440
tggcccattt tattcatgaa attccccgtg aaacggttga aaagctgata ctccatgctg  43500
tggagtcacg ggcctccaga aaaacattca acctgctttt atcttccata aactactgtg  43560
tgaacccttt tgtcaaaaaa ctactgcacg ctgtggtgaa acacaagtac atgcttatca  43620
taaagctttt gctcgagcgg cccaaaaaga agataaacct ggtagatgct gctctattca  43680
aacttgtaaa atactctact tatacagaaa tagtaaaata catgggtgag ttttctgtgg  43740
acccaaaaag ggtggtcaaa atggcagcac gactcatgag agtggacctg attaaaaaga  43800
tttctaatga tgcatgggaa gataaactag agagaatcaa gcaccttaaa cagatggtaa  43860
ataccatgaa ccacagaaat ggaaaaaatc tattgatgta caatattcac aatattactg  43920
gatataccta tctgaacacc aaagaagcat ttaacttaac aagattttat gctgtccaca  43980
atgcaacatg tttgtttaaa gaaatgtgta aaagctgttt tgtacatgat aaaatacagc  44040
tcagagaatt gcttgaagat tgtttacata ttgctaatag gcatgattat atccagattg  44100
cagaaaccgc agatgaatgt atcaaatata tagatcttat tacatttaag taaaccatgt  44160
atatatcaag taaatccaga ttaaatcagg ctaattgtaa atagttgtag ataccatata  44220
atgaatgttt tattaggata gtagttcagt taagatagta gtttagttaa gatagtagtt  44280
tagttaagat agtagttatg ttaagatagt agttctgtta agataatagt ttagttaaaa  44340
ctagttcatg ttaagttaat agttttgtta agacaatagt tcatttaagt caatagttca  44400
gttaagtcaa tagttttgtt aagtcaatag tttagttaag tcaatagttt agttaagtca  44460
atagtttagt taagtcaata gttatattaa gacattagtt ctgctaatac attagttttg  44520
ttaagataat aaaaatttat ttttttcat cagggtagag aaaatgttct ccctacagga  44580
gctctgccgg aagaacattt acattcttcc ttaccccttg gctaagcatg tacttcaaca  44640
actagggctg tactggaagg gacatggatc tcttcaacga atcggagatg accatgtact  44700
cttacagcag gacctgatct tttccatcaa cgaggcctta agaatggcag gagaggaagg  44760
aaacaatgaa gtagtaaagc tcttgttact atgggaggga aaccttcatt atgccatcat  44820
aggagcttta gagggcgacc gatatgacct tatccataaa tattatgatc aaattgggga  44880
ctgccacaag attcttcctt taatccaaga cccgcaaatc tttgaaaaat gccatgaatt  44940
gagtaactcc tgtaatattc gatgcctttt agaacatgca gtaaaacacg acatgctttc  45000
tattcttcaa aaacacaagg agcaaataag attacacatg gcattaaccc aaatactatt  45060
tgaattggcg tgtcatgaac gtaaaaatga catcattaga tggatcggtt attccctgca  45120
catacaccat ctagagacta tttttgatgt tgcattcgcc cataaaaatt tatccttata  45180
cgttttaggg tatgaacttc tcatgcacaa agtaaataca gaggctgcat atatagaatt  45240
acccaatttg ctatcatatc accttcgaac tgcggcggca ggaggtcttc ttaactttat  45300
gttagaaaca ataaagcatg gtggatatct ggataaaacg gttttatccg cggctatcag  45360
gtacaagcat aggaaaattg tggctcattt tattcatcag gttccccgta aaaccgttaa  45420
```

-continued aaaactgtta ctctatgctg tgcaggctcg ggcccccaaa aaaacactga acctactttt 45480
atcttcctta aactactccg tgcacaccat caccaaacaa ctcgtacaca atgtcgtcat 45540
ctacagttcc acgcttatcg taaagctttt actcatgcgg cgaaaaaaca agttaaacct 45600
agtagatgcc gttttagcca gacttgtaaa atattccacc tatacagaca ttgtacaatt 45660
catgggtgag ttttctgtga gcccagaaag ggtgatcaaa atggctgcac gggaatccag 45720
gacctttctg attgaaatga tctccaaagc tgcttgggga aatcacccac agacgttgat 45780
tcatcatctc aaacaactaa ccaataccat gaagcctcaa tctggaaaag accacatcat 45840
atataccatc cactatattt atctaaactc taatatgctg gtagcggagg aggaaaaaaa 45900
tatttttaaa ttagcaaaat tttatgcgaa tcataatgcg gtaaacaggt ttaaacaaat 45960
ttgtgaagac tattatatat tagatgcacg atttaaaaca cttattttag aatgttttga 46020
aattgccgtc cagaaaaact atcctagaat tgcaaatatt gtggatgact atattcgatt 46080
cctttttac aggggaaata taaccgagga agaaattcgt gaagcctatt ctttaaaaga 46140
tgctgaggtt tatgtagatt taaaatggtt acaacaagga gaaatggttt aaaccaaatc 46200
cggtttaaac taaatccaat ttaaactaca tttggtttat cattagtcat tgaaaccatc 46260
gaaaaaaaag ctatttgttt atccccataa actcatcttt tttttgtctc aaagtttgac 46320
actaaaattc agtgttttat agtgtttata attaagtgtt ttgcatgcat tgcagaaatt 46380
ttcatctttt ttaattggtt caataccaca tgtcatacaa tatgttgttt gattatcaag 46440
attaacttta tgaaaggaaa gtaagtgagc cgcaaattta aaagtaaaat atctttcatt 46500
taaaatgatc ttatgaatgt attttcgata aggaggaatg aaagcatttg ccaaaataaa 46560
tcgcataaaa ggcttggaaa aacccatatc ttctaatctt ttgtgggtat aaaccctatt 46620
ttggtgtttt acaaaaactt cattgttata atagtcgtta tagctatcaa tcattttttt 46680
aagtcctata atgcccaagg ttgcacgcat aaagccacag tttctgctcc aaaaagcatg 46740
cacctgtaaa gggtgctttt catataacca attacaaaat ttcattccgc aacagtagca 46800
tgttatttca gtgggggatg tatagaataa tccggcattc gaaaattttt cataattttt 46860
tatgtcatgg attgcgaagc tttgatttcg tgcatctatg gagctatagc ctacatattt 46920
aggttttact tcaaataatc gcaaagagat gtatggatct atcgtattta ttttaggaaa 46980
catttcataa ttttaaattc ttatatataa tataaaaaaa attacaaaca tttgtaatga 47040
tcatcctcaa ttgaaggctg agttgtaggc tttatttttc taattatacg aagaaggtag 47100
gttctcataa agccttcaag atgactattg atgtttccaa tacattttct caatgagttc 47160
ataaacccag acattttgct aatggcttgg caaagtgcca acaagttgtc cacaaagtac 47220
tggtagattg ccactagcta tagctagcta tagtgagcca acctctctgt atgtatttta 47280
tatatttcat tttttaatag atttaatatt tttataaaaa atatttagtt ttttatacaa 47340
gaatgtcgac aaaaaaaaag cccacaatta ccaagcaaga gctttactcc ttagtagcgg 47400
cagataccca gttaaataaa gcattgattg aaagaatctt tacaagtcag caaaaaaataa 47460
tacaaaatgc tttaaagcac aatcaagaag ttattatacc acccggaatc aagttcaccg 47520
tcgttacggt gaaagctaaa cctgctcgcc agggccataa tcccgccaca ggagagccta 47580
ttcaaattaa agctaaacct gaacataaag ccgtaaagat acgagcattg aaacctgtcc 47640
atgatatgtt aaactaaact ataaagtcat attcttcttt atcgttatta tcttcaatat 47700
atttttgcca atcgaaatcg aataaattca gatcctggac atttaaatac ttatcatcgt 47760
acattttaat ataatttaaa catgagttgt tgtcaaaaac ttttagcgtt tttgttaaaa 47820

-continued

```
ttatcatatg aataatttcc ttattaagag ttgccggaat aatacaaaac ctatttttag  47880
gtacatcatc catgataata gtaaaattag taaaaattgt ttcttgtttt tcttttgttt  47940
caaataaacg ttgtaaggtt aaaggtttct cgttcaatgg tttctttgaa gataaaaaga  48000
atgtataatc tggtttaaag gtatttttgg tttcaatcgt gattccatct gcttgagcat  48060
atactaaacc agaccaaata taacggtcca ctattacaat ataatttagc ttaagtagca  48120
ctgcaatttc tgcgataaat tcactacgat gttttgtaaa taatttatgt aattgttccg  48180
atgacatttc tatggtttta tttaacacct gcaatataag atcaccggtg gtcgtgtctg  48240
gattaggaaa atgtatacat atagcattat aatccatgca ttccaatgtt tcttttaatt  48300
tcattgcctg tgtgcttttt cccacaccat tgattccctc gatggcaatg agtattccac  48360
gcatgattaa taaaaggaaa aaaagaattc agtttttaac atttcttaca aatctttttt  48420
tatacaacat tgtacaacac tgcattagcg gtatatgatg ttatagcttc attaaatatt  48480
tgcttttata taatctttac caacctatat ttggtagatc actgcagatg gtcataaata  48540
ggccataact aagataaaaa ttatttcaga cgctactacg gtagtattat taaaatcatg  48600
tgtggcaatg tatgacgtct taatagataa aacatttaag gaaaacaaat ttgaataaaa  48660
aaataattgt tatgatggcg ttgttacaca aagaaaagct tatagagtgc atctatcatg  48720
agctagaaaa tggcgggaca atattgcttc taacaaaaaa tattgttgtg tcagaaattt  48780
catacattgg caatacttat aaatatttta cctttaatga caatcatgat ctgataagca  48840
aagaagatct taaaggagca acatccaaaa acattgctaa aatgatttat aattggatta  48900
taaaaaatcc tcaaaataat aagatttgga gtggtgagcc gcgtactcaa atttattttg  48960
aaaatgattt atatcataca aattacaatc ataaatgtat aaaagatttt tggaatgttt  49020
caacttcagt cggtcctcat atctttaatg atcgtagcat ttggtgtact aaatgcacat  49080
ccttttaccc atttaccaac attatgtcgc ccaatatatt ccaataaatt agatatcttt  49140
gctattaaaa tagttaaaaa ccttatagga taattaggta ctttattacg ataaattatg  49200
atattttata attagttact ttattataat taatctcttt attaatgaat tatcataaga  49260
taactaatta tttttttcca tatatcagat aataaatctg atatgggcta aaagtatgtt  49320
tcaaactatt tacaatagaa tttctgttaa gaaaacatac ataatttgaa taaaattttt  49380
ttaaatatca ccgaaacaat caacatggtg ttaatagagt ttttaacagg tttcttctat  49440
ttatatggaa agagactgtt ttccattagt aaagtcatgg acatgatatg tctagactat  49500
tataccatta ttcctgctcc tctggcgatg atgttagcgg caagactaaa aaactatgac  49560
ctcatgaaac gactgcacga atgggaaatc tctattgact acgctctact tgtagtagat  49620
gatgtgccgt ctattgacta ttgcttaagt cttggcgcta gatccccgac tagagcacaa  49680
aaaagagaac tgctgaggga caacacgttt aatcccgtgt ataagtatct tatgaactgt  49740
tccggcttcc caacaaagag agaaaaaaac attccttgtg atgttcaatg cgaaagactg  49800
caaaaaaaca ttataaaaga actggtattt aactgctctg tactgcttga aatggtactg  49860
cacacagaaa gagaatatgc atacgcccta cactgtgctg caaaacataa ccaattgccc  49920
atcctcatgt attgttggca acaatccaca gacgcggaat ctattttgtt gaaaacctgc  49980
tgttctgata agaacatcaa ttgttttaac tattgtattc tatatggcgg cgcccaaaat  50040
ttggatgctg caatggtgga agcggcaaag cacgatgccc ggatgctgat aaactactgt  50100
gtcatgcttg gtggaagatc cttaaacgaa gcaaaagaaa cggctgccat gtttggacac  50160
```

```
attgaatgcg cacaacactg ttttaaactg cagtcttacg tcgtggacac atcgaataca  50220
gacgacactg attaaagcga caatcttacg tcatgaacga ctgtcttttg agtatctata  50280
cttacattat attttttat gaaaaaaata taaaggttgt atacaaacct ttgtatacaa  50340
gaaatttgga tcattaaaca ataattaatt tggacacagg aaacgatcta gatcgatcaa  50400
aaagctattt tttttgcaca cagaacattt agataattga gagattactt tccatacttg  50460
ttaagctttt ttacacacag gaactttgga ttctgttcag gaagtttttc atagacatta  50520
tgtttacagc cagtaataat aattttgggc tttttcttaa accaccggtg gaaaacatcc  50580
agcttgtaaa gagggaaatg catgtagaga ggttttggta gtcatggtta agagatttga  50640
ctaactccat gtttcctgta aagactgccc agtcccaagc agtaaaacct ctatgatagt  50700
ctttttgagt cggatctgct ccaaatttta tgagagaaag catatttaaa gaacggcccc  50760
gtattgcggc cttcatcaca ggagtcatcc cattaaaatt cggtaaacaa attctggtcc  50820
catttttcc gaaatagccc aacacccctt ccaggattaa atgatttttt ttctcagcta  50880
aataatgtaa agcagagttt ccatctttat ccctcctatg agggttaatt atttctccag  50940
gataagattc ttgttcaaaa agaaatttta aaaagtctat acgtccgtag atgcatatcc  51000
acatgaatac cgaggatcca tttttatcgc atctattgac aatccacgga tctgttttaa  51060
aaaattcctc aaatagtgta agattcccat ttctaatatg ttttttaatc catttaacaa  51120
acaagtttc tatctccctt tctggaaaca tgtgttccat tttgaatgtc gcccctactc  51180
cactatatga ttttactcct ttaattttta atgtcctttt ttttcggact tctttggata  51240
agctgtttat taccatcttt aaatgcctta tagcggggag gagccaggcc cttttcccat  51300
atgtgcggta attcttggtg tttatgcttg cctttggcat aaccaggcca gtatttttcg  51360
atatattcag ggtttgtttt tacgtattct ttaaaggtcc gataggcttc ttgaatacag  51420
gtaggctcac cggtataatt tccatgttca tcttccttta aaaagccatt aaccctgtcc  51480
tttctccact taagattgtg ctttccaaaa atgcgatcaa gatcttgcgc ctgctggggt  51540
ggaatcataa atcccttttt aggtcgaagc tttttatttt ttccatagct tcggccatcg  51600
cgttgcgaaa cagtggttag gacgcctgat agtctttcca tgggcgtcgc atctaatcct  51660
atccatccac cctgatgaat atcaatggca acaagctctc ctttattttg ggcaagccaa  51720
gtttccaaga atgccatgct ttcttcccag ggataaggcc cgccaacacc acgggttgtc  51780
caatcttgca aggactccag gtccgacacc tggtaaggct ctaaagaaga cggttccttg  51840
tttttgtact gcaaataaga tttaatgacc catttatacc atgtgtcgaa ccgcagcgtg  51900
gcgcctccaa agtgaaagcc gtcgttgatt ttaggatatc tgcaacatat ttcaaccgta  51960
cgtttgagtt ctgcaaaagc ggccttccaa ggaagtcttt cgctgcgggt aagacggtct  52020
attttgccct gcgtgccata gcgtatggca tgtcgtgcca attgcaacaa ttctgacacc  52080
gatccgtggg ccccgatcca gtttatcgga taggcaacct ccgaagggtt taaaagatgc  52140
tcgtaaaagc gtggatcttc agatgccaag gcgtctgcaa aggggataat gctagaaaac  52200
ctgtctagac atacgttttc tgtgtttact tctaaaggta gaaaaatggt tgcgtgaggc  52260
ttttgaacct gcttgttcag cggtctgcat atgctttgaa taatgtctct aggactatgt  52320
cgcggcgctg caaaaaatac cgcgtttagt tctggaacct ctacgccctc ttgaaagagt  52380
cgacagttta ataaaataac gggttccttt gaggaacaaa attctgtaaa tgttttgagg  52440
ataacctgtc gcggcagggt tgagtgagct atcagggcat agaccccttg gtctaccaac  52500
gccgcgtata gctccttggc ctgtttaata tcacgggtaa ataccagcat tttaggagcc  52560
```

```
ggtatattgg tttttaaata ggctaaggcc attataattt gctttactat gatctgtttc  52620
gtggtctcct ctttggtact cggttggtgg gccaatttag gcgcggctac catctgcaat  52680
tcaaaatcat ttacatagcc ggcctctatg ccttctcgca gatagtagcg aaaggcaacg  52740
ccgccaaaaa gttcacgatt tttcatggaa agcggggtgt cgtacctggg cgttgccgtt  52800
aaaaaaagtc ggtgcccttt tttaaagttg agcaacacgt gggtaaaggg ccgtgtctcc  52860
cattcgccgc aaatccggtg acattcatcg ctaataataa gatcgaaatc atccaccagt  52920
agcgtggagg attggtaggt ggcaatcaca agaagagaag gggcctcccg tatccgtttt  52980
gcaataaaga caggattggt ggtcatttct atattgtcgt gatttagcac aatgcgggtc  53040
tggtcagacc ccacaagcaa aacgttcttc aaagaaattc catactgata gagtttttcc  53100
agagtctgcc gtagtaggga caggcccggc accaggtaca aaacttttcc ttgaagataa  53160
ttggagagga taagataggc gacgcgagtt ttgccgcatc ggcaggccat ctgcagaatg  53220
gccctcccac ttcgccgcag ctcctgatag cccatattgg ccgcctcctt ctgataaagt  53280
cgatcctcga ttgcagtccg tgtctcatct gtagaaaaaa ataatacgtc atctgcgaaa  53340
tgttcatctt ccacaggagt tatcaccagg tgtctcagtt tctccttgct tatcagcgga  53400
tcagagggca aagatggctc aaccactatc gtggaatcat tcatctcata ggcgggagaa  53460
tcacacaaag tatagcttat gtccagacag tttgcaacat cctcagccaa ttgttttatt  53520
ttttcgggta aaagacatac gagttctttg tttttgacgc gaaaaaactg tgcacaatat  53580
aacacccctg cttcaatttt ttgcgcatcc ttctttgtag atgtttccaa tgtgaaacaa  53640
tacttccatt catccgtaaa acaggttgta taagatccat catgaagcct agcggccaag  53700
tttcctgtgt gcccaacttt atgtaaggat tgggcctcca gccagggatg aaccgccacg  53760
taaaatcctg cgcacatgct atatcaaatt gcagtttctt aataactgta cacaggatct  53820
gaaaaacatg tgattacaaa atttagataa gaaatattta atattaaaaa tcacagaata  53880
catgtcactg tgtagagaga aagccaaaaa ctcctcttga ccgccgtggg aaatcatcca  53940
gggtagtagg ttgtgtttca taaagttgta tgccgtagtg atcaccgtgg actccagatg  54000
gttattggca tctttgcaat actttgccat cttggcagaa aagacgataa atccacaaat  54060
tctaccccag ttgataagat ccttaaacag ctcagtcaca accccagtaa actgggtttt  54120
aatttcttga acactcgtaa gagaaaaggt aattgtaacc tgtttgttca aacactcatc  54180
ataataggtt aaaatttttt ttatttgttg ttgatatggg ctaagctcat gctctgaaat  54240
atcattaatg taatatttaa tatatcccac tagtatttca ttaatgatat tatgatatat  54300
taactcttct ccctccatag cggcacccta tattttttta tttaggtttc aatgttatca  54360
caattgcgat acaattgtga tacaattgtg acacaactgt gttgtataca acaaatgtta  54420
ggccacgtat agcaacctat atgttaagaa atatttttat cccaacatta gttggaaacg  54480
agcagccgca aagaagtcat ttaaaataag ccatttaaag atttagaatt tatatgtata  54540
caactgtaca atggaagcag ttcttaccaa actcgaccag gaggaaaaaa aggctctcca  54600
aaattttcat cgttgtgctt gggaagaaac taaaaatatt ataaacgatt ttcttgaaat  54660
ccctgaggaa cgatgcacct ataaattcaa ctcatacaca aaaaaaatgg agcttttatt  54720
tacccctgaa ttccacaccg cctggcatga agttcctgag tgcagagagt tcatattaaa  54780
ctttttgaga ctcatttcgg gacatcgagt ggtattaaaa ggccctacat ttgtttttac  54840
aaaagagatc aagaatctgg gcattcctag taccatcaat gttgactttc aggccaacat  54900
```

```
tgaaaatatg gatgatctac agaagggaaa tctcatcggc aagatgaata tcaaagaagg  54960
ctaaataaaa caactaacat caaaaaacat taaaggctat gttgtggacg atgcctttgt  55020
ctcaatagtt tcgaggtcat ccaataactc atgtaacgta aaaaagttgg tccatttttt  55080
tgaaaacatt aaaagacgtt cgtcttcata aataaaaaag tcattcgaag gaaaaatgat  55140
atactcaata ccatagtctt gtaatatttt ttttaggtct ctcagggtcc agggatttac  55200
caggcttcta cgcgaagtga gcatcataaa aatatctaat attttttgcg ccataagcca  55260
gcgcggattc tcattggccc acaaatcaac aataattctc ttatcaaccg tgagcattcc  55320
tacttgattc gaagaaatga ttagatgccc agcagtccac cccatgagta gataacgcag  55380
cgttgtagaa atgtcacata tggaaggcat tcctccacaa catgaaccca aattaggatg  55440
cgtgtgaaac acaaacatag caggcttgtt ggccaccctg ctataaatat cagcaggcat  55500
catagcctcg ctgccaaaat aaatgttctc tcctgcccta taggggcttg gaatgatttc  55560
cactatctcg ggtacaccgt ttatcatatt aatgcggccg caccattcac ggtcatcgtc  55620
caaaaatttt ttgatggcac cccgaacatt gtcccagtta agcaacagag tattcacaat  55680
ctcattacgc tccgcccagt attccttaaa acttctttta gacttgctga gctgttccca  55740
ggattcgaac tcagtccaat gtttttttc ttttggggaa gacttccctt ttgaaacatt  55800
ttttgcggct ccaccatcta cactatgatt ttccaaaata atctccttca tcgtttgagt  55860
tatatgggca ttgctaagca ccttagtggt aacctgttta cctatgtgat ttagcagaaa  55920
accaagtttg tccatttgtg tctcaaccat ttattcttaa caaaacaaaa aaaattaaaa  55980
atcatcgtcg tttaaaaaga gtttgaaggc aaacgcatca tccttaacac agttctgata  56040
ctgcgtaggt cttaactcga aaaagttggt tttttctact tcattaagaa agaatttagt  56100
catctgagga aaagggtttc ccaccttata aatgcttttg cactgcatca tgaagcacaa  56160
attatctgta aagtagcgta tatattgaaa tagcatttct tttgaaaaac cgggaactct  56220
tcctcttgcc ttgtcaaagg catagttaat aaactcatcc accaactcca cagcctcctt  56280
caaaattttg tgaatgatct tttcctcggg aatgttatac acgtaatttg agataagaaa  56340
acacgcaaaa ctacagtgca tcccttcatc acgtgagata aactcattat agcttacaag  56400
ccccggcata atattctgtt ccttaagaaa ctggatcgcc acaaagtggt tttgaaataa  56460
aatgccttct acggcggcga agcccaccag ccgctcacct agagtgttcc tgtcggggtc  56520
catccactgc cgcacccact gcgccatttt ttttatgata gggtgttttt caatgccgct  56580
aaagatgcgc tgttgttcct tctcatccgg gatcagcgtt tttacctgta ttgagtaggc  56640
ttcgctatga acgcactctt gggcagcctg cattgtataa aagtataaca cttcctttac  56700
tttaatttcg cgcataaaat tggttaaaag gttttcgata acaatttcgt cggcaacaac  56760
aaagaaggct aaaatttgtt tataaaattc gcgctgtggc tttggcatgg cttcccaatc  56820
atcaatgtcc ttacacatgt ccacctcctg cgccgtccac gtcaaacttt ctaatttttt  56880
ataccagttc caacattcgg ggtgctgaat aggaaaaata gtgaaacgtt gggaattttc  56940
aattagtaat tcctccatat ttgaaataaa tattaacatc ttcaaattta ttggctgcca  57000
tggagacgtt ttttattgag acgttggcat ctgatgtgta tggaaaggcg ttaaatgttg  57060
atttagatag actatcgcag gcgcaggtta aatataccct tcaagagctt atttcctact  57120
gcagcgctct aaccatttta cattatgact attcaaccct tgcggcgcgt ctttcggtgt  57180
accagctgca ccagtcaacg gcctcctcct tctcaaaggc ggtgaggctg caggccgcac  57240
aatcctgctc acgcctgtcc ccccagtttg tggacgtcgt ttacaagtac aaagccattt  57300
```

```
ttgacagcta cattgactat agcagagatt acaagctgtc cctcctgggg atagaaacca  57360
tgaaaaattc ttatttgtta aaaaataaag atggggtcat catggaacgc ccgcaggatg  57420
cttatatgcg ggttgccatc atgatctatg ggatgggaag agtggtcaat atgaaaatga  57480
ttctgctaac ctatgacctg ctttcccagc acgtcatcac acacgcgtcg cccaccatgt  57540
tcaatgcagg caccaaaaag ccacaactct ccagctgttt cctgctaaat gtaaatgata  57600
atttagaaaa tttatatgat atggtcaaaa cggccggcat catttcaggc ggcggcggtg  57660
gaatagggct gtgcttgtca ggaatacggg caaagaatag ttttatttct ggtagtggtc  57720
ttaaaagtaa cggcatacag aattatattg tgctgcaaaa tgcttcacaa tgctacgcga  57780
accagggagg cctacgtccc ggagcctacg ccgtctactt agagctgtgg caccaagaca  57840
tctttacatt tttacaaatg cctcgcctaa aaggacaaat ggctgaacaa cggcttaatg  57900
cccctaatct caagtacggc ctatgggtcc ccgacctatt catggaaata cttgaagacc  57960
aaatacacaa cagaggcgac ggcaaatggt acctcttttc gccggatcag gcccccaatc  58020
tacataaggt ctttgatttg gaacggtcgc agcacgaaaa cgcacaccgc gaatttaaaa  58080
agctttacta tcagtatgtt gctgaaaaaa ggtacaccgg cgtcacaacg gccaaagaga  58140
ttatcaaaga gtggttcaaa acagttgttc aagtagggaa tccctatatc gggtttaaag  58200
atgccataaa tcgtaaaagt aatctttcac atgtaggcac tatcacgaac tccaatcttt  58260
gtattgaagt cacaatcccc tgctgggagg gtgataaggc tgaacaaggt gtttgtaatc  58320
tggccgcagt aaatctagcc gcctttatac gtgaaaatgg ctacgactac cgtgggctca  58380
tagaagcatc aggcaatgtc acagaaaatt tagataatat tatagataat ggctactacc  58440
ccacagaagc cacgcggaga agcaatatgc gtcaccgacc tattggcatc ggggtctttg  58500
gcctagccga cgtgtttgcg tctttaaaaa tgaaatttgg ttcacccgag gccattgcca  58560
tggatgaggc catccatgcg gccctatact acggggccat gcgacgatcc atagaacttg  58620
caaaagaaaa aggaagtcat cccagctttc cggggtctgc ggcctcaaag ggtctactgc  58680
agcccgacct atgggttcgc tgtggtgatt tagtttcctc ctgggaagaa cgcgtggcac  58740
agacgacgca gggtgtgttg acgccgaaaa ggtggtcgca gctacgcctg gcggctatgc  58800
agggacttcg aaatggatat gtcacagctc ttatgcccac cgcaacctcc tcaaattcta  58860
caggaaaaaa cgaatgtttt gagcccttta catccaatct atatacacgt agaacgttaa  58920
gcggggagtt tattgtttta aataagtatt taatagacga tttaaaagaa attaatcttt  58980
ggacagaagc cattcaacag cagctactaa atgcgggagg tagcattcag cacattttgg  59040
atataccggc cgagatccgc gatcggtata aaacctccag ggaaatgaat caaaaaattt  59100
taacaaaaca cgcggccgca cgaaacccct ttgtatccca aagtatgtcc ttgaactatt  59160
acttttatga acctgaacta agccaggtac ttacagtgct cgtcctaggc tggaaaaaag  59220
gtttaactac cggttcctat tactgtcatt ttagccctgg agcgggtacc caaaaaaaga  59280
ttataagaaa ctctgagaaa gcgtgtaatg cggactgcga ggcgtgtctt ctgtaggtgt  59340
ctcgcggtaa aagagcagcg gggaccatat ggtaaacccc aacaagagga taatgaataa  59400
aaaaagtaaa caggcatcca ttagttccat attaaatttt tttttcttct atataatgga  59460
atattttgtt gcggtagaca atgaaacctc cttgggggtt tttacttcta tagagcaatg  59520
tgaagaaacg atgaaacaat accccggcct ccattatgtc gtttttaagt atatgtgtcc  59580
ggcggatgca gaaaatacag atgttgtata tttaataccc tcgttaacct tgcatacccc  59640
```

-continued catgtttgta gaccactgtc caaatcgtac caaacaagca cgacacgtat tgaaaaaaat 59700
aaacttagtg ttcgaggaag agtctattga aaattggaag gtttcagtaa atactgtgtt 59760
cccccatgtt cacaacagat tatctgcgcc gaaactttcc atcgacgagg ctaatgaagc 59820
cgtagaaaag tttttgatac aagcaggacg actcatgtct ctgtaaatgt ctcttccttt 59880
atgggtgacg tctcttcctt tgccgaggaa gtctctgtta tgggcaagag gtttgaaaca 59940
acgcaaggac tctgcttaat ctgctgtctc acaaagggaa tcaaactacc tgctttcgta 60000
tttttaatgt agtaattacc cttgttgtga tgaattttaa gaccatagcg tagtcccagt 60060
actttattaa tgaattttaa aattgtttga gggtccgttt tattgggctt tttaagctta 60120
aactcaaagc tgatcgcgct taaatcatac tgaacaaatt catcaacgag tttcgtcatt 60180
aattgttcat tggtcaatat attagggtcc tgaacgcatt taaagccgca cttagttaat 60240
agcataatag cgtacatatg agattgaaaa ctataattaa attgtagatc atgatgctct 60300
gcgtgttgca tggcccattg atgaaagttt aattcctgag tttgtaacat agtgagcgac 60360
tcgtatactg tctttccgcg gcttatttgg acacggccag tatagttctg ttttgtcata 60420
aaactattgt attgttcaac aaatttggga gtaattttat gaccgtgcca tgcataaaat 60480
tcgagtagtt tatacttttc atacgcaaat aggtcttgct ggtctactgt gatgccttcc 60540
tttaagtttt gtttaatttg taaagcttta ttggcatcaa tggtttcagc cgaggcaatg 60600
tttacatagt cctggtgttt aatttccatt ttaatgcttg tatattgttt gactgtctcc 60660
agcttttcac ccgtcagtat aaacacctta gcgccggtgt cggcgatctg gttaataaat 60720
cgggttataa agtgattttt tgatagatgt tgtatccgca ttgtttcgag ccatagatgg 60780
tagtatggag ttttataata tatcggccta cctgtttcct tactatacgt gaaggaaagc 60840
tggtgattgc ttatggtctg aaaaagggtg tcacgttttt gtaacgtaaa catttcaatg 60900
tcttcgatgg tttctggata gtaattttgt ttcccctgta agcagatttt ataacactta 60960
ctttttaatt cacgcacgcg gcccaacatt tggcaacatg tttctacgtc acacgacata 61020
ttgttaaaaa agccgtataa aacatcaaat ctcttatctt cgtatgaaac acccgctgaa 61080
atcgtgggcg tatagataag gatatcaacg agccccccaat aatacgatac attattaaaa 61140
tgggattccc gttcatgagc agtgctttta gaactataaa acccaatttt tttttccgga 61200
aactttttttt ggataaatga ttgcaacagc cgggcctcca ttaatgaatt tgtagggata 61260
acaatttttt tgtcttctag caaatccttt aaaaggttat ttaaccaagt ttctcgtgaa 61320
gaggtaaaat aatacgtgtc atgctgggcc cttttatatt gattccagtg aaagaagata 61380
gggacatccc cgcgaaaacg ctgtagaata ttatacgttc gatttcctag gtttgcgtcc 61440
aagcatataa cataatttgc cgtttcgagc atccacatga aaatggcaaa agagggagca 61500
aagtatttgt gcaggccgct attgaattga ttaaaaatcg attctacctc atccaaaata 61560
agtaggtcta caggctcggc tgtggaggtt agccggaaaa gtgattctac ctgaatgatg 61620
actctttcgt agctgtccaa atctccagtt acttcgctgt acaatgtgaa attcggtagc 61680
cgggattgta tattttttga gaagatctgt cgaaacgtca caaaccgtat ggtttgttgt 61740
tttgaaatag aattattgcc gtagtatttt tgcaaatagt tgcgcagttg gacggtttta 61800
cctattttca tttgagcctt tacaacaagc gtagggactc gttcatattc tcgcatacta 61860
ctttcatcat agatgtgttt ttgagtatca ggcagttctt caaagagaat ggactcatga 61920
acctctatgc tctttgtcat cacttggtcc acatatgttt ccacaaaatt atttgtgccg 61980
gaaaggctgc ccatgagaag gctatgttta ttgtcatggc gacagtgttg atacactttg 62040

-continued

```
tttcccgtga ctcttaaaat tagggtattg tccttatcat gcatacgctt acatatttcg  62100
cagtaacttg gacttgtacg tttaaacaat actaaatttt tatgaacacg gaggaagcaa  62160
tgatttttac atagtgttcc tgcaaatttt aatacctctt caagttcact ttgttggata  62220
gtatcgcagg aactcggtgt tgtttctttt acatttgtga agatacaagg taaacacgtc  62280
gtttcaaagg gggttgctat aagggtatca ctctttttcg tggttgtact ggtctcaaac  62340
acctctgcaa gctcctcatt aaacatttta acacgcatgc tacctttttt atgagaccct  62400
atgatgcgaa aattttgaat acttttgttg acctgggggt caacaaaagg ataaacgtgt  62460
ttgggaagat tttctaacac tttggatgta aagactttgg cctcattatt gtttaatact  62520
gagtatgtat aaagtatgat atgaaaggag tatttaagtt ctcgcttttt atttaatccg  62580
atagaatctg ttagcaaaat ttgttcacgc gttagattga tgttataagg taaagaatat  62640
gtctcgtaaa atacatccat gatgacgtta attatcatgt caaggatgtc atagacattg  62700
tcttcgacat tatcattgtc atcaacattg tcatcagagt atgacttatt taccggaaag  62760
tcgatgtcaa attttaagcg ctgaggcaaa aacccaaata ccacttcgtg gaaacacttc  62820
tgctcaaagg gctgagccgc ctcccactcc caaaagtcat cacgacttga aaaaactcta  62880
aaaagattat tatattcatc tcgcaccacg aagtgattct ttaaggtttc gagagaatat  62940
ttatcctcta cggcttctcc ttgggagtta cagcgaagaa acttgaatgt ttcttgcatt  63000
ttgatattta aaattaaatc aattatgatg cggccgctaa tgcggcggtt gacgcggccg  63060
cgccgctgac gcagccatca tacataaagc ggcatggccg ttttataacg actagtcggc  63120
cgttatatga cgaactatat aaaaatgaat tcttttaatt agagttaagt attgttgatt  63180
gtataatcca tcatggttga gccacgcgaa cagtttttttc aagatctgct ttcagcagtg  63240
gatcaacaaa tggacactgt aaaaaatgac ataaaagaca ttatgaaaga aaaaacgtct  63300
tttatggtat cattcgaaaa ctttatagaa cgttacgata ccatggaaaa aaatattcaa  63360
gaccttcaga ataagtacga agaaatggcg gccaacctta tgaccgtcat gacggataca  63420
aaaattcagc ttggagccat tatcgcccaa cttgagattc taatgataaa tggcactcca  63480
cttccggcaa aaaagacaac aattaaggag gctatgccct taccttcatc aaacacgaat  63540
aatgaacaaa cgagtcctcc cgcctcaggc aaaacaagtg aaacacctaa aaaaaatccc  63600
acgaatgcga tgttcttcac gcgtagcgaa tgggcatcct cgaatacttt tcgagaaaag  63660
tttttaacac cagaaattca agccatattg gatgagcagt ttgcaaacaa gaccgggatc  63720
gaaagattgc atgccgaggg tctttacatg tggagaaccc aattctctga cgaacagaag  63780
aaaatggtca aagagatgat gaagaagtaa tatttttggt aaaaatattt ttatcaaaat  63840
tttttaccaa ataataaaaa tatttttact ttttttcttc ataatataca tagaatgcct  63900
acaaaagctg gcacaaaaag taccgcaaat aaaaaaacaa cgaagggctc ctccaaatct  63960
ggttcttcca gaggccacac cggcaaaacc catgcttctt cgtccatgca ttccgggatg  64020
ctctataaag atatggtaaa tattgctaga tctagaggca ttccgattta ccagaatgga  64080
tcgcgtctta ctaaaagtga attggagaaa aaaattaaac ggtcaaaatg aatataatca  64140
ggaaacttaa gcctggaaca attagccttg tgctgggacc catgtttgcc ggcaaaacta  64200
cgtttcttat tcattgcatt tacatgctcg aacgtttgga aaaaaaagta gtcttcataa  64260
aatctaccaa aaacacccga gacaaaacta ttaaaacaca ctccggtata cagctacgac  64320
ccaaacaatg taaaatcata gaaagcacac agttatctga cgtgggttct ctcaccgata  64380
```

-continued

```
tccatgcagt tgtcgtagat gaagcgcatt tttttgacga tttaatcaca tgccgcactt  64440
gggcagagga agaaaaaatt attattcttg cgggactcaa tgcttccttc gagcagaaaa  64500
tgtttccgcc catcgttcgt atttttcctt actgcagctg ggttaagtat attggccgca  64560
cctgtatgaa atgtaaccaa cataatgcat gctttaatgt gcgtaagaac gcagacaaga  64620
cgcttatcct tgcgggagga agtgaactgt acgtaacatg ttgtaacaac tgtctaaaaa  64680
atacatttat taagcagttg caacctatta aatattaaaa atcttataca ataatggatc  64740
attatcttaa aaaattacaa gatatttata cgaagctcga gggtcatccc tttcttttta  64800
gcccgtcgaa aaccaatgaa aaagagttta ttactctgct aaaccaggcc ttggcctcaa  64860
cgcagcttta ccgcagcata caacagctgt ttttaacgat gtataagcta gatcccattg  64920
ggtttattaa ctatattaaa acgagtaaac aagagtattt atgcctgtta attaatccta  64980
aactcgttac taagttttta aaaataacga gctttaaaat ttacattaat ttcaggctga  65040
aaacttttta tataagtcct aataagtata ataattttta caccgctccc tctgaagaaa  65100
agactaacca tcttctaaaa gaagaaaaaa cttgggcaaa gattgttgaa gaaggaggag  65160
aagaatccta agtcgcttac attttttttt gctattttta tagaatgtac acgcatgttg  65220
atgttgtcgg aatagctgaa gcctcagcgg ccctctacgt gcaaaaagat agggatcgct  65280
acttagacgt gctaacaacc attgaaaact ttatttacca acacaaatgc atcataacag  65340
gggaaagcgc ccacctactc tttttaaaaa aaaatattta tctttacgaa ttttactcca  65400
acaatgtggc ggagcacagc aaggctttgg cgaccctgct ttataaactt gatccggaat  65460
acctcactcg ttacacagta ctcattacca aaattcccaa ccattggtat gtgattaacg  65520
tagatcagcg agaatttgtg cgcctatatg ccatcccggc agttaaacaa cacttaccga  65580
ttcccatttt acccttctat tgcaccagcg cactcaccca gcaagaattg ttttgtttag  65640
gacctgaact gcagttaata caaatatatt ccaagctctg taaccccaac tttgtcgagg  65700
aatggcctac gttgctcgac tacgaaaaaa gcatgcggat gttatttta gaacagtttc  65760
cgcaaagatt ggaaatgacg ggcgggaaga aggaggagaa ggaaaagcat gaaagtatca  65820
ttaaaaaaat aatactagaa atggtctcta cccgtcagcg aatcgttgtt gggggttaca  65880
tacaaaaaaa cctgtacaac catgtactca agaatagaaa tcgtttacag cttattacga  65940
gcttaaatat ttatgaagaa aaagatatca tccagcaatt ttgtgattca aatggactga  66000
agatcaaaat acgtatcaac aatccgctct tgcctacaaa tccggaatta cggcgtttga  66060
ctatttattt taatcataat aatgatgatg atcagtcata tctaatagta gatatgtaca  66120
acacgggaag ctatgagcta gtgcctacaa atcagataaa cacgcttgat ggcagctttt  66180
taataggaac acccttcgtg caagcgcgat tttgttggt agagatctgg gtgcttatgc  66240
ttattgcgca gcaaactaaa aaggacacca aaaaaataat acaatttttt ataaatcaat  66300
atgaaatgct tatgaatagt ccttggccca gtatggaggc ccttttttccc tcaagcagta  66360
aaagatattt aggcaactat gtagacccta acgcgctcat aaagtgggca caactcaaat  66420
taaaaagaat accgcctttt tatcctggaa agccggatga agaatcatgt taagccgatt  66480
aaaaaatcat gttaagctgg ttgaaaaatc atgttaagct ggttgaaaaa ctcttggtga  66540
aagcacggat gtaatattaa cattggccgc tcgcatttcg tgttgaaata cgatggaaga  66600
gcgacggcta tctaccatgc cgatatcggc ctggacatca cagttcatgc acttgtagat  66660
gggatgactc gcgttataga tggcaggctc gccacagttt ctacagatgt aggagatgca  66720
gccatccgag tcgtcgtgcg atttttctat gatggtttgc atggcgccct gcgccgtaag  66780
```

cacccaatgc tccatttctc ccagacgaag acctccgtgc gatcgtttgc cgtccaacgg 66840
ctggcctgtg agggcatccg tgggcccata gcttgcaacg gcgtatcggt catccagcac 66900
aaatttttgc aggcgctggt gataggtcgg tcctatgaag atggccgcat caaagtactc 66960
gccggtctgg ccgttgaaca ttttttggca tccattgaag cgtagacctt cttgcgccag 67020
tctttctgaa agaagctgca cattaatagg caggaatgcg gtgccgtctg ttaccacccc 67080
ctgtagggca tttgctagac caaccgtggt ttctatcatt tgaccgttgg tcattcggga 67140
gggatgtgag tgggggttta caatgaggtc gggctgcaat ccgtcctctg tgaagggcat 67200
gtctgaagtg ggcagggcca gcgccgcaat gcccttgttc ccgctgcgag aactcatttt 67260
gtcgcctata ttgagatttc tttcatagcg caggcgcatg aggccaaaga tctcgtcatt 67320
aggcccatgg ggacgcatca cagcatccac gacggccggc tcatcgaagc cgtacatgac 67380
agaccggtcg atgtatttgt tgagttcgtc tttttcgccc cgtattttgg ccacttttcc 67440
tataatgatg tcgccctttt tgaccaccgt tcctacgggc acgaatccat ctacaagctt 67500
ttcgtaatta gcaccaggct taagattttt ggtgattaaa gggtcgggct tcccaaacga 67560
ctctatatcg ctttctaatt ctactttttc ttctcggtag aaggtgccgg caaagccgcc 67620
cctgtcaata aaggactgcg acacgatcac agagtcctcc tgattgtagc cgccgtagat 67680
catataagcc acaatggtat taagcccgtt gggtatgaca tagttatgtg ctatggtctt 67740
tacaagcggc atttcattgt aaaactggaa gaagcggttc atgtcgacac gatatggcca 67800
gctaaagcaa taccagcccc ccgtttgccg gccttggttt gtttcatagg taacacgcgc 67860
aggttgggta cagtttgcgt agggggacac tagggcggca aggcccaaaa tagcttgggg 67920
cacgtccacg tgtgtgaaac gacgcgttac atcatgttta tgtttgcgta gctcgatgat 67980
ggagaaggca acaagacagt tttccgcctc ctcgggggta atgaactcac agatgccctg 68040
tgctacgaga tcttcaagtg taagcgttcc ggctaaaatg tcttttgcca tttgaggcgt 68100
aaatcgcgta ttttgaatga aagggatttt atgtttttcc cagtctttat cgcctttttt 68160
tctggcctct gcggccttgt agcaggcttg attgtatttt tcaatattat tatctacaat 68220
gagtaggggg cgggtcagcc taccgacgtc caaccaaaat tctacttcgt ctaccatgct 68280
atcccagtag atggtggtat ggggatgcac aaccttgccc tcacggcgaa gcattctata 68340
ccgctgagca agctcaaagg cattggtgca gcagccgatc cattctccgt tgataaatac 68400
gcgcgctagg ccctttcgta caatgtcctt gttggaaaca tcggctaact gttgaatggc 68460
cggatctgat agaaggcgtt gttttaacga aagtacttct ccggcggtgc agacattggc 68520
agtgatggct aactgtttag acatgcctac tttttcacca gtatcggctg actgggctac 68580
gcagatgtat ccaggatagg atgcgtgcac gcgacgcatc atgtcagccc tttctgtttg 68640
tttggatgcg ttggtggtgt tatgagtatt taccgtacgc aatgctgaaa tggtatttaa 68700
taaatttttt ctttccaaac tttgagtaga tactctgttt acaatggggc gctgtcgcac 68760
catgatggtt ttatttcctg aaatgataga ctgttccata ctgcgattaa gatcggaggc 68820
ggtatttttt gataaagcgg cagaaaatgc ctcgataatg tttcgctgag taagctcctc 68880
aaaggctgtt tgtttaagaa gttctttgaa cccattgatg atgggtgcta tcacggaagt 68940
attaaaaata gccttaaagg ccttggcgag tgagacccct gagccgtgca cccgcttggt 69000
gcggtagcta tcacggtccg tgggtggaaa cacattcata atgacaagaa gtattttatg 69060
aataagcagg cctaaaaagc gcagctttcg tacacgtgta tctgcggttt ggcccatgtg 69120

-continued tggcagcaat attttgtcta aaatagtaag ttgtctttca tttaagtatt gtaccgcatt 69180
ttcatcgctt ttgtaagcag atgggtttga gacaaatttg gaaaccttct cggataaaaa 69240
ctggataatt ttttctcggt tcagctcgtg ttggaccggt tgaaatatgg ggtctaaaac 69300
atgaatggat ttttccagaa tttctatcat gaaggtattc acaagggagt tggattctag 69360
atcaaatacc acttgctcaa tgatgctgtc atcgcctgtc attccaaaca tgcgaaagat 69420
gagataccaa ggtatgcgaa gttttgagaa cttggtgcta ttgatttcaa tggtaatggc 69480
gccggtggtc atgtagcgta taataatttg agagctattt tcgaaggcac ctcccggttg 69540
ggagataaac tcgccgcgaa tgatttcatt attcccttgt tgcatggtat ggtaatggat 69600
gtgaagcgtg ttaaagcgga tgttttctaa gaggtctacg acccattccc cgcctcgggc 69660
tataaagtag ccgccgggtt cattagggtc ttctcctatt tctttttttg cggtttttga 69720
taggtgatga gtgtggcagc ggttgctgcc ccgcatgatg ggaaatgtag atacctgaaa 69780
aggaggaata cttgctcgtt ttacctcctg ccgaccattg ctgtagtgcg ccgttaaaat 69840
aacctcggcg gctagattaa ccgggcccga ataggaaagg ccacacaggc gtgccttatt 69900
gggtagtaaa tttatcttgt ttccctgtga atagtttcga tgttgcgggc gttcaatgtt 69960
cacatctgta aagttaaatt ggatctgaac tgattcccga agcttatcta tttcagtatg 70020
gtcgcgttgg tctttataag taatatccac gttaaacatt tgttttacaa tttgcggaat 70080
tccattgtcc ataagatcgt cgaagctttt gatgttatac cctatcaatc ctgtagagtt 70140
tactgcagcg gagataaagc tcagcatatc agcctctgta agctcctcat tatccacggt 70200
ttcaatgggg ccgtaggtta tttgcggccg caagggttcc atgattatga agtactacat 70260
taatattcag ttattcttta aaataaatct ttatttataa atcttattta taatataaga 70320
atgccttatg caagagacat cacaaagttt attacggcaa cggaaccaga ggtgggtctt 70380
cccctgttgg cgctgcagcg ctccaaatcc atcatagggg ttattcttct tgtaataagt 70440
ttgttattta ttttcattgg cattattata ttatcagtga gtagtggtca taccacagca 70500
gcctctatat ttatcgtatt gagtcttatc ctaggtggcg gtggtttttt tcttatttat 70560
aaagataatt cttaacccac ataaaatttg aaaaaatata gagtaagaaa atgtccaatt 70620
actattatta ctatggcggg gggagatatg attggttaaa aacagtagaa cccactaatt 70680
ttttaaaaat cgggttgcct taccaggcac acccattaca tcttcaacat caggcaacta 70740
ctcccccatc tatcttagaa aaatttaaac gagcagacat tcttcttaat gaggtgaagg 70800
ccgaaatgga cccactcatg ttacaaccag aaaccgaaaa aaaactattc cagatattga 70860
gtagtattga tatgttcaaa ggtctgcgaa aaaaagtaga attcacgtac aatgctcaaa 70920
ttgttacgaa tgcttggctt aaaatgtatg agctgctaaa taccatgaat tttaataata 70980
catctcaggc attttgcaat tgtgagcttc caggagggtt tataagtgca attaaccatt 71040
ttaattatac aatgatgcat taccctactt ttaactgggt agcttcctcc ctttacccca 71100
gttcggaaac agatgccctg gaagatcact atggtcttta tcagtgcaat ccggataact 71160
ggttgatgca atctccttta ctgaaaaaaa atatagatta taataacggg gacgtaacca 71220
tcgctagcaa tgtaaaaaac ctagcgctta gagccacaca aaggctgacg cccatccatc 71280
tatatacggc tgatgggggt attaatgtag gacatgacta caataaacag gaagaattaa 71340
atcttaagct tcactttggt caagccctta cgggtttgtt gagtcttagc aaaggcggaa 71400
acatgatact caaacactat accttaaatc atgcatttac tctttcttta atatgtgtat 71460
tttctcactt ttttgaggaa ctatacatta ccaaacctac ctcctctcgg cccacaaact 71520

-continued

```
ctgaaaccta tattgtgggt aaaaacagat tacgcttatt tacccccaag gaagaacaag  71580
tccttctaaa acggctagaa ttttttaatg atacgcccct cgtagaccta agtctttacc  71640
aaaatttact tgaaagcgtt tactttgccg tagaaacaat acatctaaaa caacaaatag  71700
aatttctaaa cttcggaatg aaatgttatc gacattttta taacaagatt aaactactta  71760
acgattattt agctccgaaa aaaaagattt ttcaggatag gtggcgtgtg cttaataagc  71820
tttatgttct tgaaaaaaag cataaactta agctttgtgc ctcctaggga tctgttgctt  71880
aatttaacag atgcaatctt aacagatgta aactaaaaag tgtgttcata caaggattgt  71940
atttatgaat atttattaac atataaggtt gtgatgtaac actgtataac ctatataact  72000
acactatgaa gcacggcgta taataattta tattgaacac gatgttgact catttatttg  72060
caaacaaata tttgtttgca agacgtttgc atgcatttac taatatgttg ttgactagtt  72120
tatttgcaaa ctagatgttt gattgcaaac tagatgtttg cacgtattta tttgaactaa  72180
tatacactcc ttgttttatt tgttatatac acagcataca taagtgtata ttgtttacac  72240
ttatgtttat aactcgacgt aataacattt tacacgcttt ttttttgcaa atcttaataa  72300
tattgtatga taaatcaaac aatgtcttat atatgtggtt tattatttta ggcgccgcaa  72360
gatgtactcc attctcattg catgcttggt gttattactc tgtctagtta tatatgtcgg  72420
tcatcgtgcc gatcatgcac gaaaatattt agaaggaatg tggcatggag atccggtttt  72480
tctaaaacag tcggggctac aatcctttta tctctacata caacctgacc atacatgttt  72540
ttttagcatt gtgaataaaa atggtgaaaa gctgatggaa accaaaatac cttgtacgat  72600
aacaaataaa atatatatgt tttttaaacc tatttttgaa tttcatgttg tgatggaaga  72660
catacatagc tacttcccta agcagtttaa ctttctgtta gatagtacag aaggtaaact  72720
tattttagaa aacaatcacg ttatttatgc tgtattgtat aaggataatt tcgccaccgc  72780
actaggaaaa acggttgaaa aatatataac acaaaattaa tcatgttttc taacaaaaag  72840
tacatcggtc ttatcaataa gaaggagggt ttgaaaaaaa aaatagatga ttatagtata  72900
ttaataattg gaatattaat tggaactaac atcttaagcc ttattataaa tataatagga  72960
gagattaata aaccaatatg ttaccaaaat gatgataaga tattttattg ccctaaagat  73020
tgggttggat ataataatgt ttgttattat tttggcaatg aagaaaaaaa ttataataat  73080
gcaagtaatt attgtaagca attaaatagt acgcttacta ataataatac tattttagta  73140
aatcttacta aaacattaaa tcttactaaa acatataatc acgaatctaa ttattgggtt  73200
aattattctt taattaaaaa tgagtcagta ctattacgtg atagtggata ttacaaaaaa  73260
caaaaacatg taagtttatt atatatttgt agtaaataat atttttaatt acttaaaatt  73320
tttatatata agtttttgat actatattat aaaacatatg ttcataaaat gataatactt  73380
attttttaa tattttctaa catagtttta agtattgatt attgggttag ttttaataaa  73440
acaataattt tagatagtaa tattactaat gataataatg atataaatgg agtatcatgg  73500
aattttttta ataattcttt taatacacta gctacatgtg gaaaagcagg taacttttgt  73560
gaatgttcta attatagtac atcaatatat aatataacaa ataattgtag cttaactatt  73620
tttcctcata atgatgtatt tgatacaaca tatcaagtag tatggaatca aataattaat  73680
tatacaataa aattattaac acctgctact cccccaaata tcacatataa ttgtactaat  73740
tttttaataa catgtaaaaa aaataatgga acaaacacta atatatattt aaatataaat  73800
gatacttttg ttaaatatac taatgaaagt atacttgaat ataactggaa taatagtaac  73860
```

```
attaacaatt ttacagctac atgtataatt aataatacaa ttagtacatc taatgaaaca  73920
acacttataa attgtactta tttaacattg tcatctaact atttttatac ttttttttaaa  73980
ttatattata ttccattaag catcataatt gggataacaa taagtattct tcttatatcc  74040
atcataactt ttttatcttt acgaaaaaga aaaaaacatg ttgaagaaat agaaagtcca  74100
ccacctgaat ctaatgaaga agaacaatgt cagcatgatg acaccacttc catacatgaa  74160
ccatctccca gagaaccatt acttcctaag ccttacagtc gttatcagta taatacacct  74220
atttactaca tgcgtccctc aacacaacca ctcaacccat ttcccttacc taaaccgtgt  74280
cctccaccca aaccatgtcc gccacccaaa ccatgtcctc cacctaaacc atgtccttca  74340
gctgaatcct attctccacc caaaccacta cctagtatcc cgctactacc caatatcccg  74400
ccattatcta cccaaaatat ttcgcttatt cacgtagata gaattattta atatgtacta  74460
tatattaatt atttaacctt tcaagctggt cttcatttaa atttaaaatc cactaataaa  74520
atgtattttc tagtagcaga tcatcgagaa catcatgtga ttcctttttct taaaaccgat  74580
ttccatcaca tgcatcaaaa tcctatacaa aaaaatcaag ctctcctaga aatcaaacag  74640
ctttttactg gagattatct catctgcaaa agcccttcta ccattctggc ctgtattgaa  74700
cgaaaaacct acaaagactt tgcggcttct ttgaaagatg gacgttataa aaatcgccaa  74760
aaaatgctgt cgctgcgaga acaaaccaac tgtcaacttt atttttttgt agaaggcccg  74820
gcatttccta accctcaaaa aaaaattaat cacgttgcct atgcaagcat tattactgct  74880
atgacgcatc ttatggttag agatcatatt tttgtcattc aaacgaaaaa tgaggcccac  74940
agttcccaaa agcttgtgca gctttttttat gccttttcta aggaaatggt gtgcgtcgtt  75000
cccacctccc tcacccccac ggatgaagag ctatgcatca agctatggtc ttctctttct  75060
ggtatttcag gcgtgatagg taaaatcttg gcaaacactt gttccgtagc tcatttggtt  75120
catggaaagc tttcatcgca gaatattgat cagttaaaaa ctccctccaa ccgaccattc  75180
cccaaaaaag taaaacgtat gcttataagc attagcaaag gaaataagga gttagaaata  75240
aaattgctct cgggggttcc caatatcggg aaaaaattag ctgccgaaat tttaaaagat  75300
catgcgcttc tttttttttct aaatcagccc gtagaatgct tggcaaatat acaaatcgtt  75360
caaaaaaccc gtacgattaa gttgggaatg aagcgagccg aagcgattca ttattttttta  75420
aactggtgtg gctctgccca tgtaaccgat gatagccaaa atatcacaga ggcgtcgcgg  75480
tccacaatgc aggtcgcgac gcagtccgcc gcaatacagc ccgctgcaac gcagccattg  75540
cacgaagtat cagatgatgc atcatcagat gcttcatcac ccgtagggta tcaaacatta  75600
tctaaagaaa tgttattgaa cacagcctga tgttaataat tcactacatc taaagaaatg  75660
ttaacctcga tactaaaaag tcattgaaca caactactgg ggcgctaagt tgtccaacac  75720
atctaaagaa atgtcaacat cctcgatgct aaaagggtca tcgagccggt caataatgtc  75780
ttccccaaaa agtccgggag aactgtaggc cgagatgtcg tccatggagc tatcttcccc  75840
agagcacaca aagtcctctc caaaaatcat aaagttaaat gcaccgggct tacttaacag  75900
cttttcgctt tgaataatag tgttgagttc tgtcagcgca aactctctca caatattcac  75960
aacccaggag ggctctttaa tttcatacag cgttaagaaa cttatacata aaaattctat  76020
agagtaaagc aaggcgctgg caggatctgt tacccgtagg tgtttaaatg tagtgtgata  76080
ttcattcaca acgttaggca gcaccttttc caaatcctcc ttttcctcgt acgacaggtg  76140
ctttacaagc ctttcaacat gtataggagg cttgttaaat gtactaacgt gccgcaaaca  76200
gttataatta tataagaaaa tacgtacggc agagtcgacc gccatgagcc ttggatcatc  76260
```

```
cattgaggta ggtggtggcg gggcaccctg gccttccctg atgtctgcgt aggagcgccc  76320
ctccatggcc cctatggcct ctatcacagc aggactgata tccaaaatct tggccgtctt  76380
gattattttt ccgtaatcga aagtccatgg ctcctgtgga ggcttgggtt gtgtttcggt  76440
ggagggcgtg gtcatatctt tctttatttg aatagaacgg atcgacatct tttccttatc  76500
gtactggtct ttataattat tataatagtc atgaactaat tcgggttgag aaagatgatc  76560
gtatataata taggtaaaaa gtccgcactt gacacatttt ttatcctgga agtcgtgtaa  76620
tcctcccttg gggcagcgtg actcgtagaa ggcataaaag gtgttaaatt ctaagctcgc  76680
ctttagggct gtttggacct tttttatgtt taattgcccc acctcatgtt gtagcacgtg  76740
gcatacagaa cagcgtagat cggcaagtgc ataatggttg tcaatttttt ttatgacgtc  76800
tttgcgtgtt acttcaatct cggcgggttt ctgcgaactg tctacggcct tgtaaacgta  76860
aatggtccac ttatgaggaa gccccctttc atcgtatagg gttgaaatgg gaagcctttt  76920
atactcaaac agccgagtcc gttggtcggc tcttcctgtg ttaggatcaa atatgttata  76980
aaatccttgc tgagcaagca gggccttttg ctcgccataa gcattttcgt acgttttgaa  77040
ttctgcaagt tcggagttaa aattaggtgc attttgtaaa tacttaagaa ataattcata  77100
ggctctaagg taaatgagag ttgaggtttt ttcctcatcc cgtcctcccc accacacccg  77160
caggctttct tcttgaaaat agatgtcatt cagacgcgtc aactgcgtaa aatcaggccg  77220
atatttagag gtataaattt tatcataaaa ttctttttgc gataatagct cggccggggt  77280
acgtcctatc acggttttaa actcatattc agcctccttg ggagtccgtg gtttgtgcat  77340
agggatgctg ccgtcaatac gggccactgt ggcagcataa tcatacatgg ggtccagcag  77400
aatctctgtc aaaagtacct tggtgtcgtc ctgcacgcta agcccttgta gcccattttg  77460
gtggataatt tttttgaaag cctcccgaaa attattagca atccactgat ccgtaatctc  77520
agatagctga tttattatac cgctatattg ctgcatcatt ttctccaaaa gaaaggtcac  77580
gtatgcattc aaagagctat ccgccttcat tccatgaatg gtaatcgtaa gaaattcttt  77640
atttttttgc gagctataaa tgagattcaa aatataggca tagatgtaga tcacagcata  77700
cagctgcgtt aaaggatcgt aatcctcttc ctttttaata ttttcgatgc tatacacgag  77760
cggcaggcag acatttacgg ctatattggc aaactgtttc acgtctacaa gctttccaaa  77820
gtggataaac gtgcaggcct tcatggtttc ctgccaaata aaaacacgga gcttactatt  77880
aagatcgccg atgatgccca catctgccgt acgatcctct tgaataaaat gggccagctc  77940
ttcgccacaa attttgcaaa agtaggagta aataagcccc tggttgtttt ctttctcctt  78000
gtttattcct gaaaatttca ttagcttggt tcgcatggtg tcgtaggacg cttctgccgc  78060
ttgaagctgt ataagcatgt ccacatgggg acaaagcagc ttaaacccgc aggctttgca  78120
tagattccaa ttggtggtat tgtttttttc cttgtagagt acacgaatac tttctaatac  78180
ttttaataac tccgcgtatt gaagacccga acgcaactgt tttaccagct tgagatgagc  78240
acatgcattt ttttcttgga gttcccactg ttttttaatg tttaggtatt ctgttgtaat  78300
aagttctgcc tcctgtttcc cacaggcttt aatgacttct tgaaggatgc tgttagggtc  78360
atccacttta ccctccattg taagaatttc acgtatagca tccgactgca ccctacctat  78420
tttttcttcc ataattttaa aatactgtct cgcctgggta atgacctctg tgagcttcat  78480
gtccacctgc tgcagaatca tttgctcctt ttcacgctgt tcagcatgtt gtaaaaactt  78540
ttgttctaca gggttccaaa gcacctccaa atagcctgct ctatataggt cataaagcaa  78600
```

-continued gggcatgtat cccgatgtaa aaaccgggga caccgagtac atcgtagaca actcttttaa 78660
aaaaaatatc acgcgcttaa tgttctcctc cggttcaatc tcctcggttt caacgatatt 78720
agatatatga ctgccctgat cctcacggtc tagctttcgg tgtaccatct cctctgctag 78780
ccgattaatg agccagctat gcccgccgct ccgcaaaaac ttataaagtt cgatatactg 78840
gtgcgtaaac tggatgatgt tttccttggt ggttacgaca accccttctc cgtttttttt 78900
ccaggtttct tgatccacgc atttcataaa tactcgaata aaattggtca aattggctcc 78960
tgaggcgacg tagcccaagg tttcaggcga gaaggagcct atctcagcca tacgcataaa 79020
acactgcggg gaaaaagttt ttagccgcaa cttaagtcca tagatttcaa tgggggcttc 79080
tgcgggaacg gccaggtgcg tcccattaat taaaaaaatt tctttgcgtg tgctagggcg 79140
aacacgtaat tccttttttt tttcactcac gatggggacc acatcggggt ctaccagcag 79200
ttgacgtatg taggcctcta tgggcatgga tagatcgggc agctttgact gctcggcgcg 79260
aacatggttc acaaaatctt ttagagtgaa aagaaagtct attaaacgta tgtttttat 79320
atcattagac cctttaaggg tagagtagat ttcatccact agtgcctcga tttcctcatt 79380
attgagcgat aagatatctg tgccacggtg gactatttgc gcgatcgtaa ttacttcctc 79440
cattagatag aaactgaata ttatatttaa aataaataca aaatgtcaaa tgaaagtttt 79500
cccgaaacgt tggaaaactt actttcaatg ttacagacca aacagcaaaa cgcaattcag 79560
tcagaggtga ttgaatggct gcacagcttt tgtgaaacct ttcacttaaa aatacactgc 79620
cataaacagt ttattcctag cggggaaaaa aaacgagcta aaatacccgc tcaagaaaca 79680
cagggaaaca cgcagccctc ccaccatgtg taccgggttg ttctctccag agcacagcca 79740
gtcaaagcac aggaatctct gctaacaacc atgtgcaacg gactggtgct agatgcaaac 79800
acatggacat gcctagccat tcctccgcct gcgccctttc aacaggcgac ccgccaggtc 79860
caacactttt accgtaacaa tttctacgaa gtggttccca tccaggatgg caccctctc 79920
acaatctacc actgggatga ccctgaatat ggcccctcct ggtgcctagc aagtacccac 79980
ggatatgatg tgagtaacta ctgttggata ggcgacaaaa ccttcgccga gcttgtatac 80040
gaattgctgc agcagcactc tacctgcgac gtcaccctgg aaaaaaataa aacgcgggga 80100
acgcgtcttt tctttgataa cttaaatccc gattactgct atacgattgg aatccggcac 80160
cataatttac agccgctcat ctatgaccct caaaatattt gggcgattca atctacaaac 80220
ctaaaaacgc ttaaaacggt atatccagaa tactacggct atataggcat tccaggaatt 80280
cagagtcaag ttcctgagct tccccagtat gatttacctt atctaatacg atcttataaa 80340
actgctatga atcaagccaa aaatgctata aaaaatggca aaaaagacaa gggatacttt 80400
aattatggct atttactcat ttcgcgagcg cctgccatta ctaaaagtac ttctaatgtt 80460
ttgttaaaat cgcctctgct ggtattttta caaaaaagtg tgtaccagaa aaaacacaat 80520
atctctaaca gccagcgact agaatttatt atactgcaaa actacttgat gcagcatttt 80580
cgagatcatt tcattgctct atttccgcag tacatatcct attatacgaa ataccaaaac 80640
atgttgaata tgattatcca tagtattgca actaaagata aagatcatcc ctttgcagga 80700
gccgtggtaa aaaaagtgtt ggaagatatt gaaaacgccg aaaacattat tgatcataca 80760
accattcaaa actatgccca tcaaagcaag tacgccatgc tttacttgtc aattatttcc 80820
catttttaat ctaatacggc caaagccgcg ggttttttaa taaactaaca tttaaaaaaa 80880
ctgttttatt aaaaattata atacttttat tatatatgga acatccatct acaaactata 80940
ctcccgaaca gcaacacgaa aaattaaaac attatgtttt aatccctaaa cacctttggt 81000
cttatattaa atacggaacg catgtccggt actacaccac acaaaatgtt ttccgagtcg 81060
gtggctttgt gcttcaaaat ccctacgaag ccgttataaa aaatgaggta aaaacagcaa 81120
taagactgca aaatagtttt aacacaaaag cgaaagggca tgtaacgtgg gccgtcccat 81180
atgataatat tagcaagcta tatgccaaac cagatgcaat tatgcttacc atacaagaaa 81240
atgttgaaaa agctcttcat gctttaaacc aaaacgtact gacgctcgca tcaaaaatac 81300
gttaaatata atttttgtag aggataaaaa gctattttag ctaaaaaata attcatatac 81360
gtttatgcag aggaagaacg gtggctttca aattcagatt gcatccacgt agaccgtagc 81420
gttttttttg cttctggttt atatcgtaaa ccgtaataaa catcatcatt tgtatccgtt 81480
ggatcttttt cccactccgg ataaaaaatc ggttttcttt tttttggtcg ttttttgcag 81540
taagctgtaa attaagggaa tatagcttat cgaaaagttg ttcctgatcc atataaatag 81600
cagcatatat taaaaaaaat aaaaaaagac gcttcaacga gtcagtacca ctgcttgcca 81660
acgatttacg ttggttggtg cattatggtg atatagtaat gagtgcctgc acaagtgctt 81720
gcacaagtgc ctgcacaagt gcttgcacaa gtgcttgcac aagtgcttac acaagtgctt 81780
gcacaagtgc ctgtacacat tactgcatcg ccaaagcacc tgcaatgcct acttcctcaa 81840
cagagtacga taactaaatg cttttaagca ccgcttgcgt cgatgtgtcc ttcggggcaa 81900
tcgggttcaa ttggatccaa tattattagt cataattacc taatacttat tcaattttat 81960
ctttttttacc ttgtaagatt taaacagcgt tttagcttgt ttaaagcaac gtttaaaaca 82020
agctaaaatg ctgtttaaaa caacgtttta aacaagttaa aacaaataag cttataaata 82080
taccatgaca aaattagccc aatggatgtt tgagcagtat gtcaaagatt taaacctaaa 82140
aaatcgaggg tccccctcgt tccgcaaatg gctcacattg caaccctcac tgctgcgcta 82200
ttcgggtgtg atgcgtgcta acgcctttga catcctaaaa tatggctatc ctatgcagca 82260
gtcaggttat acggttgcta cgcttgaaat ccactttaaa aatattaggt cttcctttgc 82320
caacatttac tggaaccgtg atagcgagga gcctgagtac gtctgctgtt gtgccaccta 82380
tcaatcgcac gatggcgaat accggtatcg atttgtttgg taccaaccct tcatagaggc 82440
ttataatgcc atagaggcgg ccctggatcc cctggaaacc attatcctga acctcattgc 82500
ggcacgagat ctagacttcg ttgttcacat atttccttat aataagggcc atgaagacta 82560
tttggcctcc acgcaactta ttctcaaaat ctttattgcg acgcttttaa tggacatttt 82620
aagaattaaa gacaacacgt tggacgttca cttaaattcc gactatatta ttgtgatgga 82680
gcggctttgg cctcacataa aggatgccat agaacacttt tttgaagccc ataaggactt 82740
actagggtac ttaattgcct ttcgcaatgg ggggaacttt gcaggaagtc ttagaccctc 82800
ctgtgggcaa aagattgttc ccctaacgat tcgagaggtc ctacaaatga atgatattaa 82860
tttagccgta tggcgggagg tgtttattat gcaggaatgt tccgacttag tcatcaatgg 82920
gatagcgccc tgtttcccca tttttaacac gtggacgtat ttgcaaggta ttaaccagat 82980
tttttttgaa aacacgtctt tgcaggagaa atttaaaaaa gattttattg cccgagagct 83040
ttccaaagaa attatcaagg gccaaaaaac gttgaatgac aaggagttta aaaagttaag 83100
cctacatcaa atccagtaca tggaatcctt tctacttatg tcggatgttg ccattatgat 83160
taccacagag tatgttggct atacccttca atccctgccg ggtattattt cgcgatccag 83220
ctatttatcc cccatcgtga aaaacatttt gatggacgaa gactctttta tgtccctact 83280
atttgaccta tgctatggcg cctacgtgtt gcataaaaaa gaaaatgtga ttcacgcgga 83340

-continued

```
tttgcacctg aataacatga cctactacca tttcaaccca accagtttta cagatcgcaa  83400
caaaccagga aaatacacct taaaggtcaa gaatcctgtg attgccttta taaccgggcc  83460
caaagtcgaa accgaaacgt acgtgttcaa gcacatagat gggttcggct gcatcattga  83520
ctttagcaga gccattatgg ggccaaacca tgcaatcaag cttgagcggc agtacggcct  83580
cgcttttgta aacacctttt accgcaatca aagtgagcat attttaaagg tattacggta  83640
ctattttcct gaaatgctaa ccaatcgcga aaacgaaata caggggggtga ttttatcaaa  83700
ctttaatttc tttttcaata gcattactgc cattgatttt tacgccattg ctagaaacct  83760
acgtagtatg ctttctttgg actatttaca cacctctgag gtgaaacgaa acgtagaaat  83820
ttcgcaaaca tttttggata catgtcaatt tttggaggaa aaggccgtgg aatttttgtt  83880
taaaaatctt catactgtct tatctggcaa gccggtcgaa aaaacggccg gggatgtgct  83940
tttacccatc gtatttaaaa aatttttata cccaaatatt cctaaaaata tattacggtc  84000
ttttaccgta atagatgtat acaattataa taatataaag cgttattctg ggaaagctat  84060
acaaacgttt ccaccctggg ctcaaaccaa agaaatcttg acgcacgccg agggtcgtac  84120
atttgaagat atttttccta gaggagaatt agtttttaaa aaggcttacg cagaaaacaa  84180
ccatttggac aaaattttac agcgtattcg tgagcagctt gctaatgaaa atttgtaagg  84240
cttgcagttc ttgtatggtc agaacctatg tcgatggaaa cattattttt cgctgcagct  84300
gcggcgaaag cgttcaaggg gatagtcaga acttgctcgt ctctagcaag gtgtaccaca  84360
ccggggaaat ggaagataag tacaagattt ttattaaaaa tgcacccttt gaccccacga  84420
attgccaaat aaaaaaggat tgcccaaatt gtcatttaga ctatttgaca caaatctgta  84480
ttggaagcca aaaaatcatt atattggtgt gccgctgtgg ctatatgagc aacagaggat  84540
aaaccatatc atcccaccga attatgacat tcctttaaaa ccgtccgcct aaatagtttt  84600
cacacctttg gtggcagact attttataaa aagtaatgtt ggttcatgaa gataaagtgt  84660
gccaaagaaa cttttataaa caaatgatta atgtaggtgc tagtcgtgtg tacttaaaca  84720
gggtattcta tagccaagta ttttctatag ccaagtattt tctatagcca gtattagtca  84780
agtatttaga tgtcagggta tttttatagc cagtattttt ctatatgtac aaactattcc  84840
agtaaacata tgtgtgttct ttattgagca gcatcatggc attaacaagt ttattaaact  84900
gctctaatgg gcattaaatg acaactcggt gcttagcaaa agtgcctata ccttttaaca  84960
attagggccg ggaggcattc ccagcttttt tctataatca gccatacagt acccctgagc  85020
ctcatacacg ggaataaggt ccttccattc cttgttggga tcggcgggcc agctctcaaa  85080
tgaggtgtga atgtaagggt cctgttcttt ttccttaatg aagcgtttaa tctccatttg  85140
atgttgttta cttttttgtt tgcggcggag cgtgttccgc accaatacgt aaaaaatacc  85200
aagaatcaca cataaaagaa ttattaaaaa aaatatcatc atcgcggggt ttaaaaaacg  85260
atcccatgca acaggaatcg ttcttaaaac cttgtctggc agggctgtaa acatgaagtc  85320
tcctcctata atcggggtgg gactgtagcc taacagttca aggtcctgtc gttctagata  85380
cttattggcg aactgcccac cctttgcccc cgttttttta ttaatcaagc agcgctgcat  85440
tttccaccat tctaaatctt caggagaaag ctcaatgcca tatatcaact ttaacgttat  85500
tgcatctttt tcaatatcct tatcaatttg gctgagcttt tgagctttaa gcgggtctag  85560
tgtgtacttc catttaaact tagtgtcctg tagtttggct acatgaaata cggaacattt  85620
cggcggggcc tttgtgacgc ccttacactg cggaagttta tcattaggac aggcgcatag  85680
atgagactgc gccacagcat cgcgaactac atcgcagacg gagtacattt tcctcctatg  85740
```

ttaaacaata aattttttc atagctgaaa tttgtgggcc tatcttttcc cttgcccgga 85800
taataattat aagggagtgt tgaaacatct gggagagaat tgcttaaaaa atgggttttt 85860
gggaggggta actgcgactg ttgtacgtcg ttggccaggg agattctata tgccgggcta 85920
aaggtgcaac gttcctgtga acaacttagt acgcgcgttg ttaatacaaa tggactggta 85980
ttagcaaacc tcgtaaactc ttccggactt gtttgttttt gtatgatgtt tagcagggag 86040
tctgcctttt cgagaatcca aagcgtcgca ttgtagtaaa ataaaaatag cgacttatcg 86100
gcaggcgttg caaaagcgcc gtatagaaaa taaagcagta agtactgggg agacaccaca 86160
ataaggttat cttgaatgat agatatcgct agctctttaa acatagtgct aaaaaaatgt 86220
atgtcgttcg tcttgaatat aggggacta tagtccatgt agggctcaca tatctcagtc 86280
aggtgaaggc ccatttcttt tatgacttct tccgggttgt acgtcgctaa caccagcgcg 86340
ggataggctt tgggcatatc cacggtaagt gttatgtttt tatcattctt atggtaggag 86400
taagatggtt gtggaaattc tgttttccac tccgggactt tgcaggtaat tctcagctca 86460
tttagagtct ggtacaggag ggcgtatgcc gcaaagccgt gtatggccac ttgtttaaag 86520
ggaattgaaa acgttttact ttcgtatgtc gacttcacag gaacaacggg aatggggtaa 86580
tatttttcta tgaggttata ccgctgcaaa tcctttttaa acctgctaaa aacatcttcc 86640
cttggtgggt tatcaaaagg aaagcaaaat gctaggtgta gcccggcccg ctggtaatcg 86700
gggtgaatga ttttaaggtt tttatacgtt aatgtgggta tggtgttaaa gatattgggg 86760
ggcatatatg aaagatcagc aacccacaca aagtccgtgc gcacccgcat ggtctgcaca 86820
tggatggcgc gcaccgtgcc cacctgcttg aagccctttt catacaaaat gtcagcaagt 86880
tcgtaggcgt cctcaacgtg gttgggggaa aacatatcaa agtcgggtct ttctccctcg 86940
ggataaattg agctgccttt aagatgcagg gcataatcaa tggcaatccc cccgtacaaa 87000
ataagctttt tctttatgat aaattcgcgg accacctcca aagccgcctc aatctccacg 87060
gcatttgcct cacgtttttg agcaatgagc cggtacttag aaacattaaa atcagtcttt 87120
agtaaagacg tcataaatag tgtttaatat atattaaagg tttgaataaa atactaaata 87180
gtaaaaatgg atgccctatt aaaggaaata gaaaagttat cgcagccatc cttgcagaaa 87240
gaaaacaatg atgtatgcga tctctgtttt atgcaaatga aaaaaatttc taactatcag 87300
cttttatgcg aagagtgcgg tcagctgaag gactggtttg aacctgaata taatgaaaaa 87360
ttcacggtat attctcgtct aaagatcgtg ggtgccaata gttcctatca ccagcgcgat 87420
ttggacaagg ccaactcaag tgactatagc tccttgcaat ttcatcacat tttagaggag 87480
ctcaaatccc taaatgttaa gtatatggat gcggggcaaa agccctttcc tattcaggtg 87540
ttaaaagaaa ctgctcacag ttataaccaa gtacaacaac atcgggtcat acgcagcatt 87600
acaaagcttc agatcttagc cagtattcta cgtagcattt gtttaaaatt aaacattgct 87660
tgtacggtgg cagacgccgc gaggtttact caacttaata ccaaagggat ctcaaggggc 87720
atggatcttc tgcgctccct atttgtagac aataaaatta ctttaaacgt tgatttaaac 87780
cctatagaca gctttattaa tagtacctac agtgccttac aaattaaaca aatccaccaa 87840
gaactgcagg aggaaaatgt ttataattta aaagaaattg ttaagagctt tatattatac 87900
gcggatgaga agaacatcgg cgtcgatctt aacaggagaa ccgttgtgat tgctacgatg 87960
tataatgttt tacgccgtgc ctactacccc atagaaattg atacggtggt gtatcaatgt 88020
aaaatacgaa aaaatacaat tacacgtgct cttaaaatgt atgaggatta ctactcccac 88080
tttaagtctc tttatgagca gtatcattta aacgcggcaa aaaaattaat ttaaactaaa 88140
cgtttaaact aaatgtttaa actaaacgtt aaaactaaac atttcgacta aagtttaaaa 88200
cctagtctaa cagcgggatg cccatttccc tggggttcca tatttcaaca attttttgac 88260
cttcgggtgt taccttgatg cagcgcatga cgagcagtgg aattttccta ttaaagagtt 88320
cttgcttagc tatatcaata ggactgctat attttttttt aagcattgta gatccattaa 88380
ttgccaattg ttgcgctcta acggcgacca accttgtggc ctcaaaggtg gttaaaacgt 88440
tggaggtaat gcgctcgtta tcgggtataa tgaccaatgt ttgcgacgag gcctgcacaa 88500
agccctcgca gatggacgga gactccacga tctcgtcctt gtcctcggac tcctcctcac 88560
tgtcgacgag gttctcctct tccgtttcca catattcctc cacgaggtca tccatgataa 88620
gatcctcgtt gtcattatca gccatattac actgttatca aatgtactgt ttaatacgca 88680
aatggattta ctacgtttta attgtatgtc ttcatgtgca ggctctagtg gaaagtaatt 88740
ttctcacaat ttttggcacc gttacacttg tgcccacaaa aacccgcgat tttttattt 88800
tatattactt ttggaagtac gagtttaacc agtcgctttc aaaccttatg cgtctatctc 88860
gccaaaaaac gctcacagcg gtgttggata ttacctttaa aaaaataaca ttaattttta 88920
ccacagaggg cgtattgcgt atggattcta cgaataagcc aggcgtgcca ctcgatatag 88980
acccccagtt cattgacctt gatagtattt taatggaact ggatcattag gacctctccc 89040
gcccatttaa atttttagtt tctacaataa taaaatgcgc gaggaatcat gggaagacca 89100
cgataccatt cagctcaccg ctcagcgcaa atacctcgcc gaggtgcaag ctctagagac 89160
ccttttgact cgagagcttt cagtctttct cacagagcca ggcagcaaaa aaacaaatat 89220
tattaataga atcacaggaa aaacctacgc acttcccagc acagagctac taagactcta 89280
cgagcatctc gagcaatgtc gcaagcaagg cgccctcatg tattttttgg aaagacaggg 89340
gacctactcg ggtctcatgt tggactatga ccttaaactc aatacaaatg ctgttccccc 89400
gctggaaccc cccgcgctat cacggctttg ccatcgaata tttgtgcata taaaaaacag 89460
cagtgtgctg cctgagggca gccataaaat ccacttcttt tttacattaa aacctgaagt 89520
ggttcagggc aaatatgggt tccatgtgct cattcctggt ctcaagctgg cggcttctac 89580
caaaaaaagc attataggat ccctacagca cgatgccacc gtacaaaaaa ttctacacga 89640
gcagggcgtt acaaatcctg agtcctgtct ggacccccac tccgcctccg ttccctcgct 89700
cctctacggc tcctccaaac taaaccacaa gccctaccaa ctgaaaaccg gctttgagtt 89760
agtctttgat agctctgatc ccgactacat tcccattcat caaataaaaa atttagaatc 89820
ttataattta gtttctgagt tgagccttac gaatgaacag ggaagccttg taagacctgt 89880
ctattgcgcg gcagacattg ccgctgagaa ggaggaagag atcccgaccg aggatcactc 89940
gctctccata ttaatgctac atgatcccga agcccggtat ttacataaaa ttttaaatct 90000
gcttcctccg gagtattatg tagagtaccc cctatggagc aacgtcgtat tcgctttggc 90060
caatacatcc gctaactatc ggcccctcgc cgaatggttt tcgcaaaaat gccctgaaaa 90120
atggaatacg ggaggaaaag agaaactaga aaaactttgg aatgatgcct cgcaccacac 90180
tgaaaagaaa atcaccaagc ggtccattat gtactgggcc cacaaacatg ccccccagca 90240
atacaaagaa attgtagaac aaggctactt ttccattctc gctgaatatg tgtatagcta 90300
taacggcatg cttgagcact acatgatcgc caaagtcatc tatgctatga tgggcaacaa 90360
gtttgtagtg gacgtggatt caaacgggaa gtacgtttgg ttcgaatttg tgctaccggg 90420
ccagccaatg aatcagggag aaatatggaa gtggcgcaag gaggtaaacc cggatgagct 90480
gcacatctat atttccgaaa acttttcaag ggtgatggac cgaatcacgg agcacatcaa 90540
ataccacctc agtcaacccc atgaaagcaa tattttaaat tattataaaa aactattaaa 90600
agcctttgaa cgctctaaaa gtaaaatctt taatgacagc tttaaaaagg gagttatcag 90660
gcaagctgag tttttatttc gccaaagaag ctttattcaa actctggata ccaatcccca 90720
cctactgggg gttggcaacg gggttctctc cattgagacc atcccggcta agctcattaa 90780
tcattttcac gagcatccca ttcatcagta cacacacata tgttatgtgc cctttaatcc 90840
cgaaaacccc tggacaaaac tattattgaa tgcactccaa gacatcatcc cagaacttga 90900
tgctaggctg tggatcatgt tctacctaag cacggccata tttcgcggcc tgaaggaggc 90960
tctgatgctt ttgtggcttg gaggcggctg caatggaaaa acttttctaa tgcgacttgt 91020
ggccatggta ttgggcgatc actatgcctc caagctcaac atcagccttc ttacaagctg 91080
cagagaaacc gcggaaaaac ccaacagtgc ctttatgcgg cttaaggggc ggggatatgg 91140
gtactttgag gaaaccaaca aaagcgaggt tctaaatacg tcgcggctga aggaaatggt 91200
aaatccgggc gatgtcaccg ctcgagagct taatcaaaaa caggaaagct ttcagatgac 91260
ggccaccatg gtcgccgcgt ccaactataa cttcatcatt gacacgacgg accacggcac 91320
atggagaaga ctgcggcatt atcggtcaaa ggtgaaattc tgccataacc ccgaccccag 91380
taacccctac gagaaaaagg aagatcctcg ctttattcac gagtacatca tggatccaga 91440
ctgccaaaac gcattcttca gcatactcgt ctatttttgg gagaagctac agaaggaata 91500
caacgggcag attaaaaaag tgttttgtcc caccattgag agcgaaacgg aggcgtacag 91560
aaagtcacaa gatacgctac ataggtttat cacagaaaga gtcgtggagt cgccctccgc 91620
agaaactgtg tacaacctat ccgaggtcgt gacggcctac gcggaatggt acaacaccaa 91680
cattaacgta aagcgccata ttgccctcga gctatcccag gagttagaaa actctgtgct 91740
agaaaaatac cttcagtggt ctcccaacaa aacgcgaatt ctaaagggtt gccgtatttt 91800
gcataaattt gaaacgctgc agcccggcga atcctacatt ggggtgtcca cggccggcac 91860
actcctaaac acacccatat gcgagccaaa aaataaatgg tgggaatggt cccctaatcc 91920
ctctgcccct cctgagaaag aagcgtctgc accaactcct tagggaatat ccttagaagc 91980
atgtctttcg gcagagccat taccggtagc aaaaaagcaa cattgagtat attatatgcc 92040
ttagcctgct cataagcgtc ctttttttc atggtatttt atgtttttaa atatttttaa 92100
ttatttttta aatacgatga acagttcgtg ctccgaaggc tgtttactaa aaatcggtgt 92160
gaatccgcat tctttaaata tggtttccca ttcggggatg gtatggaaat ccatgtctct 92220
acgaatagta tggtgcccaa gtgcgtcctg caggctgtga agccagaagg cctcctgacc 92280
ttgatgaagg tcgtacatga taagaaaacc atcaggtttc aacagatggt aaagcttgtt 92340
aaaatcgttt atcgtaagat gatgcgccgc cataggtaac cctatgagct ccacagagtt 92400
ttcatgctgg acatcgtcca tatcggtata aaacgtttca cagtaaatga gacgcttaaa 92460
cgagtatcga tgacaaacat ttatttccaa gtaggtttgc actacgtttt taggtatatc 92520
gggaatcatg ttgattaagg ttgtttcggg aaacttaatc atctgactag gcttcatttt 92580
caactcttta aaggatttcc cggagaagtg aaaatgggtc tttacgtatt tatgtaaaaa 92640
tacctgaatg ggcagagggg gctcctcctc ttcgttctcg acgcctccca aaatatttgg 92700
aatttcctga cgtggcaaaa gaaagtttat gtccacgttt acgaatccat cgaggacgga 92760
cacaaagctt ggctctaatc tccattccat atactgttta gaaacgggag atagcataat 92820

-continued cctaggcgtc acaatgcacg aagggttttt aatcaccgca tcgtggtaag aaaagtgtat 92880
tccatttctt ccagtataaa gaagcctatg ttcgtcgtag cagaaacaat taaggcggta 92940
tgcctcatac atacactgtt tcaaagtaca aacacgtttt aaaaaggttt ctgcattggc 93000
ggaggccaag cggttttgcc attggtggaa ggggttcaat cctacaatgg ccagctcgtt 93060
taaaatatct tcgcggcgcg ctaaaatctg caccatagaa gaatacttta gcattttttt 93120
ttcgcaccat tcgcgaagat gtttagctac attattaacc ttattattga taaagtatac 93180
gatggcatgt tggaagcctt caaaaataaa gagcccctcc aaaagatcat ctgccaatag 93240
aagatggatg ttggtgtaag cattgtcaat attttgtaga aacggcggaa tgcctgccaa 93300
aaccgcttca gcaagcatag ctccgttccg ttgtttactg tccaatagat tcgtaagttt 93360
tttgtccgca acagacacga cggctaggat ggttgcaatg tcagaaatgg cggcttgcca 93420
gaaataaccc gaaaagcaca tgcgcgcttc ttctatagat aaaaacgaaa agcgagaggc 93480
aatgtctccg agctgcgtga gttgaagacc tttttctcct ctggttaaaa ggcctgccac 93540
aatggcccgc tcaatggctg atgccagcgc atccgtgggg ggaggatcca gcatatcaat 93600
ctcctctgcc ttaaacacgc cttccttatt ttttttaatc gtttctacga caatgctaag 93660
aaaaatggcc ccagggcctt ccgtaatgat ttcaggatac tgctgcactg gtatttgctc 93720
aaagacgtgt tttgtgtaaa gcgggtaaaa gtgcccagga aatactctcc ctacacgccc 93780
ctttctttgc tcgatacggc tttgagccgc ggggcgcgta ataagccctc ccgcccattc 93840
gggatagtag gtttcaatgc ttctgttcca cccgggatct atgacgtact tcagcgtttc 93900
aatggtaagg cccgtttccg caacaaccgt ggaaacaatg acccttctta aaggtttttc 93960
cactttagcg gttaagggat ttttcaccca cagattctta atttccgctt tcaggccaag 94020
gtaggcctca ttttcctgcg caatcgcctc actatcgatc ggcaaaatca acattaacgg 94080
cagcttttct ttggcaaggt ccatatttgc attattcagc aacatcgaaa ggaagcgtat 94140
ttcagccata ccgggcatga aaattaaaat atctgcttcc gtgggacgat catgaatgtt 94200
ttctttatga atagtgagag ccgtttcgca ggcggtctta atgtagttgt tggtgttata 94260
cagcggccag tgggtttcca caccgtactg tcgtccttcc accaaaataa tgttttcttt 94320
tccgatacca aaataggttg agtatttatg ggtatcaatg gtggcggagg ttaaaattac 94380
aaagggaata cgcagcgccc ctatgcttcc tctttgcaac atgcgctgaa gcatactttt 94440
aatatacatg agcataaggt cgatgcctag ggctcgctca tgggcctcat ctataatcat 94500
aaaggcatag cgggaagcta tctcatcatc cgtcattgta tgtagctgcg ccaacagaac 94560
ccccgcggtt gcataaataa ggccccgatt gggtttttcc gtcagaggct tcgtttggta 94620
gcccactgtt tggcctaata tcatgtcggg gtagtgggtt gaggcgccga tgtctttggc 94680
gagggtcacc gcggttagga ctcttggctg ggtacaaata accgagcgtc ccaagtattt 94740
ttggaaagaa tgcgtgtttt catttctcag aattctgaac acgtgtacgg gtaaggccgt 94800
ggattttccg gaaccagtgc gtgactttat aatgagcacc cggtctgcga gggaggttgg 94860
aatggcccct ccaaactccg ggagacgttg ttttatccaa gtgatgatgt aatgaatagg 94920
aacatcattc ttgtgctcag cgggcacgtt atagagatga ccaggctcca ataaagtcgg 94980
ttttcccata ttctattgtt ttaaggattg attgttcata aatattttta tactctgacc 95040
aagaaattat ttttttatta agccggttat ttacgttgtt atggaacgcg aaggtccagt 95100
actgaaagtc ctccgagttg tttaatgtca agggattttt tgtaagatac gaaaaggcgt 95160
ggtgctggca cctggtgcat ggcagagact cgataaagtt cagtatccat tggatggctt 95220
catatttttc tttccagcta ggagcgtctg aaaaaaagat agcatataga tgcaaggatc 95280
gccagtattt aggtccccaa tgcaacattt ataacctttt gaaaaatctc attccatata 95340
gaggtaaata ttttttttcc atggagaatt tttttgcact cttgaaggga ttgcgccaca 95400
tcgtcaaatg tttttttgttt tccatgtatt ttggcgtaat tccagccagt atctgtgtca 95460
tggtccttaa tgtcatccgc taactgaaag gcatgtccaa aacaatgggc agccctttca 95520
atcatcccaa tgtcttcaac ggatccagtt cctaaaaccc agcccataat aaacgcgatc 95580
ttaaaaaagg gaatggtttt ttctggagtg tctactaact gaccggaacc cgcgctgttt 95640
agagagtggc ttacaaaggt acacagcagc gctcccagtt ggttgggatc cggaaacctt 95700
ggacagtgtt ccttaatcca gtcgatttgc cggcaaatat tttgaaatcc ttgcatggtt 95760
agcgccagag cgctcatctg cgccttggct acgccaaagc gggcccacac tgtatcttta 95820
tttcgccgct tcacatcgtt gtcaaaggag ggcatatcat cgataatcaa agaagctacg 95880
tgaaagtact ccgctgctag ggcggcctct gccggataaa taggcgcccc aaaggaatgt 95940
tgcaactgac aggcccgaac aatttccatc aggataatgg gacggatata cttcccacct 96000
cttagagcgt aagagcaagg ctctgttagt tgtcccttaa agtccccatc ttcaatagca 96060
ttatttaaga tggtctcaaa ctcttcacta aaggttttat aatttttagg attcagtgga 96120
tgtattccat gaaaaagcgc gacactacgc ggtgctgtga ttctaaaata cttaggtttg 96180
cgcgtatagg atattaaaat aataataaga actacaatga tggagatata gatgagatgc 96240
aacatgctga gttgtctccc cgcagggaat ggtccttttc cgcgcttgtt aacggtaccg 96300
aggaggcgtt gaaatcttta ggaaaggtgc tgtctagttt ggaatctcca attcctcccg 96360
tatatttagg tatataatta ttgtgtctag aaattgtttg ctttgaggta tcaaaatatt 96420
cagcctgacc gctatttctt ttagaataat tcggtatagg gcttgagtag ttggcaatac 96480
tcttaaaccg gggcaccaag gtaacaatat tttccatata atgggtttga tacgctttgt 96540
ttaaaaatgg gcttaccggc tttatgcttg ttagttgtgc attgagtacc ggtatgtctt 96600
ctaggatttg tggctttata gaatgattag caaacacaga atgtagtata ttagatactt 96660
gtagcatatg tctatttgcg gaaaattcct ggtattctct gccgtgttgc gaatctttgg 96720
gcggaagggg accaagcatc ggcacgtccg tgtaggtact ggtggatttt atgagttcct 96780
gctctatgtt cggtttgaca tgtggatttc ctaaaggaat acctctacct gcaatccctt 96840
tttctaccga cgcaggtaga ttgtgcgcta aacacaaaat attgtacacg tctttgtgcg 96900
gaatatatcc gttatagtgc tggcccggca tctgatcgcc aaggtgctgc tcatgcttaa 96960
tggtaccctt tgttctgagt ttaggaagat cctcgtacga aaaaaatttt gtgtgctcgc 97020
tgaacctcgt agaaggaacc gaactatttt ttgggttttt taaggaaggc aatgaggaag 97080
gctgggtcag acaatttttc tgtgtgccct ttaagctagc cacctgcgga aatgtttttt 97140
tttccgtacg aacaacattg cgcctaatta ggttttccgt atgggttgaa aaagcaggac 97200
gatgattttt aaaatgatta aaaagtttat tttttggaat ggagctgtac ggctccagat 97260
cttgcgcatc gccgtaacca atgtttttgt gctgagggtt cagcataaaa gaaaagttac 97320
gtagatcact gagttgcaat cccttttcag ccttttcagg actattagtg tattcattgt 97380
atacaggcgc ggctccattt ttgttgccgc agtaccggga atttagtata ttatcagaat 97440
accggttatg acgcggcaaa tcgctttccc aaagaggtgg atctgaccta taatcggcta 97500
acagctttga agcataatca tgatacattg tatataaaag ttaattatta tattgagaag 97560
gcataattac ttcttgtagg ggtacaagag gctttgaatc aggcaaactg acgggttttg 97620
aatcggccgg ctttggaccg gcaggtatct ttttaggttg atcttcttct agctcattag 97680
acacggatgg gggagaaata ggaggaataa tttcatctcc gcccttatat ttgtcatgga 97740
tagaagaaac aattacatcc atgtttgatt tattataaat gtcgtttaac tggtgattta 97800
aaacataata atgcaaaaat aatagggcta caatgcatat atatacgtaa atagccgtct 97860
tcgtttttcg tttttatcc accggcggat tacaaattgc aaaaaataca actaatacca 97920
ccgctgtaat gattaaggcc acaatgaaag gattttgaaa ggatgttttg aacggttcgc 97980
acgtataaat tttttctcct aaattattga tacccgcaat aaaatctaca ttcattttat 98040
atatttataa attatgaaaa atttagagtt acatctccgc cggaccaatc attgctaaaa 98100
tttgaagatt cttcaaaaag gcccgactgg ttgaatgtct tctgctcagg tttccaaaaa 98160
ttttccaaga atggattttg aacaataggc tcatcttgat tttcttcttc aaggatattt 98220
tctttgatat caagaacagc ttctttaaac tcaggtgtat cttgattaaa ctcaggttta 98280
tcctgatcaa tcgcaaaaat attatcttct tcagatatat cctgtttaat cgcaagaata 98340
gtttcttcct caggtttatc ctgatcaatc gcaagaatat tttcttcttc aggtttatcc 98400
tgaccaaact caacaatatc tttctcgcta aatccgtttt tagtgtgaag ctcttggttt 98460
tgaagagaat tatcaaaatc tattttagtt gttgtcctag accgtggcac gggatagtta 98520
tctaatggtt tacttactat agtcctcgaa tgtggcacgg gataattgtt tggtgacttg 98580
ctggttagct cttggcttgt taatagttct tgttttctca ataattccat ctctactact 98640
tctttttgat ccgctggtgt ctctttttgg tattcttcat tagaaaaatg ttcagagggt 98700
aatgtttcaa taaactttgt gagtggatag ctgctctttg atgtagaaga gcgttgaatt 98760
tgctgataaa ggagttgaac aagtcgccgg tattcactct gtcttttttc atattttta 98820
cgtagcgtgg agagatctgc taagagcgac ttgttttcag atgttaattc ttcaatttga 98880
tgaagaaggc tgcgattgta tgaactaagt cttgcatacg tttcttctaa ttctgtctcc 98940
ggctccacat aggcctgttt tcgcagaaat ttattgtata gttccattct tttttgagc 99000
agaaaggtaa gactataatc ttgcatttct ttcgtaactt tatggtagtt ttctttccgg 99060
tttttgataa taaagggcag cattttttct gttgtgataa aggtgcccag attgctaatg 99120
tagtcgcaca gtagcaattc caagatagat tctttctttt caaggcttat agattggctg 99180
tattctttag gtatgaaaga atcaacaatc gttgttacga agtttgaaaa gtttaatgtt 99240
ttgctgttaa tttgggtaat gttacaaaaa tatttgtaaa aactatctag cattttttca 99300
taaagttttt tattttgttt aacccctaaa atatagccct ttacttgata ctgatattcc 99360
gtaacaatgg aatgtttttt gtatagtgca tttttgtata aaaagttata aaaaatgttg 99420
ataaaatacg caccaagggt ttcaaaaata cttataacgt gggattcttc ctgatccatt 99480
atatcatatg taatattatt ttaataaaaa attactgacg aataacatgc aaaaaaaata 99540
tgtttaaact tattttaagc tagcacttat ttaaaagtgt tttaaacacg ttttaaattg 99600
tatgttaata cacttaaaaa ttaagccgaa atttgctcca ataaggatta cttttatcaa 99660
tgaccacctc tttactataa acggctttac ataattttaa taatgcttta gagccaaagc 99720
tgaaggcagt gggaagcggc actgtactat ggtaaaaatg ttgccgatgt tcatcctcgc 99780
ggatgtacac aagtttccta tatcctttaa acacaatatg gctaatttct tccacatact 99840
ccttatcctg tttggaatag cggttgcttt gacgggaaaa attcgacata caaatagagg 99900
catttgtaaa aatggaaaca aatgcgtttt tacgaagatt ggcgggtaaa tcggtatcat 99960
cttggcagca aataatcatc gaaataaaac agtgacgatt ttggtaaaaa aactttttaa 100020
aaatttcttt tgtaaataat gggtgcagtt cggccgcgca gtcgtctaat attaaaagta 100080
aacgaggatt aagattgata tagtttaacg taaacttttc atcctctgta aggcataagt 100140
ttttatacat atgaatgttc tgtataataa tttttttaa aagttgctga taaagcgatg 100200
taatcttttc ttcttttttt tggtccgttt gttcagcctt taagcactcc actttgcaa 100260 tatttttgtt ttccttttgc tgtatatcga tcggaagttt atgatacaat gtttttagca 100320
tatcgatgtt gtttactcga ctgtagatgg aggacatcat agtttgccgc tgccagatgg 100380
cctccaaaaa gcgttcagcg cccttgttgt catttttttt ttgcttatcg gcgagccaca 100440
agcggtagtg tattagagtt ggatgtacaa aaccctcata tgaacgattt gagggttccg 100500
agggggcaac cactaaaatt tgttcaatat ggggttgcag gattttcata atatgtttaa 100560
cgtacacggt tttgcctgtt tttgaggggc catatagcac agttgtttta tctataaaat 100620
gatgtgcttt gaactgtagt tcaggaatta gcttccctga atgggtcgtt agggccatct 100680
ctatattatt acaattctgc ttttgtatat aaaatttctt tttcgagttt attattattg 100740
ttgacccaca tatctacccg tatcgtatca tcaggcacat tgagcatttc aagcgcatta 100800
tctaactgtt tttttgtttt tatcagctcg ctttcttcat cgggggttaa atttcttta 100860 ctaagcagtt gcttaatttt ttcttcgcag tcgtctataa aatcatactc tcgagctttt 100920
ttgatatttc cagatgcttt ttctaggttt tttagctcct taaaggaaag cagtccctta 100980
atcccgctat ccgtgtgaaa ggttgaatta tagatggaga gccccggagc atccgggcca 101040
gtttcttgta tattttttgc ttttttgtgg taaatagtat ttcgtaaaat ctcttttcct 101100
atctttaggt cttcctcatg acggtccaaa atccgtttta ttatttcatt attttgatta 101160
aaataattgt agcgctctct gttggcctta aagcttccca ggagtgtcca gttgcctaat 101220
tgaatggatg aaacctctga gaaaatctgg tctttatatt tataataaaa ttcatcaacc 101280
ttttgttggt tgctgctatc caccacatca taaataatga aggcaaactc taggtcgggt 101340
ttttctgggt agatgctttc cgtagcggcc cgcaactctt cgtaattatc ctcaatgtaa 101400
taattccact tataaaaagt atcctgaggt ggaatatgct gcgaaagata tctagtaatt 101460
tttgtgttaa agagaatggg tttaaacgcc ctcggatttt caagcatatg tttaatgctt 101520
tggtgaagtt ctatatttg taatatgtgg gctgctgccc tatagccctg tggggtttgg 101580
gtgattgcat caatatcggc ctgaagctca ttaggcacat ttaatgtttt ttgcatgatg 101640
tgtaaaggga tgcgctcagg atctgctaaa tcggtgtatt ctgtgcttgt acaagtgctt 101700
gcacaggtat ctacattggt atctgcacac atgcttgcac aggtgtctac attggtatct 101760
gcacacatgc ttgcacaagt gtctacattg gtatctgcac aagtatacgc actttgagca 101820
tgaagattag gatcaaacac aaaatgttct cgtaaaaagc tatcgatcgt tgttttagct 101880
tccttgcttt tctgcgtctg ggttttgcag ctatctgcta tagataaaat tgtatttact 101940
accgattcag agggaacatc attagtttcc tgtttcaaag tatcaactaa cgttattagc 102000
tcactgagaa gagttttggt cgtgtgggta ggttttgaat aggaaggcat ccattcctgc 102060
agagctttga agacatatcc aataaagcta gtcattataa gacgtcgaat atactgctcc 102120
cgcaaatttg taaaagagca aaaggccacc ctgctatcat ttttgaactg tttgtaaggg 102180
ttcgtccttt ggtaaagctg tttaagcgtt tcttcggata tttcagtaga gggatcctcc 102240
aatacgtttt tgagaagctc atcaatatta aattctgcca tatcttagag tttattatat 102300

-continued acatattaaa gctttaatat aagggggggta taacaatgga cgaaatcatc aataaatacc 102360
aagctgttga aaaacttttt aaggaaattc agcaaggatt ggccgcgtat gatcaataca 102420
agaccttaat tagtgaaatg atgcactata ataatcatat caagcaggag tattttaact 102480
ttttaatgat tatttcacct tatcttatta gggcgcatag cggagaaacg ctgcgaaaca 102540
aagtaaataa tgaaattaaa cgtcttattt tggttgaaaa tatcaatacc aaaatatcta 102600
aaacgctggt aagtgttaat tttttactac agaaaaaact ttcaacggac ggggtgaaaa 102660
cgaaaaacat gtggtgcacc aataatccca tgctgcaggt aaaaacagcc cacaaccttt 102720
ttaagcaact atgcgacaca cagtccaaaa ctcaatgggt acaaacttta aaatataagg 102780
aatgcaagta ttgtcatacc gacatggtgt ttaacaccac gcagtttggg ctgcaatgtc 102840
ctaactgcgg ttgtattcaa gaattgatgg gaaccatttt tgatgaaaca catttttaca 102900
accatgatgg gcagaaagca aagtcaggta tctttaaccc taaccgtcac tatcggtttt 102960
ggatagaaca tattcttggt agaaatccag aacaagagtt ggggaccaaa caagatccct 103020
gcggaaccaa ggtgttgcaa caactaaaaa aaattattaa gcgcgataat aaatgcatcg 103080
cgcttttgac ggtcgaaaat attcgaaaaa tgttaaaaga gataaaccgc acagacttaa 103140
ataattgtgt ttctcttata ttgcgtaaac ttaccggagt agggccgcct caaatatcag 103200
agtcgatttt actacgaggc gaatacatat ttacagaggc aattaagata cgggaaaaag 103260
tgtgtaaaaa agggcgtatt aataggaatt attatccgta ttatatatat aaaatttttg 103320
acgccatttt gcctccaaat gataccacga atcgacgcat tttacaatat attcatttgc 103380
aaggaaatga tacgctagct aataatgata gtgagtggga atctatctgt atggagctcc 103440
ctgaaataaa atggaagccc acagatcgaa cccattgtgt tcattttttt taaagatgaa 103500 gatttttttag atgatttttt ttagtttttt aaaagacgaa aaaatttttt aaaagatgaa 103560
tattcttaaa ccccgcaaat tacttttttt taggtactgt aacgcagcac agctgaaccg 103620
ttctgaagaa gaagaaagtt aatagcagat gccgatacca caagatcagc cgtagtgata 103680
gaccccacgt aatccgtgtc ccaactaata taaaattctc ttgctctgga tacgttaata 103740
tgaccactgg gttggtattc ctcccgtggc ttcaaagcaa aggtaatcat catcgcaccc 103800
ggatcatcgg gggttttaat cgcattgcct ccgtagtgga agggtatgta agagctgcag 103860
aactttgatg gaaatttatc gataagattg ataccatgag cagttacgga aatgttttta 103920
ataataggta atgtgatcgg atacgtaacg gggctaatat cagatataga tgaacatgcg 103980
tctggaagag ctgtatctct atcctgaaag cttatctctg cgtggtgagt gggctgcata 104040
atggcgttaa caacatgtcc gaacttgtgc caatctcggt gttgatgagg attttgatcg 104100
gagatgttcc aggtaggttt taatcctata aacatatatt caatgggcca tttaagagca 104160
gacattagtt tttcatcgtg gtggttattg ttggtgtggg tcacctgcgt tttatggaca 104220
cgtatcagcg aaaagcgaac gcgttttaca aaaaggttgt gtatttcagg ggttacaaac 104280
aggttattga tgtaaagttc attattcgtg agcgagattt cattaatgac tcctgggata 104340
aaccatggtt taaagcgtat attgcgtcta ctggggcgtc cagctataaa acgtgactgg 104400
cgtacaaaaa gtccaggaaa ttcattcacc aaatcctttt gcgatgcaag ctttatggtg 104460
ataaagcgct cgccgaaggg aatggatact gagggaatag caaggttcac gttctcatta 104520
aaccaaaagc gcaacttaat ccagagcgca agagggggct gatagtattt aggggtttga 104580
ggtccattac agctgtaatg aacattacgt cttatgtcca gatacgttgc gtccgtgata 104640
ggagtaatat cttgtttacc tgctgtttgg atattgtgag agttctcggg aaaatgctgt 104700
gaaagaaatt tcgggttggt atggctacac gttcgctgcg tatcattttc atcggtaaga 104760
ataggtttgc tttggtgcgg cttgtgcaaa tcatgaatgt tgcataggag agggccactg 104820
gttccctcca ccgatacctc ctggccaacc aagtgcttat atccagtcat tttatcccct 104880
gggatgcaaa atttgcgcac aagcgttgtg acatccgaac tatattcgtc tagggaattt 104940
ccatttacat cgaatcttac gttttcataa agtcgttctc cggggtattc gcagtagtaa 105000
accaagtttc ggtacgcatt ctttgtgccg ggtacaatgg gtcttccaaa aggatctaca 105060
agcgtgtaaa cggcgccctc taagggtgtt tggttgtccc agtcatatcc gttgcgagga 105120
aacgtttgaa gctgcccatg ggcccccatc tgggacgtgc cctgaatcgg agcatcctgc 105180
caggatgaat gacatgcacc caatatatga tggcccacca tatcatggaa aaagtctccg 105240
tactggggaa taccaaaggt aagcttgttt cccaaggtgg gggtacccgt atgcgggcgt 105300
actttattgt attcaaaccc tactggaaca taaggcttaa aatgcgcatt aaaatgcacc 105360
aaatgtgttt cttcgatttg actcaaagtg ggttcgggat cgggtttccc ataacttttg 105420
ttcacatttt taatgttaga gatcctgcta ttcagcaagt cttgggccaa tataatcttg 105480
tcggccttcc catcgttagc aataagacaa aaagctcctc ctgatgccat atataatgtt 105540
ataaaaataa tttattgttt ttattaaata tggcggttta tgcgaaggat cttgataata 105600
acaaagagtt aaaccaaaaa ttaattaacg atcagcttaa aattattgac acgctcttgc 105660
tggcagaaaa aaaaaacttt ttggtgtatg aactacctgc ccttttgac ttttcctccg 105720
gcgacccttt ggccagtcag cgcgacatat actatgccat cataaaaagc ctcgaggagc 105780
gcgggtttac tgtcaaaata tgtatgaaag gggatcgtgc cctccttttc atcacctgga 105840
aaaaaataca atccattgag ataaacaaaa aagaagaata tctgcgcatg cacttcatac 105900
aagacgaaga gaaagcattt tattgtaaat ttttagagtc tagatgagct tttacgcaat 105960
gttgtacagt gttgtatata tgtcttgtaa gcatttgttg tagagtaata agtaaaagat 106020
aaataaaaat gactattaaa ataaagccca aaccattaaa aatattttta tctgttagat 106080
ttaatttaat aaatggctca tggaatgtgt ggtgcgccgc tgcatgaggt gtggccgcat 106140
gggatgtggt cgcataagat gtagctacat gggatgtggc atttgcttgc atgtaaggat 106200
catgatgtgt tgggtcttca tcccagcaat aatcgccatc tttatctagc tgaattgtat 106260
accccattat atatcactta ttattttttt ttaatgtttc atgaatttca ttataggcgg 106320
tgaaagggtc ctcaggcccc ttctgtaaaa gattatagag atcttcggac gctttatgtt 106380
tcgtgcgaat taaggcggga tataacaaaa gagagggccc cagttccaaa caaattttac 106440
ttagcgggct catattttgc accaagtttc ccactacttg cgatgtttca taacgcattt 106500
taaagagctt tatcataaaa gtgttatgca ggccggtgta gtctggccta tagttaagga 106560
aggggatttc tctggtaccg tcaaacacga tctcaagtcc tctagcaagc ccgatcaaaa 106620
tttcttcagc aatggatgag tatctaattc ctacattacg aagcgtaagc atttctataa 106680
catcatctat ttcctgcata gaggaatcta ttgtaggaat tttaatatca tctgtgctga 106740
tttgttcatt cccaagatag gtaagcagca tattaatttt ttctagcttt actagcttag 106800
tcttacgctc ataatcatga tcttttttat aaaaagagtt gggatcaccg ttggaccgta 106860
gatgattaat aaggcggtct acttgctttg tactaggttt aatacttttt tcactatact 106920
cgctttcagc atagtggttt ttacgatctc ttttagaaat agctgttttt tgagatgcct 106980
cagactctgc atattttttt ctatgcgtag aaagagaata accgcggtca ttacgtgaac 107040

-continued tactgttgca tgcaaggcct cggcgcgtct taccgctgcg cacactgcca ttgcgtatac 107100
tgccatcgcg cacactgccg ctgcgtatac tgccattgcg tatactgccg ctgcgtatgc 107160
tgccgctgcg tatgctgccg ctacatacac tatcactaca tatgctgtca gtacatacgc 107220
tatcgcggcg tatgccgccg tgtaccttat cgccgcccct acccgagggt tttttagata 107280
taatactgtg tggggagtca agcgaaaatt cagggtcatt aaagttaatg cccaatgact 107340
ttgccaatcc attaagctct tcatcaaaat gatcggtagg aaaactttgt tgcttgccca 107400
tgacctgttt ttcaagttcc tccaaattgg cttgctcatt tatatggaga ttattcataa 107460
gcgtcgtaat tccagcaaga tttgctcctt ctaaaaatgt ggtgtcctcc atcggatata 107520
ctatactatt taaaagcttt taaataaaaa tgtgtttgga agaaatgctc tcttcaagcg 107580
tgtgtagctc agatataaat gcctcctcag aaagctttcc accatactcc tttctcatcg 107640
tataggaggg cgccggttta atgtaggaaa tccactggga ggtaaaaaac cggtacaaca 107700
tatttagcag ctcgcgggcc tcccaccttt tgggctccgt atagtgcaca tcaacataag 107760
aggcggcgca tgaaaagctg caaaagttgc cgagaacgcc catctcaatc tctcctcgct 107820
cattttcacg catataggtg ggcacgaatt ttgggacagt cttgaaatag agatgacatg 107880
tccagcattt aaagctagaa tgggtaaccc atttggaaac agtggtgaat acggagggta 107940
gctttttttc gacctcggct tcatcgtcat tcgtatttaa cgtatcggtg gcagtttttt 108000
tggattgcaa gcattcttca atggtaatcc cggataagta taaaatatta ggacaattag 108060
tttccataat tttgatagtt atttttatac aacatggatt taattaaaga taaatggagg 108120
acgaaacgga actgtgtttt cggtcaaaca aggtgacgag gcttgaaatg tttgtctgca 108180
catacggggg aaaaattacc agccttgcat gttcgcatat ggagttaatt aaaatgttgc 108240
aaattgctga gccggtgaag gcattgaact gcaactttgg ccaccagtgc ctaccgggct 108300
acgaatcttt aataaagact ccgaaaaaaa ctaaaaacat gttgcgccgt ccgcgcaaaa 108360
cagaaggcga tgggacttgc ttcaatagtg ccattgaagc ctccattttg tttaaggaca 108420
agatgtataa attaaaatgt tttcctagta ccggggaaat tcaggtcccg ggcgtcattt 108480
ttccggattt tgaagacgga aaaaacatta tacagcagtg ggtagacttc ttgcaacatc 108540
aacccattga aaaaaaaatc cagattattg aatttaaaac gattatgatt aattttaagt 108600
ttcaaataaa cccagtgtct ccccgcgtca tcattcattt aaaaaaattt gcagctttgt 108660
tggaacacat ccctactcca tatcccatac gtgaaataaa gcctccatta gaagactcaa 108720
aagtatccgc aaaatttatg gtcagtccgg gaaaaaaagt acgcattaat gtttttctta 108780
aaggtaagat aaatatttta ggctgcaaca caaaggaatc cgcggagacc atttatacgt 108840
ttttgaaaga tcttatcagc gtacattggc aagaaatttt gtgcgtgtta ccggtacccg 108900
attaaagaat gttttcatta ataaggtaat cgactatgct aaaaagaata acaagaaaaa 108960
taccttgaag aactatacca aagtaggtag gttttctgca tgtcacggca tggttaaaat 109020
tgctaataat gtagtccaca aaagcattgc tcaatacgac taaaaatagt aaaaaaagga 109080
taagtgctct ttttatatcc atatacttta aaacttattt tttacactaa taatttcctg 109140
cggccgcaat ataaactgta ggtcatctat aacgcccaga cctgttaaaa gtagagtact 109200
atgttttaag ggatttaaaa tatccgccgc aagaatgtga atataatttt caaagtggtt 109260
tacaggaatg cgtaagcgtt tttttttgca ctgcggttgg tttagggtcg aatactggca 109320
ggaggtatat atattaataa gaccgcggtc gatggtttca atatcttcat agaattcaat 109380
gcgcggcgtc aaaagttttt taagatgttg acataactca tcatacgtgt aggactggag 109440
gggggaaaga agggtgtagt caaagttaaa aatgtttttt tgaagaacct ttaaagcatg 109500
ttccgcgtcc gtggtttcca aaatatgttt tatggtatga atgtcattta aatctacaaa 109560
gtctgacagc tttgtgtaga actcggtgac ggaggttatt ttctggaaat cggtttttttg 109620
aaaaagattt tcaatgtgtt tgcgggttga gttgctttgc agtccataca agacatcaaa 109680
aaattcaatc agcaaaaact tatacaaatg gttaatataa aaagctttgt tggccttatt 109740
ctgctgagga tatggttcct ctaggggata tagaatggct tggtctatat ccctaggatc 109800
aatagtcaat gttgcgatgg gaagcttttc cagcgtagcg ggaagagttt gggttggagc 109860
gtagtaaaag tatagcccgg tttttccctc tgaaagaaag cccacaaatt cttttttat 109920
attttgcagc accgctgagg gtacgatttc gtactgttta tactgtttgt tgaaaagggt 109980
aataaatttc caggtttctt caaagcttgc aatctgggtg ggccgcagat caaagtcgat 110040
gggaatgtcg tcatgaatgt aggatgatag tcttatagga aaataaatag ggcgatcggt 110100
gtctgaatcg ataagtaaag cataacaaaa gttatgcctg ttgataagtt ttttaccaac 110160
cgtgtagccg ggaatgtttt tcacgtcatg gatatcccac cagttatcct tgcacataaa 110220
ctcgctcata gactggatga cctccatcac agggtcatct tcggtaaaaa tatactgggc 110280
ctcactgttt ttcagaaatc ttttttgctg ggtgatggcc attgggtaga tcccttcgtc 110340
cgtgtcaaag ataatggcta tcttcttcga tgggctaaga attttttgta ttgtgctggg 110400
ggacacctca aacccgatgt cgccctgttt atctttaaaa aagacacagt gaaggtcgta 110460
gcatatggca acaaggtcca gaaagatgtc ctgccatgtg gtgtcccatt gaagcagttg 110520
gttttttttgt tcaacaaagg tttgtaagat aaggtttgcc agctccgcgc cgctggaaaa 110580
catgttgccg gccccattcc ccaaaatata gtactgcggt gtgttggccg cctttgcaat 110640
ttcaatggca agggccttgg gggcaagatc caaaattcga gcaagggaat aaaaaagccc 110700
ggcattgcta attccaagca tggtttgctc caccccccaca atgcaaaaaa tgtcgggctc 110760
ttttatcgta tttaaaaaca gttcatctgc tatctggtgg ggtagaaagg caatccggtt 110820
caccggtatt ttttttccat aggacaaggt atgacgcgat gtttgtgtat taagatcctc 110880
caggtcttgt tctacaaacg tgtgcttggt gaggcaggta ttgttaatat agaaccgctt 110940
tgtgcccagc agggccttcg tcttttggca gcacggcaga cagtaattta gggggtggcg 111000
gccttctagt aggcttagat gagggtagtc aggatgcggg cagctatagt aggcaggtac 111060
cccctccgtg aaattccaat actttactag ctccttgcgc ttggctggcg gcatggactt 111120
cacctcggcc tctgagtaaa tgacgggtgg ccgtgggtgc tggcatagga cggagtaaac 111180
cgttgcctgc gtgtcgtact tgcgcaggtc atacaggtcg gggtcctgtt cttgaagcgc 111240
acgtagctga gaggctccct ttccttgttg tttatcgtgc agttgagaga gtttattaac 111300
caaaattttg tcaggcccgg tgatcaagtt atctaaaaac acaaataggt aaacccaaag 111360
atagttaaac tcttcctggg taatgttaaa catttctatt ttgatatctg taaccctatg 111420
gtagatgcga atgttgcggc cgccgtagat tgtttcccac cgggccgcaa catttgtgtc 111480
aaagaggtac gcatacgtgt tttggagcaa cgcaacattg atgtccattt tgcgccccgg 111540
accggaggaa ataatgatca tccgttcgat ttcgtgggga tcatacgaat aaatcccctt 111600
tttaaataaa aaattgtaga ccccggtttg ctggaggccc cgcacggaaa taatccctgc 111660
ttgctcgtat tcccgccaac gacttttgag ctcggtaaat cccttgctag aaagcgtata 111720
gggccaaaag gtggacaccg acatggagct gatagaaatt tggatgtcct cgttggaggg 111780
aaggggcaga ctccctccac gaggaaacgc ggcaggcccc atatcattaa ttgtatgaat 111840
aataggattt atgaaattat ttagggtgga caccacggag ttaaagtcgt ggcgctcgtt 111900
ttctgaccaa ttgctttcga taaagtagtg cccattattt tgtatggtaa gaataaaggc 111960
ctttttattg ataaagcgta ttaaaataat agtgggtaca cggaatgttt tattgctgaa 112020
tttttcaggc tccgtggaag ttatgtggtg tttggaaacc acggtgggac ctgttttact 112080
ataaaagaac accaccagct gaggaatatc gggagtagct ggaaataggt cgaaaacatt 112140
gcgcacatta atttgaatat ttacgagggg tgaaatttta atcattgccg aggtgacggc 112200
caacgtgccg cgtgttagtc tattcccctc gtacttggca atgacttgtt gtgctctggc 112260
atacgtaaag tttattagtt tttgctctag gagaagcctc tttttaagac tggtcaagga 112320
tggagaaaga gcaggatact gtttttccat ttgtaaggga gattgtacca atagtttaaa 112380
ggcatcgggg gaaagaagag gccaatactt cataataagg ccgtaataga gtaagtcaaa 112440
ttggtaatta tcctctatgg caatggagat ttggcgccgc atgggggcca ctagcgtgtt 112500
gaggtctgct acaaagatgt gatgaatgtt ttttatgagc tggaagctgt cgagcgcttc 112560
cacatagagc tcatcttttt gactttccat agatgcgtcg atgttcaccc cacccacctg 112620
ttgaaactcc tttttgtagt cgcgaatgtc taacgccacc ccgctaccgc ttaacaatag 112680
gcgatacgtt acctgaagcg cattgttttg aaaaaagaaa atgtgttgtc tataaggggg 112740
gatccctgtg gcaacgtaaa tttttctcg aatgtcttta aaagtgtctt cagggaaaat 112800
actatactcg ctatacatcg tctcaatttc tggcatcatc acgtttgtct cctcgccacg 112860
atcctccaca aaaagttttt caaactcatc taaatcatcg ctatctccac ccaccacgta 112920
ttgggaaagc tttttctccc aatcctcgcc gtaaaaattt tgtaaaattt ctttgtcctt 112980
aggggttcgc tgcaggtctt tgcggcaggc ctgtaacacg tttgcaggaa cggatcccaa 113040
aaaaataaac gtcttcgtgt actcattttc cacaggatta taaagagtaa ctcgtagagg 113100
atttgttaaa aagtcatttt ggaaatccat tatacccggt atagaaaata aaatttaaaa 113160
taaaaacgga tgatatctat catggaccgt tctgagattg ttgcacggga gaacccggtg 113220
attacccaac gagttacaaa tctcctacaa accaatgctc ctctactatt catgcccatt 113280
gatatccatg aagtacgata tggagcctac acacttttca tgtatggttc cctcgaaaac 113340
ggttacaaag cagaagtaag gattgaaaac atcccagttt tctttgacgt acagattgag 113400
ttcaatgata caaaccagct ttttttaaag tcgctactga cggctgaaaa tattgtgtat 113460
gaacggctgg agacgctcac ccagcgtcct gtaatggggt accgcgagaa ggaaaaagag 113520
tttgcaccat acattcgaat attttttaaa agcctgtatg agcgacgaaa agccattact 113580
tacttaaata atatgggcta caacacggcc gcggacgaca caacctgtta ttaccgaatg 113640
gtttcccgag aattaaaact acctcttaca agttggatac agcttcagca ctattcctac 113700
gagcctcgcg gcttggtaca caggttttcc gtaacccccg aggatcttgt ttcctatcag 113760
aatgatggcc ccacagacca cagcatcgtt atggcctacg atatagagac ctatagccct 113820
gttaagggaa ccgttccgga cccaaatcag gcaaacgacg tggtgttcat gatatgcatg 113880
cgcatttttt ggattcactc cacagagcct ctagcgagca cgtgcatcac catggcaccc 113940
tgcaaaaagt cctcagagtg gaccaccatt ctatgctcct ctgaaaaaaa tttgttgtta 114000
agctttgctg aacagtttag ccgctgggct cctgatatat gcacagggtt caatgattct 114060
cggtacgact ggccctttat cgttgaaaaa tctatgcagc acggtattct agaagaaatc 114120
tttaacaaaa tgagcctttt ctggcaccaa aagctggata ccattctaaa atgctattac 114180

```
gtaaaggaaa agagagtcaa aatctcggcc gaaaaatcga tcatttcctc ctttttgcat 114240
acccctggat gcctacccat tgatgtccgc aacatgtgta tgcagcttta ccctaaagcc 114300
gaaaaaacaa gcttgaaagc gtttttagaa aattgtgggt tagattcgaa ggtagacctg 114360
ccgtaccatc tcatgtggaa gtattatgaa acacgagaca gcgaaaaaat agccgacgtg 114420
gcctattact gcattataga tgcccagcgc tgtcaggacc ttctggtgcg ccacaatgtt 114480
atccccgatc gcagagaggt aggaattctg tcatacacct cgctgtatga ctgtatctac 114540
tacgcgggag gacacaaggt atgcaatatg ctcattgcct atgccatcca tgatgaatac 114600
ggccgtattg cttgcagtac cattgcccga ggtaagcggg aacacggaaa atatcccggc 114660
gcctttgtga tagaccccgt taaagggctt gaacaggata aacccaccac aggtctcgac 114720
tttgcgtcgc tgtacccctc actcatcatg gcctacaact tttcgccaga aaaatttgta 114780
gcctctcggg atgaggcaaa tagcctcatg gccaagggtg aatctcttca ctacgtctcc 114840
tttcacttta acaatcgtct cgtggaagga tggtttgtgc ggcataataa cgttcctgat 114900
aaaatgggat tgtacccaaa agtactcatc gatctactta acaaacggac cgcccttaaa 114960
caagagctta aaaaactagg tgagaaaaaa gaatgtatcc atgaatccca tcctgggttt 115020
aaggaactac agtttcgcca tgccatggta gacgcgaagc aaaaggcgtt gaaaattttc 115080
atgaacacgt tttacggcga ggcaggtaac aatttgtcgc ccttctttct gcttcctcta 115140
gccggaggag tcaccagttc gggtcaatat aatcttaaac ttgtctataa ctttgttatc 115200
aataaaggtt acggcatcaa gtacggtgac accgactcat tatacattac atgcccagat 115260
agtctttata cagaggtaac agacgcatat ttaaacagcc aaaaaacgat aaaacattat 115320
gagcaactct gccacgaaaa agtgcttctg tctatgaaag ccatgtctac actatgcgcc 115380
gaggtgaatg aatacctgcg acaagataat ggcaccagtt acctacgtat ggcctacgag 115440
gaagtactct ttcctgtgtg ctttacaggc aagaaaaagt attatggtat tgctcatgta 115500
aacacaccca attttaatac aaaagaatta ttcatccgcg gaatagatat cattaagcag 115560
ggtcaaacaa aactcaccaa aacgatagga acgcgaatta tggaagaatc catgaaacta 115620
cgccgccctg aggaccatcg cccccctctt attgaaatcg ttaaaacggt tttgaaggat 115680
gctgtggtta acatgaagca gtggaatttt gaagacttca tccaaacaga tgcgtggaga 115740
ccggacaaag acaacaaagc agtccaaatc tttatgtctc gcatgcacgc tcggcgtgag 115800
caactaaaaa aacacggcgc tgcagcatcg caatttgctg agcccgagcc gggagaacgc 115860
ttctcctacg ttatcgtgga aaaacaggta cagtttgata tccagggcca ccgcacagat 115920
tcctccagaa agggggacaa gatggaatac gtctctgaag caaaggctaa aaatcttcct 115980
attgatatat tgttttatat caacaactat gttctaggct tgtgcgcgag attcattaat 116040
gaaaatgaag aatttcaacc ccctgacaac gtcagcaata aggatgaata cgctcagcgc 116100
cgagctaaat cctacctaca aaaattcgtg caatccattc accctaaaga caagtctgtc 116160
attaagcaag gcaatgttca tcgacagtgc tacaaataca ttcaccaaga aattaaaaaa 116220
aaaataggca tctttgccga cctttataag gaattttta acaacaccac aaaccccatc 116280
gaaagcttta ttcaaagcac tcagtttatg atacaatact ttgatggaga acaaaaagta 116340
aaccattcta tgaaaaaaat ggttgaacag catgctacgg ctagtaatcg agctggtaag 116400
cccgctggta atccagccgg caatgcgctg atgcgggcta tatttacgca gctgattacg 116460
gaagaaaaaa aaattgtaca agccttatac aataaggggg atgcaataca cgatcttctc 116520
```

acctatatca ttaacaatat aaattacaaa attgccacgt ttcagacgaa acagatgttg 116580
acgttcgagt tttccagtac tcatgtagaa ctgctattaa agctgaataa aacgtggctt 116640
attttggctg gaattcatgt ggcaaaaaaa catctgcaag ctttttgga ttcatataac 116700 aatgaatcgc cgtctagaac attcattcag caggctatag aggaagaatg tggcagtatt 116760
aaaccatctt gctacgactt tatttcctaa tacttcttaa gaaactcttt aaacaaggac 116820
ttcgcatggt caaaggttct aaacccatgg cccttatgat tcgccaaaaa agcggtttca 116880
tcaagatttt ctaacccttt cacggatgaa gaaataaggt gttcggcctc gtttgcccat 116940
tttctatgat ttttttcac ctcgggttct agatctgttt tctccatata ctcattgtgg 117000
tcatattttt ttttgggagg aggcgtgggt ggaggaatgg gtggaggaag tacacccgac 117060
tttcccgctt caaccgtttt ataaaaaaat agaagcataa tacaaagaat aaggactatc 117120
gcaaatatga taaccagtgt cccagtcgag ggcattttgt tatataagta acgttttttt 117180
tattttttat aattcgaatg aagaaccatg ttgaatagtc ttctactcaa agacattttg 117240
ttatacggta aatgagaatt tataaaatcc gaatatcact atcatactgt ttatctgaga 117300
aggtctcact gggtcctgtg atggagaacc catactctgt aatgctgggg tttataatgt 117360
ggtcaggact gacaagcaca tttctgaact gcgagagttc taggtttaga cgcagtcgta 117420
atagtcgctg tatatttgta ataaatatta gattgcgtat gaggcgagtg tcaaagcgat 117480
cctttccaat ttgtactaag gtgggctttt gtattccaac tcccacttgt ttaacgatgg 117540
accagggtcc ttcttcccga ttttgttccg tgatataggt cagcacacta ttttctgtat 117600
atgaggtatg atgtcgcata ttaatacctg gtgccattcc aactggcggt tgtgcaattc 117660
gggctgtacc gggacccaac catcgtggag ttttataaac atatcgttct agcgtattta 117720
aaaattcctt aaggttattt acgagtagca tgaagggtgc tattaaaaca ggtggatggt 117780
ttataaccat tgtcataaac cattgcattg cttcaatatc attttgtaat gcttgacggg 117840
gaggcggggc aggtaatcca cgtatgttga ataaagcggt taattgtgca ccggctgttt 117900
ggggcgtaat attttgtatt aaatttatca tcgaattggc ttgcccggca tttcctataa 117960
gatcgattaa attggttatt tgacctcgat attgttgtac ccagttttga atggcagcga 118020
tgatctcagg ggttggattg ttttgaattt caggtgtttg tattagatta ttcacttctc 118080
ttcgtgtatc ttcaagctga gtcctaaatg catttaactc gcctataatt tggtttctat 118140
caataacatt tcttaaacct cgaactgttt cagccaatcg tatagtacgc acaatttcat 118200
gtaaggcctg gtttatgtat attgacatgg gatggcccca ccgctcacgt ccacgttgaa 118260
tacctgcggc caaactagga cctgcctcgt cataatcaaa ttgtgtagga taaaggcttc 118320
caaatagcac tttattgaaa atttggtcag aaagaaattt agggcggccc atatttagcg 118380
cgttgtcccc tctaaagatg cgtgacatgt atccggcgtt gcctttggat agtaactcat 118440
tcccatattg agtaatagag accgagacat aggggtttat aagaagtttt agcataaatt 118500
ctcgagtatt tatgggggga cgattcggaa tgtttaatac ctctgcaaca tctggttgag 118560
gagccgtggt gtccagagat cgtacttttt cagccgaaat gccgtacata agacaagcaa 118620
tttcttcaaa actatagtca tagttgtaaa tattggcaag tggtatagat cgcatcagcg 118680
catttacatt gataggtata atattcatat caaacaagtt aaatatgcgc tcgcgctctc 118740
tattagagcc aagagtgcgt gtttgacctt tcggcgacac tattttgtga atatgattga 118800
tttgctcctc ttggtaagag ctttccacga aggaaattac gtcttgcaat gttttacgaa 118860
gcgaatacac tgcattcatc cctattcccg ctgttataat gggtttatcg tctctgttct 118920
cgctaataag attaactcca ccaaaagtat tttcattgta catcatcact gttttaaaac 118980
tacggatatt tatgataaat cggagagcct gaatggcgtg ggtataaaag tgttcaaatc 119040
gcgtgggagt aatttgttcg cgagcaacta ccgtttcatt atagtttttc atgataagct 119100
gtactccggg catatctgag agctgtaccg gatcatttcc cagtaatttt cttgtgccgt 119160
atagtagttt aaactcgggg gagccgcttt caaggttcgg gtaaagaaga ggatcatata 119220
cctcattatt ttctattctt aggtcatgta aataatagag cgaaagtgaa aatggcataa 119280
gaggctcctt attgtaccgg gacatatagt tttgaatgaa gtgttcttct gtttcaagat 119340
agatgggatg atcggtaagc tcgtgcagga cctccatggc agaatctgcc agagtgtgag 119400
agcctctaat gatcccgtcg atcactgcga ccagtcgctt tcgcacaaca tcgctcgtat 119460
tattttgtgc gtctcctagg ggcataagcg taacattggg acgaaatacg ccgccaattc 119520
cccgcagggc cgcctgaccg acggatagtc ctgtcgcagg aacattgtta ttattataat 119580
aaataacgga atcattattg gctcccaaga gtgccgtcag attagggcga gctagttgga 119640
catttgtgta ttgtataaat tgttttagaa gctctccctg gctaataaga atattaaaca 119700
ttttgttaaa tagtggaaga ttggctctat aatttttcttt aaggtaaatg ggaatttctg 119760
ttaaagtaga aataagatgc tgactcaggc cctggcgatt ggtatcctta ataagccgct 119820
gaagtataag tcccaaagac agaagaagca ccgactgctc tgtggggtcg cctctatgac 119880
caaagacgtt gttattgcgt gctaagtcag ggtgagcata tcccatctcc atcactgctt 119940
ggctaaagtt cccattagcg aatgcattaa taagatttag atatattttt ccgctgggag 120000
catcataaaa tcgggtaata tatgaagcta tgagctggtt aaacaccatc atcatactac 120060
gattattttg aataccatag tctgatccgt ataggcgata acgtcgaagg ttgtttgcgg 120120
catcattgac attggcatag gttctgagcg ctatgttgtc ccagtagcta agagtatttt 120180
cctcctgggc gttgttggta cgaataagat tggagagtct aaagtctcct agtgccacct 120240
gctctacacg aagtccagag ttattctcca aagcatcgta aaatacgagt ctactgaata 120300
ctcttccgta ttgttcaaag cgttcagagg attggggatt gttatttatt tgaatattag 120360
ccgcgtccct tctttgcgcc ccacctcgaa gttgcagtac attataaggc tttgtaagca 120420
aggtgtaggt tttattaatg atttggttaa ccccctccag gcccaattca ccgccaggaa 120480
gcggccttcc tccggcatcg gtaggtggtt taataagttt gtcaattaaa tgttcttcca 120540
accagtaaaa tgagccagga ttagatctat tttcatagta ttgaataatg tttttatcaa 120600
tatgcgggcg tagaagatca agaaaatact tcgtgtcggc catcaaagaa tcaattaagg 120660
aaataagacc tgtaaaatct aaatgcactt gagcggtgct ggtttcaggg aagcgaactt 120720
gaaccatttt gttaaaactg gaggtcattt cgaagatatt ggtcaacagg agctgcatga 120780
ttcgctgatt atctactaaa taccttgcgg ccaactcttg ctccggacga actcctccac 120840
cagcaggaat acccacatat ggtacaatcc aagcaaaaag agtttctgtg gttaaatttc 120900
ggtcttgggc tgctgcagcc gcttcggtag tgggatcagg gtacaccata gaaagccgca 120960
tattgatttc tttaatgact aatcctggat ttctaatctc agagatggcc ccgtgttttc 121020
ttccgagcca gtcaataaga ttggcgcggt tcacgttggc agcttgtgtc tctcgtaacc 121080
attcgataat gctttttttga atcgtatcta ggtctaaacc tttaatgtta ttacgaaagt 121140
tattaagaag tacgtaaata gcactcaata agttaagacc tgtaataacg gtttcatgaa 121200
acagaaatat tttgttaaca tctgtatctg ccagtgactc agagccttga ataagttttg 121260
aaacgatttg aattttatcg gtatgctcct ttttgagttc attgatagcc tggcgaatga 121320
gttcttggta ggaaattttg cccaattctt gttgcagact gggatcttca aacatctcac 121380
taagctgttt cctaaatttt tgtaccaaat cccactggga gttgggctgc agcattcctg 121440
tttggacatc cacagagtct atattgtata gtgccgggcg ccacttgggg gtaggctggg 121500
ttgaaggact aataaaccta tcggagggaa gtaattgtga ggattgtgta tagccatcct 121560
catcaggaag aatggagtag ttggtttgat tcatcattcc aaaatcattc atagttcgcg 121620
cttcctgaac aatgcgttga aatttttccc attcggtgcg tgtaatgaca ccgaatctgc 121680
ggtttatttc atttacaaaa tggataagcg ctttttttggt tgcttcttgt tcaccatact 121740
ctaagttaaa gtgttggtaa atgacgttta tttctttgat aagctgacga atttcggttt 121800
ctgagtagtc accaatgtta ataagctcaa taggacgcat aaagataatg cgaataagtc 121860
ctgagaagat tccttccagc tcaggaagca tcgagatctg tacattttca tctctaaagg 121920
aaaacaactt ttgataaaat tcggcgaggc ggggaaggcg gaagtaaagc tctgctgcct 121980
cgggaattac ctcgggctct agctcatcgg cacccccccaa tatcatacgc gtgggtataa 122040
gtttgtacac gggctcaggc cgttcaaaca tgtcgtaaat ccctaataca ataaaaatct 122100
tggcggccat acttttcagc atgaaggtga agaagacgtc ctcggtttcc cagcgggttg 122160
atagggcgtc gttaactctc acagtagaga ggtagacccg ctgagccgct tcctcggcag 122220
tctgtgcaag cgccatcctt tgtcctccaa tttctgattg atttagattt ttaagtccca 122280
cggaaagcgc agaatgttga agatattcaa gcaaggtttt atagatttgc aggggcgaca 122340
tgggcaccat ttgccgcagc tcctctcccc caagcatgtc cccaatccgg gcaaaggcat 122400
tgatgatatt tttaagcgcc tgaaagttag aaagagagcg cccgataagg tcgcgaatgt 122460
ttttagcctg gcttgctctg acgggacgga gggtaccaac gcttcggcct tgttggattt 122520
cagccgcaac tttttcgtag tagtggcccg caggagcatt atccgtaaag acgttggagt 122580
cgttgcctgt ggaggtggga aaactttcaa agacttgtgc aagcgtgtcc cctgttgtct 122640
cggtgaacca tcgtcctata atgcgcacgc catccagcat ctgttggact gtttgaatag 122700
aatctatgtt gtttacaaac gttttggtaa tgtttttaag ataaagatct agcccttcca 122760
gagctcgata gaatcggcgt tttacatcat actccagctc gatggcgctt acggttgcct 122820
tccagtctac ttcctgggca cctccaggat ttgggcccac gtgtcctctg gcaagatcta 122880
cagccggaga attaatgcgc gcattttttt ccgtatccaa ctgcatgagg cgtcccgcaa 122940
tagcatctcc gagaatagtg gcatagtttt cctcgtagga ttgaaactcc tgtttgttat 123000
gcgttaaatt ggagtaaatc tgggccacat aatagtaata cataaaggtg ttaattgcct 123060
ggttgaggtc aacctgcgat cgcgcggcct tgctgagccc aagctcttca actgttaggg 123120
cagcaccgcc tacccttgta cactcgcagt cctcctcgcc tccatacttt ttttgcacaa 123180
tatcggtata aaaatcaata atctgtagca agcgagagca ggagtcataa agatttttaa 123240
aattagggtc ggttttagat atctcctcca aaacattttt aacaagcgta agctgtgtta 123300
agaaggtttc gcgttcttct cgtgcggccg cattggtgta aaagccgata agacttagat 123360
caagtgcgat ggtgcccata tcattaatgc gcgaaagagc atctcgaagc ctcgttatgt 123420
tcggcgtcaa ggcaatttct ttaacaagtt tgatgcctat ttttttcaca ttttccaaaa 123480
agtcgttata ggcttgtgtg cttttattca aaaattccat gaggatgtgc tttctatcca 123540
gtctttgcgc ttcaatcctc ctatctagtg gcgttttctc ctcatcgccc cccttttttgg 123600
cacaactgtt ctcaaggatt ttgtggcgtt cattaaaggt ctgtcgcaac aggttcacgg 123660 cttttttcaaa ctcagcaatg ttttctgcgg agacaagacc actaaacctt ttgaggtcaa 123720
gctccttgtc aaactccgcc cagtttttgc tttgaaggta ctgttcaacc ttgagtccta 123780
ctttctggag agccttatta attttattcg caacagacgc agcaatacct agattacaaa 123840
gtgtgtacga aagtactttt ccaaaatttt tggttcccaa gacactattt gtatcattta 123900
aaagtttaat aatatccacc tcatccgtct gcagtttatc aagttccttt tgggtgggag 123960
ttaaaatatt gtcaataaaa ttcgttaaaa tgttgatttg caggttttgt tcatttaaaa 124020
gtcgacgata tactgcttca atcatggtga ctgcattaat gacttcctca ttgggggctg 124080
ctttggttac ctccgtcacc atgcgctcgt gaagttgctt aatggcgtcg tttaacagct 124140
tgatattttc aagtgtattt tctatactgc cgtgtacatc aagatactct gcgcgcagtc 124200
catgagttag ggagttaatg tacagaacta tttgtcgaca tatactggcg gccccttcgg 124260
tggtatctat aagcttatcc tgacctaaat caataaattc ctggttaatg gcgtctgcaa 124320
tcattttaca gacggtctcc tgtttttccg catttttttac aaaggtggaa ccggctcgag 124380
gatcgggcag ttgtttttttg atatctttaa gaatatcttc gatgggctgc tttgtgtcta 124440
ctttgaaccc tattttggca atcgccctga taattccttc tataatccgc agctttgctt 124500
tactcgatac ggagtctatg tgataatctt taatgtgttg tacaggattt ttgtcccccc 124560
cgccattaaa atatcctccc cctgaaaaag gacgagtttg tctttgtata tgatcctgta 124620
acttcgcata tatatttgct tctgatgaag gcagtggtct actagaggtt gaagatccac 124680
ggttacccat tataataaaa aaaataaaga tttaaaacta caaatatttt gctgtttata 124740
aacccaatca tataagacta actaaaacat taaatgtagg tgagataaaa gcttattttt 124800
tttaaaagtt taataaccat gagtcttacc acctcttttt cttcttcctt tagaggggtt 124860
ccataaatgg tttgaataaa attatgtgct ctaataacct tgttaaaatc aggtgccttt 124920
ccatattgtt caatatgttg cacagtcttt tgtgcaagca tatacagctt ggagtcttta 124980
ggtacctccg atgagggctc ttgctcaaac aacgtttcaa aggaggatgt gcattcattg 125040
gtttcattat catttttttc atgaatgttc tccgaagatg ctgaggattc cgtctcctct 125100
tcaaacagca catgcagaat catattccat tcttcttgag cctgatgttc agtataccct 125160
tgccctgcat atatacgagc agatttcaca atatcatact taacagtact aagcaatgtt 125220
tttatagcgg tcgtaacaat tctaccgcta ttgataatct caacagaaaa ccaattatac 125280
aggctacccg catgaaacac aacttgtgaa gatgatctta aatccgtttt gaagatgacc 125340
tccattttca tggatatatt taaaataaaa tccattcaat tttaaaatta taaaataata 125400
agaagatgcc ctctaatatg aaacagtttt gcaagatttc tgtatggcta cagcagcacg 125460
atccagattt attagaaatt atcaacaact tatgtatgct tggcaattta tccgcggcaa 125520
agtacaaaca cggagttacc ttcatttacc ccaaacaggc aaagatccgc gatgaaataa 125580
aaaaacatgc ctactccaat gacccttcac aagccataaa gaccttagaa tcactcatcc 125640
ttccatttta cattcccact ccagcggagt tcaccgggga aatcggctcc tacaccggag 125700
tgaaattaga ggttgaaaaa acggaggcga ataaagttat tttaaaaaat ggagaagcgg 125760
tcctagtacc ggcggccgat tttaagccct ttcctgatcg ccgactagcg gtctggatca 125820
tggagtcagg ctctatgccc ctggagggtc ccccctataa gcggaaaaag gagggtgggg 125880
ggaatgaccc gccggttcct aagcatatct cgccgtatac tccgcgcacg cgtattgcca 125940
ttgaggtgga aaaggccttt gatgactgta tgcgtcaaaa ctggtgtagt gtcaataatc 126000
cctatcttgc caagtcggtc tccttgctgt ctttcttgtc gctcaaccat cccaccgagt 126060
ttattaaggt actgccgctt atagactttg accccttggt gaccttttat ctacttcttg 126120
agccctataa aacgcatggg gatgactttt taattccgga aaccatttta ttcggcccta 126180
ccggatggaa tggtacagat ctgtatcaaa gtgccatgct ggagtttaaa aagtttttta 126240
cccagattac tcgccaaacc tttatggaca tagccgattc ggctactaag gaggtagatg 126300
ttcccatatg ttactcggat cccgaaaccg tacattccta tgccaatcac gtgcgtactg 126360
aaattttgca tcacaatgcc gtcaataagg ttacaacacc taacctcgtc gtgcaggcct 126420
ataatgagct cgagcaaacc aataccatac gacattacgg ccctattttc ccggaaagta 126480
ccatcaacgc actgcgtttt tggaaaaagc tgtggcagga tgaacagcga tttgttatcc 126540
acggcctgca ccgcacgttg atggatcaac ccacctatga aacctctgag tttgcagaga 126600
tcgttagaaa tttacggttt tcgcgtcccg gcaataacta tataaacgag cttaatatta 126660
caagtcccgc tatgtacggc gacaagcata ccaccggaga tattgcgccc aatgatagat 126720
ttgccatgtt ggtggccttt atcaacagta ctgacttttt atacaccgcg attcccgagg 126780
aaaaggtagg ggggaatgaa acccaaacca gtagccttac agacctagtt ccaacacggc 126840
tacactcttt tttaaatcat aatctaagca aacttaaaat cttaaaccgc gcgcagcaaa 126900
cggttagaaa tattctttca aatgattgtc ttaatcaact gaaacattat gttaaacaca 126960
cgggaaaaaa tgaaatacta aagttacttc aagaataagt atgttgatac ctgtggtgtg 127020
ttttacctgt gggtttccta ttggaaccta cgcggcaatt tttgacaagg ctcgtaccga 127080
gtatattaaa accaaaatgg gcggaacatt gccgcaaaat atcccattag atgcttctct 127140
ccagattgag ttaaaagacc tcattacagc tctgggaatc ccaatgcggg tgtgttgtcg 127200
cactcattta attactacgt tggattatcg taaatattat taatatctaa aattgaaaaa 127260
atatttttaa tgttactagt aaaaatgact acacacatct ttcacgcaga tgatctccta 127320
caagcattgc aacaagcaaa agcagaaaaa aatttttcat ctgtattttc tttagattgg 127380
gataaattac gcacagcgaa gcgtaataca acggttaaat atgttacggt caatgtcata 127440
gtaaaaggca aaaaagctcc gctaatgttt aactttcaaa atgaaaaaca tgtaggaacc 127500
attcctccca gtaccgatga agaggttata cggatgaatg ctgaaaatcc aaagtttttg 127560
gtgaaaaaac gtgacaggga tccctgtttg cagttcaaca aatacaaaat ctcgccgcca 127620
ttggaagatg atggtctcac tgttaaaaag aatgagcagg gtgaagaaat ataccccggc 127680
gacgaagaaa aatctaagtt gtttcaaatt attgaactgt tagaagaagc ctttgaagac 127740
gctgtgcaaa aaggtcctga agccatgaaa acgaaacatg ttataaaatt aattcaaaga 127800
aaaatttcta atagcgcggt taaaaacgca gacaaacctt tgccgaatcc tatcgcacgc 127860
attcgtatta aaatcaatcc cgctacaagt atactaacac caatattgct tgataaaaat 127920
aagcccatta ctttacagaa tggtaaaaca agctttgaag agttaaaaga tgaagacggc 127980
gttaaggcca atccggataa tattcataag cttatagaat cgcattctat acatgatggc 128040
atcattaatg ctagatctat ttgcatcagc aatatgggca tttcatttcc gctttgcttg 128100
gaaatgggag ttgtaaaagt ttttgaaaaa aataatggga ttgatgtgaa ctccatttat 128160
ggctcagacg atatttcaac tcttgttaat cagattgcta ttgcttaaac aatttgctca 128220
aaacaagctt ataaacgttt cttaggtatg cgatacgtaa atcctaattc tttaataagt 128280
tctttttcag tagtgatttt tagaggtact aaagtttgat ttttaaataa tccatactga 128340
tttagcttat aattcttttt ttttaacgca gctcgaattc ttattaaata agaaacggga 128400
cccgtaaaat gaagtactgc gtatggcttt tcctcggcta aggccgtaaa aagatcaagt 128460
tgatatgtgt tttttttcca ttcaataaaa agtacacact ttcgttctcc gcagactttt 128520
acagaaaaag aaagatcctt tatgcgaatg ttgggcagga cgtgttttaa aagttttttt 128580
tctggaacaa taataagaag atccacgtca ttaagcattt tctcttcgcg tcttaagcta 128640
ccaacagcaa cgatgttttt tgataaaatt tttataagtt gtccattata ttcaaacgca 128700
agtcgggagc gtaagtcatt tacaattttt tttccttgaa taagcgttaa cattttatat 128760
ttaatattaa aatcttttca ttttatatat tatatacgca aaatggcact tgatggttca 128820
agtggtggag gctctaatgt agaaacatta cttatagtag caatcattgt ggttattatg 128880
gcaatcatgc tttactattt ttggtggatg ccccgccagc aaaaaaaatg tagcaaggct 128940
gaagaatgca catgtaataa cggaagctgt tccctaaaaa caagttaaaa catgcaatta 129000
tatgcatgca tataaacgca tgcatataaa cgcatacata taaaatgcgt aaatactata 129060
taaaaaacta taacatatca atcaaggaat caacactttt ataattttcc gtaatatatt 129120
tttcatccat aatgatgtca gagtacatgg tccctatgcg aggaacagag cccataaggg 129180
taggcgcggc aataccgtaa atgggattca cggcggagtc aaccgcagca tctgtcaaga 129240
cctggactgg agacgacaag gccattcgca acaacacgtt ggaaggctct cttgcattaa 129300
gccctgcctt ttctagagag gtaacctgtc ccgttcttgt catgagatct gcgtacatga 129360
gtaaatgacg atggttggga cccttgtccc ccataaccgt tctaatttca ctaataattt 129420
tttgccgtgc cgcttctatg ccgtaaagct ccatggtgtc tcctatagag gacgatacga 129480
tggtgtatgg gtcgatgtta tcatcaagca ttgcgccaaa aatattagtc ccgtttgttt 129540
tgatggcgta gatattgtct agtcttacca gtttcccctg ggcatccaca cggtggcgca 129600
taagcttaac aacattcgca tttttgatgc ctggtattcc tctaatcgtg ctatttaata 129660
gtttatccac cacatttacg gcaatttttt catccgtagc cattcgggta ttggtactgc 129720
gtctaaaggc gctttcccgt aggtatatgc gaataatgat gggaatccct gaggccgtgt 129780
tttccacaga atgcatgatg taggtgttgg ggtgtttagc tcttagacta ttaataatac 129840
tttctagact aatgcttttt aatatcatgg ttgttttgtt taattccaag cggatacacc 129900
agtttgcaat atcctctggg ggctgtagta gaggatggtt ttccagaaaa tccgtcatcc 129960
attccacatc acttgcaaaa tcggggtaca tcacattttt ttttgtgctt gaatacgttt 130020
cgtacaatag gtgccactgc aatatcaacc gttcgaacgt tataagctct atgctgttag 130080
caatttcttg cgcatatgtt ttatttgttt ccacttccgg gttctttaga cgtaaaagca 130140
tttcagagga ttgttcagcc tctacgggct tcgcgctaaa gatctcctgg ggccgcacaa 130200
ttcccgactt gttggttccc ccggccacgg accggtggtg ggagtccagc atatattgtg 130260
tcaagggctc tgatacggac tgcgccgcca ggattcccac tgcctcaccg tagttaataa 130320
gactttgagt atattgtagc cttatgaggt ccaggatggc actcatctgc tcgcaggtaa 130380
tgtttaatgt tttaacggtt gccagttcga tgcgaataag catgcgcatc agagaggcag 130440
cccgtttaag ataaacgggt atgggcgttt gtagtcgttc ctgaatgttg ttaataaaca 130500
cgtatggaag atttttgcaa aacgttttga ccatcgcgta tttttgtaga atactttttt 130560
cgtcgaaggg aagcacgcca ctggtggagc tcagtagaat gttttttacg atgctggcca 130620
cgtttaccgg cacctgtcta acatctgtaa gcagctgact gaaattaaaa ttttcgacgt 130680
ttaggaagat ctgtcgatat ttatctctat ccttttttaag gcgtgaaaat tcttcttcaa 130740

-continued acaagggcga ttgtatcccg gtgtacttga atttgtcttc aagttcctgg tccgacagca 130800
tgatggtttc aaaccgtacg gtttcaagct ggcgcgcatc aaggccgtcc tctccgtaca 130860
actgctgcac aagacgcgta tcgatggaaa cccgtcggta ataatccaca atacaggatt 130920
gaaggccaaa gatggcttta cggttggcat agcctgtgga tgatgtcgat aatgctttgt 130980
tgatcaagtc gaatcttcca ttcatttccc caaagataaa ttcaggggag gtaaggcccg 131040
caatatagct gttgcagatg aacccgtagg cctgcgcctc cagggcaaac ctggggtagt 131100
acaccagggt cctaccgaag gaaaactggg gttgaatgcg ttgtgtatta atttcaattt 131160
ggccgatgcc cgccatgatg tgaatcatat tggggtttga gcccttggcg ccagtggcca 131220
ccatctgaaa aagcccattg gtttccggat taatggaatt cataatcggc tttaaaattc 131280
tatcgggaaa tttaagcgca ttcagctgca atttttcgta gaagtcatgc gttgtcaggc 131340
ctataggcgg catgatgtct ccatgaagca gccggttgtt tatttcctcc gactcaagca 131400
gcagttcatt gataatttct tggacctcct gatgtgcctc cggggttagg agcatgtcgg 131460
ccgtggacac tgtgaatccg gcgttgcgca cgtagtttag ggcgagctgc tgggtcgcaa 131520
atatcatttt caaggcctgc tgcggcccat acctacgcga aataaggtga tagattccac 131580
cggaggaacc cgctccgacg gcctttttgt caaggacgcc ttcaatgagt tcgccgttgc 131640
gtatttgtgt agagatgtcc tgcttgttat aatgcatgta gggtgcatac acttctgagt 131700
accatgtggg ggctcgttga taattgatgg gggtctgcct cagtagcata gatacaaccg 131760
atttgccatc cagcaggtca gttggggagt agttggcaaa acaaggtggg tcggtttggg 131820
ttgtttgaaa caaccccatg gcgtgcagct tgttcatcac atttttcccc atgggggtgt 131880
tcgtgcgtgt aagcaaaaag cttcccaccg tggagtcctg cacctgccca ttaacgggac 131940
ccgagctctt tgtggaaatg aaccagtttc gcacagaaca aagtagttcg gcctcaacgc 132000
ggctcatgac gctccaggga acccagagat tcatctgatc cccgtcaaag tccgcattat 132060
accaggcaca tgcgctgaca ttcatttgaa acgtagaaat ttttgggttt tcaagaacga 132120
caatccggtg aaccccctatg ctgcttcgtt cgagagaagg ctggcgatta aaaaacgcga 132180
cgtcgccagt gacgacgtca cggtaaagga tgtctcctac ctccagccta aagtcttgtt 132240
tgagaccctc aatgtcgtga acggattgtg ttatttgctt atacactctt gaacaaccag 132300
ggtactggcg ctttccattt aaaaaatagg gcattaatct attaatatta taatgttgca 132360
ctgtttccgc aacttgcagc gttcgtgcaa aggaaatggg atagccaacc tcgtccaggt 132420
gaaggtctga gttcccgcag atggtggacc ggctgatcga ccatacctgg ctgcccagta 132480
gggatttacg aattcttccc tccttgcgag gaagtcttcg catgatggag ggagcagggc 132540
gtgcccccat gacgatccca cgctttcccg tgcctccctg ggttgcggtg gtggaaacgg 132600
aatccaacaa aaagttatag taaagttgct gtatggtttg caaattgcgg tcaatattta 132660
aaggtatttt ttggccgcgc acgatttgta ggtccttcgg gatcagcaga ttctttcgaa 132720
ccagatactg aatcacgttg ttaatgtcgt gaaagctttg ggggcctgac ccgattccca 132780
atctgatgcc aggtcgtatg ctgatggggg ggatctgaat ggccttaagc acaagttttt 132840
cgggatggga gtttttactt cgccccagtt ttacaacggt gtcgtaggtt acgcgcgaaa 132900
aaatctctct gatgatctgc gggtacagtt tgtcaatctt gccctgctga tccgcccaaa 132960
aggtaaaata atcttccgag tccttaacaa ttttggggtg tactgcctta cagacgtagc 133020
actgctttcc ttcggtttgg cttgaagccg cttcaataag acgcttaggc ctaataaggt 133080
gctcgtacct ctttaggtca acgatgggag ccccgcagtt gagacatata acccttaacc 133140
atcgtcgtat ttcggcgatg aagagcggct gaagcaccgg agcatgcatc tgcagtatcc 133200
cagggtgtcc catacattgc ttgcgctggt gtgagcaagt gatgcattta taatggtgat 133260
cggtggttcc cattcgcgca tcatagatac ccccttcggc gggaagggtg ccctcaaata 133320
aattagaaat ggtaacctcc ataacgcctt gcctcttatg atcattgtca ccggcaatat 133380
tgaactgaac ggcggctatt tcggcatatc cagcctccat atttttgcta aatacataat 133440
aaaacttcaa atgttaaaaa aaataacatc ggttggcata tttttttgtt aaaaccaagt 133500
gttaaatgat ttctaaaaca tttatcggtt cacgaaaacc taccgcacgg gcctgaagag 133560
gaatgccagt tttgggggaa agctcggcat attccacggt aagctctttt ccataaagat 133620 gtttttttaaa taaggcgggc gtgagttttt gaaaaagagc ataacgatcc gcgtacgtca 133680
aatgcttagg agtgactaca aaccgctttt tgtttggcaa ttcgcaaacc cataaaatgg 133740
cgcctaagtc ctttcccttt tttccctgag tatagtccac taaaataaat tcagcgtcta 133800
gcagcggttt cagcttggca agatgcgctg agtggtagtt gttgtatccc ggctcatagg 133860
gcccattggc attgcgtacg atggctccct cgtagccctc cttaataaac tgcgccttaa 133920
gcctaagggc ctcatccaca ttcttcacgc taaaattttc aacttggtgg ataaaggtaa 133980
gatcttcctt ctgtttaaaa atatttgtta atagctgttg tctcttgttg gaaggcattt 134040
gaagctgatc actccaaaaa cagtcaaaca cgtaaaagtg cagctcggag gaatctgtct 134100
tcgcattcgc ctgccccgcg atccattgca gaggtttgcg gtgtaaataa agctcaccat 134160
ccaaatatac tctcacgtct ataaataaat aaagctgttt gagctctttt ttaatattgt 134220
caagacctaa aaattccttt ttcgtgcgcg aatacaagag aatgctacca tcgccctgct 134280
ggcaggccac agctcgaacg ccattacgct tgcgctgcac gatgggatct gtttcttctt 134340
caaaaaatgt cttaggaatt atattaaaat attttaccag catagggggg ataattcctc 134400
tatttgtgtg ggctccccgc ttttgtctgg catggcgatt atatttacta agggcgtcct 134460
tgaatgcctg atggactacc gttgtggcat ttttttttacc caagtttttt ccctcggtaa 134520
cacgtgtcat ttttgatatc cgcaccgccc cttcttccac aaaaaatttt gtgaaaattt 134580
cagcaacggc gtcttttaca tctgtggaaa acatctcatc tgtgatggga atgatcgtgt 134640
tgtgctgcac cacttgcaca caaataatcc atgaggcctt ttttccgctt ttcgtttcag 134700
actcaatcgg aggaaaacaa aaaatgttgt ttgaatattg cccaggaaat tgatttagca 134760
tggttttaac aataaaataa gcctatcaat ttttttataa tttgaatagt tattccaaat 134820
tcaatatggc ttctttagat aatttagtgg cacgatatca gaggtgcttt aatgaccagt 134880
ctcttaaaaa tagtactatt gaacttgaaa tacgttttca acagataaat tttttattat 134940
tcaaaaccgt atatgaggca cttgtggcac aagagatccc tagcaccatc tcccacagca 135000
tccgctgcat caaaaaagtt caccatgaaa accactgccg ggaaaaaatt ttgccgtcgg 135060
aaaatcttta cttcaaaaaa cagcctctca tgtttttttaa gttttcagag cctgcatctc 135120
tgggctgtaa ggtctcgctg gccatcgagc agcccattcg taaatttatc ttggactcct 135180
ccattctcgt tcggctcaaa aatcgtacga cctttcgggt atctgaactt tggaaaatag 135240
agcttaccat tgtaaagcag ctgatgggaa gcgaggtctc tgcaaaactt gccgctttca 135300
aaacgcttct gtttgacacc ccagagcaac aaacgacaaa aaatatgatg acgttaataa 135360
acccagatga cgaatatctt tacgaaatag aaatagagta tacaggaaag cccgaatccc 135420
taacggcggc agatgttata aaaattaaaa acacggtgtt gacacttatt tctccaaacc 135480

-continued

```
atttaatgct aacagcctac caccaggcca ttgaattcat tgcctcccat atactgtcct 135540
cagaaatcct tcttgctcgt attaagagcg ggaagtgggg gcttaaacgc ctcctccccc 135600
aggtgaaatc catgaccaaa gcggattaca tgaaatttta tccgcccgtt ggctactatg 135660
taacggacaa agcagatgga attagaggca tcgccgtcat tcaggacacg caaatttatg 135720
tggttgcaga ccagttatac agcctaggta ccaccggcat tgaacccctt aaaccaacca 135780
ttttggacgg tgaatttatg cctgaaaaaa aagaatttta tgggtttgac gtcatcatgt 135840
atgagggcaa tctattgacg caacaggggt ttgaaacaag aattgagtct ttaagcaagg 135900
gcattaaagt cttacaagcg tttaacataa aagcagaaat gaagcccttt atttcgctaa 135960
caagtgcaga tcccaacgtg ctcctcaaaa actttgaaag catttttaag aaaaaaactc 136020
gcccatattc tattgatggc atcattttag tagaacctgg caattcttat ctaaatacaa 136080
acacctttaa gtggaagccc acctgggata acacattaga ctttttggtg cgaaaatgtc 136140
cggagagttt aaacgtacca gagtacgcgc ccaaaaaagg gttttccctg catctactat 136200
ttgtaggcat ctccggagag ctttttaaaa aattagcgct aaattggtgt ccaggatata 136260
cgaaactatt ccccgttaca cagcgcaacc aaaactactt tccagtacag ttccagccat 136320
cggattttcc attggcattt ctttattacc acccagatac ctcgtcattt tctaatatag 136380
atggaaaggt ccttgaaatg cgttgtctta agagagaaat caatcacgtc agctgggaaa 136440
ttgtaaaaat ccgggaggat aggcagcagg atcttaaaac cggcgggtat tttggcaatg 136500
atttcaaaac agccgaactc acatggctta actatatgga tcccttttcc tttgaggagc 136560
tggcaaaggg cccttctgga atgtacttcg ccggtgccaa aaccggcata taccgcgctc 136620
aaacagcact tatttccttt attaaacaag aaatcatcca aaaaataagt caccaatcct 136680
gggttatcga tcttggaata ggaaaagggc aggacctagg acgttacctg gacgcaggga 136740
taaggcatct tgttgggatc gataaggatc aaaccgcgct tgcggagctt gtttatcgaa 136800
aattttcgca tgctacgacc cgacagcaca agcacgctac caacatttac gtgttgcatc 136860
aagacctcgc agagcctgcg aaagaaatca gcgaaaaggt acaccaaatt tacgggtttc 136920
ccaaggaggg agcttcttcc attgttagca acctgtttat tcactatctt atgaaaaaca 136980
cgcagcaggt ggaaaacctg gccgttctgt gccataagct tcttcagccg gggggaatgg 137040
tgtggtttac caccatgttg ggagaacagg tcttagaatt acttcatgaa aatagaatag 137100
agctcaatga agtatgggag gctcgtgaaa acgaagtggt caaatttgct attaaacgtc 137160
tctttaaaga ggatatatta caggaaactg ggcaagaaat tggagtcctg ttacccttca 137220
gcaatggcga cttctacaat gaatatcttg tgaacacagc gtttttaatt aaaatattta 137280
aacatcacgg cttttcccta gttcaaaagc agtcctttaa ggactggatt ccagaatttc 137340
aaaactttag taaaagtttg tataaaattc ttacagaagc cgataaaact tggacaagcc 137400
tttttgggtt tatttgtctg cgcaaaaatt aaatattttt tcataagaag tactacccag 137460
gttttaaaga aatagctaaa aatatcatat ggatactgcc atgcagctta aaacgtctat 137520
tggtttaatt acatgtcgta tgaacaccca aaataaccaa atagaaacta ttctggttca 137580
aaaacgttac agccttgctt tttcagaatt tattcattgt cattactcta taaatgctaa 137640
tcaaggtcat ctgattaaaa tgtttaataa catgacaatt aatgaacgac tgcttgtcaa 137700
aacactggat tttgaccgca tgtggtatca tatttggatt gaaactccag tctacgaact 137760
ataccacaaa aaataccaaa aatttaggaa aaattggctt ctcccggata atgggaaaaa 137820
gcttatttca ttaatcaacc aagcaaaggg ctcaggaaca cttctatggg aaatccctaa 137880
```

-continued gggtaagccg aaggaagacg agtcggacct tacctgtgcc atacgggagt ttgaagaaga 137940
aaccgggatt acccgcgaat attaccagat tctcccagag tttaaaaaat ctatgtcata 138000
ctttgacggt aaaacagaat ataagcatat ctacttcctt gcaatgttat gtaagtcgtt 138060
ggaggaaccc aatatgaatc tttctttaca atacgaaaac cgaattgccg aaatttctaa 138120
aatttcttgg caaaatatgg aggctgtacg ttttattagc aaacgccagt cattaaacct 138180
ggagcctatc atcgggcctg catttaattt tattaaaaac tatttacgat acaagcacta 138240
ggatgccgca ttaaaatgcc acataaggta atacactagg aatgtcgcac acgcacaaga 138300
atacaacgtc gccggagatt tattatctag tacacgtttt atgtatgtac aatccgcctt 138360
catttaatat attgagcgga tgtactatgt atttatttta acaaaaaaca ttattttttt 138420
taatcttcat catctgtttt tataaactca gtaatatcaa aagtagcttg tggggtttca 138480
gagggttcac cttggttatc ctccgtgagg ataacatgtt cttcaggttc gtcgtcactg 138540
gagaacccat catttaattc ctcttcactc aacatctgta aaaaatcttc caagctttcg 138600
ctatcgttaa aatcctcatc atccataaga ataatggtac cttcctcatc gtttcctcct 138660
tgtttcgtgt ctaaataggc ctgcatggca tttgcaaaag tatcaaaata ggctgagtca 138720
gattgctgtt ccaaaatatg gccttgcgta ttaaatgtgg ttgcatcgtt gttaaatgct 138780
tgcaaataca gtaagggatt tatatccatt attattaagc aaaaaaaatt taaattattt 138840
ttcgaccgat gttaggtaaa attaaacaat tgctataggt gttaagcaat gtttattgat 138900
tttaagtact caacaaccat gatgtaaata ctatacagca cttttggatt tttaatcaaa 138960
tccagattaa tactaacttc ttttgtgata cagttcgtaa taatagtatc ctgctcatcg 139020
ttttgtaaga tttcttttaa tatatttttt tttaccggga tactaagcaa ttgattattt 139080
tcttttaaaa actcctttg atattcaatc gtcttattca ttgaatattt gtatataact 139140
ataattacaa atgttcaatg aattgttatt catgtcggga gatggctatt taaaaatcat 139200
gtcctatttt tctttgctca ataagcatcc aaatattttc atggcgtttt attaattgtt 139260
cattattgaa cgtatcacaa agatcattta taaattgcag atagtttatt atttctttca 139320
agagagtaac aaacattact tcagcagaac atataatagg taattcagtg gcgttaaaag 139380
aattttgatc ttgttgatac gccaatggcg aggacttaag gagatttggg ggtcttgccc 139440
aaaaccctag gctgctgttc ttgtttttta gggcgtcata aagaaatgaa agcacattgc 139500
aaggcttaag ccgcgacatc tccttcccct tgggcccttt ccatattttt agatctaaga 139560
tctcatccga gcttatagag taggtatagt aaagtttttc aaaaaagcat atctgcttga 139620
agtctttttt agaacgactt tcaagaagca tttctataat gttaacaagt tttgttaggt 139680
ttaaggcctg ttcctgtgta agctcctctt gcacgtgata gactgaaaaa gtgtgcttag 139740
gaatgaaaat actccccgtg gcactggcct gttgtctgcc aggtatatag tacacgctgc 139800
tgttagcaag ctgtaccggc acaatttgcc ccacttctgc aacattattt tgcgattcgg 139860
acgagggtat gacaatagtt acgggttcag tcaataggct ttcgccgaga ataatattac 139920
tgtcattttt aataatttta acggccgcta ttaaatcaaa ggcatttaag taagaaacaa 139980
cagcagaaaa tcttacatgc atatatcctc ttccgctatt attcgtacgc ataataaaac 140040
aaggggagcg ttgtataacg ccagtaatat taagaataaa actgtttttg aaacacttac 140100
ccacataaat gttttcaagc tccttcaaaa gatgagcctc cacatttgta caaaaattgg 140160
taggatcatc aatattcaac gttgtctcaa aaattttttg gtcgatcata tctataatat 140220

-continued attctgtcta tttcaattta aataatatac gaataaataa cgagattatt ttattaaata 140280
agcaatggtg tatacacttt gtatttactt tgagatatac tttgtgtatc acaacgtgcc 140340
ctaagatgtg tgcacaagtg acggcatttt gtcgttaaaa aggtaaaacc agcggattcc 140400
atcctgcatt ccatttggtt gattacgagc ctccatttct ttttgcaaaa ggttattgcg 140460
aatgagtaag cagagcttga tggcactaat ctttgtaagg tttaaactta tgcccaattg 140520
gtcagcaatt ttttgttgct cctcccgtcc gcgtgtttcg catacggctc cccggtttag 140580
catgcgaata tcagtaatct cattcttttt taaaacctgg ataggtgggc ggattttaaa 140640
tttaagggcc tttcccttgc tttccatata gcctatgacg atgtcgtttt cttttcgttt 140700
aacattaata ttaagcatat aaagcggaat ttcatgccag gttttatctt ctcgcgaggt 140760
aataagtcgc acggagtcct ccgtggcata gcccactaga gtgttgtcat ccccaggcac 140820
gtggcttata attttaaaaa tgtccggaaa tggctgaata tctttttttg aaaaagcgat 140880
gaaaaacttt ttataaacct cgacaagggc ccccatacct gcaagattat ctataataag 140940
tgcttctagc atcgtatagt gaaatgaagc ggggtagtgg atgagtacct gctccattgg 141000
ctcatcctga aaatccttct gaaacttttc atacaatact tgaaagggtt ctttggtctg 141060
cgagtgttcg aggtatttgg taatacggat gctgtgcatc gcgggaggct gaaaatcccg 141120
aatatatgtt tcaatatcta ataccggttc ctttttatgg ttaagcaccg cagcgacgta 141180
caaatgctca ggctttgccg gcacatgcat aatggtgcaa agacgattct gtatccataa 141240
ttccttgcac tggtttttttg agtagcatag agaaatgagc gccagcgcga agttgtcctc 141300
tgagaagagt ttattatcga tggtaattcc ctgtatgagc ttgggagtgg aaacagcctt 141360
ccatagctcg gagtacgtcc acacggggcg tgccataaac aaagatataa taatattaga 141420
aattgttttt acctcttgct ccccgtatcc ataggcctca aaggtattga ggacggtggc 141480
tccgacgttt gccggcgtga tggatggact aaggggcaga ctttccaaca taggcttatc 141540
aatcttaatc tggttggtga acccatcaat ggcgtgcttt cgcagcgcct tatccccctc 141600
ctgtattaaa atgtattctt ttaatttttg tgcgtactta gcgagctctg gccctccatc 141660
gggtgttgtc gatacgtaca aataaattgt cacgttgcgc tcactggggg ggagctccat 141720
gtgtgaattt tttcgcacca ccctcccaaa tacctgaata agccggggaa tatcaagggg 141780
caatgacata atcatctcgt accgcacggc ctgaaagttc aaaccctcca caatcacctt 141840
ggacccgatg agaatacgca gctggtggcc ttccaggttg gacgaggcgt taaaaagagc 141900
caggcttcgt tcgcgtacag cgggctctat ttcgctgtgc agaatggtga accgtactgg 141960
aataaactga tggtcgctat gtgtgtgctc atcgcgaatc gcggcgcaga tggagcagcg 142020
ggtcgttccc acaggggacg aaacttcatt taaaatgcca ttactttgta aaatttcttg 142080
caagataaga acccccgaca tgcggacccg attgtggtaa attaaaattt tcccccggcc 142140
ttgccgaata atggaaagaa tgtctttcat catttgagtg tattttccgc tataaaaggc 142200
caatcccgag atgtgcgttg gtggctgcag cgacaaaaag ctgccactca cattaaaggg 142260
ggctctacgc gaaggctcaa taatctgtac cccgttttcc agaagccagt ctgtgcttgc 142320
catagaaagg gcggtggggg tttccgtcga gttaaacagg ccgtaagcct tgggttccgt 142380
ttgttttgaa aattttgggt tgggaaacac catgtcataa atgctgtacg cattactcga 142440
gattttaggg tcagggccca gctgtttaag cgtttcaagc tgatactcag acatggggca 142500
ttcgatgaaa tgtaagtacg gcaatgtttc gtctttatag gacaacatct ttccggcaaa 142560
tattctttcg gggtaaaaat tggtgttggt atccaacaaa aaagataccc ttccggtgct 142620

-continued cagtctttcc acaagagcta gggcgtcctt tttccattta acggaatgcc cactgctgtc 142680
aaacagttgc tggcgctgga ggggctggcc gttgggcagc tcatgccgcg gaaccaaaag 142740
gtttaacagg tcgacgtatt ccatgacact cccggttacg ggcgttgccg acatgaagac 142800
ggccctgggg gcctggtgag gtggaaaggc atccaggaca tactgtaaag cgatgccata 142860
attatttcgt tcctggatat tgtacacgtt gtgtatttca tccgcaatga gcagtcctcc 142920
cctaagttgc tccatgattt tttgattcac ccggatgagg ccgtttgtct cggcctcgct 142980 aatttttgc acgaactgag atatatcgtt ctcattcaat gtatcttctg cttcgtcaga 143040
acgatgaaac agagaaagca catcaaagtt tttctcttca cccttactcg taatattgaa 143100
aagcttggat gcaaattcct tatagccgta aaactgaaaa aagcctccgc ggtttctatc 143160
ggttaaacgg cgctttaacg tactaacgaa cccatttaga tgccgtgatt cgaccgacgt 143220
ggtgctgcca gactgctttg caatgtgaag aagccggtgt agctcagcga cctccttgta 143280
agaaacaaat cccagctcag gacgtcttag catttctgtt tgaatgatgg cgcgtgtaaa 143340
gcctaccaca aaaatccagg gcgcattttc aataaaattc atgtagtggt tcataaattg 143400
acgcgcgatg gcaatcgcgg caatgctttt tcccgtcccg gtctgccagt ttaataaaag 143460
acgcgagtag ggcgtgttgg gattttgaaa gttttggacg aaaagctggg cattatgcaa 143520
ttggagaccc ttgatggaag gaaagggcga cgcgtagggg tcacacggaa aaaacgctcg 143580
cccccccttc tcgcagccag gcccaccgat ctggacaaaa tgagcccgca gatcacgaat 143640
gagctctttt tggtcgacag gaggggaaat caacgattta aactcctttc ttcgcgccaa 143700
ctgctgcaaa aagtctgcgg catccaattc gggatacgcc atattatcat aaaaaaataa 143760 accttttat gaaaactttt atgtgattct gtattgcaat tgtttttat gaatactgta 143820 aataagcgta tcaacttgtt tttctaacga agaggcgtta ttcttttttt ctggatataa 143880
aataataata agtataataa ttaagactaa acagcaggca atcactatca aactcatatt 143940
atacttactt ttttataaaa agtattatat cttatgaatg cgcaagttca gctaattgtt 144000
cgtcgcttgg aatgtgggac tgcagggagg tggagttttt cctttttcta aagaataccg 144060
ggaaatggtg gtgaggctca ggttgttgta catagtagct aggaggaggt ttaggtatgc 144120
tcgacttgca gtcaatagtc cggttatagt aaacgatggc aacgatgata agaataataa 144180
tgagcaaaat caaaatgccc aggagaatcg cagttgttcc gggatatttg gcgattgtat 144240
gggctaaaag gccttgggtg ctttgtttaa ttccctcgcg ggttgacagg ttatgagaaa 144300
gcagtggaga cgtttcagtg tccatttatt acaattgaac agttatatta atctcaaata 144360
aaatataaca caaaattaat tatggccatg caaaagttat ttacgtatat ttacgagttt 144420
attgaatatc gtaagatggt gctgttggaa gaaaaggtac catatgataa gtttgttcaa 144480
atggtactta atacaggatt ttttcgtatt aacgcggaga cgctgaatca cggaatcgta 144540
tccgtgttta tctttggagc aaatggcaag tacgttcacc acggaggcga catgagaacg 144600
cttttaacga atacgcttaa tgaaaaaaaa cattatgaag aattaatttt aatcgttgat 144660
aagcccgttt taagcaaaaa aaatatttta gatataatcg tcgagcagcg cgctgcaaat 144720
cccacgattg taataaacat atatccctac cacctgttct gcattaacat tcccaaggtg 144780
agtgccattc ctaaacataa actaattact caggaggagg cgcaggagtt tttaggtcgc 144840
gaatatctgc aaccgcagga cctcatgcaa attagcgcgt cagaccccc ggtggtctgg 144900 ctgggaggaa gaccgggaga ctttgtgcaa attgagcggc cctcagagac agctatgcac 144960

-continued gctgttgtta tccgctttat caccaagtcc aaaatttgag tcccgtgttt aaagatgaca 145020
gacagctaag taagcatatc tgtaaaattg tcgatgtcct ctgtggatag agcgctttcc 145080
tctgagcagc aaattttttc atacatctcc atgggggatg gcgaggcttt aatagtatgt 145140
aggtcacgta agaactgttg tatgatggga tatttgtctt ttaaaaactg ggatgtttc 145200 ataactggaa ttatttgaaa gataaagacc ttccatccaa agtagccaac cacatttggc 145260
atttcgggac acgcggtttc ataaggcata gaatagtgaa tagtgtactg atctttttga 145320
tacagcgttt caagtagttg gcgaaatgtt tccgcgtcga gcgtgccaaa atcttgagga 145380
gcctcggtgt gctcctgtgt agagcagatc gtgatgattc cccaggcaag cgggagcatg 145440
gactctggag ggtggatatc cgtattggtc tcattattcg atcccagctg atgaatgccg 145500
cacacgcgaa acatggcctc gacgtagatg cccatagaga taggcggcga aagggcaaga 145560
ccggattgta tttgcggcat atagtaggag ggcaccgagt tttttatttt tcggttgaat 145620
ggggacttta tttctaccag cacggggatg cgtttcgtgg cctcatagcg tacgttgtta 145680
aaaattgttt tgatttccca ggactgttga gtgtatccca gcgttaggtg acaaaaccca 145740
tcggggctat tactatgtcc ggggtatccc aaataggtcc catcaatatg aatattgtca 145800
cctatgacgg tggtttggca gaacaactca agcagatctt tactaacacg ctcaaaaagg 145860
gttccccagc tacaagcagc gcggttcaaa ttcttcttaa aaagatttgc tttttccgcc 145920
aaggttatat aatagctttt gtaagggttt aaacctaaaa cgctggcaag gtcagagcca 145980
cccacctgag tgcgacgaat agcatgccag gcatcggagc gctgctgagg agagtcttta 146040
aacaggcgta caaaggtttc cattatactt gttttaacag gaattcaata taaaaagtca 146100
acacagtttg caatttttcc aatctcaaga tatagccata catttttttt tccaattggc 146160
gaatatgttt aagctcatgt gtttcaatat tagcatccgg aaatttaaat gcataaagat 146220
gttcaaaggc ctgatttata cacgtatcaa aggatctgtg gtatgttatt agcttcagca 146280
tgtgtgccag atcttcaaga tggtctaaat ttatacggtt ttccacgtgg tggatcatgt 146340
ctgccacatc ttgagccccc atccagggga tcacaaggta ctccccctta aagatgattc 146400
gtcgtttttt taaaaaatca tgaaaacgtt ttaaagcttc aagaaagggg cagttgggct 146460
ttgaccccaa aatgctgacg acgatatcct cgggcatgat gtattcgcag tgaggatagt 146520
agtttacgga ctctaattca gcggcccgcc gttttatttc gtatcttgcc cagttattca 146580
gagagtactc cacgcctccg accacaacag acatcctatc tattaaaaaa taacaataaa 146640
aaccttatga aatctatgta tagtggccgc taaaatgtct atattagaaa aaattacgtc 146700
aagtccctct gaatgcgcag agcatcttac aaacaaagat agctgtttaa gtaaaaaaat 146760
acaaaaagag ctcacctctt ttttggaaaa aaaagagaca ctcggttgcg attcggagtc 146820
ctgcgtaatt acccaccccg ccgtgaaggc ctatgcgcaa caaaagggac tggacctctc 146880
caaagaactg gagactcggt ttaaagcgcc aggacccaga aacaacacgg gtcttcttac 146940
aaacttcaat attgatgaaa cgctgcagag gtgggccata aaatacacca agtttttcaa 147000
ctgtcctttt tccatgatgg actttgagag ggtccattat aaatttaatc aagtggatat 147060
ggtaaaggta tataagggag aagagctaca atatgtagaa ggcaaagtgg tcaagcgtcc 147120
ttgtaacacc ttcggatgcg ttttaaacac ggacttttca acgggcactg gaaaacactg 147180
ggtagccatc tttgtggata tgcggggcga ctgctggagc atcgaatatt ttaattcgac 147240
gggaaattct cctccaggtc ccgttattcg ttggatggaa cgggtcaaac agcagctatt 147300
aaaaatacac cacaccgtga aaacgcttgc agttaccaac attcgtcacc aacggtcgca 147360
gaccgagtgc ggcccctaca gcctgtttta catcagggca cgcctcgaca acgtgtcata 147420
cgcccatttt atatccgcta ggattaccga cgaagacatg tataagttta gaacccatct 147480
gtttcgcatc gcataaacta ataaagtttg aattctttat aggaataaaa atggaagcgt 147540
ttgaaatcag cgatttcaaa gagcatgcga agaaaaaaag catgtgggct ggcgccctca 147600
acaaagtcac tatttcgggt cttatggggg tctttaccga agatgaggac cttatggcgt 147660
tacccattca cagagaccac tgccccgctt tgttaaaaat ttttgacgag atcatcgtaa 147720
atgccacgga tcatgaaaga gcttgccata acaaaacaaa aaaggtaact tacattaaaa 147780
tttcgtttga taaaggtgtg ttttcttgcg aaaacgatgg cccgggaatc cccattgcaa 147840
agcatgagca agccagtctt atcgccaagc gcgatgtgta tgttcccgag gtggcttcat 147900
gtcacttttt agccggaacg aacatcaata aggccaagga ctgtatcaag gggggaacca 147960
acggcgtcgg gctgaagctc gccatggtgc attcgcagtg ggccattctt accaccgccg 148020
acggcgcgca aaagtatgtt caacatatca accaacgcct agatatcatt gagcctccta 148080
ccattacacc ctccagggaa atgtttacac gtatcgagct catgcccgta taccaggaac 148140
tagggtacgc ggagcctctg tctgaaacag agcaggcgga tctttccgcc tggatttacc 148200
ttcgcgcctg ccaatgcgcg gcctacgtgg gaaaaggcac caccatttat tacaatgata 148260
agccttgccg cacgggctct gtgatggcgc tagccaaaat gtacaccctg ttgagcgcgc 148320
ctaatagcac gatacatacg gcgaccatta aggccgacgc aaagccctat agcctgcacc 148380
ccctgcaggt tgcggcggtc gtgtccccca agtttaaaaa atttgaacac gtgtccgtta 148440
tcaacggggt aaattgcgta aaaggagaac atgtcacctt tttgaaaaag actattaatg 148500
aaatggtcgt taaaaaattt caacaaacga ttaaagataa aaaccgcaaa acaacattac 148560
gagacagctg ttcaaacatc tttatcgtta tagtgggttc cattccagga atagaatgga 148620
ccggccagcg gaaggatgaa cttagcatcg cggaaaatgt ttttaaaacg cattactcca 148680
ttccttctag ttttttaaca agtatgacaa agtctatcgt ggatattctt ctgcaatcca 148740
tttctaaaaa agataaccat aaacaggtcg acgtagacaa atatacgcgt gcccgcaatg 148800
cgggaggaaa aagggcgcag gactgcatgc tactcgcggc ggaaggggat agcgcacttt 148860
ccctgctgcg cacgggacta accctgggaa agtccaaccc aagcgggccc tcctttgact 148920
tctgcggcat gatctccctg ggaggagtca tcatgaatgc ctgcaaaaag gtgacaaaca 148980
ttacaacgga ctctggagaa accattatgg tgcgcaacga acagcttacc aataataaag 149040
tgttgcaggg aatcgtgcag gtattgggtc tagacttcaa ctgccattac aaaacacagg 149100
aagagcgagc aaagctgaga tacggctgca ttgttgcgtg cgttgatcaa gatctggatg 149160
ggtgtggaaa aatccttgga ctgctgctgg cctactttca cctgttttgg cctcagctta 149220
ttatccatgg tttcgtaaaa cgactgctta ccccgctgat acgtgtgtat gaaaagggta 149280
agaccatgcc cgtggaattt tactatgaac aagagtttga tgcctgggca aaaaagcaga 149340
ccagcttagc caaccatacc gtaaaatatt acaagggatt ggcggcgcat gacacccatg 149400
aagtaaaaag catgttcaaa cattttgaca acatggtgta cacgtttacc ctggatgact 149460
cagcaaagga gttgtttcat atttattttg gcggggagtc ggagttgcga aaaagagagc 149520
tttgcaccgg cgtggtgccg ctcaccgaaa cccagacgca gtccattcat agtgtccgac 149580
gaattccttg cagcctgcat ctgcaagtag ataccaaggc ttacaagctg gatgccatcg 149640
agcggcagat tcccaacttc ttagacggga tgacgcgggc gcggcgcaaa attttagccg 149700

-continued gggggggtgaa atgcttcgcc tccaacaacc gtgaacgaaa ggtttttcag ttcgggggct 149760
acgttgcaga tcacatgttt tatcaccatg gcgacatgtc gttaaacaca agtattataa 149820
aagccgccca gtattaccca ggctcctccc acctctatcc ggtattcata ggcataggaa 149880
gttttggctc caggcacctg ggaggaaagg atgcaggatc cccaagatac atcagtgtgc 149940
agcttgcgtc tgaatttatt aaaacaatgt tccccgcgga ggactcatgg cttctcccct 150000
acgtctttga ggacggccag cgggcggaac cagagtacta cgtgcctgtg ttgccgcttg 150060
ctattatgga gtacggcgcc aacccatcgg agggctggaa gtacaccact tgggcccggc 150120
aactggaaga cattttggcc ttggtgaggg cctacgtcga caaagacaac ccaaaacacg 150180
agctactgca ctatgcaata aaacataaga ttactatact cccgctgcgg ccctccaatt 150240
acaatttcaa gggccatttg aagcggtttg gccaatacta ctacagctac ggcacgtacg 150300
tcatctcaga gcagcgaaat ataattacta ttacggagct tcctctgcgt gttcctacgg 150360
ttgcatacat cgaaagtata aaaaaatcga gtaaccgcat gacatttatt gaagaaatca 150420
tcgactacag tagttcagaa actattgaaa ttctggtgaa attaaagcca aatagtctta 150480
accgtatcgt ggaagaattt aaggagactg aagagcaaga ttccatagaa aattttctgc 150540
gcctgcgcaa ttgtttacat tcacatctaa actttgtaaa acctaaaggt ggcattatcg 150600
agtttaacac gtattatgaa attttgtatg cgtggctacc ttacaggcgt gagctttacc 150660
aaaagcgtct tatgcgtgag cacgcggtgc ttaagctgcg cattatcatg gaaactgcta 150720
ttgtacgcta catcaatgag tctgcagagc taaatctttc ccattatgag gatgaaaagg 150780
aggcaagccg cattctaagc gagcatggat ttcccccgct gaaccacacg ctgatcattt 150840
cccctgagtt tgcctctata gaggaactca atcaaaaagc actgcagggc tgttatacct 150900
atatactatc tttgcaggct cgagaattgc ttatcgcagc caaaactcgt cgggtggaaa 150960
aaataaaaaa aatgcaagct cgtcttgata aggttgagca gcttttgcaa gagtctccct 151020
ttcccggcgc cagcgtatgg ctggaggaaa ttgatgcggt ggaaaaggct attataaaag 151080
gaagaaatac tcagtggaaa tttcattaaa cgctaccggt tttatgatgt ccaataggtg 151140
ttaagcaatc agttcatcaa cattttttttc aagaatttga aaagtttgga taatgttctg 151200
aatacttttt tctaaaagag ttatcaaatc ttcttgtgag gccttatgaa taattgttaa 151260
taccatttct tgcttatggg gaacacactg ataccccaca aagctaatat caggaatcat 151320
ttcataaata tatgttttta gcagatttcc gatggtatgg gtttcatctt ttatcgtgat 151380
aatggccttt gtttttcct catccatgga aaacagcaca agttccggct gcggctcttc 151440
aaagttttca taaatttttt gaatgctttg gattcggcca ataatgatcc ggcaggcgtt 151500
ttttaaatac gtgcgaacgg cctggttgat atgtggcagc ggcaccgctg gaaagcaaag 151560
ccccaggcgg tggtgacgcg ggtctgaggt catagagctt tgcttgtaac cgctaagcgc 151620
catatattct tttttatccg ttgggtactg ttcaatgtca aggtgggaaa aatgtgtttt 151680
aacggcaaga ttaaaggcgg catgctttcg tcctatgccc tttttaatat agatatcctc 151740
tataatcaac gattttccgg gttgtaggaa gccaatctca aaggtaggat taaaaatcgg 151800
gtatttaagc ttagggcctg ccacctggat gagatcgcgg ctatagatgg ttttaacctc 151860
acagctattg tttaaactcc gcagagcaaa taccagtgtc tcgtttttcg cataaatcgg 151920
aatgaaatta atgcggtttc taataaattg ttccgtcata aacaggtccg tggaatcctc 151980
gatcttatac ccaccgggct taatatctag catataattg ggaatttcat cttgcaagac 152040
ccgcgacagg ccgtggaccg cggctctgct aatgccctta aagtccataa caacattgac 152100
cgggacgagg ggcaactgct cctcgagctg aaatagtttt ttggccgcat ttttaataaa 152160
gaggttggaa aagtctatca aaaacggttt gatttccacg ttttggaaaa ttttttccat 152220
ttgtattata aatatatcta tatatattca aattatggta gtttatgact tgctcgtttc 152280
tttaagtaag gaatccatag atgtgctacg gtttgtagag gcaaaccttg cggcgtttaa 152340
ccagcagtat attttttca atatccaaag aaaaaactcg atcacgacac cccttctcat 152400
tacgccgcag caggaaaaaa tttcgcaaat tgttgagttt ttaatggatg aatataataa 152460
gaacaataga aggccctccg ggccgccgcg tgagcagccc atgcacccat tattgccgta 152520
tcaacaatcc tcggacgaac agcccatgat gccgtatcaa cagccccgg ggaatgatga 152580
tcagccatat gagcaaatat accataaaaa acacgcgtcg cagcaagtaa atactgaact 152640
gaacgattat tatcaacata ttcttgcatt aggcgatgaa gacaaaggta tggacagcat 152700
gttaaaactt ccagaaaagg caaaaaggga tagcgatgat gaggacgaca tgttttctat 152760
aaaaaactaa cgacgtaaca attaaacaaa aataaaaatc attataaaat gaatcttgaa 152820
tacgtccaag ttgttcaaaa atttaatcaa gtactcctag aacttaccaa aaaagtatgt 152880
accgttgtgg gcgggagcaa acccacctat tggtatcacc acattagaag ggtttgctca 152940
gaatgtccat ccatgccgat gagtatgata ggtccgtatc tgaatgtcta taaagcccaa 153000
attctaacaa gggacaagaa tttttttatg aatttcgatc ccgcgcataa tgagtacacc 153060
tttatcattc aaaaactaaa agaagcagcc cgaaatatgc cggaagacga attagaacag 153120
tactgggtaa aacttttatt tttacttaaa agctacataa aatgtaagcc ctttattaat 153180
taaagaattg atgcataact aataaatggc cggtcgtgtt aaaataaaac agaaagagct 153240
catagactct actgtaaaaa acaaaaatgt gatgaatctg ttccatgaaa ttataggctc 153300
aaaaggcaat attaatttta gcgttgtctg gcccaagttt aaaaaaaatca aacagagcgt 153360
ttatgactac atttccactc tttctgtgct ggaaaaagca aacgttatgc aaaactttga 153420
agctgataag aaactgttgg aactttttgt acaaaagctg tgggctgcct atgaaggcta 153480
tttcaaatat cccgagattg aaaaatatga ggtggaaggc caggtaaatt tcaatctcgt 153540
acctcagtgc gtcctcgaaa agtttagcca gttgtatagg ataagaatca attcagagct 153600
tgtcacactc atcctaaaca gctgtgcctt tatgagtaaa tataacgatt atattctcaa 153660
aaaagatccc tacatactaa ccataacccc cggcctatgc ttttccccca ttcccaactt 153720
cgaggaccta aattttaaac atctttacaa cagtgataaa aattctcagc atgacaaaga 153780
gtttatcatg tttatattat ataagcttta tacggctgcc ctaggagtgt acaatgccat 153840
ctcgattcca gacatcgacg tagaagacct tgaaaatatc atcctatcct cggtgagcca 153900
gattaaaaaa caaattccgc gctgcaaaga cgccttcaac aaaattgaat cttcggtaca 153960
cctgttgcgc aaaaatttta acacatatta cagtgactat gtgggctcag gctacaaccc 154020
aaccatcatt atggaacagt acattaaaga catatcacag gattccaaga acatatcacc 154080
acgcatttcc taccagttta gaaccatcat caagtattac cgcgacatga ttgccaccag 154140
gcatcaaacg atggaccccc aggtattaaa cctcgtaaag cacgtcgaaa agaaattaga 154200
tatgcttgat agagaaaaaa attagtatat atagttatgg tgaatctttt tcctgttttt 154260
accttaattg tgattattac aattttaatt acgactcgag aactatccac cacgatgctt 154320
attgtttctc ttgtaacaga ttatattatt attaatacac agtatacgga acagcagcat 154380
gaaaacaata catttttcat gccgcaaaaa aattctttta acgaatctta taataaagac 154440
aaaaaatcta atatacatat tccctaccag tggctggcgc ctgaactgaa ggaagctgag 154500
agcaagtact ggtggggcaa ttatgatcct catagcgagc ccgttctcgc tggcgcatct 154560
tgaatatctt catacgtggc acgtcaccat caaaaacatt gcccaacagc acgggcttga 154620
tataaaggtg gccattgtgg tctcaacatc gcatttaaat aattttttgc caatttccgg 154680
ggcgcttaac atcgaatgta taaccttccc cagttgcggc atcaaggaga tagacctcct 154740
atgggcgcgc attaaactat ttcaacatta ctgcgccatc ggtgcccgtc ttttatggct 154800
ggtaagtgct gacatcaggc cccctgtttc agcgtggcca gccatcgccg acagtctaaa 154860
aaagggagca gatgcggtcg ttattcccta cccctcccga tggaacaatc ttatacctac 154920
cgtcatcaaa gaaatagttg tccaccaaaa aaaatgcctt gtggcggtgg atgcacgcca 154980
ccttgataca gatacccaga ttgtaggggc cgggatgggc tgcatcgtcc taaccctaaa 155040
ggcccttatg gtgcgcctaa gtattggcaa acagcccgtt aagatactgt ggcccgacct 155100
tcacggcact gccgagggca ttcctctgga gggggtggag gttggctggt ttttaaacgc 155160
ttatgcgcat aaattaaata tacgctgcct aggggctgat catattgcgc agcacttaac 155220
ttaattcttt atttaaaaag tccacgcatc cagtggcggc ctacattaag ggcctacgca 155280
cataaatata cactggctag aagtacgcct tcatttaaac cattgaatta tttatataat 155340
ggctgcaaac attattgcaa caagagccgt gccaaagatg gccagcaaaa aagagcatca 155400
atactgtctg ctagactccc aggaaaagcg tcatgggcat tatccctttt catttgaatt 155460
aaagccttat gggcaaacag gcgcaaatat cataggagta cagggctcac ttacccatgt 155520
tatcaaaatg acagtatttc catttatgat tccttttcct ttacaaaaaa ctcatataga 155580
tgattttatt ggtggacgca tttatttatt ttttaaggaa ctggacatgc aagcagtttc 155640
tgatgtaaat ggaatgcaat accacttcga gttcaaggtt gttcctgtaa gccccaacca 155700
agtagagctt cttcctgtga ataataaata taaatttaca tatgctatac cggtagtgca 155760
ataccttacc ccaatctttt atgatctttc gggaccgcta gatttcccat tagatactct 155820
ttcggtccat gtggatatcc tctccaatca tatacagctt cctatccaaa accataacct 155880
aacaacgggt gatcgtgttt ttatttctgg atataaacac ctgcaaacga ttgaattatg 155940
taaaaataac aagattttta tcaaaaatat accgccgctt tcatccgaaa aaataaaact 156000
atatatacta aaaaatcgaa tcagaattcc gctatacttt aaatctttaa aaacgtctaa 156060
gtaataacat ttttatagtc tactcctagt tccgaaatag gctgaatttc ttttttaagt 156120
cctttaaacc aaggatgtga tacaagactc ttaaaggaaa gccgcttatt ttcattaatt 156180
gttaaacatt ccgtgataaa ctgttttccc gtctctgaaa tgttctcggg aatataattt 156240
tcccgtttca ggatatcatt taaataaaaa ttttctgcac gaaatctaaa aagattaacc 156300
gcgaccatac ctatcgtcca cacggttaaa ggaagctggt agtaataacc ataataataa 156360
aattctggac acacgtattc ccatgttcca aacatattat attggggacg ggtttcgtct 156420
aatctaacag cgcttccaaa gtcaatgacc ttaatgatct tttgatttat gtctataata 156480
aggttctcat ccttaatatc cccatggata aagcccttct cataaatgtt ttgtataata 156540
agaataagct ggaatattat ttttttggct tcggtttcct caagtttttt aaagtaatga 156600
taatgaagta gatcaacact atttggaata tattctatga ttagtatatg atacatagca 156660
ttttcggtat attcgataag cttaataaca ccgggagtat cttgcagggc tttcaacacg 156720
atgacttcat ttcctggaat ttcttttta gaaacgtact taaatataat gggttgccct 156780
acttgatgac ccaaaaagac gttatttctg ccaccctcaa acatgggtct cgtcgcaatg 156840
aaatacatgt gctgcgttgt ggagatcctt tccacctttg ctgtaggata aaacgcatat 156900
tgtgcctggg gattttttaa catttttta agctgttgtt ccggcctgga catgttttat 156960
tagctttata tataaagggt tagaaggttt aatttcaata tatgccttaa tgatgggatt 157020
atattcgtaa aaggtatagc ctaatcctac gtctttgttt ttttggtaaa aaaactgttt 157080
gccctcgtag gatatgctat aggcttttac ttcggctttt acaagcggtt ggcagggatt 157140
gggcaaacgt aaatcgcgtt caaagttttc atgaaaaagc aaagcatttg tgggctgaca 157200
catcagacag ccgctttcgc cattgaaggc acattcaatg gccgcccttt ttagtaaatc 157260
gcggaaagca gaattaagat ggctcttttc aagccccctt tcgtgaaaac gctcatcaat 157320
cgtttttgt tcctgactgc cttcgggaat actataaaac attttttgat tagccaccgc 157380
gatgtacaaa aaaggctgta cggttttctc ctcgggcggt agcgcatcgt ggctaccaat 157440
gcgtataatg cgcgccttca cttgatcctc tcgggcctta tcccagtacg gctctaggat 157500
atgaacctgc cgcccgtatt tgagatccaa tccctcagct cctgttttag agacgagtaa 157560
aattttaata acctctccgt gtatattcag cggcgaattc caaagctgct ggatcatgtc 157620
gcgctcttta gataaaattt tccctgtaat aagcgtaaat cgtgttattt tggaggacag 157680
gactaacgta tgggtcggcc catcttccgc aaagttttc accataagat ctttcccatc 157740
cttatgaagg aggatggtgt tgtgcccttc ttccaatact tttaggggct gaaggcactg 157800
gtagccctct atttctaaaa agcgggccac gacgtgaagg cccaattcca caaactgtga 157860
gtaaatgagc acagggcccg gagacgtttt aatattttt agcatgcgta ctattttggg 157920
actagaattt tctgtgaagg cctctttggg cagctgctga acagcctctg ataatttttc 157980
atcctccttt actgttagca tttcggacgc gaagatgctg atcatacggg aacgcacata 158040
gtaggaggag cctgactctt gctccgatcc tggcaggcag agggcggcgg catttatttt 158100
ttcatacatt cctgagctgg cgtgcttttc cgcgttttca acgtctcggg ccagcagata 158160
ttgcctatac tgctcgggtg acatttcaac cttttctata ataagaggaa gctctgtggg 158220
gaatagcttg ttgagctcat tctggtttcc agcgtagctt atcataccca ctaggcggtt 158280
tagtagtttg tccgcgttta aagggctatt cgttgtttta ttgacataag cggtgtagaa 158340
tctttcatag tgaagaggta ataagattcg cccgcttagc atattaaaac agggcaccat 158400
ttcaaagggg tccttcgaac acggggtgcc tgttaaaaac agaatacgaa tatttttagc 158460
ttgcataata ttattgtaca gctggcgggc atttgtttta tcattggcgc tattgataat 158520
tcctctaaag aggttgtgtg cctcgtcaac gatgagcagg catccattta gggaccctcc 158580
cgcctttatg atctgctgcc ccatgttgta agcgtctagg gacacaaacc tgaagcgccg 158640
cgagattttt tgtagctctt tggagtgatc cgtcgtttcc ggatataaaa gtttaataag 158700
ctttaacaaa gactgttgga agtttgagtg caacgacttg ggtgcgatca gaatcgggtt 158760
gtaaatatgt gaaagtgaga tggcaagcga caggctcaaa atggttttcc ccatgcccat 158820
ctggtgatag atgaggaggc cccgtgtgtt ttccccctgg cctatcccaa atttaggatc 158880
cgaaaaggcg gtgtaaatta aaaactggta gtatttcagg gctcgtgcaa agcgggcagt 158940
gagtgaggtg tctttgcttt cctgaagctc tttatatttt tcatatacct cttttaggta 159000
tgcttctatt tggacgggga aggaggtgtt gttgtgcacg caagacatga ctcgttataa 159060
ggatcccata ttaaaacttc attagaagaa tagggctgct gatagctagc gctgcactta 159120
aaaatggggt agcccttttt cttgtaaatc cggtgcctgt cgtagacctg gctagaaagc 159180
gggcttagtg tatctttaat gtccacaacg atgcgtacct ttttttcatc cgatccctgc 159240
cgggtaatac gtcccaagat ttgctccatg ttgtttctgc ggggcgttgc catgatgatc 159300
gatgtcatat gcttgaagga aatgcctcta cgcccgtagc cataggtcag caagataatg 159360
gaagcgctgt gtgcctgaga aagagcggta tttgaaaccc cgccgcatag gagcgccacc 159420
tccggaacga taatttgaac atctttgaat tctttggaaa gcgcctgata aaaaatttct 159480
aaaagtttgc gaaattccac gaaaatgatg atgccatacg gctcatcggt cccccatttg 159540
tgaggctcag cggtatgcag ggagtaaagc cgctttgcct catttacgac aagttgtata 159600
cgcgaaggat cttgaagtag tttatcaatg gtggcaatgg ccgatacctt ttcattaata 159660
tacacagggc taacgaagtc aggatgtccc tgatattcga tttccctcac gtacccggaa 159720
aaggttgtgg tgggacttac agtcctctgg ggctgtccta gatggtgaat aataatcttg 159780
tccataccat cgggccggtc caggggtgta gcggacagtc ctaatatccg actaagttgt 159840
attttccaaa aaattttgta attctccggc gagtgtaatt catgtgcctc atctaacacg 159900
actagaccaa agggctcaaa gaactgctca ggcttcttgc gcagggtatt aatgattccc 159960
acgatgacgt cgtactcttt gctcgtcatg tcctttttct tgcacgctgc attattgtaa 160020
gcagctacac gtaggtgggg caggagcaat gttagctcgt cgatccactg tatttgaatc 160080
gccttggtgg gcacgatgac cagggtaggg tacaaaagtt tttgaataat gctgatcgca 160140
atacgcgttt tccccaaacc ggtatttaga tgtaggtaaa agcgcccata gggggacagg 160200
agctttttat gaatcttatc gaccatttct tgctggtagt taaatagtgg aaattctgtt 160260
tcaacgcatg ggagggcccg cagcgacacg gggcgcgtcg tgtaaaccat gttaaacatt 160320
tcaaactgct tttgcagcaa tatgggaaaa taaatgtatt ccccctgcag cgtgaaggca 160380
gtttcctgtc ttatggctat gtgctttggc tgcccgggta atgcccgcgc cgtaacggtg 160440
agcgccttaa gaacgcgccc gaaatcatgt tgtaatttac tttgtagctt cttataattt 160500
attcctattc cagcaaagga tataatggcc tccattctca cgctggacgg gttatatgca 160560
gaggttccaa aattcttacc agaggcgtta cgagagggct gtgctggcaa gaatcctcta 160620
agcttttata ttcaacaaat tttaaattta atgggatgtg acggtaacga gtaccatgtt 160680
ctttttacca gcagctccga ggaagcaaat actcatatga tcatggccgc cgtgcgtcgc 160740
catttgctgc ggacgcagca aaggcctcat gtcattatcg gagcagccga gccccctagc 160800
gtcaccgaat gtgtgaaggc attggcgcag gaaaaacgct gcgtatacac catcatcccc 160860
ctaaaaaatt ttgaaataga tcctgttgcg gtatacgatg ccatacaaag caatacctgc 160920
ttagcgtgca tttcaggcac taatgctgtt gtcaaaacgt tcaacaaact ccaggacatc 160980
agcaacgtgt taaaaggtat tcccctgcac tcagaagtga gtgatcttgt ttatcaagga 161040
tgtattcaac aaaatccgcc cgctgatagt ttttcaataa atagtctcta cggcttcctg 161100
ggagtcggtg ttttgggaat gaagaaaaag gtcatgcaag gattggggcc gctcattttt 161160
ggaggagggc tgagaggcgg aagccctaat atacccggaa ttcatgccat gtataaaacg 161220
ctaacccagc aaaggccttc tatgaaaaaa aataaataca atacatacgc tgttcatgaa 161280
aactttaaaa aacatcagca tgtatatcta cccatagggg gcgtgtctgc agaggacacg 161340
tctgcagaaa acatatctac aaaagacatg cctgttgaag gcccgaaggg actcccgggc 161400
tatattttat ttagcgttgg ccgtcgcgcc gaggagctac aaaaaaaaat tttcactaaa 161460
tttaatataa aggttggccg tgttgttgac ttacaagaga tactgtttcg tatcaaaata 161520
ccccaaaaat actgggagac attattgttc atccaattaa gagataattt gaccaaagag 161580
gacataaaaa gagttatggt tgttttgatg catttagata ccatcactcc tcgtggctct 161640
cttcctcctc cgagccactc ttcttctttt tcttaatcgt ttttgtttgt tctataataa 161700
gggaaaagaa ctccgtggga tcttgttccc cgtacaggtt atctgcgacc ataaggatgc 161760
ttagaatggt aaacaggtga gaatacataa gggtttgcgt tttaagaaaa ccctgacgtt 161820
gaatcataat tgaaaacacc ttgcaaagcc gactcatcag ttgttctgta atggcgttaa 161880
gcattttctg gaatttttct tggttttcgg gtgtgatttt atattcatgt agaaagtgtt 161940
tcacacctga ggagaagaat ctttcctcct tcgagagccc atctttgatg atgggaagtt 162000
ccttgatcag ggcaaaccat tcctcctctt gggcttgcgg attctgaaga tactgatggc 162060
agatatggtt tagaatggtg cacacgtagc taataagctc tgagctgatt ctttggttgg 162120
ttttcaaatg ttggcgaaag tagtttttca ccgaagtgca tgtaataaac gtcttcattt 162180
tcttataata tacaacagta tgttgagtct ttaatttaaa attacaagga gttttctagg 162240
tctttatgcg tataggtgtt tctttgtcgt aaattttcaa tagccgacat tgtttgtgaa 162300
gcagtgttct gagtagtgac tgtcgtgtaa ggctcagccg gatgagcagg agcactcgcg 162360
gccgcaggtg cggccgccgg cccgccagtt gccatgacta gtctgtccgt aactgggttg 162420
tccgtaactg gtttgtttgt tgctggtctg tttgttgccg gtctgcccgt gactggcttg 162480
cctacacttg ctgtagtcgc tccagctggt ttagaggtac ctggttgtgg agtgacttct 162540
acccactgct gatcttgata aggatttata aactgtatat cttcctcctc aatagcagca 162600 gctttttct ttcttgaaga gaatagatag attagaacga tgataatgat gactaagacc 162660
acgatagcaa tgagaatagt atacatatgt gtggagaaga agcttggtgt agtgactggt 162720
gacaaacact caccataatg ccgcggataa accggttgaa aaaattcaga atccatttaa 162780
gatactatta taaataatat ataaaaatgt tgtggcgcaa tgaaattaca gaatttatgg 162840
accaactttc caagtattct caagaaatct taaaaacgtt taagcaattg cgtcctagtg 162900
aatataaaca atacaatgaa tttttaacac aagttacacc gttgctgcaa aaaacccctg 162960
aaaaaattcc agagttggtt gaccatatat tcaattacct agacaacgtt gaaaaaattt 163020
gtgagctcct cgtgaatgct agctcaatta ttattagttc aaaaatacga gaacaagtaa 163080
aacacggaat gagcttcagc tataaagccg acctcgactc cttggcggac attctctctc 163140
aaaaacagta cgtgcttatg catctttcaa aaaatattgc ggccgagtat tttaatacgt 163200
gtttaaacca agggaaatcc aagttagatc tcaaagctgc ctctgtattt tatagtagtc 163260
gttcccgaac ggcaagctca gcagaactct atagaaaaat gctatacgcc tatggttcac 163320
cgcaggaaat taattattat actgaaaaag cccgaaataa gacgttggat gtggaggaga 163380
gcgacagcat ggccatcatc gaacgaacgg cccgacacaa cctttccctt atgcacccgc 163440
tagaagccat ggggcttacc tttggggcaa ccaacacgga cgccgacccg gaggatctga 163500
aggacaaaac ggtgataaat ttaacgctcc cgcaggcaac agaaagcatc acctaccatc 163560
ttaaatccct aatgcagcta aaaaaagtaa gtacggcttc aggactaaat acaaacattt 163620
tgaaagcatt tgataatatt atttccaccc ctgtgaaaaa aaataaaatg gcctccaagt 163680
tggcgcccgg gatggatgtc gtgttcacta gcgataacgg aaaaacattt tttactaaaa 163740
acattttaag caaaaacatg ctagcggggc ccaaagagcg ggtgtttgca tataataatc 163800
tcattagtaa tttaaataac tcctgtttca tacaaaatca caacgatttt ttaagacagc 163860
aggactcttg gcccttctat gacgcgcaca attttaccaa caagttttta atgcagccta 163920

```
tttttcggg gcagacccgt cctcggcttc agggagccat ggaggcggcg catgtggaaa 163980
cgcatctcac ggcattttta caaagtattc agccctctag gccacaagat ccctctgttt 164040
tggcttcccc caagttatct gctctaatct tgaactaaaa acagcctttc ttggacttaa 164100
atgatggtct accagttttt gaaataactt agagaactat gaagattttc atgaaattta 164160
aattagagat ttgcaaaggt tacttgcggt cattttctgt tgaattaaat aattattcga 164220
atagtataat gtctgaagat attcgtcgtg gtcctggcag accgccaaag aaaagggttg 164280
ttcccaactt tgagcgcaag ggcattctgg aaaaaccagt tcggccacaa agccgtctcg 164340
agttttccta tgataacccg ctgatattta aaaatctttt tatttacttt aaaaacctta 164400
aaagtaaaaa tattttggtg cgatgtaccc ccaccgagat taccttttt tcacgtgacc 164460
agtcgcaggc aagctttgtt attgccacca tcgacggaaa aaacgtgaac cattattacg 164520
ccagtgatgt cttttggcta ggcatcaaca gagagctcgt tgaaaaaatg tttaacagca 164580
ttgatcgctc tttttaaaa attaccatcg ttcaccgcta tgacaagcct gaaaccctgt 164640
tttttatctt tacggatttt gacattgaca aggagtgcac gtatcagatt acggtctcgg 164700
agcccgagct cgatatggac cttatcgaaa tggaaaaaag catcagtgaa gaaagactca 164760
agaactatcc tctgcgctgg gagtttacct ccaagcagct caagaaaaca tttagcgact 164820
tatcaaacta caccgagctc gtgaccattg aaaaactcgg cggcgatacg ccgctgcacc 164880
tgtatttcca aaagtttaac tccatctcat accacgagat gtataaatct tccaacaaga 164940
tcaacctgac ctcgaccatt cctaagtcgc aggtgttcca gataaatgtt aaaattgctc 165000
acatcaagtc gctggcctcg gctatggtca ccgacaagat ccgcattctg tgcgaagaaa 165060
atgggaacct aatctttcaa tcggaaatgg atgcccttat gttaaatacg attaccttga 165120
acaccacgat atagttcggt aacattagat gttctaatat ttagcatcta aataatacgc 165180
tgtagtccgg tcagggttgc gtcacagttt tcccattttt ttgcctcgtc ggcggtggcc 165240
accgttgccc tatcatttac gcccggtaag acaaagctaa aggcgttcag cggggcttgg 165300
caatgcccgc ccagcgtgaa ggagctcgga ggattttgcg catcccgaaa tcccttagcc 165360
atgttgttta acacttcggt tacgtcaatc gagtgaaggg atcccttggg atccgtgaat 165420
gtaaagacgc agtttctaaa gcgcatgtat gcgatggacg attcatcggg ggttttgaag 165480
gtaacagtgt tccccttgct gtacttaaag gggaccatc cggtaaaatt ataccaaatg 165540
aaagcaataa taattaaaat aaccaacaca atagttatag acaacacaaa gtctgtagtg 165600
ccgcccatta ttaaataaaa atattttaga ccgccggctt aaaatttact tattgctcat 165660
agcttaagtc tattttattc atagcttaag tttattgctc atggcttaag tctattgctt 165720
atagcttaag tctattttat tcatagctta agtctattgt tcatggctta agtttgttgc 165780
tcatagctta actccattac tgatagctta ctgatcatga cttaaataaa aatattttgc 165840
ccgcttaaaa attgtttagg tttgaaaaaa taagagatgg agggggcaac ttatcgtcat 165900
tgtgtttacc cccactggaa gacatcaaac ggtaaataat tataagaatc aaaatgatta 165960
atataagggt taaaaaagga tgattcatca cattaattaa aaacgtattt ataacgctgt 166020
tgcagttgaa attttggtat aggtcggaaa tattgcccga gcctccgtat tctgcaatgt 166080
tctgacatat ggtgagtccg gaggggcact gcttgttggt caaaatattt ctttgctccg 166140
ttgttttata ggcattttta tttccattac acggagcaaa cgcacattca ggccataggg 166200
tgccggagtt cacacaggca caatactggc tatacgcata ctcatccttt gagcacaatc 166260
cctgtttatc gcatatgctc ccaataatat tgtcatcctc cgccgtttgt tgatttgtat 166320
```

gcgagcgtaa aatagcggcc caggccttgg gctccttttt ttgcagctcg gaaatcgaag 166380
ggcctgtaca gctaaagtcg acccaaatat cattgcattt cgtggaaact ggcatgcaag 166440
acataattga aataattaat aagtatatat catggcaaca aatttttttta ttcaacctat 166500 caccgaagaa gctgaagcat actacccacc ttccgtgata acgaataaac ggaaggacct 166560
gggggtagac gtatactgtt gctccgacct agtgcttcaa cctggactaa atattgttcg 166620
cctgcatatt aaagtagcat gcgaacacat gggcaaaaaa tgcggtttta aaatcatggc 166680
gagaagcagt atgtgcaccc atgaacggct gctcatcctt gcaaacggaa ttggtttaat 166740
agacccgggt tatgtgggcg agctcatgct caagatcatt aatcttggcg acaccccggt 166800
ccaaatatgg gccaaagaat gtttggtgca gttggtggcc caaggtgacc atgtgcctga 166860
ccatatcaac atcctaaaaa gaaaccaaat atttccgctg tttgcgccta ccccaagagg 166920
cgagggtaga tttgggagca cgggcgaggc cgggattatg agaacttaat tttatttttt 166980
ttcttaacat aatgggaggc tctacaagca aaaattcctt taaaaatacg accaacatta 167040
tcagcaattc cattttcaat cagatgcaaa gttgtatttc catgttggat ggcaaaaatt 167100
acataggcgt attcggtgat ggaaatattt taaaccacgt tttccaggat ttaaacttat 167160
cattaaacac aagttgcgtg caaaagcacg taaacgagga aaatttcatt acaaatcttt 167220
cgaaccaaat tactcaaaat ttaaaagacc aagaagttgc gttaacccaa tggatggacg 167280
caggaactca cgatcagaaa acggatatag aagaaaatat aaaggtaaac ttaacaacca 167340
cacttattca aaactgcgtt tcatccctgt cgggtatgaa cgtgctggtg gtgaagggga 167400
atggcaacat tgttgaaaac gcaactcaga agcagtcgca gcaaatcatc tctaactgct 167460
tgcaggggag caagcaggcc atagacacca caaccggcat cactaacacg gtaaatcagt 167520
actcacacta cacctcaaaa aactttttttg acttcattgc agacgcaatt tcggctgttt 167580
ttaaaaacat catggtcgcg gctgtagtta tcgttctaat catcgtaggg tttatagccg 167640
tcttttactt tttgcattca cggcaccgcc atgaggagga agaagaagct gaaccactca 167700
taagcaacaa ggtattaaaa aatgctgccg tttcgtaata atttaattaa aagtaaaaaa 167760
aaaggtattg ttatagtgat ggcagatttt aattctccaa tccagtattt gaaagaagat 167820
tcgagggacc ggacctctat aggttctcta gaatacgatg aaaatgccga cacgatgata 167880
ccgagcttcg cagcaggctt ggaagagttt gaacccattc ccgactatga ccctaccaca 167940
tcaacttccc tgtattcaca attgacccac aacatggaaa aaatcgcaga ggaagaggat 168000
agtaattttc tacacgatac tagggagttt acttcactgg tccccgatga ggcagacaat 168060
aaaccggaag atgacgaaga aagcggtgca aaacctaaaa agaaaaaaca tttgtttcca 168120
aaattaagct cgcataaatc gaagtaaaaa ttgaagcgaa aaaaagtaga aaaaaaatgt 168180
ttggagcttt tgtaagccac cgtttgtggt cagatagtgg ttgtacgacc acctgcatca 168240
caaacagcat tgctaattat gtagccttcg gcgaacaaat tggatttccc tttaaatcag 168300
ctcaggtatt tattgccggc cctagaaagg ctgtgataaa tattcaggaa gatgataaag 168360
ttgagctttt aaagatgatt gttaagcaca atctttgggt tgttgctcat ggaacctact 168420
tagatgtgcc ctggtcccgt aagagtgcgt ttgttacaca ttttatacaa caagaactac 168480
ttatatgcaa ggaagtcggt attaaagggt tagttttaca cctaggcgct gtggagcctg 168540
aacttattat ggaaggacta aaaaaaatta agccggttga gggggttgtc atttacctgg 168600
aaaccccgca taacaaacat catacatata aatacagtac aattgagcag atcaaagaat 168660
tgtttttacg gatacgaaat accaggttga aacagattgg tttatgcatt gatacggctc 168720
acatctggtc ttccggtgtc aacatctcca gctataatga cgcggggcaa tggctgcgct 168780
cgctggaaaa cattcattcc gtgatcccac caagccacat tatgttccac ctaaatgatg 168840
ccgccacaga atgcggaagc ggtatagacc gacatgcaag tctttttgaa ggaatgattt 168900
ggaaatcata tagccataaa ataaagcaaa gcggtttata ttgttttgtt gaatacgtta 168960
cgcgacacca gtgtccggct atattggaga gaaacctcgg gtcttccatg caattacaaa 169020
ccgctttaac cgcagaattt actacattaa aatcgttatt aaaataagga tgagttttag 169080
cgaatgtccc ttagttatta gtgcatgcaa aaaatttcta caaaagcgta ttacaataga 169140
gaatgaagca cttataaatg ccttaataac cgctttagcg cagaccagca cgttgaatga 169200
tctttgttta ttacctattc aaacctattt gcttagttat aaaaatgctt ttgagtggat 169260
acacttcgta tgtattgcaa tcaccactat tttggataat aagtataact ggaaggactg 169320
tacggtagat attaattata tttttctcca tgtaacctat atttacaata ttaaaaccaa 169380
ggaataccta gactactgtt cttaaacttt atttttteta tatttacgcc aaagagaata 169440
tttaaagttt ttttgaaaaa aataatatat gtagataaaa ttcagttaca tgatatatgt 169500
gtaaacatgt gtggtaaaca acatatggtt atgctttata agataaatgc gcataatata 169560
tgtaaacaaa atatggttat gtgttaaatg catataaatg tattttaacg tatatcttgt 169620
gataatggat atatgcattt attaaaagag gctgtattta ttataaatct tgctaaggat 169680
gccattgtca acatatatcc catgttggac aaattgcgtt gcgatccagt tcttttttt 169740
tgattttgtt taatgctatc ctttttgaag ggatggttgt ccaccatatt tattcgatgt 169800
tcaatgaata ggtctgcttt ttcgtaaggc agtgaaggtc gttccaagac tccttgaacg 169860
atggacgtgt tttcttggat ccacttaaaa agcacgtggc attcaaaaac aggacagtga 169920
ttggatcctt ggatatgctt tggacagcca atgcttgaag agatgtagtc ccttttcttt 169980
aggacaagct tctccacgct ggggcaacag agatcgttca agttctggac ggtcgcattt 170040
ggaatgttga aacttcgtat ccattcaccc tcgggtcctc ccttatgaag aaggagtatt 170100
tgctcatggt ccttagtaat cttaaccaaa tgttggaaga tcattttttt acctgcttta 170160
aaggcctgaa gggtgtcagt tggcaaagct attgaattcg ggagtgggct ttcatcaagc 170220
gtgaaatggt gaatgtgacg cgactggaaa gaaaacgacc gttgatttat tttttcaaag 170280
attgggtcga ttccgccatg aaagaacagc tgcaagattt tagaaggcgt atttttttcc 170340
caataaaaaa tgaccacttc tcgtgggatt aaaatcgtct gtgtcccatt ttcattatat 170400
aattggccca taaagccatc aacgtcaatc aacaccaaaa gcatggtata gagagctttt 170460
agaaccggag ttcgttaaaa aaatacaaag ttcgtttaaa acgtgtaatg ttactaaaaa 170520
aatgtaatgt ttaaatgata atgataccac atgcattaat gaaaaaaact tttaaatttt 170580
tgttttaata tttgcatgaa aatggaaaca tttttagtct gtttatttca caatgcagat 170640
ggtttacatc aacagattca ggaaattttg tatttattgc ggatgcatat ttacgaaaca 170700
aatctttact taaagcagga actatcacgg cttatatatc caaataggca actttctttt 170760
gtgttactta tgcccctttc ccttctaaga aactgggatg acattgaata tttaacggac 170820
gttgtagatg ataagcagac tctacattac gcggcaaatt tgctgacaaa ctacgttcta 170880
catctatcca tgtttcaaaa gctgacaaaa ccatacttcc ttttagcggt caagcgggtc 170940
agcgaaaaac tcaacaaaaa gcagcgacat tcattttacg aggtattggt aacctccgaa 171000
accttgaata attatgaaaa cctatctaaa aacattttaa atacgttgat gtttgccgtg 171060
cgctacgtat ttaaacctac gccgaactat tcagaaattc tcgcagagtt ggaaaaaaaa 171120
aataaaattc accatattat ttttaatatg gtaattacgg attttgcgca aatccgtgaa 171180
caacaaatgg ataaacatct gtgtgaaaca aataatgagc ttcgtcagga atgtaaagaa 171240
actatttttg atttaaaggt ggtaggaaat gtttagccaa taaactcatg cccgcatttt 171300
ttacaggtac aaaatatcgt ggatggctca tcgagggcgc gtgtttgtac ttctctgtag 171360
gtacacatac gctgcttgca gttgggacac ttataaagtt gtgacgtctt ttcggcgacc 171420
ttttgctgcg aacgtagagt aatttctgtc ttctccttta aggcggcaga ggggcaaagc 171480
tcggcgaacg tcatgctacc aattgcctcc ggttttagct cgccagaaat tagcttatta 171540
agggcatcgt tatcctgttg ttggtgactt ttttttcgc agttaataat atgattgatc 171600
gtcccacaac gggttgaata ttcttctaaa aaggtttttt cttgttgctg gtacgtataa 171660
tgataacacg aggcctcgat tttttgcgcg tattcggtgc ataaatcagt atgttcctta 171720
aaaaacatat gtttttgaag cgttctaaaa aacatcattt ggatgatatc acgcatttcc 171780
aaaataatat agggttctag tcttttggaa tctttcataa ctagatcggt ggtaatattc 171840
ttagtcatac aatttattaa aaatggttta atatattgta aatatttttt aggcgtgtca 171900
gcctgtaaaa aacattcttg ttcaatctta tttgtaagga tagtattttg caaatactta 171960
tttagcaaaa atacgataga atcgcgggct atatgcattt tcatataatt ttttttaaa 172020 atttaataca aaaaaaagaa gtatagactc ttcttctagt ccggttagtt cgttggttgc 172080
ctcaacatgg agactcagaa gttgatttcc atggttaagg aagccttaga aaaatatcaa 172140
taccctctta ctgctaaaaa tattaaagta gtgatacaaa aagagcacaa tgtcgtctta 172200
cctacaggat ctataaatag catactgtac agtaactcag aactttttga gaagattgat 172260
aagacaaata ccatttatcc cccgctttgg atacggaaaa actaattgta accagtagta 172320
catttaagga tagtttaagc agtaaatgta gaataacaca gttaagcaat aaataacaag 172380
tatataggaa tatataggaa tatatagaaa tatatagaaa tagctaagct taatactaat 172440
tcagcttttt ttttaactaa aacctgaata gatgcgaagt agcggacata tacatactaa 172500
aataagccat acatttactt tcttcttgaa catgaaacct ttttttcttc tgttgttggt 172560
atataaacaa taggactgtt tgctgaggtt gtatgatctt ctacaactgc tgtctcagga 172620
tgacgatgtt tttttaaact aaaagtgtag gatggaatga gtggaatata gttatggctc 172680
gacttatcct gtttcgtaca ggaatatttt ttacaaatag aacgcaacaa gcatatgaat 172740
aaaaacagaa atgatataca ggagcataaa atagatatga acactaaggg gtagcagctt 172800
ttataacgtt ccgtattttt cttagctatc aattgattta ccgtaatatt tatctcggga 172860
aactttgttc tacaatattt tgtttggtat tccagaaact catgtcctgg cttattcccg 172920
cagcttaaaa aatgatacaa aaatgtgtta ttgttactaa aattaattct tcttaagaaa 172980
aactgcggaa gacgctttag gtacgtctgt tcctgtttta gtaggaagta gtataaggga 173040
caatttcttt ttccacacat tagattattg taatataggt aggttggggt gttggagcga 173100
ataagttttc tgagtatgtt ataatctatg acttgtaaat cgttatacct taggtccaaa 173160
aacttgagtt ctttaccaaa gccacctgca atttcagaaa tatttttcat cccgcagcgg 173220
ataatacgga tgtcctgaaa cgtctttaaa atacttgtat tgtagtgaat acttatgtta 173280
tttttttgta aataatctat gtcatgacaa gtgcatgaaa tgccagcagc attgcttggt 173340
atagtattat atgcaggaag aactatacta ctattgagaa tagtcacatt gtacttatac 173400
catgtattat tttctgatat aaagtatttg caggtgacct gtggtttaat cctacctgtt 173460
aagccacttc ctaaaaaaac aaaaaatatg aaaaccctta gcatcctgta tatactatta 173520
aaaatttata aaattttctg tttaaatttc atttagacaa aaaaataata tatatacatc 173580
agcaagaaat tatatacaga ttatataatt ttctgatttt tttttgccac aataagcatc 173640
attatatgca ttaaaatctc aatactaaac actaaaatct aaattctaag cattaaattc 173700
taagcattaa attctatgca ctaaactgta agcactaaaa tctaagtaac taaaatcaac 173760
actaaatgta tgcaacctaa aatgtaaagc attactcatc atcctcctct tcttcatcct 173820
catcatcata ggttaagata tatgtgtcat cctccatttc ttcacattca tcttcataag 173880
catcactggg tattggtgga acattggatg cagcattttt aaaatattct atgtcttctg 173940
gtgaacactc atctaatgat tttttgacag tccttttaac ttccatggga tatgattcca 174000
aatcctcttt atataagagt ttacggtagc ttttagctgc atccacattt gctggagaat 174060
ctggatttgg ctcattgagc agtgaaatta cactaagaag aatggtatca atcttttgag 174120
ccggagacca agtcattccc tgttcttcag cattgtctcc gtgtaagata gagatacata 174180
gttttccatc agagtaaata ttaggatgcc acatttcaga ggtgaatgtt aatctgggtg 174240
gtgcatatgg gtattctgga ggaaaggcga tttttgcctt gaataagcct ccctcataaa 174300
aagtgtcagg tgggcccctt aagatcacat cccattcagt catatccttc tcattcaccg 174360
aaattttgaa attctcagag ggattctcta tcaggtgtct gtactctgct attaaaaacc 174420
tggaaaccat ggttatttaa tattaattaa attccctggt ttattcctcc ttaaaagtag 174480
atgaacctct tttgtttttt attgggttca tttttactaa atttatgaac tggaaaaaac 174540
tttaacggca taattatcaa atgcgaaggg ggatccgtat aaaatcctag cttgccggta 174600
atggctatta agttaaattt ggtaccagta acactaatat ttaaaaagcc ctgatcatta 174660
actttccaca ttaaaagatt attatattcg aatgtttgtc caatatggac aactttgtca 174720
ccagatgtta catttgattt ggttgttagt ggctgaagct tggcacaatc aaaaataagc 174780
ccattaacac taagatatag aggagtgggt tgatctattt tctcatagtt taatattcca 174840
tctttccacg taatagcttg ataattatcc gcagcaatga gttgaaattt tataaatagt 174900
acaggggttt tagttgtcgt tatacattta aagggtgttt tataaaaata aaaaataata 174960
attgttaaaa gtatgataat aatcgccaaa ataatttcat acattttta taagaattat 175020 acatagtatg gtatttaaaa tattagctaa atttaaaaaa acttcatgat ttttaaaaca 175080
gggaaaaagg ggattaggtt gaataaaaaa ggtaagcact tgtctatata ttttttttac 175140
aatgttgcct tgagtcgcat ttttaactgg ctggggagta tcagagtgga atatcactgt 175200
agtaggtcta taaggtcttg ttaaaatatg atcggtcatt gttttcgtac tagtgtcatt 175260
tagggtcgac ctgatagctc gatataaagt tataggggat aacctatcaa atacagtctt 175320
atctgtgctg aaatgtatat cgtcttcttt atcactaata atattaggaa tggctgtcat 175380
taaataatta ctacttgttg ttgtgggtga aatagttgta ctggtattat tggaaatggc 175440
tgtcattaaa taattactac ttgttgttgt gggtgaaata gttgtactag tattattaga 175500
aatggctgtc gttaaataat tactacctat tacaagtaaa ctaatgctaa ctacattttt 175560
aacctcaata aacctaaaaa gccatactaa atacctaaac aacatcctgt tataatatga 175620
gcagaaaaaa aaataagtat aattagggaa ttattcttat tcgcttacta ttaagaataa 175680
ttcagaatct tatttagtta gaaactatca taaagtgaat aggactcatc gtcggatgaa 175740
gattccgttt cagagatagt ttctttttct tcctcagaat aatctgttcc tacaatagaa 175800
tcggtgtcat cctcagaaag agaagtattt aaatatggac tatctatagc aatatcctct 175860
tctatctcgc aatcctcctc ctccatttcc atagtgtgta ggagaatatt tttatcatca 175920
tgctcacttc ttttttgtt gaaagatgaa ccgtcctcaa tacggttcat gttaagttcc 175980
ttcatcttat gtataatttc cgtaatccgt gatgtttttg acatgtaaga tggttttaag 176040
gttatatcca caataacagg agaatctcta tcattttcat ttgataaact ttgatctttg 176100
atttcttcgt ctaaaattct tgtctttttt tgggtactag atgaaataga ggaattcata 176160
ttctgaaacg atatatcaag gggagctgga cgcttttttc caattaaacc gtttttcgag 176220
atactatgat tagatgaatg atctttagcc aagctgtcct tggatatact atagttagat 176280
attttacctt taaataatat tcttctatac aagttattct taggtaaaga attagtatgg 176340
attcctatat ttttatctga aggagtgtcc atatcggaga acgtcctctt acgaatattt 176400
tgaccacgag ccatttcatc cactataggc agtattttgg ctggctatgg ttctttgttg 176460
tgacaattct atgagatttg attgcaaatc aatttttagt tttaaatata ttggtaccta 176520
ggacaaagaa agtatatata gccaataatt attccactaa attgatttcc agactgatgg 176580
gtatggagcc atgttgtctc tgcagacgat cgcaaaaatg gccgtagcaa caaacaccta 176640
ctccaagtat cactatccaa tactgaaggt ctttgggctg tggtggaaaa acaatacgct 176700
aaatggccct attaaaatat gtaaccattg caacaacata atggtaggag aatatcctat 176760
gtgttacaat catggaatga gtctggatat agctttgatt cgggcagtaa aggagcgtaa 176820
tatatcctta gtccagcttt tcaccgaatg ggggggaaat attgactatg gggcactttg 176880
tgctaacact ccatctatgc aaagattatg taaaagtttg ggagccaaac caccaaaggg 176940
ccgaatgtat atggatgctc ttatacatct ttcagatacc ttgaatgata atgatctgat 177000
tagggggtat gagattttg atgataatag cgtgttggat tgtgtcaatc tcatacgact 177060
caaaataatg cttaccttga aggcccgtat acctctcatg gaacaactag accaaattgc 177120
cttaaaacaa cttctgcagc gatactggta tgccatggct gtacaacaca acttaacaat 177180
cgctatccac tattttgata atcatattcc taatataaag ccatttagtc tgcgctgtgc 177240
tttgtatttt aatgatccct ttaaaatcca tgatgcttgc agaactgtaa atatggatcc 177300
taatgagatg atgaacattg cttgtcaaca ggatttaaac tttcaaagca tttactattg 177360
ttatctttta ggggctgata ttaatcaggc tatgctaatg tctttaaagt atggtcatct 177420
ttctaatatg tggttttgca tagatttggg ggcggatgcc tttaaagagg caggggcgct 177480
tgctgagaaa aaaataaaag agtgttacaa cacatattag gtcttaatat ctttaagcga 177540
gagttgattc ccccctgtaa agatcctgat ccttatcaaa tccaaattct gttaaaaaac 177600
tacattctaa aaaatgtctc aactgttttt acatattatt gccagtagcc attgtttata 177660
tcagaaaata acccatttgt ttatcttttt ttgtggggca accattaaga cccgacgcaa 177720
aaaaagatta atcttttatc agatacctaa aacgttctat aagggagtct atgagatgga 177780
tcatattttg atggtcatag taagaagcaa gctttttggc gaaaacaacg gagttaaaga 177840
atttaacccg ctcatgtttg gataggactt ttaacagcga gccaaaacag tatttaaaaa 177900
tttggcaata gtttttttgg gatgcaataa acaaacactt gatcagtgcc cgcttcactt 177960
tctgatcaga catgtttgcc gcataacagg cctttttaaa cttagtaata taattatgtt 178020
ccgcaagcac cattaacaag ggaacgatgg gaagctgctt ttcttggtga aatttacgta 178080
aatattcgat ggccaccgct tggacgactg tgtaatttac taagttagaa atgatagctt 178140
tcatggttgt aaaaatatac ataggatttt ctttttctgt atacagtttg aaaagcttat 178200
gattacgtga aatgatggcc atttttaata caagatggta tagtgtatct ttaggtaaaa 178260
atgccttgca agccgcgatg atgtcgatgt tgtctccatg aacagcgata gaaactaatg 178320
tttccaatct aaatgttttt atctgcatta atagaagaat gcagtcaatg ttattatact 178380
taataatact gtaatacacc gaatcaatga ccgtcatctg agaatcaagc tgacttatta 178440
gtaaatttaa cgtttttttg gaggcatgac ctttgatcgc ggcactaagt gcacacagta 178500
tagcaaaatt gttaaataca ttttgattta ggagaaggag taatattttc cttcggttat 178560
agtacgcagc atctgtgatg attattggcc gataaatgtt aaaatgtgtt aacagctttt 178620
taaaaaaacg gaagtaattt ttttggatcg ctgtttgcat catcgaaata atgagataat 178680
cagggtatat aatgggtagg tcacatgcta cctctaacaa agaatagtcg cccaatctaa 178740
aggctgtgtt gaaaagcgta ctatcatcat acgtatcgag tacccctgct gttacaaacc 178800
aagcgataag atgaatgtgc cgttccttgc aagctatcgc aaatagggag tttcctatgg 178860
aatgtcgaat aatgtactcc ctattttttt ccaaaatgtt tggaaaattg tatagcgttg 178920
cggcatacag tagacactcc attctggcgt tataattttt acttttacat atgaataggt 178980
ggaagaactc gaataattct tgagaacttg ttaaatgcat aatatggtga tattttggtg 179040
tcgttaaatg gtatgagaaa atgcattcta atacatcttt tcggttatgc tttagcgcct 179100
gagctaaggc atattcaggc tcgacccata ggactagtgt ttctataatt gagatattcg 179160
cctgctttgc cagggcatac tttaagacgc tccggttaga aaaaatgttg ttatgaagat 179220
ggataaccgt atccattttt acgatgggac cattccagta tagtcctaaa tgctgtagca 179280
gatcttttgt tagttgtgaa gcgttctcgg gtgtcatata aatatgttgc agggcttttt 179340
tctgtaagga gaacatttcg tcgtaatcgt acaaaaaaaa ttaaaatttg ggcatggatg 179400
attcaaacat aacaaaatca agattttata acagtttgca ttaacctata catatatgca 179460
agtaaatgag atattatcta tcataacgaa tcaagggata tttgtatata tcaggagttt 179520
ctgaaataaa gatatgaaga ttatcatagt agtatccatc aatcacaatg caacttcctt 179580
taaggcataa tttagtaaac tcagcactcc catcttctgg atgctttaca actaacatta 179640
aaaactcctc agtcatatta tctgtaataa aataagatcc tcctggagcc atttgtagca 179700
tgtctcttat tcctacaaaa tctttttgg gatggtaaaa actcagcagt ttcaaactct 179760
tttttagttt tttttcctgg tatttaagcc atttgttata aaacagtttt cttatgaaaa 179820
tgcatttgaa aatattggga atgtttaacc atgcttcttc cgagcacatc tccagatact 179880
tactttcttt gtttcccatg tctaatttat tgctcactaa gttagtaatg aatctatttt 179940
aataatctac tttactaatc tatcttaata acctatctta taatctatct taataaccta 180000
attataacct atttataatt ggctaatgct gccggcattt catgcctatc taaacaactc 180060
ctactaagca atctactatt acatatatag attcactttt tatatttgta aatcatgaga 180120
attataaaat cattactcat ttttattgta aattagtggg tatttgtaaa aatcttcaaa 180180
cgttttaaga tagttttcta gagagaagta atctttgcca tcaatatata atgcttttcc 180240
tttaaactcc agttttgcta tgtttagtga gccgtttcta gatctttttg ggcaataaat 180300
agattttcat tggttgcatc gtccgtaagc agaaaggtac cactaggcac gttaaaaaac 180360
atacgttcta tttcatggtc ggatttttga gaatagaaaa aatctaattt tttaatccgc 180420
gttaactctt ttttatcaat ctttccagac tgttttatat atactttatt gcaaatctta 180480
caatcctcta tggcttcatt atacttattt tgcttatcct ctattgacat gtccgtattt 180540
gataggtaac ttccgttaag gcggttcccc atggttttag atagattttt aattcagttg 180600
tatactttta ttatgaggct aaaatataga agtttgatcc taaaaaaata aaaagatttt 180660
gtacatttat ttatggttta tagcggtata gaggccgata aaaggtatcc gggtagtctc 180720
ctatgatatc gtcaattttg gtataataac agttgttatg gtagtattgt ccaaaccgag 180780
tatgtatgcg ccggtgaagc gtccgcccgc taatggtaca gttccaggtt aagacaatca 180840
tatcacaccc aaaaagagag gaaacagcat aggtgcccaa aggttcatta tataacatac 180900
gccgcatata ttttagtttt ttttctccat ggtaataatc acaggttttc atgtcctgct 180960
taataggatg attccccatg tatgataata tataataaat ttagttttta gctttttcaa 181020
aaaattgggc gctcgaaact aaattttcct tatcacagcg tttggagaaa gcgtatttaa 181080
agatatatct tcttctaaca agactgcaaa aaaaatctta ccccttattt ttataatgtt 181140
catcatagcg tttgaagata tcagaaggtg ccaggtttta taaaaatatc ctttaggatt 181200
tataacgata caagggtcta taaaatatat gcgggtataa tcttataaaa tcatcgattt 181260
tttcataata ttctccgttt atacaataaa gatcataaca gatattgatg cgtagatgca 181320
ttattcgcgt gttcgttggg cagctaaagg atatcacaac gtagtttttt ttaagaaaag 181380
acgaaactac ataagtccct aagggttcat tgaatagtaa acgccatatt tgttttaaat 181440
tttgttgttc accatagtag tattcgcact ttttcaagtc ttttttaata agcctattcc 181500
ccatgtatgc ttataaataa aaatttagaa atgtgctata ttatttgttg atgaatcatg 181560
aacacgtctt atatgttgat atgttacttt aaaaacattt gtattttcaa cagacgcgtt 181620
ctattcttat taagaatgat gccgtcttta ttttaaacct tggtttaaaa tttaaagaag 181680
tatttataaa ctataatcat gggaactttt tcagtaactg cctctgcaaa aagtgacgat 181740
gctgtttgta agtatttaga agaaccaata gatgaaaatt acagaaacat attaagaaat 181800
gagcatgtta aaaaaaattt aaatgaggct ctgaatcgac atattactac ctataatcca 181860
gtagttgatt ggtgtaataa ctattcaaca ttttcatctc aggatttcga tgaatataaa 181920
atttatatac atagcgatct tatggatgga cgacctcgtc caaaaaaaac atggtgtgtc 181980
atcatgtaat gtttgttagt tttatataaa cgcaaaaata ttcttctagg agatgttgat 182040
atactaccta ttgaattcaa tatattaaag tacatttctg gctattccca ttacggtatt 182100
attattacta tttttaagag ctagatgtgg atttaagtaa taataacatt ctcccgttcc 182160
tcctagagac acctcatcaa attcccatcc tatgcaacct ttatgttgta aacataatga 182220
ttgacagcat tcatcttctt ttgaccaagt cgtccaaatc ctaccaagat ctatacgtgt 182280
ttttccaaat ggagattgaa gatcagcagt agtggcatta aacctataaa aaccaggtgc 182340
ataatcacat gaacggatcg taggatctaa tttaatatct tttatatctt gttttactgc 182400
ttctagacaa cttttatcag tacatgttcc acgtacacag tggtgtcctt tatccttaca 182460
atccgtatct gtcttacatt tttttttcgg cggtttatgt ttcagatggt aaaaacccag 182520
tattaaaata atcacaagaa taattcctat aagtacttga acaacaggat aaaacatttt 182580
aatattaaat atatttttta attaaatgaa tagatttaat ccaagtagta ttaaaatttt 182640
ttagaaatag tgttctacaa ataatgaaat gaatggtcca aaaaaaataa ggtgtacaat 182700
aatgtaatat attgttaggc taagtaaatt taatatttta aagtatttgg aaaaatattt 182760
tttaacatat gatgtctagg aatatttttt agacatttaa aaccatatag ttactttatt 182820
tattacactg aacttgaaaa gacttattac ctaaaatatt aatagatgaa gtaatattgt 182880
gtaattgagt ccataacatg ggtgggaaac aaaaatctcg taatatgaaa aataaacatc 182940
ctaaaaagag tgcaattgtt ataagtttat gtaactttat tttaaagtaa gaatataaaa 183000
atatgagtac aagaggaata ggggccatta ctaacattgg ctccaacatc ctgttgtcta 183060
caaaaaaaaa tattttttt agcaaaaaaa aatccatgga aggatattaa tacacataat 183120
tatttgacat cacattagtg tacttaccaa atagtaatat acaaccatcc taatattcac 183180
ctttatgaaa tgatcccaac ctatacggta aaatagtata ggttttaata aagaaaaaag 183240
atattctgtg gtttttattt ttgtatagtg tgtgaataca aaataaaatc ccaaatttta 183300
acctttcttt tttttctata caggatgtta gaaattagta ttggcaacgc tgctaggcga 183360
cctgcagcgg ctccgggttc ttacccctca gcagcgggca gttgccttct ttcgagccaa 183420
tactaaggag ctagaggact tcttatgctc agatgggcag tctgaggagg tactgtctgg 183480
ccccccttctt aaccgtctac tagaaccctc aggccctctt gatattttaa ccggatatca 183540
cctatttcgt cagaatccca aggcaggtca gttgcgcggc cttgaggtca agatgcttga 183600
acggttatac gatgctaata tttacaatat actgtctcgg ctgcggcctg aaaaagttcg 183660
caacaaggct attgagctat actgggtttt ccgagctatc catatttgtc atgctccttt 183720
agttttagat attgtacgat atgaggaacc ggactttgct gaactggcct ttatttgtgc 183780
tgcttacttt ggtgaacctc aggtaatgta tttgctctac aaatatatgc ctctgacccg 183840
cgcagttctt acggatgcca tccggataag tcttgagagc aacaaccagg tagggatttg 183900
ctatgcttac ttgatgggag gcagcctcaa gggactagtc tccgccccac tgcgtaaacg 183960
tctgcgcgcc aaactacgct cgcagcgcaa aaagaaggac gttctttcac cccacgactt 184020
cttactgctg ctccagtagc tttttttgcc gcaggagcac cgcggatagg agctcctcca 184080
cgctcgcgat ccggcgctgg aagcggaacc gatcgaccgc cacctgctcc cagggaccct 184140
tgcgctcgat gtcgtcggct tcccacacct cgacggctgt ggcaaaatgg acatgcttcg 184200
cgtcgttcgt ccgtttttg cgccgcctcc ccattattct tcctgtaaga ttagtgttta 184260
atacctataa taacataatt ttaagattta atataccaaa acttaaacta tttttgtata 184320
gtaactatta gcatgtctac acatgattgt tctctaaaag agaaaccggt tgatatgaac 184380
gatatatctg agaaatcagt tgtcgtggat aatgcacccg agaaaccagc tggagcgaat 184440
catatacctg agaagtcggc ccgcgaaatg acatcatcag aatggattgc tgaatattgg 184500
aaaggtataa aacgtggaaa tgacgtgcca tgttgttgtc caagaaaaat gaccagtgca 184560
gacaaaaagt tttcagtatt tggtaaggga tccctaatgc gctccatcca gaagaataat 184620
taaaaaaaat atttttttta gcaagttttt aaactattta aataaatgtg gtaaaaaaat 184680
tcacataata attaaagtga acgtgttaga attaatattt ttttataatc ggatataata 184740
tccattaaat caataaatga tagtgttgct accacactaa acaataacaa acagaaacgc 184800
acgatacctt tcctcatgat ttataatagc gtgttatcta aagatttttt tgaaaaaaat 184860
attaaatttt agttgattat ttttttcagt tacaacattg ctttagaaaa aatacctaat 184920
tactacatag caaataaagc gagcgcattg ttacaaacaa cattttttt gcgcctggat 184980
actcctatat atgagaacta taatacggta tattaatcct attaccaaca ttgtcaataa 185040
tagtatgtag gcaatgacat actttaaata ccaaatatcc atggttattt ctaaaaatct 185100
tgaaaaaacg ttaaatttta gatcggtcac ctacgacagt aatactaatt ttaataattg 185160
atgactgaaa tcataatata atgccgtgcg aaaaataatt atttttcggt taaagatacc 185220
attacataaa aaatatgcca tctactctac aagtgcttgc taaaaaggta ttggccttag 185280
gggagcataa agaaaatgaa catatatcta gagaatatta ttatcatata ttaaagtgtt 185340
gcggtttatg gtggcatgaa gctccgatta tactttgtta tgatgggagt gagcaaatga 185400
tgataaagac tccaatcttt gaagaaggca tattacttaa tactgcatta atgaaagctg 185460
tacaggagaa taattatgaa ttaataaagt tgtttactga atggggagca aacatcaatt 185520
atggattaat ttccattaat accgagcatg cccgggatct atgtcgaaaa ttaggagcta 185580
aagaaatgct tgaaggaaat gaatttatac aaattatatt caaaacatta gatgatacca 185640
ccagtagtaa tataatttta tgtcatgaat tattcaccaa caatcctctt ttagagaatg 185700
taaatatggg ggaaatgagg atgataattt attggaggat gaaaaattta acgaacctat 185760
tattaaataa tgactctatt agtgaaatat taactaaatt ctggtatggt atagcagtaa 185820
aatataatct taaggatgcg atccaatatt tttaccagag attcatggac ttcaacgagt 185880
ggcgagtaac atgtgctctt tcttttaata atgtgaatga tcttcataag atgtatataa 185940
cagagaaggt tcatatgaat aatgacgaaa tgatgaatct agcctgcagc attcaagaca 186000
gaaatttatc aaccatttac tattgttttc tattgggggg ctaacatcaa tcaagcaatg 186060
ttaacctcag tattaaatta taatattttt aacttattct tttgtataga cttaggggct 186120
gatgcctttg aagagggtaa gaccctggcg aaacaaaagg ggtataatga aatagtggaa 186180
atcttatcat tagatatcat ttatagtcca aatactgact tctcatcaaa aatagaacct 186240
gaacatatta gttctttgtt aaaaaacttt tatccaaaaa atctgttcgc ttttgatcgt 186300
tgcaaccccg gtttatatta ttcttagagg accgctacaa aaattatttt ttttcttgat 186360
caaagctcca aaataattat tagattaaag tcgcctatag cagcagccca ctccaaaaaa 186420
agtattttat agtacaaaaa acacgaaaaa tagtttgcgg ccggcggcaa actatttgtt 186480
gttgtctaaa acttaatgtt tttttaatat ttttaaatgc aaccatggat tgttggacta 186540
tcagggagaa gaactatagc tacatcatat tgtcaatact ggtaatacta ttaatatggt 186600
atcttatact taactattgt cgatcgaaaa aaaatgcagt tacaaacaac atgccgccac 186660
catacacggt gtcaagtagc tgttctcaat aatagggttg attgacgctc ttcgtaataa 186720
tatgttgatt gacgcatcat aaaatgctgt ggttgattaa tatgttgatt gtcgcctact 186780
ttattatata agtaatgatt tttgtataaa atacgggttt gtgagggctt tattttttct 186840
tattagaaca aagcatgcaa tttaaggcct acagcaagag taatttaaca cctacaacag 186900
taattttaag gtcagtaata atgtttaatt aaggcctgac cactaaaact taaacgattt 186960
tgtaaaaaaa aatgtctact ccactttctc tacagactct tgttaaaaaa gtgctggcca 187020
cacagcacat atctaaagaa cactacttta ttttgaaata ttgtggttta tggtggcatg 187080
aagcgccgat tacgatttgc attgatgagg atagccaaat attgataaaa tcggcaagct 187140
tcaaagaagg cttatcttta gatatcgcat taatgaaagt cgtgcaagaa aataaccatg 187200
atttaataga gttgtttacc aagtggggtg cagatatcaa ctctagctta gttactgtta 187260
atacggagta tacccggaac ctttgtcaga aattaggcgc aaaggaagct ttgaatgaaa 187320
gggatatttt acaaatattt tataaaacac gtcatcttaa aactagcagt aatattattt 187380
tatataatga attgttttct aataatctcc ttttccaaaa tatagagaga ttgagtttaa 187440
tagtttatag gggcttgaaa aacttatcaa tcaactttat attggatgat atttcattta 187500
gcgaaatgtt aactagatac tggtatagta tggcgatatt atataacctt actgaagcca 187560
tccaatattt ttatcaacga tataggcatt ttaaagattg gcggcttata tgtgggcttt 187620

```
cttttaacaa tttgtctgac cttcatgaag tatataactt agagaagacg gatatagaca 187680
ttgatgaaat gatgaagttg acctgtagta cgtatgatgg taattattcg actatttatt 187740
attgttttat gttgggggct gacatcaatc gggcaatgtt aacctcggta ataaactttc 187800
atattggtaa cttgttcctt tgtatagatt taggagctga tgctttcgaa gacagcatgg 187860
aactagcaaa acaaaagaat aataatatat tagtagaaat attatcattt aaaaattatt 187920
atagttcaaa tacctctctt ttatcaataa aaacgacaga tccggaaaaa attaatgcct 187980
tattagatga agaaaagtat gagtcaaaaa atatgttaat gtatgaagaa ttatctcatt 188040
gatacaaaat tattttttat aacagaactc tctgatggtg acaaatctcc gataggaata 188100
tatgacgtaa cataattatt tttttcgccc agaaaaaaat tataaatgtt attattgcca 188160
gcacttttat caactatacg tacaaaaagg tgttgaccaa aaaaataatt ttttttcttg 188220
atcaaagtat gtaaacgccc gcttacagca aggatcttaa gtgagagcca ttaaatttta 188280
ttgatagctg cttgccacca gtagaatacg gccaaaccac ctaacaggaa atacaaggcg 188340
gcccttcggc caataaggtg gataaaaatc acgcataaga cggttgtaac atagcacttt 188400
agtgcgaata tcaggaatgc caatagcatg tagataaggc accaaacatc gcagctatac 188460
atggctaaag atcaaccaga aaaggtttaa attttaacgc cggcccaaaa cttaaacttt 188520
ttttgatatt tttaagtgca gccatggatt ggtccggcca taggatgacc tatgcctacg 188580
tggcattctc attgatggca atagcaataa tatggtatat tctacttatc tattgccgat 188640
cgaaaaaaaa tgttgttaca agcggtaata cgctcgcttt agcgccaata tcgcatatgt 188700
gaaaaatgtt cgccgaaaaa aacattaaaa tttagaaccg ccgcggcatc tcaggggcgg 188760
caacattttt ttttatatgg atattgtcac acaccacctc atctatgacg caatatatta 188820
ctgctaatat caggttcccc aatagtatgt agagaaacca cacaagatag atattcatgg 188880
cgatttttga cgaaaaaaca ttaagtttta gcttctttga cgcctgtgta ctaataatgt 188940
ttaacgcctg tagtataata attgatacct acagcagtaa ttgataccta cggcgataat 189000
gtctctctgg ccgccccaaa aaaaagtatt tacggtaggg tttattaccg gcggcgtaac 189060
accagttatg gtcaattttg tctggcccgc cgcccagccg caaaaaaaaa tcaattacaa 189120
ccgcaaaaaa aaatatttcc ggccgcggcg tttcaaaaaa taatctttgc gaaataattc 189180
cgcatcttgt gaaatgaacg cctacagtaa taattttaat ctttgacacc tacagcagta 189240
gtaataattt taatctttaa cgcctgcagc agtactaata ttttaatctt taacgcctac 189300
agcagtagta ataattttaa tgtttaacgc ctacagcagt agtaat                189346
```

<210> SEQ ID NO 2
<211> LENGTH: 190459
<212> TYPE: DNA
<213> ORGANISM: Artificial Sequence
<220> FEATURE:
<223> OTHER INFORMATION: Chemically Synthesized

<400> SEQUENCE: 2

```
gaatatacca tattattgct attgccatca atgagaatgc cacgtaggca taggtcatcc     60
tatggccgga ccaatccatg gctgcactta aaaatatcaa aaaagtttaa gttttgggcc    120
ggcgttaaaa tttaaacctt ttctggttga tctttagcca tgtatagctg cgatgtttgg    180
tgccttatct acatgctatt ggcattcctg atattcgcac taaagtgcta tgttacaacc    240
gtcttatgcg tgatttttat ccaccttatt ggccgaaggg ccgccttgta tttcctgtta    300
ggtggtttgg ccgtattcta ctggtggcaa gcagctatca ataaaattta atggctctca    360
```

```
cttaagatcc ttgctgtaag cgggcgttta catactttga tcaagaaaaa aaattatttt    420
tggacccccc cccatgtttt atcaaaaatc atataataaa gtggcgacaa tcaacatatt    480
aatcaaccac agcattttat gatgtgttaa tcaacatata ccatattaat caaccacagc    540
attttatgat gcgtcaatca acatattatt acggagagcg tcaatcaata taatattgag    600
aacagcgact tgataccgtg tatggtggtg gcggcggcat gttgtttgta acagcatttt    660
tcatcattcg aagcttacaa aagatatgta taagatagca tattaatgtt attaacagta    720
atatcaataa ggcgtagcta tagatcttca ctttggtaga ccaataatcc atggttgcgc    780
ttaaaaatac caaaaaaaac attaagtttt ggagggtaag attggttttt caccattggt    840
aaagattatt attctaaatg tttaccccat agatgtgaaa caatgattct tcatatatta    900
acatattttt tgacttatac ttttcttcat ctagtaaggc gttaattttt tccggatctg    960
tcgtttttat tgataaaaga gaagagtctg gactgtaatt tttaaataat aagatattta   1020
ttaatatcca attattcgtt tggctcgcta tttccatgct ctcttcgaaa gcatcagctc   1080
ctaaatctat acaaaggaat aagttacctt cacaaaaatt cattaccgag gtaatcattg   1140
cccgattaat gtcagccccc aacataaaac aataatatat agttgtataa ttacaatcat   1200
acatacaggc caactgcatc atttcatcaa tgtctatatt tgtcttctct ttgttataaa   1260
tttcatgaag gtcaaagacg ttgttataag caaccccaca tattaaccgc caatctttaa   1320
aatgactata tcgttgataa aaatattgga tggcttcagt aagcttatat agtatcgcca   1380
tactatacca atacctagtt agcatttcgt tgaatgaaat attatccaat gtaaagttaa   1440
ttgataatgt atctagttca ccaaaaattc ttaatttcag ttgagcatta tttaggaaaa   1500
ggggattatc agataataat tcatggcata gaataatatt actgctagtt ttaacatact   1560
gtacattata aaatatttct aaaattttat tttcactcaa agctttcctc gcacctaact   1620
ttggcatagg tcctggtgca ctccatattg acagtaacca acccaaagct gatgtctgca   1680
ccccattcgg taaacagctc tattaaacca tgattgtttt cctgtacagc cttcattaat   1740
gcaacattta atgttaaacc atgtttaaaa cttgctgttt ttattaatat ttgttcatct   1800
atacaagtat gataaatcgt aattggggct tcatgccacc acaaaccaca acgctctaaa   1860
atacaataat catcttttaa cacaggctgt gtagctagta ctttttttagt aagtgcttgt   1920
aaagtagatg gcatcttcta tctgcaaaat aattatttcc gaaaaaaaaa tcaaattaaa   1980
atactaaatt ctattttttt ttttaataaa gcctgtaaat tatataataa atctcgccca   2040
ccgtattatt tccggacaca actttttata cctcattata tttttagatc tatagttttt   2100
taacaaggca ttaatttttt ctggatctgt cgtttttaaa gataaaagag agacgtttga   2160
actataataa tctttaaatg ataatatttc tactaatata tcatgattct tttgttttgc   2220
taattctaag ctctcttcga aagcattagc tcctaaatct atacaaaaga acaagttatt   2280
catataaaag ttttttaccg aggtaaccat tgcccgattg atgtcagccc ccaatacaaa   2340
acaatagtaa atggttaaaa aattgctatc tctcatacag gccagatata tcatttcatc   2400
aatattcata tcaacctttt ttatatgata catttcatga agatcagaca cgttattaaa   2460
agaaagccca catattagcc gccaatcttt aaaatgacta tatcgttgat aaaaatattg   2520
gatggcttca gtaagcttac atagtatcgc tatactatac caatatctag ttagcatttc   2580
gttgaatgtt atttcattca atataaagtt gatcgatatc ttctctagaa aacaacaaat   2640
tattactttt aattcctcta tattctggaa aaggggatta ttagataaca atttatggca   2700
```

-continued

```
taaaataata ttactactag ttttaatacg atgtatttta taaaatattt gtacaatatc   2760
catttcattc aaaatttttg cgcctaactc ccggcagaaa ttccaagtat gctccgtatt   2820
gacagtgact aagctagagt tgatgtctgc accccattca gtaaacaact ctattagatc   2880
atagttgttt tcctgcacag ttttcattaa tgcgagattt aactctaaac catctttaaa   2940
aattgctgat tttatcatca attgattatc ctcattagta gaaagcataa ttggagctcc   3000
atgccaccac aaaccacaat atttcaaaat aaagtagtgt tctttagata tgtgctgtgt   3060
ggccagtatt tttttagcaa gagcctgcag agaaattgga gtagacatat tttttttgc   3120
aaaatggttt aagtttttca agaatacaga ttggataaat taggttgttg acttagttac   3180
aggaggtatt aaatattatg tagacataaa aatgagatcc tccaaaaaaa taaacaacaa   3240
aaaaaatatg tttaatatta aaatgacaat ttctacattg cttattgctc ttattatact   3300
acttattatt attttagtag tgtttttata ctataagaaa caacaaccac cgaaaaaggt   3360
ctgtaaagta gataaagatt gtggtagtgg agagcattgt gttcgtggat catgtagctc   3420
attgagctgc ttagatgccg taaaaatgga caaacgaaat attaagatag attctaagat   3480
ttcctcatgc gaattcactc ccaattttta ccgttttacg gatactgctg ctgatgagca   3540
gcaagaattt ggaaaaacac ggcatcctat aaaaataact ccatctccaa gtgaatccca   3600
tagcccccaa gaggtgtgtg aaaaatattg ttcatgggga accgatgact gtacaggttg   3660
ggaatatgtt ggtgatgaaa aggagggaac atgttatgta tataataatc cacatcaccc   3720
ggttcttaaa tatggtaagg atcacatcat agccttacct agaaatcata aacatgcata   3780
aataaataca ttaggctcat cgtatctttt taaaatccat aaatattcgt ttgatatatg   3840
ctgaaatttt tataaaaaaa ataactattt cctataaatc atctagaaat agtcctcgtt   3900
ttgatcggtt tatatcttat aatattgtgc atcgatgcac aactgctttt tttggtcctt   3960
ctggaacatc attatatttt ctttcattaa tataccattc agatgtaaac gttgaataat   4020
ttttatggca acaatctacc attgaattat atttagtaac atctaataca tcgtttgttt   4080
tatcaggctc agctctataa tcttgataat ttttgttatc agcttctaaa gctccatcat   4140
tatttttcaa agaagtatcc ataattatgt ttggtaaaaa tactttaagt tttaatgtga   4200
tatttaaaat ggttgttata taaatttacc gcttacaggt aatctttatt cagtgtcata   4260
aactatactt ttgatgattc agtattttgt gaatcagtac atttattatc attaatattt   4320
ttaggctgtt tttccaatgt tttattgttg caatgagcct gctcctcctt tgacgaggaa   4380
gtgtctgttg gagtcatctg tttaggaaga gtatcatcca tatctattat gaagaaaata   4440
tataaatatt gatatacaat caaaaatatt tttgatcacg tctttgttat ctatcgatat   4500
tgttgataac gtcttgaata acctacatca tttttttaca taaaaaaata gatataattt   4560
ttattatatc tcaattattt taaagataat tatcaataca gcaaatatca taagctaaca   4620
tatttttcga ataatagttt tttagtaaag tattaatctt ttcaggattg gtttcttttg   4680
ataataagat aggattcgct ttataaattt ttaaagataa tatattcaca atgatagaat   4740
aaccgtatat atctgctaat gtcttactgt gttcaataac attagcccct aaatccatac   4800
aaaagaacat attttcaata caaaagtttt ttaccgagat taacattgct cgattagcgt   4860
tggctcccaa tgcaaaacag tagtaaatgg tcaaaaaatt attatcgcgc atacaggcca   4920
gctccatcat tttattaata ctcatatgaa ttttcgttgt gttacatatt tcatgaaggt   4980
caaacacatt gttgaaagaa agtgcacaaa ttaatcgcca ttcatcaaaa tgcctgtatt   5040
cttgacaaaa atattgaata gcttctttaa gattatattt taccgctatg ccataccaat   5100
```

```
atttggttag catctcacta aatgagatct catttaacat agaatttgtt gttaaatcct   5160
tcaactccca ataaatgatc atccttaaat ccaccatgtt tacattttgt aaaaaagggt   5220
tattagaaaa taattcatga cacaaaatga cattactact tgttatttta cactttgttt   5280
caaagaaaaa tcgtaaaatt tcacttgtct caagctcttc tttagctccc aattttcggc   5340
ataggtttcg agtatgctcg ttattaataa aaagtaaccc ataattaata tttgcacccc   5400
attcagtaaa caacatgatt agatcatcat tgttttcctt aactgccaat accaatgcag   5460
tattaagcct tataccctct ttaaagcata atgtccttat cattatttga ttatcatcat   5520
ctatatacat tgagatagga gcttcatgcc accataaacc ataacgctct aaaatataat   5580
aatcatcttt agatacgtgt tgcgtggcca atgccctttt agcaagtgct tgtaaagtcg   5640
atggctgcat gtttattctg ttaaaaaaaa tcaaattatc gggtaaacat aaggatcaac   5700
ccgtagttaa tatttgcagt agtatttttt aacaatgaat tataataaaa aaataattca   5760
ttactatcta ttataaaacc catctttaac tttaaagaag aactagatca tctttttttt   5820
gttgtgtcag aacttcttca atttattacc cacattttat ctaaaaaaat aaaaactaca   5880
tcatatcttg tttcttcatc aaattatcat accatttata gggtgtaggt tgggaacatt   5940
ccatcatgtg gtaatcaggg tatttatata tttttgata gtaacatcta tttggcagat    6000
gtattgtcca acaatcatgt ctaataaaat cattttcacc tatgggggaa tcatcttaaa   6060
aaccttattc ctacagattc cattttgaca gtcccagcaa aagtcacaat attttccatg   6120
agtacaccaa tgttcaagct ctctttcggg aggaatgctg ccaattttat gtttttagc    6180
ttctaactct ctgtacaaca tcagttggga aagcagaaag aagattacca ggagaaccat   6240
taaatatata atagtctgca aactacgttt gcgaatgtaa tttgcaacta aaacacaacc   6300
cacaaggtaa aatccataag ttaataactt ttgccatttt cgtatgacag cctcgtgcca   6360
ttcatggttg tgttgtgggc attctgttcg gtaaacttca tgaggcttta tagaagttac   6420
atagtaggta cagaattcat tgtgacgaaa aacactgcag ttagctatgt agtcattttc   6480
aagaatggga gaatggtttt caaagacctt attcttacag atgccatctt gacagtccca   6540
acagaaccta caatgatttg cataggtgca ccagtattca agctcctttt caggaggggt   6600
tcttgttaga tccaggagct ctagctcata tgtataaaga agagttggaa tggatagtaa   6660
agtaaatatt tgcagaccaa gcatggctac ttgtgaacaa gtggctgctc gtcaacaaat   6720
agctgtttat cagcaaatag ctgtttatca gcaacaacta attatcagca aatgctgctt   6780
gtgggtaagc caataaatag gccataccct tgaaaggaga attcagtttg ataaaaaaaa   6840
taacgagttt tctaataacc cggtcaagca tttaataaat gaatagcatc acacgtctgc   6900
atcgtgcatt ctgcctggaa aatgggccca tctctaatat atttacactg acggtgaatc   6960
atacagtgtt ccatgggata gctatgctcc tgtacaggag gcatatcttt tagaacttta   7020
ttcttacaaa gaccatcttg acaagcccag caaaaccgac aatttttcac atattgacac   7080
cagtatctaa gctcctcttc caggggattg tcggtcgaaa acccctgtag actagctagg   7140
ccagctagca gcaagccgag gtaactaaag aacctcattg tagtgttata ttacgaaaaa   7200
acatgttaaa atttggaaaa aaaagccctt tttatagatc tggaaaaaaa ttttcacaaa   7260
tctaattaaa agccttacag atcatccttt tcataaattt tcattaacaa ttggtggggg   7320
cggttgtgag gtactggatc agaacaatcc ataacatggt aatgtccatt tccttcacca   7380
tatgtacact ggttatacca gcgagaaacc tcacaagatg tcaaataact gttctcaaca   7440
```

-continued

```
atcaatggca tgctcttatt caccttgttc ttgcaaattc catgtgcaca ttcccagcaa   7500
aacttgcagt tttccatgta agtacaccag tatccaagtt cttcttgtgg aggattatcc   7560
gttgaacgaa gatgccctcc tgcctgagta ggtagtccta agacctgatt ggccagcagg   7620
ccaagaattt ccaagaagat caccaacatt gctacggctg gctgaacagc tggcagatag   7680
ctagctaatt agcaaaccaa gtgactcgcc ctctctactc ttaatatgag aatttaagat   7740
tcggtccggc tttttttccca tgttttacag ggaaaaggta tttttagcct atgaatgtac   7800
atggttccgc acattaaaaa aaataaaaga aattatttaa tattggctgt tattttcttt   7860
caactagcaa caagccaggt aactaaagaa cttcattgta gttttatatt acggaaaagg   7920
ttaaattttg gacaaaaaaa tcatatctaa ttaaaaatcc tcacagatct ttcttttcat   7980
aaattttcat taacaattgg taggggcggt tgtgaggtac tggatcagaa caatccataa   8040
catggtaatg cccatttcct tcaccatatg tacactggtt ataccagcga gaaacctcac   8100
atgttgtcaa gtagctgttt tcaataatca atggcatgct attattcacc ttgttcttgc   8160
aaattccatg tgcacattcc cagcaaaact tgcacctttc catgtaagtg caccagtatc   8220
caagttcttc ttgtggagga ttatccgttg aacgaagatg ccctcctgcc tgagtaggta   8280
gtcctacgac ctgattggcc agcaggccaa gaattcccaa gaagactacc aacattgcta   8340
cggctggctg aacagctggc agatagctag ctaattagca aaccaagtga ctcaccctct   8400
ctactcttaa tatgagaatt taagatccgg tccgacattt ttccgatatt ttacaagaaa   8460
aagatatttt tagctacaaa tacacttcat atatccctaa aaaaacaaaa atttatttaa   8520
ttttaactat tattttcttt ccactctctc tttaagattt tgtaaggatt ccagggcttt   8580
ggttcagaac aggccattac atggtgaatc ccctgtccta gatcatacat acatttattt   8640
agccagcggg aaactataca tgattgcaca tactcatttt caagaattgt tgtattctcc   8700
aatttgccct cacaaaggcc attttgacaa ttccagcaaa acttgcagtt ttctgtataa   8760
gtgcaccagt attcaagttc ttcttgtgga ggattatccg ttggatgaag ttgtccagct   8820
ggttgattag gtagccctaa gacctggttg caattcatgg tatggtagat acccttatct   8880
aaatcataca tacatttatc cagccaacgg gaaaccagac atgatttcac atactcattc   8940
ttgtaaatta ctgacccatc tattttgttt atacaagtgc cgtcttggca gtcccagcaa   9000
aattggcaac tttccatgta ggcacaccag tattcgagtt cttcctctgg aggctcctct   9060
gttggacgaa gttgtccaac gagctgactt gaaacctggc tggccagaag gccaagaatt   9120
cccaagaaga tcaccaacat tgctacggct ggctgaacag ctgactgaat agctagccaa   9180
ttagcaatcc actgtacttt tcataagatc atttaagatt cggtcggcat tttttcaata   9240
gtttgctagg aaaaaatttt taattttata gattcacact acttcattct catgcttagg   9300
aaaaaaacaa actaaatctt acaatgtatc tggatctaat gagaagctag aattcatctt   9360
ttttcaaatc ctttctggga tgttcattct ttttccactc cttccttgca attttataag   9420
gattccaggg ctttgggtca gaacagttca tgctatggta aatgtgctcc tccacatcat   9480
atctacatag gtcaccccag cgggaaacct cacaatattt tacatagtca ttctcaataa   9540
tacttgtgga gttgtttccc caaaccctgc tggtacaaat cccatcttca caatcccagc   9600
agaaccgaca gctttccaca taagtgcacc agtatccaag ttcattctct gggggttcaa   9660
atgttagagg aagatgtcca cctacccgag tagaagtgga ggatgaaacc aggttgctac   9720
tggccagcag gccaataatt cccaggataa tcaccagcat tgtgctcaac cagcaacggc   9780
tagcaacgac tagcaactga ctagcaatag ctagaaatgg ctagcaatca gtagtagcta   9840
```

```
acgctctact ctttataaga aaatttaaaa ttcgatcaga ttttttttaga attgagaatg   9900
agtaaaacgc ttatattctt tttctagcta gaaaaaataa gctagtttaa gataggattt   9960
cccttactaa cggtttaatt tttagcaaag gtataggtaa aatacacttg tacttagctg  10020
caaaaaaata agcttatggc gtataagccg ccataagttt atttaattaa aatgttaaac  10080
tctgtgataa gactggaatc ttaggcaggt ttgatgtgga gaacagcatg aaatacaaga  10140
gtgcctgtta cacgaataag ttctctcaaa ccggggatgg tcatactcac atctatgaaa  10200
tcctggtcta ggagattcat ttgatgcatg atggccgcac ccacacttat gagacactga  10260
agaactaaag ggtttaattt tgatctgaat ggtactatat aggatgatgg caatccatat  10320
caagattaga gcaatcaaaa tcacctcctc aagaagcatg atgtagcctt aaatcttaga  10380
ctgctttaaa ccttaggccc tcactatctt taatgaagga gtttaaattt tgatcccttt  10440
ttcaagaccc atttagaaga aaaaataaag tttatatcaa tctaattcat aagtcatctc  10500
tttcataaat cttcatgtat tctctatgtg gataagtatg ggatgttgga tttgcgcagt  10560
ccatttgatg atctgtatgg tttttgggtc cttcataata actacatata ccattccagc  10620
gggaaaccgt gcaatttata atccagtcat tttgatgaat aactggccaa tctgtttgaa  10680
tcctgtttcg gcagataccg tggacgcatt cccagcaaaa gtcacattgg tttgcgtaag  10740
tgcaccaata aactagctca tgttcaggag gataacgggt tggtagtaaa tcttctaatt  10800
tacgtatagg agcggcttga aggacaacca cccccagtag tactagaatc agtaccttta  10860
tagtggccac cctacactag acctctaagt tgaagacaaa gaactaaaat ttagagccgt  10920
ttaattacta ctaataatta tattttttat tgtctacaat aggattctat taaaaaataa  10980
tgatttttac caagaaatat ttttataaaa aattaatata ttttgtaata aactttattt  11040
ccaatgactg ttaaaataag gaaactatcc ttagttagtc gaggaagatg gttaggttat  11100
ttcgcaatcc gataaaatgt ttattttatc gtaggtctcg taaaatccag gaaaaaaaat  11160
tacggaagag tttaaaaaag ctaaattttt accaccctcc agaagattgt tgtcaaatat  11220
atcgtttgct agaaaatgtt cctggaggaa cttactttat tacagaaaat atgacgaatg  11280
atttaattat ggtcgtaaag gattcggtgg ataaaaaaat taaaagcatt aaattatatc  11340
ttcatggaag ttatattaag attcatcagc actattatat taatatttat atgtatctta  11400
tgagatatac ccaaatttat aaatatccct taatttgttt taacaaatat tataacatct  11460
aagtaaatat tcttggaatg gattttctta tagaatggtt acaggatatg tcagcgacag  11520
gcttaataac aaatttgtta atattttttt gttaaataaa tgaacaggcc accatttaat  11580
attacccgtt gcaaaataag aaaaaaaaac aaacttatag ttacaaatca tcttgattaa  11640
tcacatgtcg ttttaactca atgaaccatt ctaaatcttt gggttgtgaa caattcatgt  11700
tatgttgata gtgtatccta aagtgagctt catacataca ccggtcatgc caccgggaaa  11760
ctgtacaatt aacaatataa tcattttgcg taataatagg gtggtcacta aacactttat  11820
ttttacacat tccatcttta caggtccagc agaagtcaca gtgttttgca taggtgcacc  11880
agaacttgag atccctttca ggaggcctac gcatttgcat cggattatct gtggaaagag  11940
gtaggttcat tattatgttc gtcatcaaaa ttcctaaaag aacatagaag ccaagaaaga  12000
taagcagtct tgtagcggct tgcattcgca ttcgtgagta ttgtttgcga acatagctta  12060
tgagagcaat ggtagctatc atacaaagac aagtatgttt gatattctca gtgtcaatga  12120
ccctatcctc ctttatttgc attaactcat caaaccaatc ataatatgtg ggatttgtac  12180
```

-continued

```
agctcatgat gtgaaagcgg cgtatcctag agtctgtaaa gtagctacat ctttcattat  12240
agcgagaaac cctacatatt tgtatgtaat catttttttt gatgagaggg tgtttttcaa  12300
aaaccttatt tttacaaacc ccgtgtcgac aattccagca gaagtcacac gattttgcat  12360
aggtgcacca atactcaagc tctctctttg gaggtctccg ggtcattggt aactctcctg  12420
ttcctggaaa agattggctt tgaatgaccg gctgcatgac cgccagtacc aaaaggaaca  12480
caatcacctt catggctgca acttataagt tgcaacttat gggttgcaat actgcaacgt  12540
ataggttgca ccttatagat cgcgactcaa aaggtatgaa aaccttaccc tcaatacaga  12600
atttaagttt taatcctgat aatgtatctg tttatgaaaa aaaatttttt ttactcatgt  12660
atgaattctt atacgaatca taatatgtag gctgagaata ataattcata tacggtgttg  12720
cgggctcaat aaaaatttg ttaccacaaa aaataaatgc tggattttta agatatatat  12780
ctattaatga ctaaaccctt tatacgctgt aggctgaaaa caatccatat aatgaatata  12840
cggtgatttg ggtttaataa aatacataca acggtcaaaa tagcgggcaa tactacattg  12900
actaatataa tcattttgtt taataagagg catatcatcc cacactttat ttttacaaat  12960
accgttccta cattcccagc agaaatcaca gtgttttcca tacgtgcacc agtattcaag  13020
ctctcttata ggaggcgtat aagtccttgg taaattttgt ttcatataaa agatggaaag  13080
gggtcgattt aaacccggct gagatagcca aatcaaaata cataaaagag caagtagttt  13140
catagtggta tttagatgta aatttttata gtatgcaaat acaatgtaac ctacaaatac  13200
aatactaaat acaaggtaaa aacaacaatg tcttataatg attggccaat aatcaccccc  13260
ccccccccca tttttccatg aatatttcat ttcctgtata gggtctagga tgtgaacact  13320
ccatgttatg atgattaggc attttaactg atatttcata aaaacacccc caggaattgc  13380
gattaactat acagtttaca atcgaattca tcgaattaga ctcatttgtt atcttatttt  13440
tacaaatgcc attttgacaa tcccagcaga agtcacaatt ctttacatac gtacaccaat  13500
atggaagctc ctccttagga ggatgctggg ttcttggtaa ttctggtaat tcatgtgcaa  13560
gaatgaggac tgagtagccc aacaaaagtc ctagaacctt catgttgtgt ccaaatggca  13620
cctgtcattt taaaaaagat ttaaattttg ctaccgcaaa aaaaatccag tatgtatttt  13680
tttaatacat ataattattg aagtcttata agataaagcc gagaacacta tattttgtat  13740
agatgatgta tccggtattc aaactctctt ataagtacat gtaggaaatg gtcaattatt  13800
caagattggc tgagataaca acaaaaccaa aatactcaaa agcataagta atttcatggt  13860
tgtactcagt cgtagatttt tgcagatcgc aaatgcaacg caaccagcaa atacaaagct  13920
aaatacaagg taaaaacaat aataccttat aatgattggc caattcttat ccctccattt  13980
ttccatgaac atttcatgtt cataaagtct aggatacgaa caacatttca tgctatgatg  14040
attaggtatt ttaagtgata tttcataaaa acaccacggg gttgttggtg attgataggt  14100
aagaataagg atggttgaat aacctagtaa aagtcctaga aaaaccttca tattgcgttc  14160
ataccacaga tgttatttaa aaaaaatata aattttacag tatgtgatat acacatacca  14220
caaaaatgtt cttatattaa ctaaaatatg tgggcagaga gcaattcata taatgaatat  14280
atggtatttt aggctcaata aagtacatac aacgatcaat aaaacgggta atactacatt  14340
tactgatgta atcattttga acaataagag gcatatcatc caaaacctta tttttacaaa  14400
taccattctt acaatcccag cagaaatcac agtgttttcc atacgtacac caatattcaa  14460
gttctctcat aggaggcgta taggtccttg gtaaaatttg tttcgtataa aagatggaaa  14520
ggggtcgatt taaaactggc tgtgctaacc aaaccaaaat actcaaaaga acgaaaagtt  14580
```

tcatggttgt actcagacgc agattcttac aaagcgcaca tacaaagcag cctgtatatg 14640
caataccaat gatgaaatag agacagtatt gctttataga taattgttga tggtcacccc 14700
cccccccccc ccatgtttgc atgaatattt catttcctgt atagggtcta ggatgtaaac 14760
attccatgct aaagtgatta ggcattttag atgaaatttc atataaacag gattgagtct 14820
tggaatcacg gaaaactcta cagtttacaa tagaatgatt ggagtcaatg aaacgagatt 14880
ccgttatctt atttttgcaa atgccatctt gacagtccca acagaaatcg cattgtggta 14940
catacgtaca ccaatatgaa agctcactct tgggaggatg ctgggttctt ggtaagtctg 15000
gtaattcatg tgcgagaatg aggactgagt agcccaacaa aagtcccaga agaaccttca 15060
tgttgcgtct aaatgacacc tgcacttaca aaaaaaaatt taaattttga atataacaca 15120
aaaaaaccac cttaaaattt cttatattat ttcttggatc tgccccgacg tcatacaatg 15180
tattaaaatt atagaccaat catctttttg tatataggct aatcatcttt atatatagat 15240
tttagatgtt tgcttgttgt atcaacttaa ctgctagcga agaaaatgga taaaaacttt 15300
ctgtattttt ataggttgaa atcattttat gcacatcgct aggatctaat attttatttt 15360
gaagaaccga atgtgggctt aaaatttttt tcttagaaaa aagtagaatc ataatattgc 15420
tatgtttttg tttaatgatt tcttgtatct tttttgtata cgggttggca cccaaaccta 15480
tacaaaaata tacattactc aaataactac cttctataca taatcttttt tccccacgta 15540
ttttcctatt tatttcccta tttatggaat taaaggatat caatctctct aaggcacggt 15600
caaggtctgc gcctaaggca aaacaataat atatacctaa tttattccca gggcgtgcac 15660
aggcaagaaa catcatgacg tttagcccta aacgtatatt ttcctgaaaa tacgcatgat 15720
gaacttcatc aatattacct aagtatatgg ccgtttgtaa acgccaaaga tctaaatgag 15780
gaaatttttt actaagataa tgaataggtt ttgtgagatt aaaatctatg gcgaacttat 15840
accaaaattt taatacaagt gtatttctcg tcatttcttc ttctttttca tctaaatata 15900
agataaaacg attgtaaaca aagtctatca ataggtgaaa atcattgcta ttaaagctgt 15960
cgagaatcaa aatattgtca taataaattt cgatcgccag taaaaccttt tttcgtttga 16020
cgagataaac aaacatatta tacaacccta catctaaaaa ttctggattg gctcctagtt 16080
ggatacacag gtctttagtc tgcttcgttt tggcacacat gatgccaaaa ttaatatcag 16140
caccccataa aacaaataac ttgattagat cagtctggtt ttccttcaca gcttttacta 16200
aggctctgtc aagctcatag ctgtcgacat cagagcatga catagagcca ccggttacca 16260
ttttacattg cttacaaaaa cctatgggtc cgttttccca ccatagtcca agctgttgta 16320
gaataaaaat atcatcctca tgataatttg aaaaagcctt ggtttctatc aagacttttt 16380
ttgtaagaac ctgtaaagag ttcatcgtat tattatgaat aacaggagta aacgtaatca 16440
attataaaag tgattttttc gaaaaaaact ttagatggtt gaaaatgata atgtacatgt 16500
tcatacaaaa aatagatgca gtgatgtcta aaatcaaaat ttaattttct atgtaaaaag 16560
tacagactta cttatttggg ttaaattgtt tattttaaac tttaattaac cgtttgagtt 16620
agcgatgttt gatttatctt ccatactcat ccgggggggg ggggtcctta tagctctgac 16680
attattgtgg attattgaat ataatgaata cttcatagat gctaaacatt ttaatagtag 16740
ttctgaggct taattgtact ctataaattt ataaaaactt tttgatcaaa atttaatttc 16800
ttataaaaag agtacagacg tcgcttgttt aagcttcatc atgtttcatt cattactttc 16860
tacaattacg ggggggggga gtcccctcat agctttagta ttgctatggt ttactaatta 16920

```
ttatgtagaa tttatagaag catatgtacc tgaaagtata cctactctat aaaattaaat  16980
aatttcagta tatttttttt atgaatagaa cggaaatgat ataaaaataa tttaatattg  17040
caaaaaaaat tcataatgtt ggtatgtatt ataaacataa tagcatgtgt aatttataaa  17100
ctgactcctc tatataatta ttagatgagg taccaaccta cttatgatat gccgatgata  17160
gatattgtat actataaaac aaaattattt taaatgtatt catggataca ttataacatt  17220
tttaccgcaa attgtctctc agcgaagaaa atgaatgaaa cgtttctgta tattcatagg  17280
ttgaaattat tttacgcact tcactaggtt ctaatatttt cttatgaagt attgaatggg  17340
ggcttaaaag tcctttctta aaaagaagtt tcatcataac attcttttct tgtctaagaa  17400
gagtttcttg tatttttttt gtataaggat tggcacccaa acttatacaa aaatgtacat  17460
tactccaaat accataattt gaaaagaaag ttatttccct atttacttca tgattaatga  17520
aacctatcaa cgtctctaag gccgtattga tatttgcgcc taaggcaaaa caatagtata  17580
tacccaattt attttgaggg tacatacaag caagcgacat catgtcattt ggatctaaac  17640
gtatattttc ctgaaaatat gcatgatgga tttcatcaac attacctaag tatacagccg  17700
tttttaaacg ccaataatct aggtgaggaa atttcttact aagaaaacga ataggtttta  17760
taagattaaa ctctatggcg atcttaaacc aaaattttaa tacatatgta tttttttatca  17820
tttttcttt ttcatctaaa tttaagataa aacgattgta aataaagtct atcaacacgt  17880
aaaaatcatg gctatcaaaa ctgtcgagaa tcgaaatatt gtcataataa atatctatag  17940
ctaataagac cttttgttgt ttaattagat caacaaacat attatacaac cctacatcta  18000
aaaattttgg atcagctcct agttgaatac acagaacttt cgtcctttcc gtcttggcac  18060
atatgatgcc ataattaatg ttggcacccc ataaaacaaa taacttgatt agatcagtct  18120
ggtttttctt cacagccctc accaaggctc tgtcaagctc atagctgtca acatcagaac  18180
atgacataga gccactggtt accattttac attgtttaca aaaacctatg ggtccgtttt  18240
cccaccataa tccaagctgc tgtaaaataa aaatatcatc ctcatgataa tttgaaaaag  18300
ccttgttttc tatcaagact ttttttgtaa gaacctgtaa agaattcatc gtattatcat  18360
gaatgaaagc agtaaatgta atcaattata aaattgactt attgaagaga aatgttaaat  18420
gagtgaaatc ggtgtttatg atgatgtaca tgatcatacg aagaaacacg ttcactggtg  18480
tccatgatca aaatttaatg ttttacgtaa aaagtacaga tgttaactgt ttagtttaaa  18540
cataaattta acctttagtt taaaccctag ttaatgatgt ttaatatttc ttctatactc  18600
attcagggaa gtgtaatgat tctaatactg ttgttatgga ttattaatga aaactttaca  18660
gatgctggag ggaataattt taatcatact gttttaatgt agctatataa gctttcatca  18720
aaatttaatt tttttataa aaatacacga attaaactaa agtctaaact ttagtttgac  18780
tatttgagtt aatgatgctt aacttatctt ccatgcttat caaggggggg tcctaatagt  18840
tttgatacta ttgttgtgga ttgttgaata taataaatac tttatagatg ctgaaatgtt  18900
tgaaaataat agtacatcaa tgttgtaagt ttgatcaaaa tttaatttct cataaaaaag  18960
gtacacatca acattgctca tttaagtttc atgatgtttg attcattact tcctacaatt  19020
actggggggg gggggggtc tttaatagct ttagcattgt tatggtttgc tgactattat  19080
gtagaattca tagaagcacg tttagatagt aatatcactg cagtgtagat tatgaaatac  19140
atactaaact aatttcagta tatttttttt gttcatataa gttaaggtac aaaaatgatt  19200
aaacattgca aaaaaagaaa atcacaatgc tattatacat agtgatcata gtggcttgta  19260
tcatttctaa actagttcca aatgaatatt gggcaataca tctatttttt atcattatga  19320
```

tttttatggt atatatgtat gaaaagttag atatacatca aaaatctcag ttctggaatt 19380
ataccatgtc aggcttatct ggacataacg tacaggtaac atgtaagtgt tactaaatac 19440
tatgaagtat ctattttttt tgttgtaaaa aaaagaactt gatagtattt tttaaaaaat 19500
aaaataatta attgtacgtc aacttcctta ttttattctt taaaaataac tcgtaagtat 19560
tatttatcta ttttttgaaa aaatagatgt aatcggtttc atcatttagg tgtgtatttc 19620
tttttagcat ctatcaagaa ttcattgttt agtgatatga aaacaatgaa tgatcattat 19680
cttctattta acaaccacct aaataaatga acgtcttttt catcttaact gattaccaaa 19740
agttattttg cgaaaaggca tacatatgat caatatcaga cctacaatga atatttccat 19800
aatatccctt tattgtaata attctatttt tgcattccga tatctcatca tctgtgctat 19860
tatatgtttc cataactgtt tcatcatcaa acataaatcc tgttaaatag gcaaaagact 19920
ttaatcccgg atagattttt accattttcc tgagagccgt gtatagcttg taataaatgg 19980
ccaaaaaatat gcaataaagc gtagaaagag agtaattttt ggcataaaag attttgaagg 20040
tttgatgaat ggctaaatcg catataatat aagatacgat tttaaagcgc acctgttcac 20100
gcagatttgt tgaaaaattc gtggaaagat ttaacaaata aaaggttatt aatagttgct 20160
catcattccc cttatacgac atcgtcagac gctctaatat tttactacta ggcacatctg 20220
ccacatgttg aacatttaaa gcctgttctt cttctgtgtt acggcaaaag agccgtgcgt 20280
attcaggtga agctccccag gataacaacg tccttgctac ggctaaattt tttttgacga 20340
tgacttttat cagaaataag tctttatttt tgcattgatc actatgcgaa tttgtatagt 20400
tgacgccgtt gcattgagta cattgatata atgttttaca attccagcgt agccctaaat 20460
ggtataaaag aactgtattt tcgacataag catgctgatt aacgatgttt ttgagacaac 20520
acgtcgttaa ggacaccata ttgtctccaa tttgttagat aaaagtcttt actaaaaaaa 20580
tagattttta gttttaacaa tcgagatttt attatttgga tgcatcatca aaaagattta 20640
taagtataag aggttgtata agaaaaaaat gatgttatac tatttatgtt aaaatttaat 20700
ttatcatata aaaagtacag atttaatcag ttggttaaac tatttagtta attaaactaa 20760
atagtttaac catttagtca gactacttgg ttagcaatgt ttgagctttc ttccattctt 20820
atccgggggg gggggtccta atcgttctaa tactattgtg gatagttgaa tataatgaag 20880
actttataga tgctataatg atgaattcta gtatgcctgt ataaaataat taaccttttt 20940
gatcaaaatt taattttttt ataaaaagct acagagtagt gttttattaa acgtggctta 21000
tttaaaagtt acacaatgtt aaaatctcta cttactttaa ttctttgtgg ggttttatta 21060
actttatcca tattatggct tactacttac catgtagaac ttatagaggc aatagatgat 21120
ttctacgact gaaatataga atagtccatt ttctatttgt aaaataatga tttatattct 21180
ttcctaaaaa tgatacttta tatggtttga aaacaaatat taacaacttg attttttttt 21240
ctataaataa actataaatg aaaatagtaa aactcataga gtcttataag tgaacatctt 21300
cataatgtta ctcaaacgtt ggactattaa aaaatattcc gtgtgcatta ttgcttttaa 21360
tcagtatgat tactttatac gaagccgcta ttaaaacgct tatcacacac cgaaaacaaa 21420
ttttaaaaca ccccgatagc cgtgaaattt tactagcttt ggggttgtac tgggataaaa 21480
ctcatattct tgttaaatgt cgtgaatgtg ggaatatgag tcttaccgga aaacacagta 21540
caaaatgtat taacattaat tgtctactta ttcttgccat aaaaaaaaga ataagcgtat 21600
tgttgatacc ttgataggaa tgggcgcgga tgtaacatat atacatcttt taaagaataa 21660

```
gataaaactg tcatacaacc agctgtctat gcttaaaagc aactcgcaga tttcattgaa  21720
ggagcttcat gctatatgct atcttttata tggtcggctt cccaaaaaaa ttaaacaagg  21780
gatgcgactg tgtaaaacaa tggcgggact atgtggtgaa cttttatgtg catttttagc  21840
tccgtaaatg ataatatgta tttaaaacaa acagatatta ccaaaatata ttctatgtac  21900
ataatatctg ggaaattatt ttttttctc atacccttaa atataaaaat attgggtttc  21960
ttcactaaac tttagaggta aaaatttttc tttgttttgc accatcatgt atgggtttag  22020
gctgtcccag ggattgttta tttgaatatt tcctaaatag gaacacaacg ccatgatcat  22080
atatctttca ttctggtaag ctttttgata catcttcaaa gatgccgtac ctccgagtgt  22140
gtaacagcaa acaaacgtcc gtacttttcc atgggtcgca gcccattcca ttccgtagct  22200
cagcatcttt tgctgtattt ttttattcgc tttataaaaa aagtttttca tccattccac  22260
gttctcataa aaacaggcac ttaaaaagag cactaggggt agtgtagtct tattatagaa  22320
tgtaggaatg tatgttttag ttattttttt caacgcgtgt tccatactat gttttaccgc  22380
cataaaaata caaaaccaat accaactttt tctataaaag gttttgctgt acacatataa  22440
acgagcaaaa tatatttcaa actctatatt ctttttataa aaaaactcga gacagtcgtt  22500
tatgttacga ctttttctaa atacctcaaa aacagtaatt aattcactgt cgctgtggaa  22560
atgttcgtaa gctaactgtt taatgtcttt aggggtcaat tctttttttg ggagcagtgg  22620
tttgagattc ggcaaaggtc gtctaaagta gtgagcgaac ttttcattcg ctccccaaca  22680
caaaagccga taagccagca tgtagttatc acgttttacc gcgtaaataa gcaaatagtt  22740
tatattgata catgtaccat gttgctgccc gtttggacat atgttgccgc attctgaaca  22800
cttatgaatg agatcatagt tcttacaaca taaccccaaa cgggttagta cttctttgtc  22860
acgttttaaa aactcgacat gattctttaa tgttaatgct ttgagcgcaa tgttaaataa  22920
actctgcatt ttattaaaat gaggttagta tcatgtttta gtataaaatt tagcggctgt  22980
ttacataatg ctaaataaac ttaacgttcc tactaaacca aaaaaaatca aattgactaa  23040
gtcatagaga atttgacgat gttggtaggt aatttttaa catggtatat attttttag  23100
ggtcggttat attaggtaat aaaagaggac gtgccgttaa agtattttgc ttaagatcct  23160
ttagatcctt acaaaaatat agattgttcg tctgatgatg ccactgtgtt gcagtgatgg  23220
cttgatcaat atcacctccc aagacaaaac agtagtatat cgttaaaaag ttgtaatctt  23280
tcatacaagc caactgcatc attttatcga tgtccatatg aacgatcttt tgctcgtata  23340
tttcatgaag gtcaaataca ttgttgaagt aaatggcgca catgagtcgc cacatactaa  23400
ggtgcccata tgtttgatag aaaaaggaga tagctctttt aagcttatat tttactgcta  23460
tggcatagca gtatttaacg aatacgttca tgggtacatt atctaagata taaaatatga  23520
aaaactttaa ctctcgatga atctcttccc ccatttcctg tacatttaga gcttccaaca  23580
taggattttt atcaaatatt tcatgacata aaataatgtt attgctcgtt ttatgacgca  23640
ttaaaccggt gaaaatttcc ttattattta aactatcttt agctcctaac tttcgacaca  23700
gctcctgagt ttgttccgtc ctagcacagg tcagcccata ataaatgttt gctccccact  23760
cggtgaacag ccttattacg tcatagttat tttcttttat ggccatgatt aatgccacat  23820
caagatgaag aagttccccc ttaaaggggg ttgagcttaa aataacgtaa ttacagtagt  23880
gacataagct aatgggcttg ttttgccacc ataagccaca atattttaaa atataatgat  23940
actcctcagg cacgctctgt ttggccacag cctttttggc cagggtttgc aaggagagca  24000
tgataacttc ttgaaaaaaa aactcaaatt aagttcctac ttttttaaaa tattagtatg  24060
```

gacagatcta ccatcatatg aaggaattct ttcatcgtta aacactgaag agataatact 24120
ttcatcgtat agagaatatc atgtcaatcc atatattgaa tgttatatat cattaaaccc 24180
atcattaata tagtgtttat gtgctatgga caggtttttt gaatgataat cttttaacat 24240
acgttttata acttcgggat cagtttcttt taaagataaa gaatcattca tgttataaca 24300
atttaatgat aacatgctgg caatgaacga gttgtctttt tgatgcgcta gagtctttcc 24360
ctcctcaaag gcattggcgc ctaagtctat acaaaagaat atgtttccga tattatagaa 24420
ctgaatagaa tgaaacatgg cctgattgat atcagcccct aagacgacgc aacagtaata 24480
aatcgttaaa tagttatagt tcttgcgaca ggcccacttt agcatttcat tcatgtctat 24540
gcgaatcctc tccttttcgt acacttcgtg aagttcaaac acattattgt aaaaaagggc 24600
gcacataagc cgccaccgat gtagatgagc atatctctga taaaaatagc aaatcgcctc 24660
cttaaggtta cattctattg ccatcgcgta ccaatattta gtaaacatct cgcttaatat 24720
atcggtttct accattaatc cctccagttg ttcataaatc attcccttta cttcaaaacg 24780
atttatggta tctaaaatgg gattattaga aaatacctca tggcagaaaa tgatgttact 24840
gctagttaga tcacgtttca atgtgtaaaa aaatcgtaaa atttcctggt catttaactg 24900
ttctttggca cctagctgcc tgcacaggtc tcgggtgtgc tccgtgttga cagaaagcaa 24960
accgtagttg atgtttgcac cccactcggt gaacaattct attagatcgt gattgttttc 25020
ctccacagct ttcaccaagg ccgcgttaag atttgtgccg ttcttaaaat acggcgtcca 25080
tattttcttt tgatgataca tgatagggcc attatgccac catagaccgc agcacttcaa 25140
aaaatgagga tggcatttgg ccggatactg gctggccagc accttttttgg tgagagtctg 25200
cagagagagg accatatttc ttttttttga aaaaatcaaa ttaaaaaaat catgcttgtt 25260
tagcatacat gtaatattgt tataattacg ttataattac gttataatta cgttataact 25320
atattataac aatggtataa caatggtata acaatgttat aacaatgtta taacgatgta 25380
tcattgatgt catcattcaa ctaggccaac atacttttta atttatagtt ttttaataga 25440
tgatatattt tgttaggatc tgcttctttt aacgttaata gcgaggagtc tgcactataa 25500
atgtctaatg ataaatgatg agatatcaaa tagtaattcc gttgctctgc tagggccttt 25560
gcctcttcaa aggcgtcggc tcccagatct atacaaaaga acaagttatc catattataa 25620
aatcgtacgc aggcaagcat agctgaatta atattagctc ctaagagaaa acaataatat 25680
atggttaaaa aattgttatc ttttgtgcag gccatccgca tcatttcatc cacgtccatg 25740
cggatctttt ccttttcata caaattatgt aggtcaaaca gcttattaaa acaaagagca 25800
cagattaacc accacgtatt tagatactta aaatgttggt aaacataaga aatggcctcc 25860
ctaagattat cctgcaatgc cactataaaa cagtatatcg ttaacatatc accatccgac 25920
atattactta atatgtcggt gtcttctact aacctttca acttccaata tatggatgac 25980
cttatttccc ttataatgac ataggctgga aagggattat cattaaaaag tttaagacat 26040
aagataatat tactgctagt agtgccaggg tgtattaatt taaagaacat gtgcataatc 26100
ttctttttat ccacgcggta cttggctcct aattcccagc aaaattctcg aacaggcggc 26160
gtattggcgc aaattaaccc atagttgatg tctgcgcccc attctgtaaa cagttttatt 26220
aactgatagt tgttttcctt tgtagccaac attagtgccg tattaaggtc caagccgtct 26280
gcaaagcttg gcagctttat cagcatatgt ttgcaatcaa gggaaattgg ggccttatac 26340
caccatagtc cgcagcgttc taagataaca tggtactcaa tagatacttg ctgtctggct 26400

-continued agtacctttt tggcgaagga ttgtaaggaa ggaaacatcc tgtttctttt tttttaaaaa 26460
tcaattatct ttgttcataa tcaagaaaaa tccccatatt tattgagtga taattttttta 26520 acatgcaatt tattttttca gggtccgtaa cgatcgacaa cagagaaata accggattgt 26580
aatgctttaa tgataaggca tgggctatca gataattttc cttttgttct gccaaagctt 26640
tgccctcctc aaaggcatcg gcacccaggt ctatacaaaa gaacaggttt ccaagattat 26700
agttttgtat ggaaacaagc atggcttgat tgatgttggc tcccatgata aaacagtagt 26760
aaatggccga atagctataa tcttggatgc aggctatgtg catcatttca tcaatatcca 26820
tgcggaccct ttctatttcg tacagctcgt gaaggtcgaa cacgttgttg taaaaaaggg 26880
cgcacatgag ccgccaccta tgtagacgcg ggtatttctg gtaaaagtag cggatagcat 26940
ctttgaggtc atagtccacc gctatcgcgt accagtattt ggttaaaaca gtgctaaagc 27000
tatcatcatg gtccagcatg aaggttatct ccatgagccc tcttaactcc cacatgattt 27060 ccccccctcag atccagatta tctataatcc ttaaattggg gttattggaa aacacctcgt 27120
ggcaaaagat aatattgcta ctggttttat cgcgcgttgt atcaaagaaa atttttaaaa 27180
tatactctct ttctaaatat tctttggctc ccagctcttt gcacagatca cgggtatttt 27240
ccgtgagagc acaaatcatt ccatagttaa tatctgcacc ccattcagta aacagcttta 27300
tcaagtcatg attattctcc ttcacggctt tcatcagtcc tatgtttaac tcgatacctt 27360
gactaaaaca ggttgacctt ataaataatt tattgcgtcg aatatgaagc ataatggggc 27420
cattatgcca ccacaggcca caacacttca ggacatgata ttgatctacc ggtatacact 27480
gcccggccag tactttcttc gtgagggatt gcagggaagg caacatgcct ttccatcctt 27540
tgacggaaat caaattatct actaataact atcagtgttt atattaagta tttagatatt 27600
atcccgggct ggatacgtag tatcgctatt cacatgtact tccaactcta gccggagcct 27660
gcagggtcat ttatttttaa tattgattct tttttgtatt taatcattta gagaaggtca 27720
tcataggagc cagatgttct ctctccagaa cttatgtcga aaaacattac ctaaccgtaa 27780
acttcctgaa ttttttgacg aatatatatt acaactgctg ggattatact gggaaaacca 27840
tggaactatt caacgagcag gaaacaactg tgtgcttata cagcaacata ccctcattcc 27900
cgtaaatgaa gccctgagaa cagcagcatc tgaagaaaat tatgagatcg tgagcctttt 27960
attagcgtgg gaggggaacc tttactatgc tattataggg gctctagagg gcaaccgcca 28020
cgacttaatt cgtaaatatg atgaccaaat caaggaccat catgaaattc tgccattcat 28080
tgacgatcca gtcatatttc acaaatgcca tatcatgcgg caatgctttt ttgattgtat 28140
tttatatcaa gctgtaaaat atagtaagtt tcgcgttctt ctttacttta aacatagatt 28200
agaggatgat ttgcccttca ctcatttact tattgaaaag gcatgtaaag atcataatta 28260
tgaagttatt aaatggatat atgaaaacct acatatctac aatatgatag ataccttttga 28320 atgtgctatt gcccataagg atctacatct atattgtttg ggtatagat ttatatataa 28380 cagaatcgta cccgataagt atcatcattt agatattcgc atgctttcaa gcctacaact 28440
cctacataag gtggcagcca aaggatactt agattttatc ctagaaacct taaagtatga 28500
tcataataaa gataatataa atattattct aacacaagct gcaacctata accatagaaa 28560
aattttaatc tatttcattc ctcaatcaac ccacgcacag atagaacaat gtttactagt 28620
ggcgataaaa gcaaaatctt ccaggaaaac cttgaactta ctactgtctc acctaaacct 28680
ttccatcaac ctcatcaaaa aaataagcca ttatgttgcc acttacaatt caacaaatat 28740
aataggcatt ctgagtatgc ggcggaaaaa gaagatatat ttagatatca tattgacaaa 28800

```
atttgtaaaa aaagctattt ttaataagtt tgtcgttcga tgtatggata cattttctat  28860
aaacccggaa agaatcctta aaatagccgc gcgaataaat aggatgatgt tagtgaaaaa  28920
aatatctgaa catgtttgga aaaatcatgc ggttagactt aaatacctta aacatgcggt  28980
acacacgatg aagcataaag atgggaaaaa tagactcatg aactttatct atgatcgctg  29040
ttattaccat atgcaagggg aagaaatctt tagcctcgca agattttatg caatccatca  29100
tgcaccaaag ttgtttgacg ttttttatga ttgttgtatc ctagatacga tacgattcaa  29160
aagccttctt ttagattgtt cacatatcat aggtaaaaac gctcatgatg ctaccaatat  29220
caacatcgtg aacaagtata tcggcaacct gtttgttatg ggagttctta gcaaaaaaga  29280
aatcttacag gactatccat ccatttattc taaacaatac atgccttagt ttattttttt  29340
tgcggccgaa acattattct taccctagaa aacgcttata gtcatcttaa atcataggta  29400
aggaagatca tcatattttt tgaaacgtaa tttttttaacg catgatctat gatttcaggg  29460
tccgtgcttt taggcaacgg ggtggtggcc ggactataaa tctttaggga taaaatgttc  29520
tttataagct catacccttc ccctaaagct gtagtaccct cttcgaaaac atcagccccc  29580
agatctatac aaaagaacat gttttctata ttatagtact gtattgagct aagcatggct  29640
tgattgatgt tggcgcccag gacatagcag tagtacatgg ttgaaaggtt gtggtctttg  29700
atgcaggcga tccgcatcat ctcttctatg tccatatgga tcttgtcctt ttcatacgcc  29760
tcatgaaggt caaacacatt attaaaacaa agagcacatg ttaaccgcca cgtattcagg  29820
tgtgtatatt tttggtaaaa atactgtatg gcctctttca ggttatagcg tatggctata  29880
gcgtaccagt atttgagtag taatgtactg agcgaaaact cattatttag cagatcggtt  29940
tttactatta actcccttaa ctcccagaaa atttctatcc tcatttttat attatttact  30000
ttttgtaata tcggattgtt ggaaaacacc tcatggcata aaataatgtt actactagtt  30060
ttatgaaact ttagatctat aaaaatttgt aaaatttctt cttcattcaa ggtttccttg  30120
gcacctagct ctcgacagag gtcccaggtg tgctccgtgt tgacagatac cagcccgtag  30180
ttgatgtccg ccccccactc tgcaaacagt tttataaggt tgtagttgtt ttcccttaca  30240
gccttcacta acgccgtatt taggtttaag ccctctttaa tacctgctga ttttatgagc  30300
cttaggttat gatcaaacgt gatcggagca tcatgccacc ataggtcata acactttaaa  30360
agataatgtt ggttcgtggg cacgcattgt ccagccaaca cctttttggt cagagattgc  30420
agggaaggca acatgtctct tcatctttta aaaaaaaatc aaattaatta gccgaataaa  30480
tttttctttc gagggctttt taaaagagct ctttaagagc tctttaagag ctttttaaga  30540
gattaaaaaa ttattcttgc tggcattctg ccaagtatgc ggcattccta tcatctatag  30600
tatattatga gaatattccc aaatgatgga taagtttttt gatttataat cttttaataa  30660
actgcttatt tcttcggggt cctttaagtt tagtggcaag gaagcatctg agctgtaaat  30720
atccaaagcc aaactatggc tcagaaaatt ataacctttt tgttccgcta tggcacgacc  30780
ctcttcaaag gcattaccac ccaaatctat acagaaaaat atattaccga tgttataata  30840
ttgtactgaa gtaagcatag cttggttgat gttgcccccc agcgcgtaac agtaatatat  30900
tgttaatgga ttgttatcct tggtagaagc cagacatatc atgtcatgga cgtctatttg  30960
gatgttttcc ttgtggtaca tctcatgaag ctcatatatt ttgttataat acaggagaca  31020
ttttaatcgc cattcattaa gatccgtata tttctcatct agaaaacaaa tggcgtcctt  31080
acaatcgtat tgtactgctt tggcgtacca atacttcact agtaaaccat ttaactcgtc  31140
```

cgtttctttt atttctatga gcccccatag tcttttataa attaagcccc ttaattgtat 31200
aacaaatttg ttttctaaaa taggattatt cataaaaatt tcatggcaca aaataatact 31260
gccgctggtt ttattgtgca ttatcctggt aaaaatacgg aaaatatcgt tgtcctctag 31320
agtttctttg gcgcctagct gtctacacaa ctctcggatg tgcttcgtat tgatagaaag 31380
caaaccatag ttgatatttg cgccccactc tgtaaagagc tttatcagac tatagttgtt 31440
ttccttaaca gctattatta atgccacacg aaggtctata tcttctccta aaaatcctga 31500
ttttatttgt attcggccac gatccataca aagcttgaga ggagcatcat gccaccatag 31560
gccacaatat ttcaaaatgc agtgttcatc tattgacaaa cactggctgg ctatcgtctt 31620
tttgacgagg gtctgcagag agagcggcaa cgacatgttt ctttttcacc aaaaaaaatc 31680
aaatgttctc gtctttaaag gttaattcat gttcttaaaa tgttcatttc atgatagtga 31740
ttaataatat ggtttaataa cgctagaagg cttgtttata agacagtcat aagcagtcta 31800
taagacagtc tataagcagt ctataagaca gtctatgact tagtctataa ctataatttc 31860
tggatgggct gtaagatact cttcggctcg tttcagattt tttgaagtat atgtctttag 31920
catatcatat atttcctggg gttcggttac atctaatacc aaggtcacat cacggctgaa 31980
aagctgcttt actaagaaaa tgttgctcaa gttatacata taagctttgt gcgcaatgag 32040
ttgtgcccta tcaaaatcgg cagcccccaa atcaatacag aaaaacatgt ttaaagtatt 32100
attgttatag atagaaagat tcatgccata atcgagacta gcccccaacc tatgacagta 32160
ataaatggcc gcgtaatttt tttcccgcaa gcaagcaaat ttcatcatca gattagggct 32220
gatgcaaatc tctttttcac gacacaactc gtgtatgtca aaaatgttat taaaataaag 32280
gctacaagct acccgccaat agaggtgatt tttatgcctt ttatagaaat agtgaatagc 32340
ctttgtaaaa ttatgtcgta atgccagggc aaaccaaaac tttgttaata ggtggtgcgc 32400
cgtatccccc gtcaacggaa tgtttgaaca ggtgtacgta actgtgtcta aagtggttct 32460
agttacggtt tccaagagtg gattatgaca aaacatgtca taacccagca gaactcctgc 32520
acaggatttt agcctggcca cttcttttaa aatttccaga agacggggtt cggatacagg 32580
cgttaagcct cccagttccg cacacagccg ctttagatac acggcaggaa cacgtataag 32640
cccatattca ggatttgcgc cccaatccac aaataaacgt ataagttcaa gattatcgct 32700
cttcacggcc tttactagcg ccgcttcgag acaaagatca tcctcagaaa aacactgtaa 32760
atgtttatac gaaaaaactt gcttacaatt gttacatagg tgaataggac ctaaatccca 32820
ccacaaacca aaacgctgca acgtataatc atagtcactt gaaagataat tgcatgccac 32880
aactttttg gccaacgttt gtaaagacaa catactaagt ttaaaacatc ttaaatctaa 32940
gctagctaac tttcaagaaa accctctatc cctaagaata tatcttataa ctagacttat 33000
agcagtaaaa atcaactttg gttattcttt ttaatataaa acgtctaatt acttgcaaag 33060
gactataaag cccattttcc tcagctagaa tttttatttt ttaatgaagt agggggatat 33120
gttttccctt caagaccttt gccgaaagca tctttttatt cttcccgatg tttttggcga 33180
gcatgtacta caacgattag gactgtattg gagatgtcac ggctcccttc aacgcatagg 33240
agacgaccac atactcatac gacgggatct catcctttcc accaacgagg ccttaagaat 33300
ggcgggagag gaaggaaaca atgaagtagt aaagctcttg ttactgtgga agggaaatct 33360
tcattacgcc gtcataggag ccttgcaggg tgatcaatat gacctgatcc ataagtatga 33420
aaaccaaatc ggcgactttc attttatctt accattgatt caagacgcga atacgtttga 33480
aaaatgccac gctttagaac gtttttgtgg tgtttcatgt ctgctaaaac atgctacaaa 33540

```
atacaacatg ctccctattc tccaaaaata ccaagaagag ctgtctatga gagcgtatct  33600
tcacgaaacc ctatttgaac tagcatgcct atggcagagg tatgatgtcc ttaaatggat  33660
agagcaaacc atacatgttt acgacctaaa gattatgttt aatattgcca tctccaagag  33720
ggatctgact atgtactcct taggatatat tttccttttt gatagaggga acaccgaagc  33780
tacgttgcta acgcaacatc tcaagaagac agcggccaaa gggctcctcc actttgtgct  33840
agaaacgtta aaatacggcg gcaacataga taccgtcctg acccaagccg taaagtacaa  33900
tcatagaaaa cttttagatt attttctgcg tcaactacct cgtaaacata ttgaaaaact  33960
tttgttgctg gccgtgcagg aaaaggcttc taaaaaaaca ttgaacttac tgttgtcaca  34020
tttaaactac tccgtgaaac gcatcaaaaa actaccgcgc tatgtgatag agtacgagtc  34080
caccttggtg ataaagattt tattaaaaaa aagagtgaac ctgatagatg ccatgttgga  34140
aaagatggta agatattttt ctgcgacgaa agtgaggacg atcatggatg agctttcgat  34200
tagtccggaa agagtcatta agatggctat acagaaaatg agaacggata tcgtaatcca  34260
tacttcttat gtttgggagg atgatctaga acgtcttact cgtcttaaaa atatggtata  34320
caccataaag tacgaacatg ggaaaaaaat gttaattaaa gtcatgcacg gcatatacaa  34380
aaacttatta tacggcgaaa gggaaaaagt catgttttat ttagccaagc tctatgttgc  34440
tcaaaacgcg gccacccaat tcagagacat ttgtaaggac tgttacaaac tggatgtggc  34500
acggtttaaa ccgcggttta agcaactaat attagactgt ttagaaatta ttactaaaaa  34560
atcttgctat agtatcctgg aaatcttaga aaaacatatt atttccctgt ttactatgaa  34620
agttatgact gaagaagaaa aaaacctatg tttagaaata ttatataaag taattcatta  34680
taaaacaata caatgttaaa attcaataga tatccatcat taatattgat tatattttcg  34740
aatattatct tctatggtgc aagataatca tctagcgcgt gaaacatgtc ctcttctctt  34800
caggaacttt gtcgaaaaaa gctgcctgac tgcatacttc cagagttttt tgacgactat  34860
gtattgcaac tgttaggact gcactggcaa gatcatggtt cccttcagcg tatcgagaag  34920
aaccagatac ttgttcaaca ggaacccatc catatcaatg aagcactcaa agtagcagca  34980
tcggaaggga actatgaaat cgtagagctg ttgttgtcat gggaggcaga tccccgctac  35040
gccgtcgtag gagccctaga aagcaaatac tatgacctgg tttacaaata ctatgaccaa  35100
gttaaagact gccatgatat cttgccgctg attcaaaatc cggaaacatt cgaaagatgt  35160
catgagttaa acagcacctg ttcactgaaa tgcttattca agcatgctgt gataaatgac  35220
atgctgccga ttcttcaaaa atatacagac tatctggata ggtgggagta ttgcagccag  35280
atgctgttcg aactggcatg tagtaaaaaa aaatatgaga tggttgtgtg gatagaggga  35340
gttctaggcg tcggcaaagt tacatctctt ttcaccattg cgattagcaa cagagaccta  35400
cagctgtatt ctctgggcta ctcaattatc cttgagaatt tgtactcctg tggacaggac  35460
cccaagtttt tactaaatca tttcctgcga gacgtttcaa taaaagggct tctacccttt  35520
gtaatcaaaa ccatagaata tggtggaagc aaggagatag ccataactct ggctaaaaaa  35580
tatcagcata aacatatttt gaaatacttc gaaacctggg aaagctaggt tcagtatggt  35640
gtactcacta ttgtagtgaa tcgtatcctg taaattttgt aaaaaagctt aaacttttga  35700
ccacatcata ttgttttaga aatctcaaac cagtgaacaa cagtcttatc atacattaaa  35760
attccagtaa aatttatatt ttttttggta aacaaatgtt ttctcttcaa gacatctgtc  35820
ggaaacatct ttttcaactt cctgacgctt ttgatgaata tatattacaa gcgctaggac  35880
```

-continued

```
tatactggga aaaacacgga tctcttcaac gaataagaaa ggacgctgtg tttgtacagc  35940
gaaacatcgt cctttctacc aatgaggccc tgagaatcgc agcctcagag ggaaacgaaa  36000
gggtaataaa acttctgtta tcatgggagg gaaattttca ttatgtgatc ataggagctc  36060
tagagggtga ccaatatgac ctaattcata agtatgatag tcaaattaaa gactaccaca  36120
tgattttatc attgatccaa aatgcaaata cctttgaaaa gtgtcatcag ttatccaata  36180
gtaatatgtg gtgtcttata cagaatgcta taaaatataa tatgctccct attctccaaa  36240
aacacagaaa tattctgaca catgagggag agaatcagga attgtttgag atggcatgtg  36300
aggaacagaa atatgacata gttttatgga taggacaaac cctaatgtta aatgagccgg  36360
agtttatttt tgatatcgcc ttcgaacgga tagatttttc tttattaaca atgggttata  36420
gccttctttt tgataacaag atgagtagta tagacattca tgatcaagaa gatcttactt  36480
cattaccaac agaacacctc gaaaaagcag ccactaaggg atgtttcttc tttatgctag  36540
aaactttaaa acatggtgga aatgtaaata tggcagtctt atctaaagct gttgagtata  36600
atcatagaaa aattttagac cattttattc ggcggcaaaa atgtttatca cgtgaagaga  36660
ttgaaaacct attattaacc gccataacca attgtgcatc cataaaaacg ttaaacttac  36720
tcttgtctta cctaaactat tccgtaaaaa atatcattgg aaaaatagta caacatgtca  36780
taaaagatgg tgattatacc atcatattac ttttaaaaaa aaagaaaata aacctagtgg  36840
aacctgtttt aacaggtttt atagattatt actatagcta ttgttttata aaacatttta  36900
tccaagagtt tgctattcgt ccggaaaaac tgattaaaat ggccgcgcga aaaggtaaac  36960
taaatatgat tatcgaattc cttaacgaaa aatatgttca taaagatgat cttggaacta  37020
tatttaaata tctcaaaacc ctagtatgta ccatgaaaca taaaaaagga aaagagacat  37080
taattgttct tattcataaa atatatcaag atattcatct ggagactaaa gaaaaattta  37140
aattattaag attttatgtc atgcatgatg caactatcca atttctatct atgtgcaaag  37200
actgttttaa tttagccggt tttaaaccat ttgttttaga atgtttggat attgctatta  37260
aaaaaaatta ccctgatatg atacaatata tagaaattct atcgaaatct gagtaaaatt  37320
tatttttttg atcagagtaa gaaaatgttc tccctccagg agatctgtcg aaagaacatc  37380
tactttctac ctgactggct cggtgagcat gtgattcagc gactaggtct gtactgggaa  37440
aaacatggtt ctcttcagcg aatcggagac aactatgtac ttatacaaca ggacctcatc  37500
atccccatca atgaagccct aagaatggca ggggaggagg ggaatgatga ggtggtacaa  37560
ctcctattac tatgggaggg aaacattcat tatgccatca taggagcttt ggagagtgac  37620
cattatagcc taatacgtaa gctctatgac caaatcgaag actgtcacga catccttccc  37680
ttgattcaag acccaaaact ctttgaaaaa tgccatgaat tagataaatc ttgtaacatt  37740
ttatgtctcg tattacacgc cgtaaaaaac gatatgcttt gcattcttca agagtataaa  37800
atgcatctaa gtggagagga tattcaagtg gtgtttgaaa cagcatgccg ttcacaaaaa  37860
aacgatattg tgtcatggat gggacaaaat attgcaatat acaaccccga agttattttt  37920
gatattgcct ttgataagat gaatgtgtcc ttattatcta tagggtatac gcttcttttc  37980
aatcatcata taaataatac gaacgaaaat attaattctt tattgacaca acatcttgaa  38040
tgggctgccg gcatgggcct tcttcatttt atgctggaaa ctttaaagta tggcggggat  38100
gtaacgataa tagtcttgtc tgaggccgta aaatatgacc acagaaagat tttagattat  38160
tttctccgtc gaaaaaactt gtaccaagaa gatcttgaag aactattatt gttggcgata  38220
cgtgcagatt gttctaaaaa gaccttaaac ttgttattat cttacttaaa ctattccata  38280
```

aacaatatcc gtaaaaaaat attacaatgt gtaaaagaat atgaaacgac cgttattata 38340
aaaattttac ggaaaagaaa gataaatctg atagagccca ttttggcaga ctttatagga 38400
tatcatagct atacctatat ggtagatttt atgcgtgagt tttccatcca tccggaaaaa 38460
atgatcaaaa tggctgcacg agaatcgagg gaggacttga tcataaaatt ttccaaaaaa 38520
gtttgcaaag agcctaaaga tagacttcac tatctcaaaa gcttagtgta tactatgcga 38580
cataaagaag gcaaacaact gttaatttat acaatccata acttatacaa agcttgtcat 38640
ctagagagta aagaaatgtt taatttggca cgattttatg cacggcataa tgcagtgatc 38700
cagttcaaat cgatttgcca cgatctctcc aagctcaata ttaatatcaa aaacttgttg 38760
ttagaatgtt taggtattgc tattaaaaaa aattactttc aacttatcaa aacaatagaa 38820
acggatatgc gttatgagta acatttttag atgagggaag attctaccaa actaactaag 38880
acctttcgct agaatgtatc ttattgttaa tatagatgag atatgtcatt gtgaaaaaat 38940
agattaggta ggttgtgaaa aacagattaa acttaaaatt atgtgtatta tgtaaaattt 39000
tagaaataaa aatttatttt ttttattgag ggtacggaaa atgttctccc tacaggacct 39060
ctgtcggaag aacattttct tccttccaaa tgattttagc aagcataccc tacaatggct 39120
gggattatat tggaaagagc atggatccgt ccatcgagca gaaaaagaca gcataatgat 39180
acagaatgaa ttggttcttt ctatcaatga tgctttacag cttgcaggag aggaggggga 39240
cacagatgta gtacagctct tgttattatg ggagggaaat ctgcattatg ccatcatagg 39300
agccttgaag actgaaaaat ataacctaat atgtgagtat catagccaaa ttcaggactg 39360
gcatattctc ctacccatga ttcaagatcc agaaacattc gaaaaatgtc atgatttaag 39420
ccttggatgt gactttattt gccttctcca acatgctgta aaatacaaca tgctttctat 39480
tcttgtcaaa tataaggagg atctactaaa tgcaaggatt aggcatcgta tccaatccct 39540
gtttgttttg gcatgcgaaa atcggagaat tgaaattatt gattggatag gccaaaatct 39600
gccaattcct gaacctgatg ccatttttag cattgctgtt gctacaagag atttagaact 39660
gttttcctta gggtacaaga ttatttttga ttacatgcaa agacagggaa tcattcaatt 39720
aaccaatgga gttcgcatgg ttgtgctaaa tcgtcacatt agcatggcaa tagataatgg 39780
tcttttacct tttgttctgg aaactttaaa acatggtggg aatatacata gagccttatc 39840
ttatgcagta acacacaata gaagaaaaat tctggattat cttattcgcc agaaaaatat 39900
agcccctaat acaattgaaa gacttttata tctggccgtg aaaaatcaat cttccaggaa 39960
aactttgaac ttgttgctat cttacataaa ttacaaggtg aaaaatgtta aaaagctggt 40020
agagcatgta gtaaatgaga aatccactct tgtgttaaaa attttattag aaaaaaagga 40080
aaatctagtg gatgctgttt taacaagact tgtaaaacat tctacatatt tccaggtgag 40140
agaatttatc caggagtttt ccatcagccc agaaaaattc attaaaatag ctgtgcggga 40200
aaagaaaaat gtgttaatcg aggctatttc tgaagatatt tgggaaaatc ccacagaaag 40260
aattacttat ctcaaacaga tagtgcacac cataaaatat gaaagtggaa ggcgattttt 40320
ggtagacatc attcacagca tttaccaaag ttactcacta aaacacgaag atattcttaa 40380
actggcaaca ttttatgtca aacacaatgc aatcacccat tttaaagacc tctgcaaata 40440
tctttggctg aacagaggaa cagaaagtaa gaaactgttt ttagagtgtt tagaaattgc 40500
tgatgagaag gagtttcctg atattaaaag tattgtgagt gaatatatta actacttgtt 40560
tactgcagga gctattacca aggaagaaat catgcaagcc tatgatgctt tagagtagcc 40620

```
atgtattaac attctgaaag tagaataaaa tatactatat actaaaaacc aaattagcca  40680
tttttaacta tcttcttctt aaaaactctg gataaaaatt tatttttttt aatttgggta  40740
gggaaaatgt tctcccttca ggacctctgt cggaagaaca ccttcttcct tccaagtgat  40800
tttagcaagc ataccctgca tttgctgggg ttatactgga aggggcatgg atctatccaa  40860
aggataaaga atgatggtgt gcttatagag catgatctta ctctttccat caatgaagcc  40920
ttaattcttg caggagaaga gggaaacaat gaagtagtaa agctcttgtt actatgggaa  40980
ggaaatcttc attatgccat cataggagct ttgaggactg agaactataa cctagtatgt  41040
gagtaccata gtcaaattca ggactggcat gttctcctcc ctttgattca agatccagaa  41100
acattcgaaa aatgtcatga tttaagcctt gaatgtgatc tttcatgcct tctccaacat  41160
gctgtaaaat ataacatgct ttcgattctt gttaaatata aagaggatct actaaatgta  41220
ctatttaggc aacaaattca aggactattt attttagcat gtgaaaatcg gaagcttgag  41280
attcttacgt ggatgggtca aaatctgcca attcctgatc ctgagcctat tttagcatt  41340
gctgttgtca caaaagattt agaaatgttt tccttagggt acaagattgt tttgaatac  41400
atggaaaacc aaggacttca tttaacccag gtagttcgta tggttatgct aaatcatcac  41460
tttggcatgg taataaataa aggactttta ccctttgtgc tggaaatttt aaattatggt  41520
gggaatgtaa atagagcctt atcttatgct gtcacacaaa ataaaagaaa gattttagac  41580
catgttgttc gccaaaagaa tataccccat aaaaccattg aaagaatgtt gcatctggct  41640
gtaaaaaagc atgctcccag gaaaactctg aacttgttac tatcttacat aaattacaag  41700
gtgaaaaatg ttaaaaagtt gttagaacat gtagtgaaat acaactctac tcttgtgata  41760
agactcttgt tagaaaaaaa gaaaaacctg ctggatgcta ctttgacaag atatgtcaaa  41820
gattctacat actttcaggt gaaagaattt atgcaagact tctccatcag cccagaaaaa  41880
ttcattaaaa tagctgtgcg ggaaaagaga aatgtgttga tcaagggtat ttctgaagat  41940
atttgggaaa atcccgcgga aagaatcagg aatcttaagc agatagtgtg taccataaaa  42000
tatgaaagtg gaagacaatt cctgataaat atcattcaca ccatttacca gagttattct  42060
ttgaaacctg aagaaattct taaattggca acattttatg tcaaacacaa tgcaaccacc  42120
cattttaaag atctctgcaa atatctttgg ctgaacagaa gaacagaaag taagaaactg  42180
tttttagagt gcttggaaat tgctgataag aaggagtttc ctgatattaa aagtattgtg  42240
agtgaataca ttaactattt gtttactgca ggagctatta ccaaggaaga aatcatgcaa  42300
gcctatgctt tggagtatgc catgtattaa atttctgaat cagtaagcaa tagatagatt  42360
ttagaatatg ctgtattaag ttagtttctg aataagtaat taatagatag attttagttt  42420
atgtaaaaat gttaacattt gttcataagt tttagatacc attttagagt tacttttta  42480
gatattacta ttttagccat tattatctta aataatcact attttagata ggtccccgta  42540
ttaaaaacca aattaaccat tatctatgtt tttaataata ctttttaaaa accctccata  42600
aaaatttatt ttttttcata aaagtagaga aaatgttctc cctacaggat ctctgtcgga  42660
agaacctttt tcttccactt gagcccttag gcaagcatgt ggttcaacgg ctgggattat  42720
actgggaagg ccatggttca gttaaacgag tgggtgattg ctttatatgt gtagaccaga  42780
tttggatgct atcaatccat aaggctatac aaattgcagc ctcggaagga aatgagaaca  42840
ttgtcaagct tttcttacta tggaagggga gtctacaata tgccatcata ggagccttag  42900
agggcaggca atatgatctg attcaaaaat attacaacca aattggggac tgccatcaga  42960
ttctaccact gattcaagat ccagaaattt acgaaagatg tcatgaatta aatgttacat  43020
```

-continued

```
gtacctttca atgcttattt caacatgcta taagagataa catgctgccc attttccaaa  43080
aatatggaga agatctgaat ggaaacagga gaatggttca acttctgtat gagatggcat  43140
gccgattaca aaattatgat atcatcaaat ggataggatc taacctgcat gtttataact  43200
tggaagccat ttttagcatt gcttttgtta gaaaggattt aactttgtat tctttaggct  43260
acatgcttct tctgggtaga atgagtactg aagatagaaa ctttatctca atcataacac  43320
gccatcttga atacgcatca aaaaagggac tttttgactt tgtactagaa tctttgaaat  43380
atggaggtca agtggataca gtgttgtttc aggctgtaaa atacaaccat aggaaaattt  43440
tggcccattt tattcatgaa attccccgtg aaacggttga aaagctgata ctccatgctg  43500
tggagtcacg ggcctccaga aaaacattca acctgctttt atcttccata aactactgtg  43560
tgaacccttt tgtcaaaaaa ctactgcacg ctgtggtgaa acacaagtac atgcttatca  43620
taaagctttt gctcgagcgg cccaaaaaga agataaacct ggtagatgct gctctattca  43680
aacttgtaaa atactctact tatacagaaa tagtaaaata catgggtgag ttttctgtgg  43740
acccaaaaag ggtggtcaaa atggcagcac gactcatgag agtggacctg attaaaaaga  43800
tttctaatga tgcatgggaa gataaactag agagaatcaa gcaccttaaa cagatggtaa  43860
ataccatgaa ccacagaaat ggaaaaaatc tattgatgta caatattcac aatattactg  43920
gatataccta tctgaacacc aaagaagcat ttaacttaac aagattttat gctgtccaca  43980
atgcaacatg tttgtttaaa gaaatgtgta aaagctgttt tgtacatgat aaaatacagc  44040
tcagagaatt gcttgaagat tgtttacata ttgctaatag gcatgattat atccagattg  44100
cagaaaccgc agatgaatgt atcaaatata tagatcttat tacatttaag taaaccatgt  44160
atatatcaag taaatccaga ttaaatcagg ctaattgtaa atagttgtag ataccatata  44220
atgaatgttt tattaggata gtagttcagt taagatagta gtttagttaa gatagtagtt  44280
tagttaagat agtagttatg ttaagatagt agttctgtta agataatagt ttagttaaaa  44340
ctagttcatg ttaagttaat agttttgtta agacaatagt tcatttaagt caatagttca  44400
gttaagtcaa tagttttgtt aagtcaatag tttagttaag tcaatagttt agttaagtca  44460
atagtttagt taagtcaata gttatattaa gacattagtt ctgctaatac attagttttg  44520
ttaagataat aaaaatttat ttttttcat cagggtagag aaaatgttct ccctacagga  44580
gctctgccgg aagaacattt acattcttcc ttaccccttg gctaagcatg tacttcaaca  44640
actagggctg tactggaagg gacatggatc tcttcaacga atcggagatg accatgtact  44700
cttacagcag gacctgatct tttccatcaa cgaggcctta agaatggcag gagaggaagg  44760
aaacaatgaa gtagtaaagc tcttgttact atgggaggga aaccttcatt atgccatcat  44820
aggagcttta gagggcgacc gatatgacct tatccataaa tattatgatc aaattgggga  44880
ctgccacaag attcttcctt taatccaaga cccgcaaatc tttgaaaaat gccatgaatt  44940
gagtaactcc tgtaatattc gatgcctttt agaacatgca gtaaaacacg acatgctttc  45000
tattcttcaa aaacacaagg agcaaataag attacacatg gcattaaccc aaatactatt  45060
tgaattggcg tgtcatgaac gtaaaaatga catcattaga tggatcggtt attccctgca  45120
catacaccat ctagagacta tttttgatgt tgcattcgcc cataaaaatt tatccttata  45180
cgttttaggg tatgaacttc tcatgcacaa agtaaataca gaggctgcat atatagaatt  45240
acccaatttg ctatcatatc accttcgaac tgcggcggca ggaggtcttc ttaactttat  45300
gttagaaaca ataaagcatg gtggatatct ggataaaacg gttttatccg cggctatcag  45360
```

gtacaagcat aggaaaattg tggctcattt tattcatcag gttccccgta aaaccgttaa 45420
aaaactgtta ctctatgctg tgcaggctcg ggcccccaaa aaaacactga acctactttt 45480
atcttcctta aactactccg tgcacaccat caccaaacaa ctcgtacaca atgtcgtcat 45540
ctacagttcc acgcttatcg taaagctttt actcatgcgg cgaaaaaaca agttaaacct 45600
agtagatgcc gttttagcca gacttgtaaa atattccacc tatacagaca ttgtacaatt 45660
catgggtgag ttttctgtga gcccagaaag ggtgatcaaa atggctgcac gggaatccag 45720
gacctttctg attgaaatga tctccaaagc tgcttgggga aatcacccac agacgttgat 45780
tcatcatctc aaacaactaa ccaataccat gaagcctcaa tctggaaaag accacatcat 45840
atataccatc cactatattt atctaaactc taatatgctg gtagcggagg aggaaaaaaa 45900
tatttttaaa ttagcaaaat tttatgcgaa tcataatgcg gtaaacaggt ttaaacaaat 45960
ttgtgaagac tattatatat tagatgcacg atttaaaaca cttattttag aatgttttga 46020
aattgccgtc cagaaaaact atcctagaat tgcaaatatt gtggatgact atattcgatt 46080
cctttttac aggggaaata taaccgagga agaaattcgt gaagcctatt ctttaaaaga 46140
tgctgaggtt tatgtagatt taaaatggtt acaacaagga gaaatggttt aaaccaaatc 46200
cggtttaaac taaatccaat ttaaactaca tttggtttat cattagtcat tgaaaccatc 46260
gaaaaaaaag ctatttgttt atccccataa actcatcttt tttttgtctc aaagtttgac 46320
actaaaattc agtgttttat agtgtttata attaagtgtt ttgcatgcat tgcagaaatt 46380
ttcatctttt ttaattggtt caataccaca tgtcatacaa tatgttgttt gattatcaag 46440
attaacttta tgaaaggaaa gtaagtgagc cgcaaattta aaagtaaaat atctttcatt 46500
taaaatgatc ttatgaatgt attttcgata aggaggaatg aaagcatttg ccaaaataaa 46560
tcgcataaaa ggcttggaaa aacccatatc ttctaatctt ttgtgggtat aaaccctatt 46620
ttggtgtttt acaaaaactt cattgttata atagtcgtta tagctatcaa tcattttttt 46680
aagtcctata atgcccaagg ttgcacgcat aaagccacag tttctgctcc aaaaagcatg 46740
cacctgtaaa gggtgctttt catataacca attacaaaat ttcattccgc aacagtagca 46800
tgttatttca gtgggggatg tatagaataa tccggcattc gaaaattttt cataattttt 46860
tatgtcatgg attgcgaagc tttgatttcg tgcatctatg gagctatagc ctacatattt 46920
aggttttact tcaaataatc gcaaagagat gtatggatct atcgtattta ttttaggaaa 46980
catttcataa ttttaaattc ttatatataa tataaaaaaa attacaaaca tttgtaatga 47040
tcatcctcaa ttgaaggctg agttgtaggc tttatttttc taattatacg aagaaggtag 47100
gttctcataa agccttcaag atgactattg atgtttccaa tacattttct caatgagttc 47160
ataaacccag acattttgct aatggcttgg caaagtgcca acaagttgtc cacaaagtac 47220
tggtagattg ccactagcta tagctagcta tagtgagcca acctctctgt atgtatttta 47280
tatatttcat tttttaatag atttaatatt tttataaaaa atatttagtt ttttatacaa 47340
gaatgtcgac aaaaaaaaag cccacaatta ccaagcaaga gctttactcc ttagtagcgg 47400
cagataccca gttaaataaa gcattgattg aaagaatctt tacaagtcag caaaaaaataa 47460
tacaaaatgc tttaaagcac aatcaagaag ttattatacc acccggaatc aagttcaccg 47520
tcgttacggt gaaagctaaa cctgctcgcc agggccataa tcccgccaca ggagagccta 47580
ttcaaattaa agctaaacct gaacataaag ccgtaaagat acgagcattg aaacctgtcc 47640
atgatatgtt aaactaaact ataaagtcat attcttcttt atcgttatta tcttcaatat 47700
atttttgcca atcgaaatcg aataaattca gatcctggac atttaaatac ttatcatcgt 47760
acattttaat ataatttaaa catgagttgt tgtcaaaaac ttttagcgtt tttgttaaaa 47820
ttatcatatg aataatttcc ttattaagag ttgccggaat aatacaaaac ctatttttag 47880
gtacatcatc catgataata gtaaaattag taaaaattgt ttcttgtttt tcttttgttt 47940
caaataaacg ttgtaaggtt aaaggtttct cgttcaatgg tttctttgaa gataaaaaga 48000
atgtataatc tggtttaaag gtatttttgg tttcaatcgt gattccatct gcttgagcat 48060
atactaaacc agaccaaata taacggtcca ctattacaat ataatttagc ttaagtagca 48120
ctgcaatttc tgcgataaat tcactacgat gttttgtaaa taatttatgt aattgttccg 48180
atgacatttc tatggtttta tttaacacct gcaatataag atcaccggtg gtcgtgtctg 48240
gattaggaaa atgtatacat atagcattat aatccatgca ttccaatgtt tcttttaatt 48300
tcattgcctg tgtgcttttt cccacaccat tgattccctc gatggcaatg agtattccac 48360
gcatgattaa taaaaggaaa aaaagaattc agtttttaac atttcttaca aatctttttt 48420
tatacaacat tgtacaacac tgcattagcg gtatatgatg ttatagcttc attaaatatt 48480
tgcttttata taatctttac caacctatat ttggtagatc actgcagatg gtcataaata 48540
ggccataact aagataaaaa ttatttcaga cgctactacg gtagtattat taaaatcatg 48600
tgtggcaatg tatgacgtct taatagataa aacatttaag gaaaacaaat ttgaataaaa 48660
aaataattgt tatgatggcg ttgttacaca aagaaaagct tatagagtgc atctatcatg 48720
agctagaaaa tggcgggaca atattgcttc taacaaaaaa tattgttgtg tcagaaattt 48780
catacattgg caatacttat aaatatttta cctttaatga caatcatgat ctgataagca 48840
aagaagatct taaaggagca acatccaaaa acattgctaa aatgatttat aattggatta 48900
taaaaaatcc tcaaaataat aagatttgga gtggtgagcc gcgtactcaa atttattttg 48960
aaaatgattt atatcataca aattacaatc ataaatgtat aaaagatttt tggaatgttt 49020
caacttcagt cggtcctcat atctttaatg atcgtagcat ttggtgtact aaatgcacat 49080
ccttttaccc atttaccaac attatgtcgc ccaatatatt ccaataaatt agatatcttt 49140
gctattaaaa tagttaaaaa ccttatagga taattaggta ctttattacg ataaattatg 49200
atattttata attagttact ttattataat taatctcttt attaatgaat tatcataaga 49260
taactaatta tttttttcca tatatcagat aataaatctg atatgggcta aaagtatgtt 49320
tcaaactatt tacaatagaa tttctgttaa gaaaacatac ataatttgaa taaaattttt 49380
ttaaatatca ccgaaacaat caacatggtg ttaatagagt ttttaacagg tttcttctat 49440
ttatatggaa agagactgtt ttccattagt aaagtcatgg acatgatatg tctagactat 49500
tataccatta ttcctgctcc tctggcgatg atgttagcgg caagactaaa aaactatgac 49560
ctcatgaaac gactgcacga atgggaaatc tctattgact acgctctact tgtagtagat 49620
gatgtgccgt ctattgacta ttgcttaagt cttggcgcta gatccccgac tagagcacaa 49680
aaaagagaac tgctgaggga caacacgttt aatcccgtgt ataagtatct tatgaactgt 49740
tccggcttcc caacaaagag agaaaaaaac attccttgtg atgttcaatg cgaaagactg 49800
caaaaaaaca ttataaaaga actggtattt aactgctctg tactgcttga aatggtactg 49860
cacacagaaa gagaatatgc atacgcccta cactgtgctg caaaacataa ccaattgccc 49920
atcctcatgt attgttggca acaatccaca gacgcggaat ctattttgtt gaaaacctgc 49980
tgttctgata agaacatcaa ttgttttaac tattgtattc tatatggcgg cgcccaaaat 50040
ttggatgctg caatggtgga agcggcaaag cacgatgccc ggatgctgat aaactactgt 50100
gtcatgcttg gtggaagatc cttaaacgaa gcaaaagaaa cggctgccat gtttggacac 50160
attgaatgcg cacaacactg ttttaaactg cagtcttacg tcgtggacac atcgaataca 50220
gacgacactg attaaagcga caatcttacg tcatgaacga ctgtcttttg agtatctata 50280
cttacattat attttttat gaaaaaaata taaaggttgt atacaaacct ttgtatacaa 50340
gaaatttgga tcattaaaca ataattaatt tggacacagg aaacgatcta gatcgatcaa 50400
aaagctattt tttttgcaca cagaacattt agataattga gagattactt tccatacttg 50460
ttaagctttt ttacacacag gaactttgga ttctgttcag gaagtttttc atagacatta 50520
tgtttacagc cagtaataat aattttgggc tttttcttaa accaccggtg gaaaacatcc 50580
agcttgtaaa gagggaaatg catgtagaga ggttttggta gtcatggtta agagatttga 50640
ctaactccat gtttcctgta aagactgccc agtcccaagc agtaaaacct ctatgatagt 50700
ctttttgagt cggatctgct ccaaatttta tgagagaaag catatttaaa gaacggcccc 50760
gtattgcggc cttcatcaca ggagtcatcc cattaaaatt cggtaaacaa attctggtcc 50820 catttttcc gaaatagccc aacacccctt ccaggattaa atgatttttt ttctcagcta 50880
aataatgtaa agcagagttt ccatctttat ccctcctatg agggttaatt atttctccag 50940
gataagattc ttgttcaaaa agaaatttta aaaagtctat acgtccgtag atgcatatcc 51000
acatgaatac cgaggatcca tttttatcgc atctattgac aatccacgga tctgttttaa 51060
aaaattcctc aaatagtgta agattcccat ttctaatatg ttttttaatc catttaacaa 51120
acaagttttc tatctccctt tctggaaaca tgtgttccat tttgaatgtc gcccctactc 51180
cactatatga ttttactcct ttaattttta atgtcctttt ttttcggact tctttggata 51240
agctgtttat taccatcttt aaatgcctta tagcggggag gagccaggcc cttttcccat 51300
atgtgcggta attcttggtg tttatgcttg cctttggcat aaccaggcca gtatttttcg 51360
atatattcag ggtttgtttt tacgtattct ttaaaggtcc gataggcttc ttgaatacag 51420
gtaggctcac cggtataatt tccatgttca tcttccttta aaaagccatt aaccctgtcc 51480
tttctccact taagattgtg ctttccaaaa atgcgatcaa gatcttgcgc ctgctggggt 51540
ggaatcataa atccctttt aggtcgaagc tttttatttt ttccatagct tcggccatcg 51600
cgttgcgaaa cagtggttag gacgcctgat agtctttcca tgggcgtcgc atctaatcct 51660
atccatccac cctgatgaat atcaatggca acaagctctc ctttattttg ggcaagccaa 51720
gtttccaaga atgccatgct ttcttcccag ggataaggcc cgccaacacc acgggttgtc 51780
caatcttgca aggactccag gtccgacacc tggtaaggct ctaaagaaga cggttccttg 51840
tttttgtact gcaaataaga tttaatgacc catttatacc atgtgtcgaa ccgcagcgtg 51900
gcgcctccaa agtgaaagcc gtcgttgatt ttaggatatc tgcaacatat ttcaaccgta 51960
cgtttgagtt ctgcaaaagc ggccttccaa ggaagtcttt cgctgcgggt aagacggtct 52020
attttgccct gcgtgccata gcgtatggca tgtcgtgcca attgcaacaa ttctgacacc 52080
gatccgtggg ccccgatcca gtttatcgga taggcaacct ccgaagggtt taaaagatgc 52140
tcgtaaaagc gtggatcttc agatgccaag gcgtctgcaa aggggataat gctagaaaac 52200
ctgtctagac atacgttttc tgtgtttact tctaaaggta gaaaaatggt tgcgtgaggc 52260
ttttgaacct gcttgttcag cggtctgcat atgctttgaa taatgtctct aggactatgt 52320
cgcggcgctg caaaaaatac cgcgtttagt tctggaacct ctacgccctc ttgaaagagt 52380
cgacagttta ataaaataac gggttccttt gaggaacaaa attctgtaaa tgttttgagg 52440
ataacctgtc gcggcagggt tgagtgagct atcagggcat agaccccttg gtctaccaac 52500
gccgcgtata gctccttggc ctgtttaata tcacgggtaa ataccagcat tttaggagcc 52560
ggtatattgg tttttaaata ggctaaggcc attataattt gctttactat gatctgtttc 52620
gtggtctcct ctttggtact cggttggtgg gccaatttag gcgcggctac catctgcaat 52680
tcaaaatcat ttacatagcc ggcctctatg ccttctcgca gatagtagcg aaaggcaacg 52740
ccgccaaaaa gttcacgatt tttcatggaa agcggggtgt cgtacctggg cgttgccgtt 52800
aaaaaaagtc ggtgcccttt tttaaagttg agcaacacgt gggtaaaggg ccgtgtctcc 52860
cattcgccgc aaatccggtg acattcatcg ctaataataa gatcgaaatc atccaccagt 52920
agcgtggagg attggtaggt ggcaatcaca agaagagaag gggcctcccg tatccgtttt 52980
gcaataaaga caggattggt ggtcatttct atattgtcgt gatttagcac aatgcgggtc 53040
tggtcagacc ccacaagcaa aacgttcttc aaagaaattc catactgata gagtttttcc 53100
agagtctgcc gtagtaggga caggcccggc accaggtaca aaacttttcc ttgaagataa 53160
ttggagagga taagataggc gacgcgagtt ttgccgcatc ggcaggccat ctgcagaatg 53220
gccctcccac ttcgccgcag ctcctgatag cccatattgg ccgcctcctt ctgataaagt 53280
cgatcctcga ttgcagtccg tgtctcatct gtagaaaaaa ataatacgtc atctgcgaaa 53340
tgttcatctt ccacaggagt tatcaccagg tgtctcagtt tctccttgct tatcagcgga 53400
tcagagggca aagatggctc aaccactatc gtggaatcat tcatctcata ggcgggagaa 53460
tcacacaaag tatagcttat gtccagacag tttgcaacat cctcagccaa ttgttttatt 53520
ttttcgggta aaagacatac gagttctttg tttttgacgc gaaaaaactg tgcacaatat 53580
aacaccccctg cttcaatttt ttgcgcatcc ttctttgtag atgtttccaa tgtgaaacaa 53640
tacttccatt catccgtaaa acaggttgta taagatccat catgaagcct agcggccaag 53700
tttcctgtgt gcccaacttt atgtaaggat tgggcctcca gccagggatg aaccgccacg 53760
taaaatcctg cgcacatgct atatcaaatt gcagtttctt aataactgta cacaggatct 53820
gaaaaacatg tgattacaaa atttagataa gaaatattta atattaaaaa tcacagaata 53880
catgtcactg tgtagagaga aagccaaaaa ctcctcttga ccgccgtggg aaatcatcca 53940
gggtagtagg ttgtgtttca taaagttgta tgccgtagtg atcaccgtgg actccagatg 54000
gttattggca tctttgcaat actttgccat cttggcagaa aagacgataa atccacaaat 54060
tctaccccag ttgataagat ccttaaacag ctcagtcaca accccagtaa actgggtttt 54120
aatttcttga acactcgtaa gagaaaaggt aattgtaacc tgtttgttca aacactcatc 54180
ataataggtt aaaatttttt ttatttgttg ttgatatggg ctaagctcat gctctgaaat 54240
atcattaatg taatatttaa tatatcccac tagtatttca ttaatgatat tatgatatat 54300
taactcttct ccctccatag cggcacccta tatttttta tttaggtttc aatgttatca 54360
caattgcgat acaattgtga tacaattgtg acacaactgt gttgtataca acaaatgtta 54420
ggccacgtat agcaacctat atgttaagaa atatttttat cccaacatta gttggaaacg 54480
agcagccgca aagaagtcat ttaaaataag ccatttaaag atttagaatt tatatgtata 54540
caactgtaca atggaagcag ttcttaccaa actcgaccag gaggaaaaaa aggctctcca 54600
aaattttcat cgttgtgctt gggaagaaac taaaaatatt ataaacgatt ttcttgaaat 54660
ccctgaggaa cgatgcacct ataaattcaa ctcatacaca aaaaaaatgg agcttttatt 54720
tacccctgaa ttccacaccg cctggcatga agttcctgag tgcagagagt tcatattaaa 54780
ctttttgaga ctcatttcgg gacatcgagt ggtattaaaa ggccctacat ttgtttttac 54840

```
aaaagagatc aagaatctgg gcattcctag taccatcaat gttgactttc aggccaacat  54900
tgaaaatatg gatgatctac agaagggaaa tctcatcggc aagatgaata tcaaagaagg  54960
ctaaataaaa caactaacat caaaaaacat taaaggctat gttgtggacg atgcctttgt  55020
ctcaatagtt tcgaggtcat ccaataactc atgtaacgta aaaaagttgg tccatttttt  55080
tgaaaacatt aaaagacgtt cgtcttcata aataaaaaag tcattcgaag gaaaaatgat  55140
atactcaata ccatagtctt gtaatatttt ttttaggtct ctcagggtcc agggatttac  55200
caggcttcta cgcgaagtga gcatcataaa aatatctaat attttttgcg ccataagcca  55260
gcgcggattc tcattggccc acaaatcaac aataattctc ttatcaaccg tgagcattcc  55320
tacttgattc gaagaaatga ttagatgccc agcagtccac cccatgagta gataacgcag  55380
cgttgtagaa atgtcacata tggaaggcat tcctccacaa catgaaccca aattaggatg  55440
cgtgtgaaac acaaacatag caggcttgtt ggccaccctg ctataaatat cagcaggcat  55500
catagcctcg ctgccaaaat aaatgttctc tcctgcccta taggggcttg gaatgatttc  55560
cactatctcg ggtacaccgt ttatcatatt aatgcggccg caccattcac ggtcatcgtc  55620
caaaaatttt ttgatggcac cccgaacatt gtcccagtta agcaacagag tattcacaat  55680
ctcattacgc tccgcccagt attccttaaa acttctttta gacttgctga gctgttccca  55740
ggattcgaac tcagtccaat gttttttttc ttttggggaa gacttccctt ttgaaacatt  55800
ttttgcggct ccaccatcta cactatgatt ttccaaaata atctccttca tcgtttgagt  55860
tatatgggca ttgctaagca ccttagtggt aacctgttta cctatgtgat ttagcagaaa  55920
accaagtttg tccatttgtg tctcaaccat ttattcttaa caaaacaaaa aaaattaaaa  55980
atcatcgtcg tttaaaaaga gtttgaaggc aaacgcatca tccttaacac agttctgata  56040
ctgcgtaggt cttaactcga aaaagttggt tttttctact tcattaagaa agaatttagt  56100
catctgagga aaagggtttc ccaccttata aatgcttttg cactgcatca tgaagcacaa  56160
attatctgta aagtagcgta tatattgaaa tagcatttct tttgaaaaac cgggaactct  56220
tcctcttgcc ttgtcaaagg catagttaat aaactcatcc accaactcca cagcctcctt  56280
caaaattttg tgaatgatct tttcctcggg aatgttatac acgtaatttg agataagaaa  56340
acacgcaaaa ctacagtgca tcccttcatc acgtgagata aactcattat agcttacaag  56400
ccccggcata atattctgtt ccttaagaaa ctggatcgcc acaaagtggt tttgaaataa  56460
aatgccttct acggcggcga agcccaccag ccgctcacct agagtgttcc tgtcggggtc  56520
catccactgc cgcacccact gcgccatttt ttttatgata gggtgttttt caatgccgct  56580
aaagatgcgc tgttgttcct tctcatccgg gatcagcgtt tttacctgta ttgagtaggc  56640
ttcgctatga acgcactctt gggcagcctg cattgtataa aagtataaca cttcctttac  56700
tttaatttcg cgcataaaat tggttaaaag gttttcgata acaatttcgt cggcaacaac  56760
aaagaaggct aaaatttgtt tataaaattc gcgctgtggc tttggcatgg cttcccaatc  56820
atcaatgtcc ttacacatgt ccacctcctg cgccgtccac gtcaaacttt ctaatttttt  56880
ataccagttc caacattcgg ggtgctgaat aggaaaaata gtgaaacgtt gggaattttc  56940
aattagtaat tcctccatat ttgaaataaa tattaacatc ttcaaattta ttggctgcca  57000
tggagacgtt ttttattgag acgttggcat ctgatgtgta tggaaaggcg ttaaatgttg  57060
atttagatag actatcgcag gcgcaggtta aatataccct tcaagagctt atttcctact  57120
gcagcgctct aaccatttta cattatgact attcaaccct tgcggcgcgt ctttcggtgt  57180
accagctgca ccagtcaacg gcctcctcct tctcaaaggc ggtgaggctg caggccgcac  57240
```

aatcctgctc acgcctgtcc ccccagtttg tggacgtcgt ttacaagtac aaagccattt 57300
ttgacagcta cattgactat agcagagatt acaagctgtc cctcctgggg atagaaacca 57360
tgaaaaattc ttatttgtta aaaaataaag atggggtcat catggaacgc ccgcaggatg 57420
cttatatgcg ggttgccatc atgatctatg ggatgggaag agtggtcaat atgaaaatga 57480
ttctgctaac ctatgacctg ctttcccagc acgtcatcac acacgcgtcg cccaccatgt 57540
tcaatgcagg caccaaaaag ccacaactct ccagctgttt cctgctaaat gtaaatgata 57600
atttagaaaa tttatatgat atggtcaaaa cggccggcat catttcaggc ggcggcggtg 57660
gaatagggct gtgcttgtca ggaatacggg caaagaatag ttttatttct ggtagtggtc 57720
ttaaaagtaa cggcatacag aattatattg tgctgcaaaa tgcttcacaa tgctacgcga 57780
accagggagg cctacgtccc ggagcctacg ccgtctactt agagctgtgg caccaagaca 57840
tctttacatt tttacaaatg cctcgcctaa aaggacaaat ggctgaacaa cggcttaatg 57900
cccctaatct caagtacggc ctatgggtcc ccgacctatt catggaaata cttgaagacc 57960
aaatacacaa cagaggcgac ggcaaatggt acctcttttc gccggatcag gcccccaatc 58020
tacataaggt ctttgatttg gaacggtcgc agcacgaaaa cgcacaccgc gaatttaaaa 58080
agctttacta tcagtatgtt gctgaaaaaa ggtacaccgg cgtcacaacg gccaaagaga 58140
ttatcaaaga gtggttcaaa acagttgttc aagtagggaa tccctatatc gggtttaaag 58200
atgccataaa tcgtaaaagt aatctttcac atgtaggcac tatcacgaac tccaatcttt 58260
gtattgaagt cacaatcccc tgctgggagg gtgataaggc tgaacaaggt gtttgtaatc 58320
tggccgcagt aaatctagcc gcctttatac gtgaaaatgg ctacgactac cgtgggctca 58380
tagaagcatc aggcaatgtc acagaaaatt tagataatat tatagataat ggctactacc 58440
ccacagaagc cacgcggaga agcaatatgc gtcaccgacc tattggcatc ggggtctttg 58500
gcctagccga cgtgtttgcg tctttaaaaa tgaaatttgg ttcacccgag gccattgcca 58560
tggatgaggc catccatgcg gccctatact acggggccat gcgacgatcc atagaacttg 58620
caaaagaaaa aggaagtcat cccagctttc cggggtctgc ggcctcaaag ggtctactgc 58680
agcccgacct atgggttcgc tgtggtgatt tagtttcctc ctgggaagaa cgcgtggcac 58740
agacgacgca gggtgtgttg acgccgaaaa ggtggtcgca gctacgcctg gcggctatgc 58800
agggacttcg aaatggatat gtcacagctc ttatgcccac cgcaacctcc tcaaattcta 58860
caggaaaaaa cgaatgtttt gagcccttta catccaatct atatacacgt agaacgttaa 58920
gcggggagtt tattgtttta aataagtatt taatagacga tttaaaagaa attaatcttt 58980
ggacagaagc cattcaacag cagctactaa atgcgggagg tagcattcag cacattttgg 59040
atataccggc cgagatccgc gatcggtata aaacctccag ggaaatgaat caaaaaattt 59100
taacaaaaca cgcggccgca cgaaacccct ttgtatccca aagtatgtcc ttgaactatt 59160
acttttatga acctgaacta agccaggtac ttacagtgct cgtcctaggc tggaaaaaag 59220
gtttaactac cggttcctat tactgtcatt ttagccctgg agcgggtacc caaaaaaaga 59280
ttataagaaa ctctgagaaa gcgtgtaatg cggactgcga ggcgtgtctt ctgtaggtgt 59340
ctcgcggtaa aagagcagcg gggaccatat ggtaaacccc aacaagagga taatgaataa 59400
aaaaagtaaa caggcatcca ttagttccat attaaatttt tttttcttct atataatgga 59460
atattttgtt gcggtagaca atgaaacctc cttgggggtt tttacttcta tagagcaatg 59520
tgaagaaacg atgaaacaat accccggcct ccattatgtc gtttttaagt atatgtgtcc 59580

-continued

```
ggcggatgca gaaaatacag atgttgtata tttaataccc tcgttaacct tgcatacccc  59640
catgtttgta gaccactgtc caaatcgtac caaacaagca cgacacgtat tgaaaaaaat  59700
aaacttagtg ttcgaggaag agtctattga aaattggaag gtttcagtaa atactgtgtt  59760
cccccatgtt cacaacagat tatctgcgcc gaaactttcc atcgacgagg ctaatgaagc  59820
cgtagaaaag tttttgatac aagcaggacg actcatgtct ctgtaaatgt ctcttccttt  59880
atgggtgacg tctcttcctt tgccgaggaa gtctctgtta tgggcaagag gtttgaaaca  59940
acgcaaggac tctgcttaat ctgctgtctc acaaagggaa tcaaactacc tgctttcgta  60000
tttttaatgt agtaattacc cttgttgtga tgaattttaa gaccatagcg tagtcccagt  60060
actttattaa tgaattttaa aattgtttga gggtccgttt tattgggctt tttaagctta  60120
aactcaaagc tgatcgcgct taaatcatac tgaacaaatt catcaacgag tttcgtcatt  60180
aattgttcat tggtcaatat attagggtcc tgaacgcatt taaagccgca cttagttaat  60240
agcataatag cgtacatatg agattgaaaa ctataattaa attgtagatc atgatgctct  60300
gcgtgttgca tggcccattg atgaaagttt aattcctgag tttgtaacat agtgagcgac  60360
tcgtatactg tctttccgcg gcttatttgg acacggccag tatagttctg ttttgtcata  60420
aaactattgt attgttcaac aaatttggga gtaattttat gaccgtgcca tgcataaaat  60480
tcgagtagtt tatacttttc atacgcaaat aggtcttgct ggtctactgt gatgccttcc  60540
tttaagtttt gtttaatttg taaagcttta ttggcatcaa tggtttcagc cgaggcaatg  60600
tttacatagt cctggtgttt aatttccatt ttaatgcttg tatattgttt gactgtctcc  60660
agcttttcac ccgtcagtat aaacacctta gcgccggtgt cggcgatctg gttaataaat  60720
cgggttataa agtgattttt tgatagatgt tgtatccgca ttgtttcgag ccatagatgg  60780
tagtatggag ttttataata tatcggccta cctgtttcct tactatacgt gaaggaaagc  60840
tggtgattgc ttatggtctg aaaaagggtg tcacgttttt gtaacgtaaa catttcaatg  60900
tcttcgatgg tttctggata gtaattttgt ttcccctgta agcagatttt ataacactta  60960
ctttttaatt cacgcacgcg gcccaacatt tggcaacatg tttctacgtc acacgacata  61020
ttgttaaaaa agccgtataa aacatcaaat ctcttatctt cgtatgaaac acccgctgaa  61080
atcgtgggcg tatagataag gatatcaacg agcccccaat aatacgatac attattaaaa  61140
tgggattccc gttcatgagc agtgctttta gaactataaa acccaatttt tttttccgga  61200
aacttttttt ggataaatga ttgcaacagc cgggcctcca ttaatgaatt tgtagggata  61260
acaatttttt tgtcttctag caaatccttt aaaaggttat ttaaccaagt ttctcgtgaa  61320
gaggtaaaat aatacgtgtc atgctgggcc cttttatatt gattccagtg aaagaagata  61380
gggacatccc cgcgaaaacg ctgtagaata ttatacgttc gatttcctag gtttgcgtcc  61440
aagcatataa cataatttgc cgtttcgagc atccacatga aaatggcaaa agagggagca  61500
aagtatttgt gcaggccgct attgaattga ttaaaaatcg attctacctc atccaaaata  61560
agtaggtcta caggctcggc tgtggaggtt agccggaaaa gtgattctac ctgaatgatg  61620
actctttcgt agctgtccaa atctccagtt acttcgctgt acaatgtgaa attcggtagc  61680
cgggattgta tattttttga gaagatctgt cgaaacgtca caaaccgtat ggtttgttgt  61740
tttgaaatag aattattgcc gtagtatttt tgcaaatagt tgcgcagttg gacggtttta  61800
cctattttca tttgagcctt tacaacaagc gtagggactc gttcatattc tcgcatacta  61860
ctttcatcat agatgtgttt ttgagtatca ggcagttctt caaagagaat ggactcatga  61920
acctctatgc tctttgtcat cacttggtcc acatatgttt ccacaaaatt atttgtgccg  61980
```

gaaaggctgc ccatgagaag gctatgttta ttgtcatggc gacagtgttg atacactttg 62040
tttcccgtga ctcttaaaat tagggtattg tccttatcat gcatacgctt acatatttcg 62100
cagtaacttg gacttgtacg tttaaacaat actaaatttt tatgaacacg gaggaagcaa 62160
tgatttttac atagtgttcc tgcaaatttt aatacctctt caagttcact ttgttggata 62220
gtatcgcagg aactcggtgt tgtttctttt acatttgtga agatacaagg taaacacgtc 62280
gtttcaaagg gggttgctat aagggtatca ctctttttcg tggttgtact ggtctcaaac 62340
acctctgcaa gctcctcatt aaacatttta acacgcatgc taccttttttt atgagaccct 62400
atgatgcgaa aattttgaat acttttgttg acctgggggt caacaaaagg ataaacgtgt 62460
ttgggaagat tttctaacac tttggatgta aagactttgg cctcattatt gtttaatact 62520
gagtatgtat aaagtatgat atgaaaggag tatttaagtt ctcgcttttt atttaatccg 62580
atagaatctg ttagcaaaat ttgttcacgc gttagattga tgttataagg taaagaatat 62640
gtctcgtaaa atacatccat gatgacgtta attatcatgt caaggatgtc atagacattg 62700
tcttcgacat tatcattgtc atcaacattg tcatcagagt atgacttatt taccggaaag 62760
tcgatgtcaa attttaagcg ctgaggcaaa aacccaaata ccacttcgtg gaaacacttc 62820
tgctcaaagg gctgagccgc ctcccactcc caaaagtcat cacgacttga aaaaactcta 62880
aaaagattat tatattcatc tcgcaccacg aagtgattct ttaaggtttc gagagaatat 62940
ttatcctcta cggcttctcc ttgggagtta cagcgaagaa acttgaatgt ttcttgcatt 63000
ttgatattta aaattaaatc aattatgatg cggccgctaa tgcggcggtt gacgcggccg 63060
cgccgctgac gcagccatca tacataaagc ggcatggccg ttttataacg actagtcggc 63120
cgttatatga cgaactatat aaaaatgaat tcttttaatt agagttaagt attgttgatt 63180
gtataatcca tcatggttga gccacgcgaa cagtttttttc aagatctgct ttcagcagtg 63240
gatcaacaaa tggacactgt aaaaaatgac ataaaagaca ttatgaaaga aaaaacgtct 63300
tttatggtat cattcgaaaa ctttatagaa cgttacgata ccatggaaaa aaatattcaa 63360
gaccttcaga ataagtacga agaaatggcg gccaacctta tgaccgtcat gacggataca 63420
aaaattcagc ttggagccat tatcgcccaa cttgagattc taatgataaa tggcactcca 63480
cttccggcaa aaaagacaac aattaaggag gctatgccct taccttcatc aaacacgaat 63540
aatgaacaaa cgagtcctcc cgcctcaggc aaaacaagtg aaacacctaa aaaaaatccc 63600
acgaatgcga tgttcttcac gcgtagcgaa tgggcatcct cgaatacttt tcgagaaaag 63660
tttttaacac cagaaattca agccatattg gatgagcagt ttgcaaacaa gaccgggatc 63720
gaaagattgc atgccgaggg tctttacatg tggagaaccc aattctctga cgaacagaag 63780
aaaatggtca aagagatgat gaagaagtaa tatttttggt aaaaatattt ttatcaaaat 63840
tttttaccaa ataataaaaa tatttttact ttttttcttc ataatataca tagaatgcct 63900
acaaaagctg gcacaaaaag taccgcaaat aaaaaaaacaa cgaagggctc ctccaaatct 63960
ggttcttcca gaggccacac cggcaaaacc catgcttctt cgtccatgca ttccgggatg 64020
ctctataaag atatggtaaa tattgctaga tctagaggca ttccgattta ccagaatgga 64080
tcgcgtctta ctaaaagtga attggagaaa aaaattaaac ggtcaaaatg aatataatca 64140
ggaaacttaa gcctggaaca attagccttg tgctgggacc catgtttgcc ggcaaaacta 64200
cgtttcttat tcattgcatt tacatgctcg aacgtttgga aaaaaaagta gtcttcataa 64260
aatctaccaa aaacacccga gacaaaacta ttaaaacaca ctccggtata cagctacgac 64320

```
ccaaacaatg taaaatcata gaaagcacac agttatctga cgtgggttct ctcaccgata  64380
tccatgcagt tgtcgtagat gaagcgcatt tttttgacga tttaatcaca tgccgcactt  64440
gggcagagga agaaaaaatt attattcttg cgggactcaa tgcttccttc gagcagaaaa  64500
tgtttccgcc catcgttcgt atttttcctt actgcagctg ggttaagtat attggccgca  64560
cctgtatgaa atgtaaccaa cataatgcat gctttaatgt gcgtaagaac gcagacaaga  64620
cgcttatcct tgcgggagga agtgaactgt acgtaacatg ttgtaacaac tgtctaaaaa  64680
atacatttat taagcagttg caacctatta aatattaaaa atcttataca ataatggatc  64740
attatcttaa aaaattacaa gatatttata cgaagctcga gggtcatccc tttcttttta  64800
gcccgtcgaa aaccaatgaa aaagagttta ttactctgct aaaccaggcc ttggcctcaa  64860
cgcagcttta ccgcagcata caacagctgt ttttaacgat gtataagcta gatcccattg  64920
ggtttattaa ctatattaaa acgagtaaac aagagtattt atgcctgtta attaatccta  64980
aactcgttac taagttttta aaaataacga gctttaaaat ttacattaat ttcaggctga  65040
aaacttttta tataagtcct aataagtata ataattttta caccgctccc tctgaagaaa  65100
agactaacca tcttctaaaa gaagaaaaaa cttgggcaaa gattgttgaa gaaggaggag  65160
aagaatccta agtcgcttac attttttttt gctattttta tagaatgtac acgcatgttg  65220
atgttgtcgg aatagctgaa gcctcagcgg ccctctacgt gcaaaaagat agggatcgct  65280
acttagacgt gctaacaacc attgaaaact ttatttacca acacaaatgc atcataacag  65340
gggaaagcgc ccacctactc tttttaaaaa aaaatattta tctttacgaa ttttactcca  65400
acaatgtggc ggagcacagc aaggctttgg cgaccctgct ttataaactt gatccggaat  65460
acctcactcg ttacacagta ctcattacca aaattcccaa ccattggtat gtgattaacg  65520
tagatcagcg agaatttgtg cgcctatatg ccatcccggc agttaaacaa cacttaccga  65580
ttcccatttt accccttctat tgcaccagcg cactcaccca gcaagaattg ttttgtttag  65640
gacctgaact gcagttaata caaatatatt ccaagctctg taaccccaac tttgtcgagg  65700
aatggcctac gttgctcgac tacgaaaaaa gcatgcggat gttattttta gaacagtttc  65760
cgcaaagatt ggaaatgacg ggcgggaaga aggaggagaa ggaaaagcat gaaagtatca  65820
ttaaaaaaat aatactagaa atggtctcta cccgtcagcg aatcgttgtt gggggttaca  65880
tacaaaaaaa cctgtacaac catgtactca agaatagaaa tcgtttacag cttattacga  65940
gcttaaatat ttatgaagaa aaagatatca tccagcaatt ttgtgattca aatggactga  66000
agatcaaaat acgtatcaac aatccgctct tgcctacaaa tccggaatta cggcgtttga  66060
ctatttattt taatcataat aatgatgatg atcagtcata tctaatagta gatatgtaca  66120
acacgggaag ctatgagcta gtgcctacaa atcagataaa cacgcttgat ggcagctttt  66180
taataggaac acccttcgtg caagcgcgat ttttgttggt agagatctgg gtgcttatgc  66240
ttattgcgca gcaaactaaa aaggacacca aaaaaataat acaatttttt ataaatcaat  66300
atgaaatgct tatgaatagt ccttggccca gtatggaggc ccttttttccc tcaagcagta  66360
aaagatattt aggcaactat gtagacccta acgcgctcat aaagtgggca caactcaaat  66420
taaaaagaat accgcctttt tatcctggaa agccggatga agaatcatgt taagccgatt  66480
aaaaaatcat gttaagctgg ttgaaaaatc atgttaagct ggttgaaaaa ctcttggtga  66540
aagcacggat gtaatattaa cattggccgc tcgcatttcg tgttgaaata cgatggaaga  66600
gcgacggcta tctaccatgc cgatatcggc ctggacatca cagttcatgc acttgtagat  66660
gggatgactc gcgttataga tggcaggctc gccacagttt ctacagatgt aggagatgca  66720
```

```
gccatccgag tcgtcgtgcg atttttctat gatggtttgc atggcgccct gcgccgtaag  66780
cacccaatgc tccatttctc ccagacgaag acctccgtgc gatcgtttgc cgtccaacgg  66840
ctggcctgtg agggcatccg tgggcccata gcttgcaacg gcgtatcggt catccagcac  66900
aaatttttgc aggcgctggt gataggtcgg tcctatgaag atggccgcat caaagtactc  66960
gccggtctgg ccgttgaaca ttttttggca tccattgaag cgtagacctt cttgcgccag  67020
tctttctgaa agaagctgca cattaatagg caggaatgcg gtgccgtctg ttaccacccc  67080
ctgtagggca tttgctagac caaccgtggt ttctatcatt tgaccgttgg tcattcggga  67140
gggatgtgag tgggggttta caatgaggtc gggctgcaat ccgtcctctg tgaagggcat  67200
gtctgaagtg ggcagggcca gcgccgcaat gcccttgttc ccgctgcgag aactcatttt  67260
gtcgcctata ttgagatttc tttcatagcg caggcgcatg aggccaaaga tctcgtcatt  67320
aggcccatgg ggacgcatca cagcatccac gacggccggc tcatcgaagc cgtacatgac  67380
agaccggtcg atgtatttgt tgagttcgtc tttttcgccc cgtattttgg ccacttttcc  67440
tataatgatg tcgccctttt tgaccaccgt tcctacgggc acgaatccat ctacaagctt  67500
ttcgtaatta gcaccaggct taagattttt ggtgattaaa gggtcgggct tcccaaacga  67560
ctctatatcg ctttctaatt ctacttttc ttctcggtag aaggtgccgg caaagccgcc  67620
cctgtcaata aaggactgcg acacgatcac agagtcctcc tgattgtagc cgccgtagat  67680
catataagcc acaatggtat taagcccgtt gggtatgaca tagttatgtg ctatggtctt  67740
tacaagcggc atttcattgt aaaactggaa gaagcggttc atgtcgacac gatatggcca  67800
gctaaagcaa taccagcccc ccgtttgccg gccttggttt gtttcatagg taacacgcgc  67860
aggttgggta cagtttgcgt agggggacac tagggcggca aggcccaaaa tagcttgggg  67920
cacgtccacg tgtgtgaaac gacgcgttac atcatgttta tgtttgcgta gctcgatgat  67980
ggagaaggca acaagacagt tttccgcctc ctcgggggta atgaactcac agatgccctg  68040
tgctacgaga tcttcaagtg taagcgttcc ggctaaaatg tcttttgcca tttgaggcgt  68100
aaatcgcgta ttttgaatga aagggatttt atgtttttcc cagtctttat cgcctttttt  68160
tctggcctct gcggccttgt agcaggcttg attgtatttt tcaatattat tatctacaat  68220
gagtaggggg cgggtcagcc taccgacgtc caaccaaaat tctacttcgt ctaccatgct  68280
atcccagtag atggtggtat ggggatgcac aaccttgccc tcacggcgaa gcattctata  68340
ccgctgagca agctcaaagg cattggtgca gcagccgatc cattctccgt tgataaatac  68400
gcgcgctagg ccctttcgta caatgtcctt gttggaaaca tcggctaact gttgaatggc  68460
cggatctgat agaaggcgtt gttttaacga aagtacttct ccggcggtgc agacattggc  68520
agtgatggct aactgtttag acatgcctac tttttcacca gtatcggctg actgggctac  68580
gcagatgtat ccaggatagg atgcgtgcac gcgacgcatc atgtcagccc tttctgtttg  68640
tttggatgcg ttggtggtgt tatgagtatt taccgtacgc aatgctgaaa tggtatttaa  68700
taaatttttt ctttccaaac tttgagtaga tactctgttt acaatggggc gctgtcgcac  68760
catgatggtt ttatttcctg aaatgataga ctgttccata ctgcgattaa gatcggaggc  68820
ggtatttttt gataaagcgg cagaaaatgc ctcgataatg tttcgctgag taagctcctc  68880
aaaggctgtt tgtttaagaa gttctttgaa cccattgatg atgggtgcta tcacggaagt  68940
attaaaaata gccttaaagg ccttggcgag tgagacccct gagccgtgca cccgcttggt  69000
gcggtagcta tcacggtccg tgggtggaaa cacattcata atgacaagaa gtattttatg  69060
```

```
aataagcagg cctaaaaagc gcagctttcg tacacgtgta tctgcggttt ggcccatgtg  69120
tggcagcaat attttgtcta aaatagtaag ttgtctttca tttaagtatt gtaccgcatt  69180
ttcatcgctt ttgtaagcag atgggtttga gacaaatttg gaaaccttct cggataaaaa  69240
ctggataatt ttttctcggt tcagctcgtg ttggaccggt tgaaatatgg ggtctaaaac  69300
atgaatggat ttttccagaa tttctatcat gaaggtattc acaagggagt tggattctag  69360
atcaaatacc acttgctcaa tgatgctgtc atcgcctgtc attccaaaca tgcgaaagat  69420
gagataccaa ggtatgcgaa gttttgagaa cttggtgcta ttgatttcaa tggtaatggc  69480
gccggtggtc atgtagcgta taataatttg agagctattt tcgaaggcac ctcccggttg  69540
ggagataaac tcgccgcgaa tgatttcatt attcccttgt tgcatggtat ggtaatggat  69600
gtgaagcgtg ttaaagcgga tgttttctaa gaggtctacg acccattccc cgcctcgggc  69660
tataaagtag ccgccgggtt cattagggtc ttctcctatt tctttttttg cggtttttga  69720
taggtgatga gtgtggcagc ggttgctgcc ccgcatgatg ggaaatgtag atacctgaaa  69780
aggaggaata cttgctcgtt ttacctcctg ccgaccattg ctgtagtgcg ccgttaaaat  69840
aacctcggcg gctagattaa ccgggcccga ataggaaagg ccacacaggc gtgccttatt  69900
gggtagtaaa tttatcttgt ttccctgtga atagtttcga tgttgcgggc gttcaatgtt  69960
cacatctgta aagttaaatt ggatctgaac tgattcccga agcttatcta tttcagtatg  70020
gtcgcgttgg tctttataag taatatccac gttaaacatt tgttttacaa tttgcggaat  70080
tccattgtcc ataagatcgt cgaagctttt gatgttatac cctatcaatc ctgtagagtt  70140
tactgcagcg gagataaagc tcagcatatc agcctctgta agctcctcat tatccacggt  70200
ttcaatgggg ccgtaggtta tttgcggccg caagggttcc atgattatga agtactacat  70260
taatattcag ttattcttta aaataaatct ttatttataa atcttattta taatataaga  70320
atgccttatg caagagacat cacaaagttt attacggcaa cggaaccaga ggtgggtctt  70380
cccctgttgg cgctgcagcg ctccaaatcc atcatagggg ttattcttct tgtaataagt  70440
ttgttattta ttttcattgg cattattata ttatcagtga gtagtggtca taccacagca  70500
gcctctatat ttatcgtatt gagtcttatc ctaggtggcg gtggtttttt tcttatttat  70560
aaagataatt cttaacccac ataaaatttg aaaaaatata gagtaagaaa atgtccaatt  70620
actattatta ctatggcggg gggagatatg attggttaaa aacagtagaa cccactaatt  70680
ttttaaaaat cgggttgcct taccaggcac acccattaca tcttcaacat caggcaacta  70740
ctcccccatc tatcttagaa aaatttaaac gagcagacat tcttcttaat gaggtgaagg  70800
ccgaaatgga cccactcatg ttacaaccag aaaccgaaaa aaaactattc cagatattga  70860
gtagtattga tatgttcaaa ggtctgcgaa aaaaagtaga attcacgtac aatgctcaaa  70920
ttgttacgaa tgcttggctt aaaatgtatg agctgctaaa taccatgaat tttaataata  70980
catctcaggc attttgcaat tgtgagcttc caggagggtt tataagtgca attaaccatt  71040
ttaattatac aatgatgcat taccctactt ttaactgggt agcttcctcc ctttacccca  71100
gttcggaaac agatgccctg gaagatcact atggtcttta tcagtgcaat ccggataact  71160
ggttgatgca atctccttta ctgaaaaaaa atatagatta taataacggg gacgtaacca  71220
tcgctagcaa tgtaaaaaac ctagcgctta gagccacaca aaggctgacg cccatccatc  71280
tatatacggc tgatgggggt attaatgtag gacatgacta caataaacag gaagaattaa  71340
atcttaagct tcactttggt caagccctta cgggtttgtt gagtcttagc aaaggcggaa  71400
acatgatact caaacactat accttaaatc atgcatttac tctttcttta atatgtgtat  71460
```

tttctcactt ttttgaggaa ctatacatta ccaaacctac ctcctctcgg cccacaaact 71520
ctgaaaccta tattgtgggt aaaaacagat tacgcttatt tacccccaag gaagaacaag 71580
tccttctaaa acggctagaa ttttttaatg atacgcccct cgtagaccta agtctttacc 71640
aaaatttact tgaaagcgtt tactttgccg tagaaacaat acatctaaaa caacaaatag 71700
aatttctaaa cttcggaatg aaatgttatc gacattttta taacaagatt aaactactta 71760
acgattattt agctccgaaa aaaaagattt ttcaggatag gtggcgtgtg cttaataagc 71820
tttatgttct tgaaaaaaag cataaactta agctttgtgc ctcctaggga tctgttgctt 71880
aatttaacag atgcaatctt aacagatgta aactaaaaag tgtgttcata caaggattgt 71940
atttatgaat atttattaac atataaggtt gtgatgtaac actgtataac ctatataact 72000
acactatgaa gcacggcgta taataattta tattgaacac gatgttgact catttatttg 72060
caaacaaata tttgtttgca agacgtttgc atgcatttac taatatgttg ttgactagtt 72120
tatttgcaaa ctagatgttt gattgcaaac tagatgtttg cacgtattta tttgaactaa 72180
tatacactcc ttgttttatt tgttatatac acagcataca taagtgtata ttgtttacac 72240
ttatgtttat aactcgacgt aataacattt tacacgcttt ttttttgcaa atcttaataa 72300
tattgtatga taaatcaaac aatgtcttat atatgtggtt tattatttta ggcgccgcaa 72360
gatgtactcc attctcattg catgcttggt gttattactc tgtctagtta tatatgtcgg 72420
tcatcgtgcc gatcatgcac gaaaatattt agaaggaatg tggcatggag atccggtttt 72480
tctaaaacag tcggggctac aatcctttta tctctacata caacctgacc atacatgttt 72540
ttttagcatt gtgaataaaa atggtgaaaa gctgatggaa accaaaatac cttgtacgat 72600
aacaaataaa atatatatgt tttttaaacc tatttttgaa tttcatgttg tgatggaaga 72660
catacatagc tacttcccta agcagtttaa ctttctgtta gatagtacag aaggtaaact 72720
tattttagaa aacaatcacg ttatttatgc tgtattgtat aaggataatt tcgccaccgc 72780
actaggaaaa acggttgaaa aatatataac acaaaattaa tcatgttttc taacaaaaag 72840
tacatcggtc ttatcaataa gaaggagggt ttgaaaaaaa aaatagatga ttatagtata 72900
ttaataattg gaatattaat tggaactaac atcttaagcc ttattataaa tataatagga 72960
gagattaata aaccaatatg ttaccaaaat gatgataaga tattttattg ccctaaagat 73020
tgggttggat ataataatgt ttgttattat tttggcaatg aagaaaaaaa ttataataat 73080
gcaagtaatt attgtaagca attaaatagt acgcttacta ataataatac tattttagta 73140
aatcttacta aaacattaaa tcttactaaa acatataatc acgaatctaa ttattgggtt 73200
aattattctt taattaaaaa tgagtcagta ctattacgtg atagtggata ttacaaaaaa 73260
caaaaacatg taagtttatt atatatttgt agtaaataat atttttaatt acttaaaatt 73320
tttatatata agtttttgat actatattat aaaacatatg ttcataaaat gataatactt 73380 attttttaa tattttctaa catagtttta agtattgatt attgggttag ttttaataaa 73440
acaataattt tagatagtaa tattactaat gataataatg atataaatgg agtatcatgg 73500
aattttttta ataattcttt taatacacta gctacatgtg gaaaagcagg taacttttgt 73560
gaatgttcta attatagtac atcaatatat aatataacaa ataattgtag cttaactatt 73620
tttcctcata atgatgtatt tgatacaaca tatcaagtag tatggaatca aataattaat 73680
tatacaataa aattattaac acctgctact cccccaaata tcacatataa ttgtactaat 73740
tttttaataa catgtaaaaa aaataatgga acaaacacta atatatattt aaatataaat 73800
gatacttttg ttaaatatac taatgaaagt atacttgaat ataactggaa taatagtaac 73860
attaacaatt ttacagctac atgtataatt aataatacaa ttagtacatc taatgaaaca 73920
acacttataa attgtactta tttaacattg tcatctaact atttttatac ttttttttaaa 73980 ttatattata ttccattaag catcataatt gggataacaa taagtattct tcttatatcc 74040
atcataactt ttttatcttt acgaaaaaga aaaaaacatg ttgaagaaat agaaagtcca 74100
ccacctgaat ctaatgaaga agaacaatgt cagcatgatg acaccacttc catacatgaa 74160
ccatctccca gagaaccatt acttcctaag ccttacagtc gttatcagta taatacacct 74220
atttactaca tgcgtccctc aacacaacca ctcaacccat ttcccttacc taaaccgtgt 74280
cctccaccca aaccatgtcc gccacccaaa ccatgtcctc cacctaaacc atgtccttca 74340
gctgaatcct attctccacc caaaccacta cctagtatcc cgctactacc caatatcccg 74400
ccattatcta cccaaaatat ttcgcttatt cacgtagata gaattattta atatgtacta 74460
tatattaatt atttaacctt tcaagctggt cttcatttaa atttaaaatc cactaataaa 74520
atgtattttc tagtagcaga tcatcgagaa catcatgtga ttccttttct taaaaccgat 74580
ttccatcaca tgcatcaaaa tcctatacaa aaaaatcaag ctctcctaga aatcaaacag 74640
ctttttactg gagattatct catctgcaaa agcccttcta ccattctggc ctgtattgaa 74700
cgaaaaacct acaaagactt tgcggcttct ttgaaagatg gacgttataa aaatcgccaa 74760
aaaatgctgt cgctgcgaga acaaaccaac tgtcaacttt atttttttgt agaaggcccg 74820
gcatttccta accctcaaaa aaaaattaat cacgttgcct atgcaagcat tattactgct 74880
atgacgcatc ttatggttag agatcatatt tttgtcattc aaacgaaaaa tgaggcccac 74940
agttcccaaa agcttgtgca gctttttat gccttttcta aggaaatggt gtgcgtcgtt 75000
cccacctccc tcacccccac ggatgaagag ctatgcatca agctatggtc ttctctttct 75060
ggtatttcag gcgtgatagg taaaatcttg gcaaacactt gttccgtagc tcatttggtt 75120
catggaaagc tttcatcgca gaatattgat cagttaaaaa ctccctccaa ccgaccattc 75180
cccaaaaaag taaaacgtat gcttataagc attagcaaag gaaataagga gttagaaata 75240
aaattgctct cgggggttcc caatatcggg aaaaaattag ctgccgaaat tttaaaagat 75300
catgcgcttc ttttttttct aaatcagccc gtagaatgct tggcaaatat acaaatcgtt 75360
caaaaaaccc gtacgattaa gttgggaatg aagcgagccg aagcgattca ttattttta 75420 aactggtgtg gctctgccca tgtaaccgat gatagccaaa atatcacaga ggcgtcgcgg 75480
tccacaatgc aggtcgcgac gcagtccgcc gcaatacagc ccgctgcaac gcagccattg 75540
cacgaagtat cagatgatgc atcatcagat gcttcatcac ccgtagggta tcaaacatta 75600
tctaaagaaa tgttattgaa cacagcctga tgttaataat tcactacatc taaagaaatg 75660
ttaacctcga tactaaaaag tcattgaaca caactactgg ggcgctaagt tgtccaacac 75720
atctaaagaa atgtcaacat cctcgatgct aaaagggtca tcgagccggt caataatgtc 75780
ttccccaaaa agtccgggag aactgtaggc cgagatgtcg tccatggagc tatcttcccc 75840
agagcacaca aagtcctctc caaaaatcat aaagttaaat gcaccgggct tacttaacag 75900
cttttcgctt tgaataatag tgttgagttc tgtcagcgca aactctctca caatattcac 75960
aacccaggag ggctctttaa tttcatacag cgttaagaaa cttatacata aaaattctat 76020
agagtaaagc aaggcgctgg caggatctgt tacccgtagg tgtttaaatg tagtgtgata 76080
ttcattcaca acgttaggca gcaccttttc caaatcctcc ttttcctcgt acgacaggtg 76140
ctttacaagc ctttcaacat gtataggagg cttgttaaat gtactaacgt gccgcaaaca 76200
gttataatta tataagaaaa tacgtacggc agagtcgacc gccatgagcc ttggatcatc 76260
cattgaggta ggtggtggcg gggcaccctg gccttccctg atgtctgcgt aggagcgccc 76320
ctccatggcc cctatggcct ctatcacagc aggactgata tccaaaatct tggccgtctt 76380
gattattttt ccgtaatcga aagtccatgg ctcctgtgga ggcttgggtt gtgtttcggt 76440
ggagggcgtg gtcatatctt tctttatttg aatagaacgg atcgacatct tttccttatc 76500
gtactggtct ttataattat tataatagtc atgaactaat tcgggttgag aaagatgatc 76560
gtatataata taggtaaaaa gtccgcactt gacacatttt ttatcctgga agtcgtgtaa 76620
tcctcccttg gggcagcgtg actcgtagaa ggcataaaag gtgttaaatt ctaagctcgc 76680
ctttagggct gtttggacct tttttatgtt taattgcccc acctcatgtt gtagcacgtg 76740
gcatacagaa cagcgtagat cggcaagtgc ataatggttg tcaatttttt ttatgacgtc 76800
tttgcgtgtt acttcaatct cggcgggttt ctgcgaactg tctacggcct tgtaaacgta 76860
aatggtccac ttatgaggaa gccccctttc atcgtatagg gttgaaatgg gaagcctttt 76920
atactcaaac agccgagtcc gttggtcggc tcttcctgtg ttaggatcaa atatgttata 76980
aaatccttgc tgagcaagca gggccttttg ctcgccataa gcattttcgt acgttttgaa 77040
ttctgcaagt tcggagttaa aattaggtgc attttgtaaa tacttaagaa ataattcata 77100
ggctctaagg taaatgagag ttgaggtttt ttcctcatcc cgtcctcccc accacacccg 77160
caggctttct tcttgaaaat agatgtcatt cagacgcgtc aactgcgtaa aatcaggccg 77220
atatttagag gtataaattt tatcataaaa ttctttttgc gataatagct cggccggggt 77280
acgtcctatc acggttttaa actcatattc agcctccttg ggagtccgtg gtttgtgcat 77340
agggatgctg ccgtcaatac gggccactgt ggcagcataa tcatacatgg ggtccagcag 77400
aatctctgtc aaaagtacct tggtgtcgtc ctgcacgcta agcccttgta gcccattttg 77460
gtggataatt tttttgaaag cctcccgaaa attattagca atccactgat ccgtaatctc 77520
agatagctga tttattatac cgctatattg ctgcatcatt ttctccaaaa gaaaggtcac 77580
gtatgcattc aaagagctat ccgccttcat tccatgaatg gtaatcgtaa gaaattcttt 77640
attttttgc gagctataaa tgagattcaa aatataggca tagatgtaga tcacagcata 77700
cagctgcgtt aaaggatcgt aatcctcttc ctttttaata ttttcgatgc tatacacgag 77760
cggcaggcag acatttacgg ctatattggc aaactgtttc acgtctacaa gctttccaaa 77820
gtggataaac gtgcaggcct tcatggtttc ctgccaaata aaaacacgga gcttactatt 77880
aagatcgccg atgatgccca catctgccgt acgatcctct tgaataaaat gggccagctc 77940
ttcgccacaa attttgcaaa agtaggagta aataagcccc tggttgtttt ctttctcctt 78000
gtttattcct gaaaatttca ttagcttggt tcgcatggtg tcgtaggacg cttctgccgc 78060
ttgaagctgt ataagcatgt ccacatgggg acaaagcagc ttaaacccgc aggctttgca 78120
tagattccaa ttggtggtat tgttttttc cttgtagagt acacgaatac tttctaatac 78180
ttttaataac tccgcgtatt gaagacccga acgcaactgt tttaccagct tgagatgagc 78240
acatgcattt ttttcttgga gttcccactg ttttttaatg tttaggtatt ctgttgtaat 78300
aagttctgcc tcctgtttcc cacaggcttt aatgacttct tgaaggatgc tgttagggtc 78360
atccacttta ccctccattg taagaatttc acgtatagca tccgactgca ccctacctat 78420
tttttcttcc ataattttaa aatactgtct cgcctgggta atgacctctg tgagcttcat 78480
gtccacctgc tgcagaatca tttgctcctt ttcacgctgt tcagcatgtt gtaaaaactt 78540

-continued ttgttctaca gggttccaaa gcacctccaa atagcctgct ctatataggt cataaagcaa 78600
gggcatgtat cccgatgtaa aaaccgggga caccgagtac atcgtagaca actcttttaa 78660
aaaaaatatc acgcgcttaa tgttctcctc cggttcaatc tcctcggttt caacgatatt 78720
agatatatga ctgccctgat cctcacggtc tagctttcgg tgtaccatct cctctgctag 78780
ccgattaatg agccagctat gcccgccgct ccgcaaaaac ttataaagtt cgatatactg 78840
gtgcgtaaac tggatgatgt tttccttggt ggttacgaca accccttctc cgtttttttt 78900
ccaggtttct tgatccacgc atttcataaa tactcgaata aaattggtca aattggctcc 78960
tgaggcgacg tagcccaagg tttcaggcga gaaggagcct atctcagcca tacgcataaa 79020
acactgcggg gaaaaagttt ttagccgcaa cttaagtcca tagatttcaa tgggggcttc 79080
tgcgggaacg gccaggtgcg tcccattaat taaaaaaatt tctttgcgtg tgctagggcg 79140
aacacgtaat tccttttttt tttcactcac gatggggacc acatcggggt ctaccagcag 79200
ttgacgtatg taggcctcta tgggcatgga tagatcgggc agctttgact gctcggcgcg 79260
aacatggttc acaaaatctt ttagagtgaa aagaaagtct attaaacgta tgttttttat 79320
atcattagac cctttaaggg tagagtagat ttcatccact agtgcctcga tttcctcatt 79380
attgagcgat aagatatctg tgccacggtg gactatttgc gcgatcgtaa ttacttcctc 79440
cattagatag aaactgaata ttatatttaa aataaataca aaatgtcaaa tgaaagtttt 79500
cccgaaacgt tggaaaactt actttcaatg ttacagacca aacagcaaaa cgcaattcag 79560
tcagaggtga ttgaatggct gcacagcttt tgtgaaacct ttcacttaaa aatacactgc 79620
cataaacagt ttattcctag cggggaaaaa aaacgagcta aaatacccgc tcaagaaaca 79680
cagggaaaca cgcagccctc ccaccatgtg taccgggttg ttctctccag agcacagcca 79740
gtcaaagcac aggaatctct gctaacaacc atgtgcaacg gactggtgct agatgcaaac 79800
acatggacat gcctagccat tcctccgcct gcgccctttc aacaggcgac ccgccaggtc 79860
caacactttt accgtaacaa tttctacgaa gtggttccca tccaggatgg cacccttctc 79920
acaatctacc actgggatga ccctgaatat ggcccctcct ggtgcctagc aagtacccac 79980
ggatatgatg tgagtaacta ctgttggata ggcgacaaaa ccttcgccga gcttgtatac 80040
gaattgctgc agcagcactc tacctgcgac gtcaccctgg aaaaaaataa aacgcgggga 80100
acgcgtcttt tctttgataa cttaaatccc gattactgct atacgattgg aatccggcac 80160
cataatttac agccgctcat ctatgaccct caaaatattt gggcgattca atctacaaac 80220
ctaaaaacgc ttaaaacggt atatccagaa tactacggct atataggcat tccaggaatt 80280
cagagtcaag ttcctgagct tccccagtat gatttacctt atctaatacg atcttataaa 80340
actgctatga atcaagccaa aaatgctata aaaaatggca aaaaagacaa gggatacttt 80400
aattatggct atttactcat ttcgcgagcg cctgccatta ctaaaagtac ttctaatgtt 80460
ttgttaaaat cgcctctgct ggtattttta caaaaaagtg tgtaccagaa aaaacacaat 80520
atctctaaca gccagcgact agaatttatt atactgcaaa actacttgat gcagcatttt 80580
cgagatcatt tcattgctct atttccgcag tacatatcct attatacgaa ataccaaaac 80640
atgttgaata tgattatcca tagtattgca actaaagata aagatcatcc ctttgcagga 80700
gccgtggtaa aaaaagtgtt ggaagatatt gaaaacgccg aaaacattat tgatcataca 80760
accattcaaa actatgccca tcaaagcaag tacgccatgc tttacttgtc aattatttcc 80820
catttttaat ctaatacggc caaagccgcg ggttttttaa taaactaaca tttaaaaaaa 80880
ctgttttatt aaaaattata atacttttat tatatatgga acatccatct acaaactata 80940

```
ctcccgaaca gcaacacgaa aaattaaaac attatgtttt aatccctaaa cacctttggt  81000
cttatattaa atacggaacg catgtccggt actacaccac acaaaatgtt ttccgagtcg  81060
gtggctttgt gcttcaaaat ccctacgaag ccgttataaa aaatgaggta aaaacagcaa  81120
taagactgca aaatagtttt aacacaaaag cgaaagggca tgtaacgtgg gccgtcccat  81180
atgataatat tagcaagcta tatgccaaac cagatgcaat tatgcttacc atacaagaaa  81240
atgttgaaaa agctcttcat gctttaaacc aaaacgtact gacgctcgca tcaaaaatac  81300
gttaaatata atttttgtag aggataaaaa gctattttag ctaaaaaata attcatatac  81360
gtttatgcag aggaagaacg gtggctttca aattcagatt gcatccacgt agaccgtagc  81420
gttttttttg cttctggttt atatcgtaaa ccgtaataaa catcatcatt tgtatccgtt  81480
ggatcttttt cccactccgg ataaaaaatc ggttttcttt tttttggtcg ttttttgcag  81540
taagctgtaa attaagggaa tatagcttat cgaaaagttg ttcctgatcc atataaatag  81600
cagcatatat taaaaaaaat aaaaaaagac gcttcaacga gtcagtacca ctgcttgcca  81660
acgatttacg ttggttggtg cattatggtg atatagtaat gagtgcctgc acaagtgctt  81720
gcacaagtgc ctgcacaagt gcttgcacaa gtgcttgcac aagtgcttac acaagtgctt  81780
gcacaagtgc ctgtacacat tactgcatcg ccaaagcacc tgcaatgcct acttcctcaa  81840
cagagtacga taactaaatg cttttaagca ccgcttgcgt cgatgtgtcc ttcggggcaa  81900
tcgggttcaa ttggatccaa tattattagt cataattacc taatacttat tcaattttat  81960
ctttttacc ttgtaagatt taaacagcgt tttagcttgt ttaaagcaac gtttaaaaca  82020
agctaaaatg ctgtttaaaa caacgtttta aacaagttaa aacaaataag cttataaata  82080
taccatgaca aaattagccc aatggatgtt tgagcagtat gtcaaagatt taaacctaaa  82140
aaatcgaggg tccccctcgt tccgcaaatg gctcacattg caaccctcac tgctgcgcta  82200
ttcgggtgtg atgcgtgcta acgcctttga catcctaaaa tatggctatc ctatgcagca  82260
gtcaggttat acggttgcta cgcttgaaat ccactttaaa aatattaggt cttcctttgc  82320
caacatttac tggaaccgtg atagcgagga gcctgagtac gtctgctgtt gtgccaccta  82380
tcaatcgcac gatggcgaat accggtatcg atttgtttgg taccaaccct tcatagaggc  82440
ttataatgcc atagaggcgg ccctggatcc cctggaaacc attatcctga acctcattgc  82500
ggcacgagat ctagacttcg ttgttcacat atttccttat aataagggcc atgaagacta  82560
tttggcctcc acgcaactta ttctcaaaat ctttattgcg acgcttttaa tggacatttt  82620
aagaattaaa gacaacacgt tggacgttca cttaaattcc gactatatta ttgtgatgga  82680
gcggctttgg cctcacataa aggatgccat agaacacttt tttgaagccc ataaggactt  82740
actagggtac ttaattgcct ttcgcaatgg ggggaacttt gcaggaagtc ttagaccctc  82800
ctgtgggcaa aagattgttc ccctaacgat tcgagaggtc ctacaaatga atgatattaa  82860
tttagccgta tggcgggagg tgtttattat gcaggaatgt tccgacttag tcatcaatgg  82920
gatagcgccc tgtttcccca tttttaacac gtggacgtat ttgcaaggta ttaaccagat  82980
ttttttgaa aacacgtctt tgcaggagaa atttaaaaaa gattttattg cccgagagct  83040
ttccaaagaa attatcaagg gccaaaaaac gttgaatgac aaggagttta aaaagttaag  83100
cctacatcaa atccagtaca tggaatcctt tctacttatg tcggatgttg ccattatgat  83160
taccacagag tatgttggct atacccttca atccctgccg ggtattattt cgcgatccag  83220
ctatttatcc cccatcgtga aaaacatttt gatggacgaa gactctttta tgtccctact  83280
```

```
atttgaccta tgctatggcg cctacgtgtt gcataaaaaa gaaaatgtga ttcacgcgga  83340
tttgcacctg aataacatga cctactacca tttcaaccca accagtttta cagatcgcaa  83400
caaaccagga aaatacacct taaaggtcaa gaatcctgtg attgccttta taaccgggcc  83460
caaagtcgaa accgaaacgt acgtgttcaa gcacatagat gggttcggct gcatcattga  83520
ctttagcaga gccattatgg ggccaaacca tgcaatcaag cttgagcggc agtacggcct  83580
cgcttttgta aacacctttt accgcaatca aagtgagcat attttaaagg tattacggta  83640
ctattttcct gaaatgctaa ccaatcgcga aaacgaaata caggggtga ttttatcaaa  83700
ctttaatttc tttttcaata gcattactgc cattgatttt tacgccattg ctagaaacct  83760
acgtagtatg ctttctttgg actatttaca cacctctgag gtgaaacgaa acgtagaaat  83820
ttcgcaaaca tttttggata catgtcaatt tttggaggaa aaggccgtgg aatttttgtt  83880
taaaaatctt catactgtct tatctggcaa gccggtcgaa aaaacggccg gggatgtgct  83940
tttacccatc gtatttaaaa aatttttata cccaaatatt cctaaaaata tattacggtc  84000
ttttaccgta atagatgtat acaattataa taatataaag cgttattctg ggaaagctat  84060
acaaacgttt ccaccctggg ctcaaaccaa agaaatcttg acgcacgccg agggtcgtac  84120
atttgaagat atttttccta gaggagaatt agtttttaaa aaggcttacg cagaaaacaa  84180
ccatttggac aaaattttac agcgtattcg tgagcagctt gctaatgaaa atttgtaagg  84240
cttgcagttc ttgtatggtc agaacctatg tcgatggaaa cattattttt cgctgcagct  84300
gcggcgaaag cgttcaaggg gatagtcaga acttgctcgt ctctagcaag gtgtaccaca  84360
ccggggaaat ggaagataag tacaagattt ttattaaaaa tgcacccttt gaccccacga  84420
attgccaaat aaaaaaggat tgcccaaatt gtcatttaga ctatttgaca caaatctgta  84480
ttggaagcca aaaaatcatt atattggtgt gccgctgtgg ctatatgagc aacagaggat  84540
aaaccatatc atcccaccga attatgacat tcctttaaaa ccgtccgcct aaatagtttt  84600
cacacctttg gtggcagact attttataaa aagtaatgtt ggttcatgaa gataaagtgt  84660
gccaaagaaa cttttataaa caaatgatta atgtaggtgc tagtcgtgtg tacttaaaca  84720
gggtattcta tagccaagta ttttctatag ccaagtattt tctatagcca gtattagtca  84780
agtatttaga tgtcagggta tttttatagc cagtattttt ctatatgtac aaactattcc  84840
agtaaacata tgtgtgttct ttattgagca gcatcatggc attaacaagt ttattaaact  84900
gctctaatgg gcattaaatg acaactcggt gcttagcaaa agtgcctata ccttttaaca  84960
attagggccg ggaggcattc ccagcttttt tctataatca gccatacagt accccctgagc  85020
ctcatacacg ggaataaggt ccttccattc cttgttggga tcggcgggcc agctctcaaa  85080
tgaggtgtga atgtaagggt cctgttcttt ttccttaatg aagcgtttaa tctccatttg  85140
atgttgttta cttttttgtt tgcggcggag cgtgttccgc accaatacgt aaaaaaatacc  85200
aagaatcaca cataaaagaa ttattaaaaa aaatatcatc atcgcggggt ttaaaaaacg  85260
atcccatgca acaggaatcg ttcttaaaac cttgtctggc agggctgtaa acatgaagtc  85320
tcctcctata atcggggtgg gactgtagcc taacagttca aggtcctgtc gttctagata  85380
cttattggcg aactgcccac cctttgcccc cgttttttta ttaatcaagc agcgctgcat  85440
tttccaccat tctaaatctt caggagaaag ctcaatgcca tatatcaact ttaacgttat  85500
tgcatctttt tcaatatcct tatcaatttg gctgagcttt tgagctttaa gcgggtctag  85560
tgtgtacttc catttaaact tagtgtcctg tagtttggct acatgaaata cggaacattt  85620
cggcggggcc tttgtgacgc ccttacactg cggaagttta tcattaggac aggcgcatag  85680
```

atgagactgc gccacagcat cgcgaactac atcgcagacg gagtacattt tcctcctatg 85740
ttaaacaata aattttttc atagctgaaa tttgtgggcc tatcttttcc cttgcccgga 85800
taataattat aagggagtgt tgaaacatct gggagagaat tgcttaaaaa atgggttttt 85860
gggaggggta actgcgactg ttgtacgtcg ttggccaggg agattctata tgccgggcta 85920
aaggtgcaac gttcctgtga acaacttagt acgcgcgttg ttaatacaaa tggactggta 85980
ttagcaaacc tcgtaaactc ttccggactt gtttgttttt gtatgatgtt tagcagggag 86040
tctgcctttt cgagaatcca aagcgtcgca ttgtagtaaa ataaaaatag cgacttatcg 86100
gcaggcgttg caaaagcgcc gtatagaaaa taaagcagta agtactgggg agacaccaca 86160
ataaggttat cttgaatgat agatatcgct agctctttaa acatagtgct aaaaaaatgt 86220
atgtcgttcg tcttgaatat agggggacta tagtccatgt agggctcaca tatctcagtc 86280
aggtgaaggc ccatttcttt tatgacttct tccgggttgt acgtcgctaa caccagcgcg 86340
ggataggctt tgggcatatc cacggtaagt gttatgtttt tatcattctt atggtaggag 86400
taagatggtt gtggaaattc tgttttccac tccgggactt tgcaggtaat tctcagctca 86460
tttagagtct ggtacaggag ggcgtatgcc gcaaagccgt gtatggccac ttgtttaaag 86520
ggaattgaaa acgttttact ttcgtatgtc gacttcacag gaacaacggg aatggggtaa 86580
tatttttcta tgaggttata ccgctgcaaa tcctttttaa acctgctaaa aacatcttcc 86640
cttggtgggt tatcaaaagg aaagcaaaat gctaggtgta gcccggcccg ctggtaatcg 86700
gggtgaatga ttttaaggtt tttatacgtt aatgtgggta tggtgttaaa gatattgggg 86760
ggcatatatg aaagatcagc aacccacaca aagtccgtgc gcacccgcat ggtctgcaca 86820
tggatggcgc gcaccgtgcc cacctgcttg aagccctttt catacaaaat gtcagcaagt 86880
tcgtaggcgt cctcaacgtg gttgggggaa aacatatcaa agtcgggtct ttctccctcg 86940
ggataaattg agctgccttt aagatgcagg gcataatcaa tggcaatccc cccgtacaaa 87000
ataagctttt tctttatgat aaattcgcgg accacctcca aagccgcctc aatctccacg 87060
gcatttgcct cacgttttg agcaatgagc cggtacttag aaacattaaa atcagtcttt 87120
agtaaagacg tcataaatag tgtttaatat atattaaagg tttgaataaa atactaaata 87180
gtaaaaatgg atgccctatt aaaggaaata gaaaagttat cgcagccatc cttgcagaaa 87240
gaaaacaatg atgtatgcga tctctgtttt atgcaaatga aaaaaatttc taactatcag 87300
cttttatgcg aagagtgcgg tcagctgaag gactggtttg aacctgaata taatgaaaaa 87360
ttcacggtat attctcgtct aaagatcgtg ggtgccaata gttcctatca ccagcgcgat 87420
ttggacaagg ccaactcaag tgactatagc tccttgcaat ttcatcacat tttagaggag 87480
ctcaaatccc taaatgttaa gtatatggat gcggggcaaa agccctttcc tattcaggtg 87540
ttaaaagaaa ctgctcacag ttataaccaa gtacaacaac atcgggtcat acgcagcatt 87600
acaaagcttc agatcttagc cagtattcta cgtagcattt gtttaaaatt aaacattgct 87660
tgtacggtgg cagacgccgc gaggtttact caacttaata ccaaagggat ctcaaggggc 87720
atggatcttc tgcgctccct atttgtagac aataaaatta ctttaaacgt tgatttaaac 87780
cctatagaca gctttattaa tagtacctac agtgccttac aaattaaaca aatccaccaa 87840
gaactgcagg aggaaaatgt ttataattta aaagaaattg ttaagagctt tatattatac 87900
gcggatgaga agaacatcgg cgtcgatctt aacaggagaa ccgttgtgat tgctacgatg 87960
tataatgttt tacgccgtgc ctactacccc atagaaattg atacggtggt gtatcaatgt 88020

```
aaaatacgaa aaaatacaat tacacgtgct cttaaaatgt atgaggatta ctactcccac  88080
tttaagtctc tttatgagca gtatcattta aacgcggcaa aaaaattaat ttaaactaaa  88140
cgtttaaact aaatgtttaa actaaacgtt aaaactaaac atttcgacta aagtttaaaa  88200
cctagtctaa cagcgggatg cccatttccc tggggttcca tatttcaaca attttttgac  88260
cttcgggtgt taccttgatg cagcgcatga cgagcagtgg aattttccta ttaaagagtt  88320
cttgcttagc tatatcaata ggactgctat attttttttt aagcattgta gatccattaa  88380
ttgccaattg ttgcgctcta acggcgacca accttgtggc ctcaaaggtg gttaaaacgt  88440
tggaggtaat gcgctcgtta tcgggtataa tgaccaatgt ttgcgacgag gcctgcacaa  88500
agccctcgca gatggacgga gactccacga tctcgtcctt gtcctcggac tcctcctcac  88560
tgtcgacgag gttctcctct tccgtttcca catattcctc cacgaggtca tccatgataa  88620
gatcctcgtt gtcattatca gccatattac actgttatca aatgtactgt ttaatacgca  88680
aatggattta ctacgtttta attgtatgtc ttcatgtgca ggctctagtg gaaagtaatt  88740
ttctcacaat ttttggcacc gttacacttg tgcccacaaa aacccgcgat ttttttattt  88800
tatattactt ttggaagtac gagtttaacc agtcgctttc aaaccttatg cgtctatctc  88860
gccaaaaaac gctcacagcg gtgttggata ttacctttaa aaaaataaca ttaattttta  88920
ccacagaggg cgtattgcgt atggattcta cgaataagcc aggcgtgcca ctcgatatag  88980
acccccagtt cattgacctt gatagtattt taatggaact ggatcattag gacctctccc  89040
gcccatttaa atttttagtt tctacaataa taaaatgcgc gaggaatcat gggaagacca  89100
cgataccatt cagctcaccg ctcagcgcaa atacctcgcc gaggtgcaag ctctagagac  89160
ccttttgact cgagagcttt cagtctttct cacagagcca ggcagcaaaa aaacaaatat  89220
tattaataga atcacaggaa aaacctacgc acttcccagc acagagctac taagactcta  89280
cgagcatctc gagcaatgtc gcaagcaagg cgccctcatg tatttttttgg aaagacaggg  89340
gacctactcg ggtctcatgt tggactatga ccttaaactc aatacaaatg ctgttccccc  89400
gctggaaccc cccgcgctat cacggctttg ccatcgaata tttgtgcata taaaaaacag  89460
cagtgtgctg cctgagggca gccataaaat ccacttcttt tttacattaa aacctgaagt  89520
ggttcagggc aaatatgggt tccatgtgct cattcctggt ctcaagctgg cggcttctac  89580
caaaaaaagc attataggat ccctacagca cgatgccacc gtacaaaaaa ttctacacga  89640
gcagggcgtt acaaatcctg agtcctgtct ggacccccac tccgcctccg ttccctcgct  89700
cctctacggc tcctccaaac taaaccacaa gccctaccaa ctgaaaaccg gctttgagtt  89760
agtctttgat agctctgatc ccgactacat tcccattcat caaataaaaa atttagaatc  89820
ttataattta gtttctgagt tgagccttac gaatgaacag ggaagccttg taagacctgt  89880
ctattgcgcg gcagacattg ccgctgagaa ggaggaagag atcccgaccg aggatcactc  89940
gctctccata ttaatgctac atgatcccga agcccggtat ttacataaaa ttttaaatct  90000
gcttcctccg gagtattatg tagagtaccc cctatggagc aacgtcgtat tcgctttggc  90060
caatacatcc gctaactatc ggcccctcgc cgaatggttt tcgcaaaaat gccctgaaaa  90120
atggaatacg ggaggaaaag agaaactaga aaaactttgg aatgatgcct cgcaccacac  90180
tgaaaagaaa atcaccaagc ggtccattat gtactgggcc cacaaacatg ccccccagca  90240
atacaaagaa attgtagaac aaggctactt ttccattctc gctgaatatg tgtatagcta  90300
taacggcatg cttgagcact acatgatcgc caaagtcatc tatgctatga tgggcaacaa  90360
gtttgtagtg gacgtggatt caaacgggaa gtacgtttgg ttcgaatttg tgctaccggg  90420
```

ccagccaatg aatcagggag aaatatggaa gtggcgcaag gaggtaaacc cggatgagct 90480
gcacatctat atttccgaaa acttttcaag ggtgatggac cgaatcacgg agcacatcaa 90540
ataccacctc agtcaacccc atgaaagcaa tattttaaat tattataaaa aactattaaa 90600
agcctttgaa cgctctaaaa gtaaaatctt taatgacagc tttaaaaagg gagttatcag 90660
gcaagctgag tttttatttc gccaaagaag ctttattcaa actctggata ccaatcccca 90720
cctactgggg gttggcaacg gggttctctc cattgagacc atcccggcta agctcattaa 90780
tcattttcac gagcatccca ttcatcagta cacacacata tgttatgtgc cctttaatcc 90840
cgaaaacccc tggacaaaac tattattgaa tgcactccaa gacatcatcc cagaacttga 90900
tgctaggctg tggatcatgt tctacctaag cacggccata tttcgcggcc tgaaggaggc 90960
tctgatgctt ttgtggcttg gaggcggctg caatggaaaa acttttctaa tgcgacttgt 91020
ggccatggta ttgggcgatc actatgcctc caagctcaac atcagccttc ttacaagctg 91080
cagagaaacc gcggaaaaac ccaacagtgc ctttatgcgg cttaaggggc ggggatatgg 91140
gtactttgag gaaaccaaca aaagcgaggt tctaaatacg tcgcggctga aggaaatggt 91200
aaatccgggc gatgtcaccg ctcgagagct taatcaaaaa caggaaagct ttcagatgac 91260
ggccaccatg gtcgccgcgt ccaactataa cttcatcatt gacacgacgg accacggcac 91320
atggagaaga ctgcggcatt atcggtcaaa ggtgaaattc tgccataacc ccgaccccag 91380
taacccctac gagaaaaagg aagatcctcg ctttattcac gagtacatca tggatccaga 91440
ctgccaaaac gcattcttca gcatactcgt ctatttttgg gagaagctac agaaggaata 91500
caacgggcag attaaaaaag tgttttgtcc caccattgag agcgaaacgg aggcgtacag 91560
aaagtcacaa gatacgctac ataggtttat cacagaaaga gtcgtggagt cgccctccgc 91620
agaaactgtg tacaacctat ccgaggtcgt gacggcctac gcggaatggt acaacaccaa 91680
cattaacgta aagcgccata ttgccctcga gctatcccag gagttagaaa actctgtgct 91740
agaaaaatac cttcagtggt ctcccaacaa aacgcgaatt ctaaagggtt gccgtatttt 91800
gcataaattt gaaacgctgc agcccggcga atcctacatt ggggtgtcca cggccggcac 91860
actcctaaac acacccatat gcgagccaaa aaataaatgg tgggaatggt cccctaatcc 91920
ctctgcccct cctgagaaag aagcgtctgc accaactcct tagggaatat ccttagaagc 91980
atgtctttcg gcagagccat taccggtagc aaaaaagcaa cattgagtat attatatgcc 92040
ttagcctgct cataagcgtc cttttttttc atggtatttt atgtttttaa atatttttaa 92100
ttatttttta aatacgatga acagttcgtg ctccgaaggc tgtttactaa aaatcggtgt 92160
gaatccgcat tctttaaata tggtttccca ttcggggatg gtatggaaat ccatgtctct 92220
acgaatagta tggtgcccaa gtgcgtcctg caggctgtga agccagaagg cctcctgacc 92280
ttgatgaagg tcgtacatga taagaaaacc atcaggtttc aacagatggt aaagcttgtt 92340
aaaatcgttt atcgtaagat gatgcgccgc cataggtaac cctatgagct ccacagagtt 92400
ttcatgctgg acatcgtcca tatcggtata aaacgtttca cagtaaatga gacgcttaaa 92460
cgagtatcga tgacaaacat ttatttccaa gtaggtttgc actacgtttt taggtatatc 92520
gggaatcatg ttgattaagg ttgtttcggg aaacttaatc atctgactag gcttcatttt 92580
caactcttta aaggatttcc cggagaagtg aaaatgggtc tttacgtatt tatgtaaaaa 92640
tacctgaatg ggcagagggg gctcctcctc ttcgttctcg acgcctccca aaatatttgg 92700
aatttcctga cgtggcaaaa gaaagtttat gtccacgttt acgaatccat cgaggacgga 92760
cacaaagctt ggctctaatc tccattccat atactgttta gaaacgggag atagcataat 92820
cctaggcgtc acaatgcacg aagggttttt aatcaccgca tcgtggtaag aaaagtgtat 92880
tccatttctt ccagtataaa gaagcctatg ttcgtcgtag cagaaacaat taaggcggta 92940
tgcctcatac atacactgtt tcaaagtaca aacacgtttt aaaaaggttt ctgcattggc 93000
ggaggccaag cggttttgcc attggtggaa ggggttcaat cctacaatgg ccagctcgtt 93060
taaaatatct tcgcggcgcg ctaaaatctg caccatagaa gaatacttta gcattttttt 93120
ttcgcaccat tcgcgaagat gtttagctac attattaacc ttattattga taaagtatac 93180
gatggcatgt tggaagcctt caaaaataaa gagcccctcc aaaagatcat ctgccaatag 93240
aagatggatg ttggtgtaag cattgtcaat attttgtaga aacggcggaa tgcctgccaa 93300
aaccgcttca gcaagcatag ctccgttccg ttgtttactg tccaatagat tcgtaagttt 93360
tttgtccgca acagacacga cggctaggat ggttgcaatg tcagaaatgg cggcttgcca 93420
gaaataaccc gaaaagcaca tgcgcgcttc ttctatagat aaaaacgaaa agcgagaggc 93480
aatgtctccg agctgcgtga gttgaagacc tttttctcct ctggttaaaa ggcctgccac 93540
aatggcccgc tcaatggctg atgccagcgc atccgtgggg ggaggatcca gcatatcaat 93600
ctcctctgcc ttaaacacgc cttccttatt ttttttaatc gtttctacga caatgctaag 93660
aaaaatggcc ccagggcctt ccgtaatgat ttcaggatac tgctgcactg gtatttgctc 93720
aaagacgtgt tttgtgtaaa gcgggtaaaa gtgcccagga aatactctcc ctacacgccc 93780
ctttctttgc tcgatacggc tttgagccgc ggggcgcgta ataagccctc ccgcccattc 93840
gggatagtag gtttcaatgc ttctgttcca cccgggatct atgacgtact tcagcgtttc 93900
aatggtaagg cccgtttccg caacaaccgt ggaaacaatg acccttctta aaggtttttc 93960
cactttagcg gttaagggat ttttcaccca cagattctta atttccgctt tcaggccaag 94020
gtaggcctca ttttcctgcg caatcgcctc actatcgatc ggcaaaatca acattaacgg 94080
cagcttttct ttggcaaggt ccatatttgc attattcagc aacatcgaaa ggaagcgtat 94140
ttcagccata ccgggcatga aaattaaaat atctgcttcc gtgggacgat catgaatgtt 94200
ttctttatga atagtgagag ccgtttcgca ggcggtctta atgtagttgt tggtgttata 94260
cagcggccag tgggtttcca caccgtactg tcgtccttcc accaaaataa tgttttcttt 94320
tccgatacca aaataggttg agtatttatg ggtatcaatg gtggcggagg ttaaaattac 94380
aaagggaata cgcagcgccc ctatgcttcc tctttgcaac atgcgctgaa gcatactttt 94440
aatatacatg agcataaggt cgatgcctag ggctcgctca tgggcctcat ctataatcat 94500
aaaggcatag cgggaagcta tctcatcatc cgtcattgta tgtagctgcg ccaacagaac 94560
ccccgcggtt gcataaataa ggccccgatt gggtttttcc gtcagaggct tcgtttggta 94620
gcccactgtt tggcctaata tcatgtcggg gtagtgggtt gaggcgccga tgtctttggc 94680
gagggtcacc gcggttagga ctcttggctg ggtacaaata accgagcgtc ccaagtattt 94740
ttggaaagaa tgcgtgtttt catttctcag aattctgaac acgtgtacgg gtaaggccgt 94800
ggattttccg gaaccagtgc gtgactttat aatgagcacc cggtctgcga gggaggttgg 94860
aatggcccct ccaaactccg ggagacgttg ttttatccaa gtgatgatgt aatgaatagg 94920
aacatcattc ttgtgctcag cgggcacgtt atagagatga ccaggctcca ataaagtcgg 94980
ttttcccata ttctattgtt ttaaggattg attgttcata aatattttta tactctgacc 95040
aagaaattat ttttttatta agccggttat ttacgttgtt atggaacgcg aaggtccagt 95100
actgaaagtc ctccgagttg tttaatgtca agggattttt tgtaagatac gaaaaggcgt 95160
ggtgctggca cctggtgcat ggcagagact cgataaagtt cagtatccat tggatggctt 95220
catatttttc tttccagcta ggagcgtctg aaaaaaagat agcatataga tgcaaggatc 95280
gccagtattt aggtccccaa tgcaacattt ataacctttt gaaaaatctc attccatata 95340
gaggtaaata tttttttcc atggagaatt tttttgcact cttgaaggga ttgcgccaca 95400
tcgtcaaatg ttttttgttt tccatgtatt ttggcgtaat tccagccagt atctgtgtca 95460
tggtccttaa tgtcatccgc taactgaaag gcatgtccaa aacaatgggc agccctttca 95520
atcatcccaa tgtcttcaac ggatccagtt cctaaaaccc agcccataat aaacgcgatc 95580
ttaaaaaagg gaatggtttt ttctggagtg tctactaact gaccggaacc cgcgctgttt 95640
agagagtggc ttacaaaggt acacagcagc gctcccagtt ggttgggatc cggaaacctt 95700
ggacagtgtt ccttaatcca gtcgatttgc cggcaaatat tttgaaatcc ttgcatggtt 95760
agcgccagag cgctcatctg cgccttggct acgccaaagc gggcccacac tgtatcttta 95820
tttcgccgct tcacatcgtt gtcaaaggag ggcatatcat cgataatcaa agaagctacg 95880
tgaaagtact ccgctgctag ggcggcctct gccggataaa taggcgcccc aaaggaatgt 95940
tgcaactgac aggcccgaac aatttccatc aggataatgg gacggatata cttcccacct 96000
cttagagcgt aagagcaagg ctctgttagt tgtcccttaa agtccccatc ttcaatagca 96060
ttatttaaga tggtctcaaa ctcttcacta aaggttttat aatttttagg attcagtgga 96120
tgtattccat gaaaaagcgc gacactacgc ggtgctgtga ttctaaaata cttaggtttg 96180
cgcgtatagg atattaaaat aataataaga actacaatga tggagatata gatgagatgc 96240
aacatgctga gttgtctccc cgcagggaat ggtccttttc cgcgcttgtt aacggtaccg 96300
aggaggcgtt gaaatcttta ggaaaggtgc tgtctagttt ggaatctcca attcctcccg 96360
tatatttagg tatataatta ttgtgtctag aaattgtttg ctttgaggta tcaaaatatt 96420
cagcctgacc gctatttctt ttagaataat tcggtatagg gcttgagtag ttggcaatac 96480
tcttaaaccg gggcaccaag gtaacaatat tttccatata atgggtttga tacgctttgt 96540
ttaaaaatgg gcttaccggc tttatgcttg ttagttgtgc attgagtacc ggtatgtctt 96600
ctaggatttg tggctttata gaatgattag caaacacaga atgtagtata ttagatactt 96660
gtagcatatg tctatttgcg gaaaattcct ggtattctct gccgtgttgc gaatctttgg 96720
gcggaagggg accaagcatc ggcacgtccg tgtaggtact ggtggatttt atgagttcct 96780
gctctatgtt cggtttgaca tgtggatttc ctaaaggaat acctctacct gcaatccctt 96840
tttctaccga cgcaggtaga ttgtgcgcta aacacaaaat attgtacacg tctttgtgcg 96900
gaatatatcc gttatagtgc tggcccggca tctgatcgcc aaggtgctgc tcatgcttaa 96960
tggtaccctt tgttctgagt ttaggaagat cctcgtacga aaaaaatttt gtgtgctcgc 97020
tgaacctcgt agaaggaacc gaactatttt ttgggttttt taaggaaggc aatgaggaag 97080
gctgggtcag acaatttttc tgtgtgccct ttaagctagc cacctgcgga aatgtttttt 97140
tttccgtacg aacaacattg cgcctaatta ggttttccgt atgggttgaa aaagcaggac 97200
gatgattttt aaaatgatta aaaagtttat tttttggaat ggagctgtac ggctccagat 97260
cttgcgcatc gccgtaacca atgtttttgt gctgagggtt cagcataaaa gaaaagttac 97320
gtagatcact gagttgcaat cccttttcag ccttttcagg actattagtg tattcattgt 97380
atacaggcgc ggctccattt ttgttgccgc agtaccggga atttagtata ttatcagaat 97440
accggttatg acgcggcaaa tcgctttccc aaagaggtgg atctgaccta taatcggcta 97500
acagctttga agcataatca tgatacattg tatataaaag ttaattatta tattgagaag 97560
gcataattac ttcttgtagg ggtacaagag gctttgaatc aggcaaactg acgggttttg 97620
aatcggccgg ctttggaccg gcaggtatct ttttaggttg atcttcttct agctcattag 97680
acacggatgg gggagaaata ggaggaataa tttcatctcc gcccttatat ttgtcatgga 97740
tagaagaaac aattacatcc atgtttgatt tattataaat gtcgtttaac tggtgattta 97800
aaacataata atgcaaaaat aatagggcta caatgcatat atatacgtaa atagccgtct 97860
tcgtttttcg tttttatcc accggcggat tacaaattgc aaaaaataca actaatacca 97920
ccgctgtaat gattaaggcc acaatgaaag gatttgaaa ggatgttttg aacggttcgc 97980
acgtataaat tttttctcct aaattattga tacccgcaat aaaatctaca ttcattttat 98040
atatttataa attatgaaaa atttagagtt acatctccgc cggaccaatc attgctaaaa 98100
tttgaagatt cttcaaaaag gcccgactgg ttgaatgtct tctgctcagg tttccaaaaa 98160
ttttccaaga atggattttg aacaataggc tcatcttgat tttcttcttc aaggatattt 98220
tctttgatat caagaacagc ttctttaaac tcaggtgtat cttgattaaa ctcaggttta 98280
tcctgatcaa tcgcaaaaat attatcttct tcagatatat cctgtttaat cgcaagaata 98340
gtttcttcct caggtttatc ctgatcaatc gcaagaatat tttcttcttc aggtttatcc 98400
tgaccaaact caacaatatc tttctcgcta aatccgtttt tagtgtgaag ctcttggttt 98460
tgaagagaat tatcaaaatc tattttagtt gttgtcctag accgtggcac gggatagtta 98520
tctaatggtt tacttactat agtcctcgaa tgtggcacgg gataattgtt tggtgacttg 98580
ctggttagct cttggcttgt taatagttct tgttttctca ataattccat ctctactact 98640
tctttttgat ccgctggtgt ctctttttgg tattcttcat tagaaaaatg ttcagagggt 98700
aatgtttcaa taaactttgt gagtggatag ctgctctttg atgtagaaga gcgttgaatt 98760
tgctgataaa ggagttgaac aagtcgccgg tattcactct gtcttttttc atattttta 98820
cgtagcgtgg agagatctgc taagagcgac ttgttttcag atgttaattc ttcaatttga 98880
tgaagaaggc tgcgattgta tgaactaagt cttgcatacg tttcttctaa ttctgtctcc 98940
ggctccacat aggcctgttt tcgcagaaat ttattgtata gttccattct tttttgagc 99000
agaaaggtaa gactataatc ttgcatttct ttcgtaactt tatggtagtt ttctttccgg 99060
tttttgataa taaagggcag catttttct gttgtgataa aggtgcccag attgctaatg 99120
tagtcgcaca gtagcaattc caagatagat tctttctttt caaggcttat agattggctg 99180
tattctttag gtatgaaaga atcaacaatc gttgttacga agtttgaaaa gtttaatgtt 99240
ttgctgttaa tttgggtaat gttacaaaaa tatttgtaaa aactatctag catttttca 99300
taaagtttt tattttgttt aacccctaaa atatagccct ttacttgata ctgatattcc 99360
gtaacaatgg aatgtttttt gtatagtgca tttttgtata aaaagttata aaaaatgttg 99420
ataaaatacg caccaagggt ttcaaaaata cttataacgt gggattcttc ctgatccatt 99480
atatcatatg taatattatt ttaataaaaa attactgacg aataacatgc aaaaaaaata 99540
tgtttaaact tattttaagc tagcacttat ttaaaagtgt tttaaacacg ttttaaattg 99600
tatgttaata cacttaaaaa ttaagccgaa atttgctcca ataaggatta cttttatcaa 99660
tgaccacctc tttactataa acggctttac ataattttaa taatgcttta gagccaaagc 99720
tgaaggcagt gggaagcggc actgtactat ggtaaaaatg ttgccgatgt tcatcctcgc 99780
ggatgtacac aagtttccta tatcctttaa acacaatatg gctaatttct tccacatact 99840
ccttatcctg tttggaatag cggttgcttt gacgggaaaa attcgacata caaatagagg 99900

```
catttgtaaa aatggaaaca aatgcgtttt tacgaagatt ggcgggtaaa tcggtatcat  99960
cttggcagca aataatcatc gaaataaaac agtgacgatt ttggtaaaaa aactttttaa 100020
aaatttcttt tgtaaataat gggtgcagtt cggccgcgca gtcgtctaat attaaaagta 100080
aacgaggatt aagattgata tagtttaacg taaacttttc atcctctgta aggcataagt 100140
ttttatacat atgaatgttc tgtataataa tttttttaa aagttgctga taaagcgatg 100200
taatcttttc ttcttttttt tggtccgttt gttcagcctt taagcactcc actttgcaa 100260
tatttttgtt ttcctttgc tgtatatcga tcggaagttt atgatacaat gtttttagca 100320
tatcgatgtt gtttactcga ctgtagatgg aggacatcat agtttgccgc tgccagatgg 100380
cctccaaaaa gcgttcagcg cccttgttgt cattttttt ttgcttatcg gcgagccaca 100440
agcggtagtg tattagagtt ggatgtacaa aaccctcata tgaacgattt gagggttccg 100500
agggggcaac cactaaaatt tgttcaatat ggggttgcag gattttcata atatgtttaa 100560
cgtacacggt tttgcctgtt tttgaggggc catatagcac agttgtttta tctataaaat 100620
gatgtgcttt gaactgtagt tcaggaatta gcttccctga atgggtcgtt agggccatct 100680
ctatattatt acaattctgc ttttgtatat aaaatttctt tttcgagttt attattattg 100740
ttgacccaca tatctacccg tatcgtatca tcaggcacat tgagcatttc aagcgcatta 100800
tctaactgtt tttttgtttt tatcagctcg ctttcttcat cgggggttaa attttcttta 100860
ctaagcagtt gcttaatttt ttcttcgcag tcgtctataa aatcatactc tcgagctttt 100920
ttgatatttc cagatgcttt ttctaggttt tttagctcct taaaggaaag cagtccctta 100980
atcccgctat ccgtgtgaaa ggttgaatta tagatggaga gccccggagc atccgggcca 101040
gtttcttgta tattttttgc ttttttgtgg taaatagtat ttcgtaaaat ctcttttcct 101100
atctttaggt cttcctcatg acggtccaaa atccgtttta ttatttcatt attttgatta 101160
aaataattgt agcgctctct gttggcctta aagcttccca ggagtgtcca gttgcctaat 101220
tgaatggatg aaacctctga gaaaatctgg tctttatatt tataataaaa ttcatcaacc 101280
ttttgttggt tgctgctatc caccacatca taaataatga aggcaaactc taggtcgggt 101340
ttttctgggt agatgctttc cgtagcggcc cgcaactctt cgtaattatc ctcaatgtaa 101400
taattccact tataaaaagt atcctgaggt ggaatatgct gcgaaagata tctagtaatt 101460
tttgtgttaa agagaatggg tttaaacgcc ctcggatttt caagcatatg tttaatgctt 101520
tggtgaagtt ctatatttg taatatgtgg gctgctgccc tatagccctg tggggtttgg 101580
gtgattgcat caatatcggc ctgaagctca ttaggcacat ttaatgtttt ttgcatgatg 101640
tgtaaaggga tgcgctcagg atctgctaaa tcggtgtatt ctgtgcttgt acaagtgctt 101700
gcacaggtat ctacattggt atctgcacac atgcttgcac aggtgtctac attggtatct 101760
gcacacatgc ttgcacaagt gtctacattg gtatctgcac aagtatacgc actttgagca 101820
tgaagattag gatcaaacac aaaatgttct cgtaaaaagc tatcgatcgt tgttttagct 101880
tccttgcttt tctgcgtctg ggttttgcag ctatctgcta tagataaaat tgtatttact 101940
accgattcag agggaacatc attagtttcc tgtttcaaag tatcaactaa cgttattagc 102000
tcactgagaa gagttttggt cgtgtgggta ggttttgaat aggaaggcat ccattcctgc 102060
agagctttga agacatatcc aataaagcta gtcattataa gacgtcgaat atactgctcc 102120
cgcaaatttg taaaagagca aaaggccacc ctgctatcat ttttgaactg tttgtaaggg 102180
ttcgtccttt ggtaaagctg tttaagcgtt tcttcggata tttcagtaga gggatcctcc 102240
```

aatacgtttt tgagaagctc atcaatatta aattctgcca tatcttagag tttattatat 102300
acatattaaa gctttaatat aagggggggta taacaatgga cgaaatcatc aataaatacc 102360
aagctgttga aaaacttttt aaggaaattc agcaaggatt ggccgcgtat gatcaataca 102420
agaccttaat tagtgaaatg atgcactata ataatcatat caagcaggag tattttaact 102480
ttttaatgat tatttcacct tatcttatta gggcgcatag cggagaaacg ctgcgaaaca 102540
aagtaaataa tgaaattaaa cgtcttattt tggttgaaaa tatcaatacc aaaatatcta 102600
aaacgctggt aagtgttaat tttttactac agaaaaaact ttcaacggac ggggtgaaaa 102660
cgaaaaacat gtggtgcacc aataatccca tgctgcaggt aaaaacagcc cacaaccttt 102720
ttaagcaact atgcgacaca cagtccaaaa ctcaatgggt acaaacttta aaatataagg 102780
aatgcaagta ttgtcatacc gacatggtgt ttaacaccac gcagtttggg ctgcaatgtc 102840
ctaactgcgg ttgtattcaa gaattgatgg gaaccatttt tgatgaaaca catttttaca 102900
accatgatgg gcagaaagca aagtcaggta tctttaaccc taaccgtcac tatcggtttt 102960
ggatagaaca tattcttggt agaaatccag aacaagagtt ggggaccaaa caagatccct 103020
gcggaaccaa ggtgttgcaa caactaaaaa aaattattaa gcgcgataat aaatgcatcg 103080
cgcttttgac ggtcgaaaat attcgaaaaa tgttaaaaga gataaaccgc acagacttaa 103140
ataattgtgt ttctcttata ttgcgtaaac ttaccggagt agggccgcct caaatatcag 103200
agtcgatttt actacgaggc gaatacatat ttacagaggc aattaagata cgggaaaaag 103260
tgtgtaaaaa agggcgtatt aataggaatt attatccgta ttatatatat aaaatttttg 103320
acgccatttt gcctccaaat gataccacga atcgacgcat tttacaatat attcatttgc 103380
aaggaaatga tacgctagct aataatgata gtgagtggga atctatctgt atggagctcc 103440
ctgaaataaa atggaagccc acagatcgaa cccattgtgt tcattttttt taaagatgaa 103500 gatttttttag atgatttttt ttagtttttt aaaagacgaa aaaatttttt aaaagatgaa 103560
tattcttaaa ccccgcaaat tactttttttt taggtactgt aacgcagcac agctgaaccg 103620
ttctgaagaa gaagaaagtt aatagcagat gccgatacca caagatcagc cgtagtgata 103680
gaccccacgt aatccgtgtc ccaactaata taaaattctc ttgctctgga tacgttaata 103740
tgaccactgg gttggtattc ctcccgtggc ttcaaagcaa aggtaatcat catcgcaccc 103800
ggatcatcgg gggttttaat cgcattgcct ccgtagtgga agggtatgta agagctgcag 103860
aactttgatg gaaatttatc gataagattg ataccatgag cagttacgga aatgttttta 103920
ataataggta atgtgatcgg atacgtaacg gggctaatat cagatataga tgaacatgcg 103980
tctggaagag ctgtatctct atcctgaaag cttatctctg cgtggtgagt gggctgcata 104040
atggcgttaa caacatgtcc gaacttgtgc caatctcggt gttgatgagg attttgatcg 104100
gagatgttcc aggtaggttt taatcctata aacatatatt caatgggcca tttaagagca 104160
gacattagtt tttcatcgtg gtggttattg ttggtgtggg tcacctgcgt tttatggaca 104220
cgtatcagcg aaaagcgaac gcgttttaca aaaaggttgt gtatttcagg ggttacaaac 104280
aggttattga tgtaaagttc attattcgtg agcgagattt cattaatgac tcctgggata 104340
aaccatggtt taaagcgtat attgcgtcta ctggggcgtc cagctataaa acgtgactgg 104400
cgtacaaaaa gtccaggaaa ttcattcacc aaatcctttt gcgatgcaag ctttatggtg 104460
ataaagcgct cgccgaaggg aatggatact gagggaatag caaggttcac gttctcatta 104520
aaccaaaagc gcaacttaat ccagagcgca agaggggggct gatagtattt aggggtttga 104580
ggtccattac agctgtaatg aacattacgt cttatgtcca gatacgttgc gtccgtgata 104640
ggagtaatat cttgtttacc tgctgtttgg atattgtgag agttctcggg aaaatgctgt 104700
gaaagaaatt tcgggttggt atggctacac gttcgctgcg tatcattttc atcggtaaga 104760
ataggtttgc tttggtgcgg cttgtgcaaa tcatgaatgt tgcataggag agggccactg 104820
gttccctcca ccgatacctc ctggccaacc aagtgcttat atccagtcat tttatcccct 104880
gggatgcaaa atttgcgcac aagcgttgtg acatccgaac tatattcgtc tagggaattt 104940
ccatttacat cgaatcttac gttttcataa agtcgttctc cggggtattc gcagtagtaa 105000
accaagtttc ggtacgcatt ctttgtgccg ggtacaatgg gtcttccaaa aggatctaca 105060
agcgtgtaaa cggcgccctc taagggtgtt tggttgtccc agtcatatcc gttgcgagga 105120
aacgtttgaa gctgcccatg ggcccccatc tgggacgtgc cctgaatcgg agcatcctgc 105180
caggatgaat gacatgcacc caatatatga tggcccacca tatcatggaa aaagtctccg 105240
tactggggaa taccaaaggt aagcttgttt cccaaggtgg gggtacccgt atgcgggcgt 105300
actttattgt attcaaaccc tactggaaca taaggcttaa aatgcgcatt aaaatgcacc 105360
aaatgtgttt cttcgatttg actcaaagtg ggttcgggat cgggtttccc ataacttttg 105420
ttcacatttt taatgttaga gatcctgcta ttcagcaagt cttgggccaa tataatcttg 105480
tcggccttcc catcgttagc aataagacaa aaagctcctc ctgatgccat atataatgtt 105540
ataaaaataa tttattgttt ttattaaata tggcggttta tgcgaaggat cttgataata 105600
acaaagagtt aaaccaaaaa ttaattaacg atcagcttaa aattattgac acgctcttgc 105660
tggcagaaaa aaaaaacttt ttggtgtatg aactacctgc ccctttttgac ttttcctccg 105720
gcgacccttt ggccagtcag cgcgacatat actatgccat cataaaaagc ctcgaggagc 105780
gcgggtttac tgtcaaaata tgtatgaaag gggatcgtgc cctccttttc atcacctgga 105840
aaaaaataca atccattgag ataaacaaaa aagaagaata tctgcgcatg cacttcatac 105900
aagacgaaga gaaagcattt tattgtaaat ttttagagtc tagatgagct tttacgcaat 105960
gttgtacagt gttgtatata tgtcttgtaa gcatttgttg tagagtaata agtaaaagat 106020
aaataaaaat gactattaaa ataaagccca aaccattaaa aatattttta tctgttagat 106080
ttaatttaat aaatggctca tggaatgtgt ggtgcgccgc tgcatgaggt gtggccgcat 106140
gggatgtggt cgcataagat gtagctacat gggatgtggc atttgcttgc atgtaaggat 106200
catgatgtgt tgggtcttca tcccagcaat aatcgccatc tttatctagc tgaattgtat 106260
accccattat atatcactta ttattttttt ttaatgtttc atgaatttca ttataggcgg 106320
tgaaagggtc ctcaggcccc ttctgtaaaa gattatagag atcttcggac gctttatgtt 106380
tcgtgcgaat taaggcggga tataacaaaa gagagggccc cagttccaaa caaattttac 106440
ttagcgggct catattttgc accaagtttc ccactacttg cgatgtttca taacgcattt 106500
taaagagctt tatcataaaa gtgttatgca ggccggtgta gtctggccta tagttaagga 106560
aggggatttc tctggtaccg tcaaacacga tctcaagtcc tctagcaagc ccgatcaaaa 106620
tttcttcagc aatggatgag tatctaattc ctacattacg aagcgtaagc atttctataa 106680
catcatctat ttcctgcata gaggaatcta ttgtaggaat tttaatatca tctgtgctga 106740
tttgttcatt cccaagatag gtaagcagca tattaatttt ttctagcttt actagcttag 106800
tcttacgctc ataatcatga tcttttttat aaaaagagtt gggatcaccg ttggaccgta 106860
gatgattaat aaggcggtct acttgctttg tactaggttt aatacttttt tcactatact 106920
cgctttcagc atagtggttt ttacgatctc ttttagaaat agctgttttt tgagatgcct 106980
cagactctgc atattttttt ctatgcgtag aaagagaata accgcggtca ttacgtgaac 107040
tactgttgca tgcaaggcct cggcgcgtct taccgctgcg cacactgcca ttgcgtatac 107100
tgccatcgcg cacactgccg ctgcgtatac tgccattgcg tatactgccg ctgcgtatgc 107160
tgccgctgcg tatgctgccg ctacatacac tatcactaca tatgctgtca gtacatacgc 107220
tatcgcggcg tatgccgccg tgtaccttat cgccgcccct acccgagggt tttttagata 107280
taatactgtg tggggagtca agcgaaaatt cagggtcatt aaagttaatg cccaatgact 107340
ttgccaatcc attaagctct tcatcaaaat gatcggtagg aaaactttgt tgcttgccca 107400
tgacctgttt ttcaagttcc tccaaattgg cttgctcatt tatatggaga ttattcataa 107460
gcgtcgtaat tccagcaaga tttgctcctt ctaaaaatgt ggtgtcctcc atcggatata 107520
ctatactatt taaaagcttt taaataaaaa tgtgtttgga agaaatgctc tcttcaagcg 107580
tgtgtagctc agatataaat gcctcctcag aaagctttcc accatactcc tttctcatcg 107640
tataggaggg cgccggttta atgtaggaaa tccactggga ggtaaaaaac cggtacaaca 107700
tatttagcag ctcgcgggcc tcccaccttt tgggctccgt atagtgcaca tcaacataag 107760
aggcggcgca tgaaaagctg caaaagttgc cgagaacgcc catctcaatc tctcctcgct 107820
cattttcacg catataggtg ggcacgaatt ttgggacagt cttgaaatag agatgacatg 107880
tccagcattt aaagctagaa tgggtaaccc atttggaaac agtggtgaat acggagggta 107940
gctttttttc gacctcggct tcatcgtcat tcgtatttaa cgtatcggtg gcagtttttt 108000
tggattgcaa gcattcttca atggtaatcc cggataagta taaaatatta ggacaattag 108060
tttccataat tttgatagtt atttttatac aacatggatt taattaaaga taaatggagg 108120
acgaaacgga actgtgtttt cggtcaaaca aggtgacgag gcttgaaatg tttgtctgca 108180
catacggggg aaaaattacc agccttgcat gttcgcatat ggagttaatt aaaatgttgc 108240
aaattgctga gccggtgaag gcattgaact gcaactttgg ccaccagtgc ctaccgggct 108300
acgaatcttt aataaagact ccgaaaaaaa ctaaaaacat gttgcgccgt ccgcgcaaaa 108360
cagaaggcga tgggacttgc ttcaatagtg ccattgaagc ctccattttg tttaaggaca 108420
agatgtataa attaaaatgt tttcctagta ccggggaaat tcaggtcccg ggcgtcattt 108480
ttccggattt tgaagacgga aaaaacatta tacagcagtg ggtagacttc ttgcaacatc 108540
aacccattga aaaaaaaatc cagattattg aatttaaaac gattatgatt aattttaagt 108600
ttcaaataaa cccagtgtct ccccgcgtca tcattcattt aaaaaaattt gcagctttgt 108660
tggaacacat ccctactcca tatcccatac gtgaaataaa gcctccatta gaagactcaa 108720
aagtatccgc aaaatttatg gtcagtccgg gaaaaaaagt acgcattaat gtttttctta 108780
aaggtaagat aaatatttta ggctgcaaca caaaggaatc cgcggagacc atttatacgt 108840
ttttgaaaga tcttatcagc gtacattggc aagaaatttt gtgcgtgtta ccggtacccg 108900
attaaagaat gttttcatta ataaggtaat cgactatgct aaaaagaata acaagaaaaa 108960
taccttgaag aactatacca aagtaggtag gttttctgca tgtcacggca tggttaaaat 109020
tgctaataat gtagtccaca aaagcattgc tcaatacgac taaaaatagt aaaaaaagga 109080
taagtgctct ttttatatcc atatacttta aaacttattt tttacactaa taatttcctg 109140
cggccgcaat ataaactgta ggtcatctat aacgcccaga cctgttaaaa gtagagtact 109200
atgttttaag ggatttaaaa tatccgccgc aagaatgtga atataatttt caaagtggtt 109260
tacaggaatg cgtaagcgtt ttttttgca ctgcggttgg tttagggtcg aatactggca 109320
ggaggtatat atattaataa gaccgcggtc gatggtttca atatcttcat agaattcaat 109380
gcgcggcgtc aaaagttttt taagatgttg acataactca tcatacgtgt aggactggag 109440
gggggaaaga agggtgtagt caaagttaaa aatgtttttt tgaagaacct ttaaagcatg 109500
ttccgcgtcc gtggtttcca aaatatgttt tatggtatga atgtcattta aatctacaaa 109560
gtctgacagc tttgtgtaga actcggtgac ggaggttatt ttctggaaat cggttttttg 109620
aaaaagattt tcaatgtgtt tgcgggttga gttgctttgc agtccataca agacatcaaa 109680
aaattcaatc agcaaaaact tatacaaatg gttaatataa aaagctttgt tggccttatt 109740
ctgctgagga tatggttcct ctaggggata tagaatggct tggtctatat ccctaggatc 109800
aatagtcaat gttgcgatgg gaagcttttc cagcgtagcg ggaagagttt gggttggagc 109860
gtagtaaaag tatagcccgg tttttccctc tgaaagaaag cccacaaatt ctttttttat 109920
attttgcagc accgctgagg gtacgatttc gtactgttta tactgtttgt tgaaaagggt 109980
aataaatttc caggtttctt caaagcttgc aatctgggtg ggccgcagat caaagtcgat 110040
gggaatgtcg tcatgaatgt aggatgatag tcttatagga aaataaatag ggcgatcggt 110100
gtctgaatcg ataagtaaag cataacaaaa gttatgcctg ttgataagtt ttttaccaac 110160
cgtgtagccg ggaatgtttt tcacgtcatg gatatcccac cagttatcct tgcacataaa 110220
ctcgctcata gactggatga cctccatcac agggtcatct tcggtaaaaa tatactgggc 110280
ctcactgttt ttcagaaatc ttttttgctg ggtgatggcc attgggtaga tcccttcgtc 110340
cgtgtcaaag ataatggcta tcttcttcga tgggctaaga attttttgta ttgtgctggg 110400
ggacacctca aacccgatgt cgccctgttt atctttaaaa aagacacagt gaaggtcgta 110460
gcatatggca acaaggtcca gaaagatgtc ctgccatgtg gtgtcccatt gaagcagttg 110520
gttttttgt tcaacaaagg tttgtaagat aaggtttgcc agctccgcgc cgctggaaaa 110580
catgttgccg gccccattcc ccaaaatata gtactgcggt gtgttggccg cctttgcaat 110640
ttcaatggca agggccttgg gggcaagatc caaaattcga gcaagggaat aaaaaagccc 110700
ggcattgcta attccaagca tggtttgctc cacccccaca atgcaaaaaa tgtcgggctc 110760
ttttatcgta tttaaaaaca gttcatctgc tatctggtgg ggtagaaagg caatccggtt 110820
caccggtatt ttttttccat aggacaaggt atgacgcgat gtttgtgtat taagatcctc 110880
caggtcttgt tctacaaacg tgtgcttggt gaggcaggta ttgttaatat agaaccgctt 110940
tgtgcccagc agggccttcg tcttttggca gcacggcaga cagtaattta gggggtggcg 111000
gccttctagt aggcttagat gagggtagtc aggatgcggg cagctatagt aggcaggtac 111060
cccctccgtg aaattccaat actttactag ctccttgcgc ttggctggcg gcatggactt 111120
cacctcggcc tctgagtaaa tgacgggtgg ccgtgggtgc tggcatagga cggagtaaac 111180
cgttgcctgc gtgtcgtact tgcgcaggtc atacaggtcg gggtcctgtt cttgaagcgc 111240
acgtagctga gaggctccct ttccttgttg tttatcgtgc agttgagaga gtttattaac 111300
caaaattttg tcaggcccgg tgatcaagtt atctaaaaac acaaataggt aaacccaaag 111360
atagttaaac tcttcctggg taatgttaaa catttctatt ttgatatctg taaccctatg 111420
gtagatgcga atgttgcggc cgccgtagat tgtttcccac cgggccgcaa catttgtgtc 111480
aaagaggtac gcatacgtgt tttggagcaa cgcaacattg atgtccattt tgcgccccgg 111540
accggaggaa ataatgatca tccgttcgat ttcgtgggga tcatacgaat aaatcccctt 111600
tttaaataaa aaattgtaga ccccggtttg ctggaggccc cgcacggaaa taatccctgc 111660
ttgctcgtat tcccgccaac gacttttgag ctcggtaaat cccttgctag aaagcgtata 111720
gggccaaaag gtggacaccg acatggagct gatagaaatt tggatgtcct cgttggaggg 111780
aaggggcaga ctccctccac gaggaaacgc ggcaggcccc atatcattaa ttgtatgaat 111840
aataggattt atgaaattat ttagggtgga caccacggag ttaaagtcgt ggcgctcgtt 111900
ttctgaccaa ttgctttcga taaagtagtg cccattattt tgtatggtaa gaataaaggc 111960
ctttttattg ataaagcgta ttaaaataat agtgggtaca cggaatgttt tattgctgaa 112020
tttttcaggc tccgtggaag ttatgtggtg tttggaaacc acggtgggac ctgttttact 112080
ataaaagaac accaccagct gaggaatatc gggagtagct ggaaataggt cgaaaacatt 112140
gcgcacatta atttgaatat ttacgagggg tgaaatttta atcattgccg aggtgacggc 112200
caacgtgccg cgtgttagtc tattcccctc gtacttggca atgacttgtt gtgctctggc 112260
atacgtaaag tttattagtt tttgctctag gagaagcctc tttttaagac tggtcaagga 112320
tggagaaaga gcaggatact gtttttccat ttgtaaggga gattgtacca atagtttaaa 112380
ggcatcgggg gaaagaagag gccaatactt cataataagg ccgtaataga gtaagtcaaa 112440
ttggtaatta tcctctatgg caatggagat ttggcgccgc atgggggcca ctagcgtgtt 112500
gaggtctgct acaaagatgt gatgaatgtt ttttatgagc tggaagctgt cgagcgcttc 112560
cacatagagc tcatcttttt gactttccat agatgcgtcg atgttcaccc cacccacctg 112620
ttgaaactcc tttttgtagt cgcgaatgtc taacgccacc ccgctaccgc ttaacaatag 112680
gcgatacgtt acctgaagcg cattgttttg aaaaaagaaa atgtgttgtc tataaggggg 112740
gatccctgtg gcaacgtaaa ttttttctcg aatgtcttta aaagtgtctt cagggaaaat 112800
actatactcg ctatacatcg tctcaatttc tggcatcatc acgtttgtct cctcgccacg 112860
atcctccaca aaaagttttt caaactcatc taaatcatcg ctatctccac ccaccacgta 112920
ttgggaaagc tttttctccc aatcctcgcc gtaaaaattt tgtaaaattt ctttgtcctt 112980
aggggttcgc tgcaggtctt tgcggcaggc ctgtaacacg tttgcaggaa cggatcccaa 113040
aaaaataaac gtcttcgtgt actcattttc cacaggatta taaagagtaa ctcgtagagg 113100
atttgttaaa aagtcatttt ggaaatccat tatacccggt atagaaaata aaatttaaaa 113160
taaaaacgga tgatatctat catggaccgt tctgagattg ttgcacggga gaacccggtg 113220
attacccaac gagttacaaa tctcctacaa accaatgctc ctctactatt catgcccatt 113280
gatatccatg aagtacgata tggagcctac acacttttca tgtatggttc cctcgaaaac 113340
ggttacaaag cagaagtaag gattgaaaac atcccagttt tctttgacgt acagattgag 113400
ttcaatgata caaaccagct ttttttaaag tcgctactga cggctgaaaa tattgtgtat 113460
gaacggctgg agacgctcac ccagcgtcct gtaatggggt accgcgagaa ggaaaaagag 113520
tttgcaccat acattcgaat atttttaaa agcctgtatg agcgacgaaa agccattact 113580
tacttaaata atatgggcta caacacggcc gcggacgaca caacctgtta ttaccgaatg 113640
gtttcccgag aattaaaact acctcttaca agttggatac agcttcagca ctattcctac 113700
gagcctcgcg gcttggtaca caggttttcc gtaacccccg aggatcttgt ttcctatcag 113760
aatgatggcc ccacagacca cagcatcgtt atggcctacg atatagagac ctatagccct 113820
gttaagggaa ccgttccgga cccaaatcag gcaaacgacg tggtgttcat gatatgcatg 113880
cgcatttttt ggattcactc cacagagcct ctagcgagca cgtgcatcac catggcaccc 113940
tgcaaaaagt cctcagagtg gaccaccatt ctatgctcct ctgaaaaaaa tttgttgtta 114000
agctttgctg aacagtttag ccgctgggct cctgatatat gcacagggtt caatgattct 114060
cggtacgact ggccctttat cgttgaaaaa tctatgcagc acggtattct agaagaaatc 114120
tttaacaaaa tgagcctttt ctggcaccaa aagctggata ccattctaaa atgctattac 114180
gtaaaggaaa agagagtcaa aatctcggcc gaaaaatcga tcatttcctc ctttttgcat 114240
acccctggat gcctacccat tgatgtccgc aacatgtgta tgcagcttta ccctaaagcc 114300
gaaaaaacaa gcttgaaagc gtttttagaa aattgtgggt tagattcgaa ggtagacctg 114360
ccgtaccatc tcatgtggaa gtattatgaa acacgagaca gcgaaaaaat agccgacgtg 114420
gcctattact gcattataga tgcccagcgc tgtcaggacc ttctggtgcg ccacaatgtt 114480
atccccgatc gcagagaggt aggaattctg tcatacacct cgctgtatga ctgtatctac 114540
tacgcgggag gacacaaggt atgcaatatg ctcattgcct atgccatcca tgatgaatac 114600
ggccgtattg cttgcagtac cattgcccga ggtaagcggg aacacggaaa atatcccggc 114660
gcctttgtga tagaccccgt taaagggctt gaacaggata aacccaccac aggtctcgac 114720
tttgcgtcgc tgtacccctc actcatcatg gcctacaact tttcgccaga aaaatttgta 114780
gcctctcggg atgaggcaaa tagcctcatg gccaagggtg aatctcttca ctacgtctcc 114840
tttcacttta acaatcgtct cgtggaagga tggtttgtgc ggcataataa cgttcctgat 114900
aaaatgggat tgtacccaaa agtactcatc gatctactta acaaacggac cgcccttaaa 114960
caagagctta aaaaactagg tgagaaaaaa gaatgtatcc atgaatccca tcctgggttt 115020
aaggaactac agtttcgcca tgccatggta gacgcgaagc aaaaggcgtt gaaaattttc 115080
atgaacacgt tttacggcga ggcaggtaac aatttgtcgc ccttctttct gcttcctcta 115140
gccggaggag tcaccagttc gggtcaatat aatcttaaac ttgtctataa ctttgttatc 115200
aataaaggtt acggcatcaa gtacggtgac accgactcat tatacattac atgcccagat 115260
agtctttata cagaggtaac agacgcatat ttaaacagcc aaaaaacgat aaaacattat 115320
gagcaactct gccacgaaaa agtgcttctg tctatgaaag ccatgtctac actatgcgcc 115380
gaggtgaatg aatacctgcg acaagataat ggcaccagtt acctacgtat ggcctacgag 115440
gaagtactct ttcctgtgtg ctttacaggc aagaaaaagt attatggtat tgctcatgta 115500
aacacaccca attttaatac aaaagaatta ttcatccgcg gaatagatat cattaagcag 115560
ggtcaaacaa aactcaccaa aacgatagga acgcgaatta tggaagaatc catgaaacta 115620
cgccgccctg aggaccatcg ccccccctctt attgaaatcg ttaaaacggt tttgaaggat 115680
gctgtggtta acatgaagca gtggaatttt gaagacttca tccaaacaga tgcgtggaga 115740
ccggacaaag acaacaaagc agtccaaatc tttatgtctc gcatgcacgc tcggcgtgag 115800
caactaaaaa aacacggcgc tgcagcatcg caatttgctg agcccgagcc gggagaacgc 115860
ttctcctacg ttatcgtgga aaaacaggta cagtttgata tccagggcca ccgcacagat 115920
tcctccagaa agggggacaa gatggaatac gtctctgaag caaaggctaa aaatcttcct 115980
attgatatat tgttttatat caacaactat gttctaggct tgtgcgcgag attcattaat 116040
gaaaatgaag aatttcaacc ccctgacaac gtcagcaata aggatgaata cgctcagcgc 116100
cgagctaaat cctacctaca aaaattcgtg caatccattc accctaaaga caagtctgtc 116160
attaagcaag gcaatgttca tcgacagtgc tacaaataca ttcaccaaga aattaaaaaa 116220
aaaataggca tctttgccga cctttataag gaattttta acaacaccac aaaccccatc 116280
gaaagcttta ttcaaagcac tcagtttatg atacaatact ttgatggaga acaaaaagta 116340
aaccattcta tgaaaaaaat ggttgaacag catgctacgg ctagtaatcg agctggtaag 116400
cccgctggta atccagccgg caatgcgctg atgcgggcta tatttacgca gctgattacg 116460
gaagaaaaaa aaattgtaca agccttatac aataaggggg atgcaataca cgatcttctc 116520
acctatatca ttaacaatat aaattacaaa attgccacgt ttcagacgaa acagatgttg 116580
acgttcgagt tttccagtac tcatgtagaa ctgctattaa agctgaataa aacgtggctt 116640
attttggctg gaattcatgt ggcaaaaaaa catctgcaag cttttttgga ttcatataac 116700
aatgaatcgc cgtctagaac attcattcag caggctatag aggaagaatg tggcagtatt 116760
aaaccatctt gctacgactt tatttcctaa tacttcttaa gaaactcttt aaacaaggac 116820
ttcgcatggt caaaggttct aaacccatgg cccttatgat tcgccaaaaa agcggtttca 116880
tcaagatttt ctaacccttt cacggatgaa gaaataaggt gttcggcctc gtttgcccat 116940
tttctatgat ttttttcac ctcgggttct agatctgttt tctccatata ctcattgtgg 117000
tcatattttt ttttgggagg aggcgtgggt ggaggaatgg gtggaggaag tacacccgac 117060
tttcccgctt caaccgtttt ataaaaaaat agaagcataa tacaaagaat aaggactatc 117120
gcaaatatga taaccagtgt cccagtcgag ggcattttgt tatataagta acgttttttt 117180
tatttttat aattcgaatg aagaaccatg ttgaatagtc ttctactcaa agacattttg 117240
ttatacggta aatgagaatt tataaaatcc gaatatcact atcatactgt ttatctgaga 117300
aggtctcact gggtcctgtg atggagaacc catactctgt aatgctgggg tttataatgt 117360
ggtcaggact gacaagcaca tttctgaact gcgagagttc taggtttaga cgcagtcgta 117420
atagtcgctg tatatttgta ataaatatta gattgcgtat gaggcgagtg tcaaagcgat 117480
cctttccaat ttgtactaag gtgggctttt gtattccaac tcccacttgt ttaacgatgg 117540
accagggtcc ttcttcccga ttttgttccg tgatataggt cagcacacta ttttctgtat 117600
atgaggtatg atgtcgcata ttaatacctg gtgccattcc aactggcggt tgtgcaattc 117660
gggctgtacc gggacccaac catcgtggag ttttataaac atatcgttct agcgtattta 117720
aaaattcctt aaggttattt acgagtagca tgaagggtgc tattaaaaca ggtggatggt 117780
ttataaccat tgtcataaac cattgcattg cttcaatatc attttgtaat gcttgacggg 117840
gaggcggggc aggtaatcca cgtatgttga ataaagcggt taattgtgca ccggctgttt 117900
ggggcgtaat attttgtatt aaatttatca tcgaattggc ttgcccggca tttcctataa 117960
gatcgattaa attggttatt tgacctcgat attgttgtac ccagttttga atggcagcga 118020
tgatctcagg ggttggattg ttttgaattt caggtgtttg tattagatta ttcacttctc 118080
ttcgtgtatc ttcaagctga gtcctaaatg catttaactc gcctataatt tggtttctat 118140
caataacatt tcttaaacct cgaactgttt cagccaatcg tatagtacgc acaatttcat 118200
gtaaggcctg gtttatgtat attgacatgg gatggcccca ccgctcacgt ccacgttgaa 118260
tacctgcggc caaactagga cctgcctcgt cataatcaaa ttgtgtagga taaaggcttc 118320
caaatagcac tttattgaaa atttggtcag aaagaaattt agggcggccc atatttagcg 118380
cgttgtcccc tctaaagatg cgtgacatgt atccggcgtt gcctttggat agtaactcat 118440
tcccatattg agtaatagag accgagacat aggggtttat aagaagtttt agcataaatt 118500
ctcgagtatt tatgggggga cgattcggaa tgtttaatac ctctgcaaca tctggttgag 118560
gagccgtggt gtccagagat cgtacttttt cagccgaaat gccgtacata agacaagcaa 118620
tttcttcaaa actatagtca tagttgtaaa tattggcaag tggtatagat cgcatcagcg 118680
catttacatt gataggtata atattcatat caaacaagtt aaatatgcgc tcgcgctctc 118740
tattagagcc aagagtgcgt gtttgacctt tcggcgacac tattttgtga atatgattga 118800
tttgctcctc ttggtaagag ctttccacga aggaaattac gtcttgcaat gttttacgaa 118860
gcgaatacac tgcattcatc cctattcccg ctgttataat gggtttatcg tctctgttct 118920
cgctaataag attaactcca ccaaaagtat tttcattgta catcatcact gttttaaaac 118980
tacggatatt tatgataaat cggagagcct gaatggcgtg ggtataaaag tgttcaaatc 119040
gcgtgggagt aatttgttcg cgagcaacta ccgtttcatt atagtttttc atgataagct 119100
gtactccggg catatctgag agctgtaccg gatcatttcc cagtaatttt cttgtgccgt 119160
atagtagttt aaactcgggg gagccgcttt caaggttcgg gtaaagaaga ggatcatata 119220
cctcattatt ttctattctt aggtcatgta aataatagag cgaaagtgaa aatggcataa 119280
gaggctcctt attgtaccgg gacatatagt tttgaatgaa gtgttcttct gtttcaagat 119340
agatgggatg atcggtaagc tcgtgcagga cctccatggc agaatctgcc agagtgtgag 119400
agcctctaat gatcccgtcg atcactgcga ccagtcgctt tcgcacaaca tcgctcgtat 119460
tattttgtgc gtctcctagg ggcataagcg taacattggg acgaaatacg ccgccaattc 119520
cccgcagggc cgcctgaccg acggatagtc ctgtcgcagg aacattgtta ttattataat 119580
aaataacgga atcattattg gctcccaaga gtgccgtcag attagggcga gctagttgga 119640
catttgtgta ttgtataaat tgttttagaa gctctccctg gctaataaga atattaaaca 119700
ttttgttaaa tagtggaaga ttggctctat aatttttcttt aaggtaaatg ggaatttctg 119760
ttaaagtaga aataagatgc tgactcaggc cctggcgatt ggtatcctta ataagccgct 119820
gaagtataag tcccaaagac agaagaagca ccgactgctc tgtggggtcg cctctatgac 119880
caaagacgtt gttattgcgt gctaagtcag ggtgagcata tcccatctcc atcactgctt 119940
ggctaaagtt cccattagcg aatgcattaa taagatttag atatattttt ccgctgggag 120000
catcataaaa tcgggtaata tatgaagcta tgagctggtt aaacaccatc atcatactac 120060
gattattttg aataccatag tctgatccgt ataggcgata acgtcgaagg ttgtttgcgg 120120
catcattgac attggcatag gttctgagcg ctatgttgtc ccagtagcta agagtatttt 120180
cctcctgggc gttgttggta cgaataagat tggagagtct aaagtctcct agtgccacct 120240
gctctacacg aagtccagag ttattctcca aagcatcgta aaatacgagt ctactgaata 120300
ctcttccgta ttgttcaaag cgttcagagg attggggatt gttatttatt tgaatattag 120360
ccgcgtccct tctttgcgcc ccacctcgaa gttgcagtac attataaggc tttgtaagca 120420
aggtgtaggt tttattaatg atttggttaa ccccctccag gcccaattca ccgccaggaa 120480
gcggccttcc tccggcatcg gtaggtggtt taataagttt gtcaattaaa tgttcttcca 120540
accagtaaaa tgagccagga ttagatctat tttcatagta ttgaataatg tttttatcaa 120600
tatgcgggcg tagaagatca agaaaatact tcgtgtcggc catcaaagaa tcaattaagg 120660
aaataagacc tgtaaaatct aaatgcactt gagcggtgct ggtttcaggg aagcgaactt 120720
gaaccatttt gttaaaactg gaggtcattt cgaagatatt ggtcaacagg agctgcatga 120780
ttcgctgatt atctactaaa taccttgcgg ccaactcttg ctccggacga actcctccac 120840
cagcaggaat acccacatat ggtacaatcc aagcaaaaag agtttctgtg gttaaatttc 120900
ggtcttgggc tgctgcagcc gcttcggtag tgggatcagg gtacaccata gaaagccgca 120960
tattgatttc tttaatgact aatcctggat ttctaatctc agagatggcc ccgtgttttc 121020
ttccgagcca gtcaataaga ttggcgcggt tcacgttggc agcttgtgtc tctcgtaacc 121080
attcgataat gctttttttga atcgtatcta ggtctaaacc tttaatgtta ttacgaaagt 121140
tattaagaag tacgtaaata gcactcaata agttaagacc tgtaataacg gtttcatgaa 121200

-continued acagaaatat tttgttaaca tctgtatctg ccagtgactc agagccttga ataagttttg 121260
aaacgatttg aattttatcg gtatgctcct ttttgagttc attgatagcc tggcgaatga 121320
gttcttggta ggaaattttg cccaattctt gttgcagact gggatcttca aacatctcac 121380
taagctgttt cctaaatttt tgtaccaaat cccactggga gttgggctgc agcattcctg 121440
tttggacatc cacagagtct atattgtata gtgccgggcg ccacttgggg gtaggctggg 121500
ttgaaggact aataaaccta tcggagggaa gtaattgtga ggattgtgta tagccatcct 121560
catcaggaag aatggagtag ttggtttgat tcatcattcc aaaatcattc atagttcgcg 121620
cttcctgaac aatgcgttga aatttttccc attcggtgcg tgtaatgaca ccgaatctgc 121680
ggtttatttc atttacaaaa tggataagcg ctttttttggt tgcttcttgt tcaccatact 121740
ctaagttaaa gtgttggtaa atgacgttta tttctttgat aagctgacga atttcggttt 121800
ctgagtagtc accaatgtta ataagctcaa taggacgcat aaagataatg cgaataagtc 121860
ctgagaagat tccttccagc tcaggaagca tcgagatctg tacattttca tctctaaagg 121920
aaaacaactt ttgataaaat tcggcgaggc ggggaaggcg gaagtaaagc tctgctgcct 121980
cgggaattac ctcgggctct agctcatcgg caccccccaa tatcatacgc gtgggtataa 122040
gtttgtacac gggctcaggc cgttcaaaca tgtcgtaaat ccctaataca ataaaaatct 122100
tggcggccat acttttcagc atgaaggtga agaagacgtc ctcggtttcc cagcgggttg 122160
atagggcgtc gttaactctc acagtagaga ggtagacccg ctgagccgct tcctcggcag 122220
tctgtgcaag cgccatcctt tgtcctccaa tttctgattg atttagattt ttaagtccca 122280
cggaaagcgc agaatgttga agatattcaa gcaaggtttt atagatttgc aggggcgaca 122340
tgggcaccat ttgccgcagc tcctctcccc caagcatgtc cccaatccgg gcaaaggcat 122400
tgatgatatt tttaagcgcc tgaaagttag aaagagagcg cccgataagg tcgcgaatgt 122460
ttttagcctg gcttgctctg acgggacgga gggtaccaac gcttcggcct tgttggattt 122520
cagccgcaac tttttcgtag tagtggcccg caggagcatt atccgtaaag acgttggagt 122580
cgttgcctgt ggaggtggga aaactttcaa agacttgtgc aagcgtgtcc cctgttgtct 122640
cggtgaacca tcgtcctata atgcgcacgc catccagcat ctgttggact gtttgaatag 122700
aatctatgtt gtttacaaac gttttggtaa tgtttttaag ataaagatct agcccttcca 122760
gagctcgata gaatcggcgt tttacatcat actccagctc gatggcgctt acggttgcct 122820
tccagtctac ttcctgggca cctccaggat ttgggcccac gtgtcctctg gcaagatcta 122880
cagccggaga attaatgcgc gcattttttt ccgtatccaa ctgcatgagg cgtcccgcaa 122940
tagcatctcc gagaatagtg gcatagtttt cctcgtagga ttgaaactcc tgtttgttat 123000
gcgttaaatt ggagtaaatc tgggccacat aatagtaata cataaaggtg ttaattgcct 123060
ggttgaggtc aacctgcgat cgcgcggcct tgctgagccc aagctcttca actgttaggg 123120
cagcaccgcc tacccttgta cactcgcagt cctcctcgcc tccatacttt ttttgcacaa 123180
tatcggtata aaaatcaata atctgtagca agcgagagca ggagtcataa agatttttaa 123240
aattagggtc ggttttagat atctcctcca aaacattttt aacaagcgta agctgtgtta 123300
agaaggtttc gcgttcttct cgtgcggccg cattggtgta aaagccgata agacttagat 123360
caagtgcgat ggtgcccata tcattaatgc gcgaaagagc atctcgaagc ctcgttatgt 123420
tcggcgtcaa ggcaatttct ttaacaagtt tgatgcctat ttttttcaca ttttccaaaa 123480
agtcgttata ggcttgtgtg cttttattca aaaattccat gaggatgtgc tttctatcca 123540
gtctttgcgc ttcaatcctc ctatctagtg gcgttttctc ctcatcgccc cccttttttgg 123600 cacaactgtt ctcaaggatt ttgtggcgtt cattaaaggt ctgtcgcaac aggttcacgg 123660
ctttttcaaa ctcagcaatg ttttctgcgg agacaagacc actaaacctt ttgaggtcaa 123720
gctccttgtc aaactccgcc cagtttttgc tttgaaggta ctgttcaacc ttgagtccta 123780
ctttctggag agccttatta attttattcg caacagacgc agcaatacct agattacaaa 123840
gtgtgtacga aagtactttt ccaaaatttt tggttcccaa gacactattt gtatcattta 123900
aaagtttaat aatatccacc tcatccgtct gcagtttatc aagttccttt tgggtgggag 123960
ttaaaatatt gtcaataaaa ttcgttaaaa tgttgatttg caggttttgt tcatttaaaa 124020
gtcgacgata tactgcttca atcatggtga ctgcattaat gacttcctca ttgggggctg 124080
ctttggttac ctccgtcacc atgcgctcgt gaagttgctt aatggcgtcg tttaacagct 124140
tgatattttc aagtgtattt tctatactgc cgtgtacatc aagatactct gcgcgcagtc 124200
catgagttag ggagttaatg tacagaacta tttgtcgaca tatactggcg gccccttcgg 124260
tggtatctat aagcttatcc tgacctaaat caataaattc ctggttaatg gcgtctgcaa 124320
tcattttaca gacggtctcc tgtttttccg cattttttac aaaggtggaa ccggctcgag 124380
gatcgggcag ttgtttttttg atatctttaa gaatatcttc gatgggctgc tttgtgtcta 124440
ctttgaaccc tattttggca atcgccctga taattccttc tataatccgc agctttgctt 124500
tactcgatac ggagtctatg tgataatctt taatgtgttg tacaggattt ttgtcccccc 124560
cgccattaaa atatcctccc cctgaaaaag gacgagtttg tctttgtata tgatcctgta 124620
acttcgcata tatatttgct tctgatgaag gcagtggtct actagaggtt gaagatccac 124680
ggttacccat tataataaaa aaaataaaga tttaaaacta caaatatttt gctgtttata 124740
aacccaatca tataagacta actaaaacat taaatgtagg tgagataaaa gcttattttt 124800
tttaaaagtt taataaccat gagtcttacc acctcttttt cttcttcctt tagaggggtt 124860
ccataaatgg tttgaataaa attatgtgct ctaataacct tgttaaaatc aggtgccttt 124920
ccatattgtt caatatgttg cacagtcttt tgtgcaagca tatacagctt ggagtcttta 124980
ggtacctccg atgagggctc ttgctcaaac aacgtttcaa aggaggatgt gcattcattg 125040
gtttcattat catttttttc atgaatgttc tccgaagatg ctgaggattc cgtctcctct 125100
tcaaacagca catgcagaat catattccat tcttcttgag cctgatgttc agtataccct 125160
tgccctgcat atatacgagc agatttcaca atatcatact taacagtact aagcaatgtt 125220
tttatagcgg tcgtaacaat tctaccgcta ttgataatct caacagaaaa ccaattatac 125280
aggctacccg catgaaacac aacttgtgaa gatgatctta aatccgtttt gaagatgacc 125340
tccattttca tggatatatt taaaataaaa tccattcaat tttaaaatta taaaataata 125400
agaagatgcc ctctaatatg aaacagtttt gcaagatttc tgtatggcta cagcagcacg 125460
atccagattt attagaaatt atcaacaact tatgtatgct tggcaattta tccgcggcaa 125520
agtacaaaca cggagttacc ttcatttacc ccaaacaggc aaagatccgc gatgaaataa 125580
aaaaacatgc ctactccaat gacccttcac aagccataaa gaccttagaa tcactcatcc 125640
ttccatttta cattcccact ccagcggagt tcaccgggga aatcggctcc tacaccggag 125700
tgaaattaga ggttgaaaaa acggaggcga ataaagttat tttaaaaaat ggagaagcgg 125760
tcctagtacc ggcggccgat tttaagccct ttcctgatcg ccgactagcg gtctggatca 125820
tggagtcagg ctctatgccc ctggagggtc cccccctataa gcggaaaaag gagggtgggg 125880
ggaatgaccc gccggttcct aagcatatct cgccgtatac tccgcgcacg cgtattgcca 125940
ttgaggtgga aaaggccttt gatgactgta tgcgtcaaaa ctggtgtagt gtcaataatc 126000
cctatcttgc caagtcggtc tccttgctgt ctttcttgtc gctcaaccat cccaccgagt 126060
ttattaaggt actgccgctt atagactttg accccttggt gaccttttat ctacttcttg 126120
agccctataa aacgcatggg gatgactttt taattccgga aaccatttta ttcggcccta 126180
ccggatggaa tggtacagat ctgtatcaaa gtgccatgct ggagtttaaa aagtttttta 126240
cccagattac tcgccaaacc tttatggaca tagccgattc ggctactaag gaggtagatg 126300
ttcccatatg ttactcggat cccgaaaccg tacattccta tgccaatcac gtgcgtactg 126360
aaattttgca tcacaatgcc gtcaataagg ttacaacacc taacctcgtc gtgcaggcct 126420
ataatgagct cgagcaaacc aataccatac gacattacgg ccctattttc ccggaaagta 126480
ccatcaacgc actgcgtttt tggaaaaagc tgtggcagga tgaacagcga tttgttatcc 126540
acggcctgca ccgcacgttg atggatcaac ccacctatga aacctctgag tttgcagaga 126600
tcgttagaaa tttacggttt tcgcgtcccg gcaataacta tataaacgag cttaatatta 126660
caagtcccgc tatgtacggc gacaagcata ccaccggaga tattgcgccc aatgatagat 126720
ttgccatgtt ggtggccttt atcaacagta ctgacttttt atacaccgcg attcccgagg 126780
aaaaggtagg ggggaatgaa acccaaacca gtagccttac agacctagtt ccaacacggc 126840
tacactcttt tttaaatcat aatctaagca aacttaaaat cttaaaccgc gcgcagcaaa 126900
cggttagaaa tattctttca aatgattgtc ttaatcaact gaaacattat gttaaacaca 126960
cgggaaaaaa tgaaatacta aagttacttc aagaataagt atgttgatac ctgtggtgtg 127020
ttttacctgt gggtttccta ttggaaccta cgcggcaatt tttgacaagg ctcgtaccga 127080
gtatattaaa accaaaatgg gcggaacatt gccgcaaaat atcccattag atgcttctct 127140
ccagattgag ttaaaagacc tcattacagc tctgggaatc ccaatgcggg tgtgttgtcg 127200
cactcattta attactacgt tggattatcg taaatattat taatatctaa aattgaaaaa 127260
atatttttaa tgttactagt aaaaatgact acacacatct ttcacgcaga tgatctccta 127320
caagcattgc aacaagcaaa agcagaaaaa aatttttcat ctgtattttc tttagattgg 127380
gataaattac gcacagcgaa gcgtaataca acggttaaat atgttacggt caatgtcata 127440
gtaaaaggca aaaaagctcc gctaatgttt aactttcaaa atgaaaaaca tgtaggaacc 127500
attcctccca gtaccgatga agaggttata cggatgaatg ctgaaaatcc aaagtttttg 127560
gtgaaaaaac gtgacaggga tccctgtttg cagttcaaca aatacaaaat ctcgccgcca 127620
ttggaagatg atggtctcac tgttaaaaag aatgagcagg gtgaagaaat ataccccggc 127680
gacgaagaaa aatctaagtt gtttcaaatt attgaactgt tagaagaagc ctttgaagac 127740
gctgtgcaaa aaggtcctga agccatgaaa acgaaacatg ttataaaatt aattcaaaga 127800
aaaatttcta atagcgcggt taaaaacgca gacaaacctt tgccgaatcc tatcgcacgc 127860
attcgtatta aaatcaatcc cgctacaagt atactaacac caatattgct tgataaaaat 127920
aagcccatta ctttacagaa tggtaaaaca agctttgaag agttaaaaga tgaagacggc 127980
gttaaggcca atccggataa tattcataag cttatagaat cgcattctat acatgatggc 128040
atcattaatg ctagatctat ttgcatcagc aatatgggca tttcatttcc gctttgcttg 128100
gaaatgggag ttgtaaaagt ttttgaaaaa aataatggga ttgatgtgaa ctccatttat 128160
ggctcagacg atatttcaac tcttgttaat cagattgcta ttgcttaaac aatttgctca 128220
aaacaagctt ataaacgttt cttaggtatg cgatacgtaa atcctaattc tttaataagt 128280
tctttttcag tagtgatttt tagaggtact aaagtttgat ttttaaataa tccatactga 128340
tttagcttat aattcttttt ttttaacgca gctcgaattc ttattaaata agaaacggga 128400
cccgtaaaat gaagtactgc gtatggcttt tcctcggcta aggccgtaaa aagatcaagt 128460
tgatatgtgt ttttttcca ttcaataaaa agtacacact ttcgttctcc gcagactttt 128520
acagaaaaag aaagatcctt tatgcgaatg ttgggcagga cgtgttttaa aagttttttt 128580
tctggaacaa taataagaag atccacgtca ttaagcattt tctcttcgcg tcttaagcta 128640
ccaacagcaa cgatgttttt tgataaaatt tttataagtt gtccattata ttcaaacgca 128700
agtcgggagc gtaagtcatt tacaattttt tttccttgaa taagcgttaa cattttatat 128760
ttaatattaa aatcttttca ttttatatat tatatacgca aaatggcact tgatggttca 128820
agtggtggag gctctaatgt agaaacatta cttatagtag caatcattgt ggttattatg 128880
gcaatcatgc tttactattt ttggtggatg ccccgccagc aaaaaaaatg tagcaaggct 128940
gaagaatgca catgtaataa cggaagctgt tccctaaaaa caagttaaaa catgcaatta 129000
tatgcatgca tataaacgca tgcatataaa cgcatacata taaaatgcgt aaatactata 129060
taaaaaacta taacatatca atcaaggaat caacactttt ataattttcc gtaatatatt 129120
tttcatccat aatgatgtca gagtacatgg tccctatgcg aggaacagag cccataaggg 129180
taggcgcggc aataccgtaa atgggattca cggcggagtc aaccgcagca tctgtcaaga 129240
cctggactgg agacgacaag gccattcgca acaacacgtt ggaaggctct cttgcattaa 129300
gccctgcctt ttctagagag gtaacctgtc ccgttcttgt catgagatct gcgtacatga 129360
gtaaatgacg atggttggga cccttgtccc ccataaccgt tctaatttca ctaataattt 129420
tttgccgtgc cgcttctatg ccgtaaagct ccatggtgtc tcctatagag gacgatacga 129480
tggtgtatgg gtcgatgtta tcatcaagca ttgcgccaaa aatattagtc ccgtttgttt 129540
tgatggcgta gatattgtct agtcttacca gtttcccctg ggcatccaca cggtggcgca 129600
taagcttaac aacattcgca tttttgatgc ctggtattcc tctaatcgtg ctatttaata 129660
gtttatccac cacatttacg gcaatttttt catccgtagc cattcgggta ttggtactgc 129720
gtctaaaggc gctttcccgt aggtatatgc gaataatgat gggaatccct gaggccgtgt 129780
tttccacaga atgcatgatg taggtgttgg ggtgtttagc tcttagacta ttaataatac 129840
tttctagact aatgcttttt aatatcatgg ttgttttgtt taattccaag cggatacacc 129900
agtttgcaat atcctctggg ggctgtagta gaggatggtt ttccagaaaa tccgtcatcc 129960
attccacatc acttgcaaaa tcggggtaca tcacattttt ttttgtgctt gaatacgttt 130020
cgtacaatag gtgccactgc aatatcaacc gttcgaacgt tataagctct atgctgttag 130080
caatttcttg cgcatatgtt ttatttgttt ccacttccgg gttctttaga cgtaaaagca 130140
tttcagagga ttgttcagcc tctacgggct tcgcgctaaa gatctcctgg ggccgcacaa 130200
ttcccgactt gttggttccc ccggccacgg accggtggtg ggagtccagc atatattgtg 130260
tcaagggctc tgatacggac tgcgccgcca ggattcccac tgcctcaccg tagttaataa 130320
gactttgagt atattgtagc cttatgaggt ccaggatggc actcatctgc tcgcaggtaa 130380
tgtttaatgt tttaacggtt gccagttcga tgcgaataag catgcgcatc agagaggcag 130440
cccgtttaag ataaacgggt atgggcgttt gtagtcgttc ctgaatgttg ttaataaaca 130500
cgtatggaag atttttgcaa aacgttttga ccatcgcgta tttttgtaga atactttttt 130560
cgtcgaaggg aagcacgcca ctggtggagc tcagtagaat gttttttacg atgctggcca 130620
cgtttaccgg cacctgtcta acatctgtaa gcagctgact gaaattaaaa ttttcgacgt 130680
ttaggaagat ctgtcgatat ttatctctat cctttttaag gcgtgaaaat tcttcttcaa 130740
acaagggcga ttgtatcccg gtgtacttga atttgtcttc aagttcctgg tccgacagca 130800
tgatggtttc aaaccgtacg gtttcaagct ggcgcgcatc aaggccgtcc tctccgtaca 130860
actgctgcac aagacgcgta tcgatggaaa cccgtcggta ataatccaca atacaggatt 130920
gaaggccaaa gatggcttta cggttggcat agcctgtgga tgatgtcgat aatgctttgt 130980
tgatcaagtc gaatcttcca ttcatttccc caaagataaa ttcaggggag gtaaggcccg 131040
caatatagct gttgcagatg aacccgtagg cctgcgcctc cagggcaaac ctggggtagt 131100
acaccagggt cctaccgaag gaaaactggg gttgaatgcg ttgtgtatta atttcaattt 131160
ggccgatgcc cgccatgatg tgaatcatat tggggtttga gcccttggcg ccagtggcca 131220
ccatctgaaa aagcccattg gtttccggat taatggaatt cataatcggc tttaaaattc 131280
tatcgggaaa tttaagcgca ttcagctgca atttttcgta gaagtcatgc gttgtcaggc 131340
ctataggcgg catgatgtct ccatgaagca gccggttgtt tatttcctcc gactcaagca 131400
gcagttcatt gataatttct tggacctcct gatgtgcctc cggggttagg agcatgtcgg 131460
ccgtggacac tgtgaatccg gcgttgcgca cgtagtttag ggcgagctgc tgggtcgcaa 131520
atatcatttt caaggcctgc tgcggcccat acctacgcga aataaggtga tagattccac 131580
cggaggaacc cgctccgacg gccttttttgt caaggacgcc ttcaatgagt tcgccgttgc 131640
gtatttgtgt agagatgtcc tgcttgttat aatgcatgta gggtgcatac acttctgagt 131700
accatgtggg ggctcgttga taattgatgg gggtctgcct cagtagcata gatacaaccg 131760
atttgccatc cagcaggtca gttggggagt agttggcaaa acaaggtggg tcggtttggg 131820
ttgtttgaaa caaccccatg gcgtgcagct tgttcatcac atttttcccc atgggggtgt 131880
tcgtgcgtgt aagcaaaaag cttcccaccg tggagtcctg cacctgccca ttaacgggac 131940
ccgagctctt tgtggaaatg aaccagtttc gcacagaaca aagtagttcg gcctcaacgc 132000
ggctcatgac gctccaggga acccagagat tcatctgatc cccgtcaaag tccgcattat 132060
accaggcaca tgcgctgaca ttcatttgaa acgtagaaat ttttgggttt tcaagaacga 132120
caatccggtg aacccctatg ctgcttcgtt cgagagaagg ctggcgatta aaaaacgcga 132180
cgtcgccagt gacgacgtca cggtaaagga tgtctcctac ctccagccta aagtcttgtt 132240
tgagaccctc aatgtcgtga acggattgtg ttatttgctt atacactctt gaacaaccag 132300
ggtactggcg ctttccattt aaaaaatagg gcattaatct attaatatta taatgttgca 132360
ctgtttccgc aacttgcagc gttcgtgcaa aggaaatggg atagccaacc tcgtccaggt 132420
gaaggtctga gttcccgcag atggtggacc ggctgatcga ccatacctgg ctgcccagta 132480
gggatttacg aattcttccc tccttgcgag gaagtcttcg catgatggag ggagcagggc 132540
gtgcccccat gacgatccca cgctttcccg tgcctccctg ggttgcggtg gtggaaacgg 132600
aatccaacaa aaagttatag taaagttgct gtatggtttg caaattgcgg tcaatattta 132660
aaggtatttt ttggccgcgc acgatttgta ggtccttcgg gatcagcaga ttctttcgaa 132720
ccagatactg aatcacgttg ttaatgtcgt gaaagctttg ggggcctgac ccgattccca 132780
atctgatgcc aggtcgtatg ctgatggggg ggatctgaat ggccttaagc acaagttttt 132840
cgggatggga gtttttactt cgccccagtt ttacaacggt gtcgtaggtt acgcgcgaaa 132900
aaatctctct gatgatctgc gggtacagtt tgtcaatctt gccctgctga tccgcccaaa 132960
aggtaaaata atcttccgag tccttaacaa ttttggggtg tactgcctta cagacgtagc 133020
actgctttcc ttcggtttgg cttgaagccg cttcaataag acgcttaggc ctaataaggt 133080
gctcgtacct ctttaggtca acgatgggag ccccgcagtt gagacatata acccttaacc 133140
atcgtcgtat ttcggcgatg aagagcggct gaagcaccgg agcatgcatc tgcagtatcc 133200
cagggtgtcc catacattgc ttgcgctggt gtgagcaagt gatgcattta taatggtgat 133260
cggtggttcc cattcgcgca tcatagatac ccccttcggc gggaagggtg ccctcaaata 133320
aattagaaat ggtaacctcc ataacgcctt gcctcttatg atcattgtca ccggcaatat 133380
tgaactgaac ggcggctatt tcggcatatc cagcctccat atttttgcta aatacataat 133440
aaaacttcaa atgttaaaaa aaataacatc ggttggcata tttttttgtt aaaaccaagt 133500
gttaaatgat ttctaaaaca tttatcggtt cacgaaaacc taccgcacgg gcctgaagag 133560
gaatgccagt tttgggggaa agctcggcat attccacggt aagctctttt ccataaagat 133620
gtttttttaaa taaggcgggc gtgagttttt gaaaaagagc ataacgatcc gcgtacgtca 133680
aatgcttagg agtgactaca aaccgctttt tgtttggcaa ttcgcaaacc cataaaatgg 133740
cgcctaagtc ctttcccttt tttccctgag tatagtccac taaaataaat tcagcgtcta 133800
gcagcggttt cagcttggca agatgcgctg agtggtagtt gttgtatccc ggctcatagg 133860
gcccattggc attgcgtacg atggctccct cgtagccctc cttaataaac tgcgccttaa 133920
gcctaagggc ctcatccaca ttcttcacgc taaaatttc aacttggtgg ataaaggtaa 133980
gatcttcctt ctgtttaaaa atatttgtta atagctgttg tctcttgttg gaaggcattt 134040
gaagctgatc actccaaaaa cagtcaaaca cgtaaaagtg cagctcggag gaatctgtct 134100
tcgcattcgc ctgccccgcg atccattgca gaggtttgcg gtgtaaataa agctcaccat 134160
ccaaatatac tctcacgtct ataaataaat aaagctgttt gagctctttt ttaatattgt 134220
caagacctaa aaattccttt ttcgtgcgcg aatacaagag aatgctacca tcgccctgct 134280
ggcaggccac agctcgaacg ccattacgct tgcgctgcac gatgggatct gtttcttctt 134340
caaaaaatgt cttaggaatt atattaaaat attttaccag catagggggg ataattcctc 134400
tatttgtgtg ggctccccgc ttttgtctgg catggcgatt atatttacta agggcgtcct 134460
tgaatgcctg atggactacc gttgtggcat ttttttttacc caagtttttt ccctcggtaa 134520
cacgtgtcat ttttgatatc cgcaccgccc cttcttccac aaaaaatttt gtgaaaattt 134580
cagcaacggc gtcttttaca tctgtggaaa acatctcatc tgtgatggga atgatcgtgt 134640
tgtgctgcac cacttgcaca caaataatcc atgaggcctt ttttccgctt ttcgtttcag 134700
actcaatcgg aggaaaacaa aaaatgttgt ttgaatattg cccaggaaat tgatttagca 134760
tggttttaac aataaaataa gcctatcaat ttttttataa tttgaatagt tattccaaat 134820
tcaatatggc ttctttagat aatttagtgg cacgatatca gaggtgcttt aatgaccagt 134880
ctcttaaaaa tagtactatt gaacttgaaa tacgttttca acagataaat tttttattat 134940
tcaaaaccgt atatgaggca cttgtggcac aagagatccc tagcaccatc tcccacagca 135000
tccgctgcat caaaaaagtt caccatgaaa accactgccg ggaaaaaatt ttgccgtcgg 135060
aaaatcttta cttcaaaaaa cagcctctca tgttttttaa gttttcagag cctgcatctc 135120
tgggctgtaa ggtctcgctg gccatcgagc agcccattcg taaatttatc ttggactcct 135180
ccattctcgt tcggctcaaa aatcgtacga cctttcgggt atctgaactt tggaaaatag 135240
agcttaccat tgtaaagcag ctgatgggaa gcgaggtctc tgcaaaactt gccgctttca 135300
aaacgcttct gtttgacacc ccagagcaac aaacgacaaa aaatatgatg acgttaataa 135360
acccagatga cgaatatctt tacgaaatag aaatagagta tacaggaaag cccgaatccc 135420
taacggcggc agatgttata aaaattaaaa acacggtgtt gacacttatt tctccaaacc 135480
atttaatgct aacagcctac caccaggcca ttgaattcat tgcctcccat atactgtcct 135540
cagaaatcct tcttgctcgt attaagagcg ggaagtgggg gcttaaacgc ctcctccccc 135600
aggtgaaatc catgaccaaa gcggattaca tgaaatttta tccgcccgtt ggctactatg 135660
taacggacaa agcagatgga attagaggca tcgccgtcat tcaggacacg caaatttatg 135720
tggttgcaga ccagttatac agcctaggta ccaccggcat tgaacccctt aaaccaacca 135780
ttttggacgg tgaatttatg cctgaaaaaa aagaatttta tgggtttgac gtcatcatgt 135840
atgagggcaa tctattgacg caacaggggt ttgaaacaag aattgagtct ttaagcaagg 135900
gcattaaagt cttacaagcg tttaacataa aagcagaaat gaagcccttt atttcgctaa 135960
caagtgcaga tcccaacgtg ctcctcaaaa actttgaaag catttttaag aaaaaaactc 136020
gcccatattc tattgatggc atcattttag tagaacctgg caattcttat ctaaatacaa 136080
acacctttaa gtggaagccc acctgggata acacattaga ctttttggtg cgaaaatgtc 136140
cggagagttt aaacgtacca gagtacgcgc ccaaaaaagg gtttccctg catctactat 136200 ttgtaggcat ctccggagag ctttttaaaa aattagcgct aaattggtgt ccaggatata 136260
cgaaactatt ccccgttaca cagcgcaacc aaaactactt tccagtacag ttccagccat 136320
cggattttcc attggcattt ctttattacc acccagatac ctcgtcattt tctaatatag 136380
atggaaaggt ccttgaaatg cgttgtctta agagagaaat caatcacgtc agctgggaaa 136440
ttgtaaaaat ccgggaggat aggcagcagg atcttaaaac cggcgggtat tttggcaatg 136500
atttcaaaac agccgaactc acatggctta actatatgga tccctttcc tttgaggagc 136560 tggcaaaggg cccttctgga atgtacttcg ccggtgccaa aaccggcata taccgcgctc 136620
aaacagcact tatttccttt attaaacaag aaatcatcca aaaaataagt caccaatcct 136680
gggttatcga tcttggaata ggaaaagggc aggacctagg acgttacctg gacgcaggga 136740
taaggcatct tgttgggatc gataaggatc aaaccgcgct tgcggagctt gtttatcgaa 136800
aattttcgca tgctacgacc cgacagcaca agcacgctac caacatttac gtgttgcatc 136860
aagacctcgc agagcctgcg aaagaaatca gcgaaaaggt acaccaaatt tacgggtttc 136920
ccaaggaggg agcttcttcc attgttagca acctgtttat tcactatctt atgaaaaaca 136980
cgcagcaggt ggaaaacctg gccgttctgt gccataagct tcttcagccg gggggaatgg 137040
tgtggtttac caccatgttg ggagaacagg tcttagaatt acttcatgaa aatagaatag 137100
agctcaatga agtatgggag gctcgtgaaa acgaagtggt caaatttgct attaaacgtc 137160
tctttaaaga ggatatatta caggaaactg ggcaagaaat tggagtcctg ttacccttca 137220
gcaatggcga cttctacaat gaatatcttg tgaacacagc gtttttaatt aaaatattta 137280
aacatcacgg cttttcccta gttcaaaagc agtcctttaa ggactggatt ccagaatttc 137340
aaaactttag taaaagtttg tataaaattc ttacagaagc cgataaaact tggacaagcc 137400
tttttgggtt tatttgtctg cgcaaaaatt aaatattttt tcataagaag tactacccag 137460
gttttaaaga aatagctaaa aatatcatat ggatactgcc atgcagctta aaacgtctat 137520
tggtttaatt acatgtcgta tgaacaccca aaataaccaa atagaaacta ttctggttca 137580
aaaacgttac agccttgctt tttcagaatt tattcattgt cattactcta taaatgctaa 137640
tcaaggtcat ctgattaaaa tgtttaataa catgacaatt aatgaacgac tgcttgtcaa 137700
aacactggat tttgaccgca tgtggtatca tatttggatt gaaactccag tctacgaact 137760
ataccacaaa aaataccaaa aatttaggaa aaattggctt ctcccggata atgggaaaaa 137820
gcttatttca ttaatcaacc aagcaaaggg ctcaggaaca cttctatggg aaatccctaa 137880
gggtaagccg aaggaagacg agtcggacct tacctgtgcc atacgggagt ttgaagaaga 137940
aaccgggatt acccgcgaat attaccagat tctcccagag tttaaaaaat ctatgtcata 138000
ctttgacggt aaaacagaat ataagcatat ctacttcctt gcaatgttat gtaagtcgtt 138060
ggaggaaccc aatatgaatc tttctttaca atacgaaaac cgaattgccg aaatttctaa 138120
aatttcttgg caaaatatgg aggctgtacg ttttattagc aaacgccagt cattaaacct 138180
ggagcctatc atcgggcctg catttaattt tattaaaaac tatttacgat acaagcacta 138240
ggatgccgca ttaaaatgcc acataaggta atacactagg aatgtcgcac acgcacaaga 138300
atacaacgtc gccggagatt tattatctag tacacgtttt atgtatgtac aatccgcctt 138360
catttaatat attgagcgga tgtactatgt atttatttta acaaaaaaca ttattttttt 138420
taatcttcat catctgtttt tataaactca gtaatatcaa aagtagcttg tggggtttca 138480
gagggttcac cttggttatc ctccgtgagg ataacatgtt cttcaggttc gtcgtcactg 138540
gagaacccat catttaattc ctcttcactc aacatctgta aaaaatcttc caagctttcg 138600
ctatcgttaa aatcctcatc atccataaga ataatggtac cttcctcatc gtttcctcct 138660
tgtttcgtgt ctaaataggc ctgcatggca tttgcaaaag tatcaaaata ggctgagtca 138720
gattgctgtt ccaaaatatg gccttgcgta ttaaatgtgg ttgcatcgtt gttaaatgct 138780
tgcaaataca gtaagggatt tatatccatt attattaagc aaaaaaaatt taaattattt 138840
ttcgaccgat gttaggtaaa attaaacaat tgctataggt gttaagcaat gtttattgat 138900
tttaagtact caacaaccat gatgtaaata ctatacagca cttttggatt tttaatcaaa 138960
tccagattaa tactaacttc ttttgtgata cagttcgtaa taatagtatc ctgctcatcg 139020
ttttgtaaga tttcttttaa tatatttttt tttaccggga tactaagcaa ttgattattt 139080
tcttttaaaa actccttttg atattcaatc gtcttattca ttgaatattt gtatataact 139140
ataattacaa atgttcaatg aattgttatt catgtcggga gatggctatt taaaaatcat 139200
gtcctatttt tctttgctca ataagcatcc aaatattttc atggcgtttt attaattgtt 139260
cattattgaa cgtatcacaa agatcattta taaattgcag atagtttatt atttctttca 139320
agagagtaac aaacattact tcagcagaac atataatagg taattcagtg gcgttaaaag 139380
aattttgatc ttgttgatac gccaatggcg aggacttaag gagatttggg ggtcttgccc 139440
aaaaccctag gctgctgttc ttgtttttta gggcgtcata aagaaatgaa agcacattgc 139500
aaggcttaag ccgcgacatc tccttcccct tgggcccttt ccatattttt agatctaaga 139560
tctcatccga gcttatagag taggtatagt aaagtttttc aaaaaagcat atctgcttga 139620
agtctttttt agaacgactt tcaagaagca tttctataat gttaacaagt tttgttaggt 139680
ttaaggcctg ttcctgtgta agctcctctt gcacgtgata gactgaaaaa gtgtgcttag 139740
gaatgaaaat actccccgtg gcactggcct gttgtctgcc aggtatatag tacacgctgc 139800
tgttagcaag ctgtaccggc acaatttgcc ccacttctgc aacattattt tgcgattcgg 139860
acgagggtat gacaatagtt acgggttcag tcaataggct ttcgccgaga ataatattac 139920
tgtcattttt aataatttta acggccgcta ttaaatcaaa ggcatttaag taagaaacaa 139980
cagcagaaaa tcttacatgc atatatcctc ttccgctatt attcgtacgc ataataaaac 140040
aaggggagcg ttgtataacg ccagtaatat taagaataaa actgtttttg aaacacttac 140100
ccacataaat gttttcaagc tccttcaaaa gatgagcctc cacatttgta caaaaattgg 140160
taggatcatc aatattcaac gttgtctcaa aaattttttg gtcgatcata tctataatat 140220
attctgtcta tttcaattta aataatatac gaataaataa cgagattatt ttattaaata 140280
agcaatggtg tatacacttt gtatttactt tgagatatac tttgtgtatc acaacgtgcc 140340
ctaagatgtg tgcacaagtg acggcatttt gtcgttaaaa aggtaaaacc agcggattcc 140400
atcctgcatt ccatttggtt gattacgagc ctccatttct ttttgcaaaa ggttattgcg 140460
aatgagtaag cagagcttga tggcactaat ctttgtaagg tttaaactta tgcccaattg 140520
gtcagcaatt ttttgttgct cctcccgtcc gcgtgtttcg catacggctc cccggtttag 140580
catgcgaata tcagtaatct cattcttttt taaaacctgg ataggtgggc ggattttaaa 140640
tttaagggcc tttcccttgc tttccatata gcctatgacg atgtcgtttt cttttcgttt 140700
aacattaata ttaagcatat aaagcggaat ttcatgccag gttttatctt ctcgcgaggt 140760
aataagtcgc acggagtcct ccgtggcata gcccactaga gtgttgtcat ccccaggcac 140820
gtggcttata attttaaaaa tgtccggaaa tggctgaata tctttttttg aaaaagcgat 140880
gaaaaacttt ttataaacct cgacaagggc ccccatacct gcaagattat ctataataag 140940
tgcttctagc atcgtatagt gaaatgaagc ggggtagtgg atgagtacct gctccattgg 141000
ctcatcctga aaatccttct gaaacttttc atacaatact tgaaagggtt ctttggtctg 141060
cgagtgttcg aggtatttgg taatacggat gctgtgcatc gcgggaggct gaaaatcccg 141120
aatatatgtt tcaatatcta ataccggttc ctttttatgg ttaagcaccg cagcgacgta 141180
caaatgctca ggctttgccg gcacatgcat aatggtgcaa agacgattct gtatccataa 141240
ttccttgcac tggtttttttg agtagcatag agaaatgagc gccagcgcga agttgtcctc 141300
tgagaagagt ttattatcga tggtaattcc ctgtatgagc ttgggagtgg aaacagcctt 141360
ccatagctcg gagtacgtcc acacggggcg tgccataaac aaagatataa taatattaga 141420
aattgttttt acctcttgct ccccgtatcc ataggcctca aaggtattga ggacggtggc 141480
tccgacgttt gccggcgtga tggatggact aaggggcaga ctttccaaca taggcttatc 141540
aatcttaatc tggttggtga acccatcaat ggcgtgcttt cgcagcgcct tatccccctc 141600
ctgtattaaa atgtattctt ttaatttttg tgcgtactta gcgagctctg gccctccatc 141660
gggtgttgtc gatacgtaca aataaattgt cacgttgcgc tcactggggg ggagctccat 141720
gtgtgaattt tttcgcacca ccctcccaaa tacctgaata agccggggaa tatcaagggg 141780
caatgacata atcatctcgt accgcacggc ctgaaagttc aaaccctcca caatcacctt 141840
ggacccgatg agaatacgca gctggtggcc ttccaggttg gacgaggcgt taaaaagagc 141900
caggcttcgt tcgcgtacag cgggctctat ttcgctgtgc agaatggtga accgtactgg 141960
aataaactga tggtcgctat gtgtgtgctc atcgcgaatc gcggcgcaga tggagcagcg 142020
ggtcgttccc acaggggacg aaacttcatt taaaatgcca ttactttgta aaatttcttg 142080
caagataaga accccccgaca tgcggacccg attgtggtaa attaaaattt tcccccggcc 142140
ttgccgaata atggaaagaa tgtctttcat catttgagtg tattttccgc tataaaaggc 142200
caatcccgag atgtgcgttg gtggctgcag cgacaaaaag ctgccactca cattaaaggg 142260
ggctctacgc gaaggctcaa taatctgtac cccgttttcc agaagccagt ctgtgcttgc 142320
catagaaagg gcggtggggg tttccgtcga gttaaacagg ccgtaagcct tgggttccgt 142380
ttgttttgaa aattttgggt tgggaaacac catgtcataa atgctgtacg cattactcga 142440
gattttaggg tcagggccca gctgtttaag cgtttcaagc tgatactcag acatggggca 142500
ttcgatgaaa tgtaagtacg gcaatgtttc gtctttatag gacaacatct ttccggcaaa 142560
tattctttcg gggtaaaaat tggtgttggt atccaacaaa aaagataccc ttccggtgct 142620
cagtctttcc acaagagcta gggcgtcctt tttccattta acggaatgcc cactgctgtc 142680
aaacagttgc tggcgctgga ggggctggcc gttgggcagc tcatgccgcg gaaccaaaag 142740
gtttaacagg tcgacgtatt ccatgacact cccggttacg ggcgttgccg acatgaagac 142800
ggccctgggg gcctggtgag gtggaaaggc atccaggaca tactgtaaag cgatgccata 142860
attatttcgt tcctggatat tgtacacgtt gtgtatttca tccgcaatga gcagtcctcc 142920
cctaagttgc tccatgattt tttgattcac ccggatgagg ccgtttgtct cggcctcgct 142980 aatttttgc acgaactgag atatatcgtt ctcattcaat gtatcttctg cttcgtcaga 143040
acgatgaaac agagaaagca catcaaagtt tttctcttca cccttactcg taatattgaa 143100
aagcttggat gcaaattcct tatagccgta aaactgaaaa aagcctccgc ggtttctatc 143160
ggttaaacgg cgctttaacg tactaacgaa cccatttaga tgccgtgatt cgaccgacgt 143220
ggtgctgcca gactgctttg caatgtgaag aagccggtgt agctcagcga cctccttgta 143280
agaaacaaat cccagctcag gacgtcttag catttctgtt tgaatgatgg cgcgtgtaaa 143340
gcctaccaca aaaatccagg gcgcattttc aataaaattc atgtagtggt tcataaattg 143400
acgcgcgatg gcaatcgcgg caatgctttt tcccgtcccg gtctgccagt ttaataaaag 143460
acgcgagtag ggcgtgttgg gattttgaaa gttttggacg aaaagctggg cattatgcaa 143520
ttggagaccc ttgatggaag gaaagggcga cgcgtagggg tcacacggaa aaaacgctcg 143580
cccccccttc tcgcagccag gcccaccgat ctggacaaaa tgagcccgca gatcacgaat 143640
gagctctttt tggtcgacag gaggggaaat caacgattta aactcctttc ttcgcgccaa 143700
ctgctgcaaa aagtctgcgg catccaattc gggatacgcc atattatcat aaaaaaataa 143760
acctttttat gaaaactttt atgtgattct gtattgcaat tgtttttat gaatactgta 143820 aataagcgta tcaacttgtt tttctaacga agaggcgtta ttcttttttt ctggatataa 143880
aataataata agtataataa ttaagactaa acagcaggca atcactatca aactcatatt 143940
atacttactt ttttataaaa agtattatat cttatgaatg cgcaagttca gctaattgtt 144000
cgtcgcttgg aatgtgggac tgcagggagg tggagttttt cctttttcta aagaataccg 144060
ggaaatggtg gtgaggctca ggttgttgta catagtagct aggaggaggt ttaggtatgc 144120
tcgacttgca gtcaatagtc cggttatagt aaacgatggc aacgatgata agaataataa 144180
tgagcaaaat caaaatgccc aggagaatcg cagttgttcc gggatatttg gcgattgtat 144240
gggctaaaag gccttgggtg ctttgtttaa ttccctcgcg ggttgacagg ttatgagaaa 144300
gcagtggaga cgtttcagtg tccatttatt acaattgaac agttatatta atctcaaata 144360
aaatataaca caaaattaat tatggccatg caaaagttat ttacgtatat ttacgagttt 144420
attgaatatc gtaagatggt gctgttggaa gaaaaggtac catatgataa gtttgttcaa 144480
atggtactta atacaggatt ttttcgtatt aacgcggaga cgctgaatca cggaatcgta 144540
tccgtgttta tctttggagc aaatggcaag tacgttcacc acggaggcga catgagaacg 144600
cttttaacga atacgcttaa tgaaaaaaaa cattatgaag aattaatttt aatcgttgat 144660
aagcccgttt taagcaaaaa aaatatttta gatataatcg tcgagcagcg cgctgcaaat 144720
cccacgattg taataaacat atatccctac cacctgttct gcattaacat tcccaaggtg 144780
agtgccattc ctaaacataa actaattact caggaggagg cgcaggagtt tttaggtcgc 144840
gaatatctgc aaccgcagga cctcatgcaa attagcgcgt cagaccccc ggtggtctgg 144900 ctgggaggaa gaccgggaga ctttgtgcaa attgagcggc cctcagagac agctatgcac 144960
gctgttgtta tccgctttat caccaagtcc aaaatttgag tcccgtgttt aaagatgaca 145020
gacagctaag taagcatatc tgtaaaattg tcgatgtcct ctgtggatag agcgctttcc 145080
tctgagcagc aaattttttc atacatctcc atgggggatg gcgaggcttt aatagtatgt 145140
aggtcacgta agaactgttg tatgatggga tatttgtctt ttaaaaactg gggatgtttc 145200
ataactggaa ttatttgaaa gataaagacc ttccatccaa agtagccaac cacatttggc 145260
atttcgggac acgcggtttc ataaggcata gaatagtgaa tagtgtactg atctttttga 145320
tacagcgttt caagtagttg gcgaaatgtt tccgcgtcga gcgtgccaaa atcttgagga 145380
gcctcggtgt gctcctgtgt agagcagatc gtgatgattc cccaggcaag cgggagcatg 145440
gactctggag ggtggatatc cgtattggtc tcattattcg atcccagctg atgaatgccg 145500
cacacgcgaa acatggcctc gacgtagatg cccatagaga taggcggcga aagggcaaga 145560
ccggattgta tttgcggcat atagtaggag ggcaccgagt tttttatttt tcggttgaat 145620
ggggacttta tttctaccag cacggggatg cgtttcgtgg cctcatagcg tacgttgtta 145680
aaaattgttt tgatttccca ggactgttga gtgtatccca gcgttaggtg acaaaaccca 145740
tcggggctat tactatgtcc ggggtatccc aaataggtcc catcaatatg aatattgtca 145800
cctatgacgg tggtttggca gaacaactca agcagatctt tactaacacg ctcaaaaagg 145860
gttccccagc tacaagcagc gcggttcaaa ttcttcttaa aaagatttgc tttttccgcc 145920
aaggttatat aatagctttt gtaagggttt aaacctaaaa cgctggcaag gtcagagcca 145980
cccacctgag tgcgacgaat agcatgccag gcatcggagc gctgctgagg agagtcttta 146040
aacaggcgta caaaggtttc cattatactt gttttaacag gaattcaata taaaaagtca 146100
acacagtttg caatttttcc aatctcaaga tatagccata catttttttt tccaattggc 146160
gaatatgttt aagctcatgt gtttcaatat tagcatccgg aaatttaaat gcataaagat 146220
gttcaaaggc ctgatttata cacgtatcaa aggatctgtg gtatgttatt agcttcagca 146280
tgtgtgccag atcttcaaga tggtctaaat ttatacggtt ttccacgtgg tggatcatgt 146340
ctgccacatc ttgagccccc atccagggga tcacaaggta ctcccccctta aagatgattc 146400 gtcgtttttt taaaaaatca tgaaaacgtt ttaaagcttc aagaaagggg cagttgggct 146460
ttgaccccaa aatgctgacg acgatatcct cgggcatgat gtattcgcag tgaggatagt 146520
agtttacgga ctctaattca gcggcccgcc gttttatttc gtatcttgcc cagttattca 146580
gagagtactc cacgcctccg accacaacag acatcctatc tattaaaaaa taacaataaa 146640
aaccttatga aatctatgta tagtggccgc taaaatgtct atattagaaa aaattacgtc 146700
aagtccctct gaatgcgcag agcatcttac aaacaaagat agctgtttaa gtaaaaaaat 146760
acaaaaagag ctcacctctt ttttggaaaa aaaagagaca ctcggttgcg attcggagtc 146820
ctgcgtaatt acccaccccg ccgtgaaggc ctatgcgcaa caaaagggac tggacctctc 146880
caaagaactg gagactcggt ttaaagcgcc aggacccaga aacaacacgg gtcttcttac 146940
aaacttcaat attgatgaaa cgctgcagag gtgggccata aaatacacca agtttttcaa 147000
ctgtcctttt tccatgatgg actttgagag ggtccattat aaatttaatc aagtggatat 147060
ggtaaaggta tataagggag aagagctaca atatgtagaa ggcaaagtgg tcaagcgtcc 147120
ttgtaacacc ttcggatgcg ttttaaacac ggacttttca acgggcactg gaaaacactg 147180
ggtagccatc tttgtggata tgcggggcga ctgctggagc atcgaatatt ttaattcgac 147240
gggaaattct cctccaggtc ccgttattcg ttggatggaa cgggtcaaac agcagctatt 147300
aaaaatacac cacaccgtga aaacgcttgc agttaccaac attcgtcacc aacggtcgca 147360
gaccgagtgc ggcccctaca gcctgtttta catcagggca cgcctcgaca acgtgtcata 147420
cgcccatttt atatccgcta ggattaccga cgaagacatg tataagttta gaacccatct 147480
gtttcgcatc gcataaacta ataaagtttg aattctttat aggaataaaa atggaagcgt 147540
ttgaaatcag cgatttcaaa gagcatgcga agaaaaaaag catgtgggct ggcgccctca 147600
acaaagtcac tatttcgggt cttatggggg tctttaccga agatgaggac cttatggcgt 147660
tacccattca cagagaccac tgccccgctt tgttaaaaat ttttgacgag atcatcgtaa 147720
atgccacgga tcatgaaaga gcttgccata acaaaacaaa aaaggtaact tacattaaaa 147780
tttcgtttga taaaggtgtg ttttcttgcg aaaacgatgg cccgggaatc cccattgcaa 147840
agcatgagca agccagtctt atcgccaagc gcgatgtgta tgttcccgag gtggcttcat 147900
gtcacttttt agccggaacg aacatcaata aggccaagga ctgtatcaag gggggaacca 147960
acggcgtcgg gctgaagctc gccatggtgc attcgcagtg ggccattctt accaccgccg 148020
acggcgcgca aaagtatgtt caacatatca accaacgcct agatatcatt gagcctccta 148080
ccattacacc ctccagggaa atgtttacac gtatcgagct catgcccgta taccaggaac 148140
tagggtacgc ggagcctctg tctgaaacag agcaggcgga tctttccgcc tggatttacc 148200
ttcgcgcctg ccaatgcgcg gcctacgtgg gaaaaggcac caccatttat tacaatgata 148260
agccttgccg cacgggctct gtgatggcgc tagccaaaat gtacaccctg ttgagcgcgc 148320
ctaatagcac gatacatacg gcgaccatta aggccgacgc aaagccctat agcctgcacc 148380
ccctgcaggt tgcggcggtc gtgtccccca agtttaaaaa atttgaacac gtgtccgtta 148440
tcaacggggt aaattgcgta aaaggagaac atgtcacctt tttgaaaaag actattaatg 148500
aaatggtcgt taaaaaattt caacaaacga ttaaagataa aaaccgcaaa acaacattac 148560
gagacagctg ttcaaacatc tttatcgtta tagtgggttc cattccagga atagaatgga 148620
ccggccagcg gaaggatgaa cttagcatcg cggaaaatgt ttttaaaacg cattactcca 148680
ttccttctag tttttaaca agtatgacaa agtctatcgt ggatattctt ctgcaatcca 148740
tttctaaaaa agataaccat aaacaggtcg acgtagacaa atatacgcgt gcccgcaatg 148800
cgggaggaaa aagggcgcag gactgcatgc tactcgcggc ggaaggggat agcgcacttt 148860
ccctgctgcg cacgggacta accctgggaa agtccaaccc aagcgggccc tcctttgact 148920
tctgcggcat gatctccctg ggaggagtca tcatgaatgc ctgcaaaaag gtgacaaaca 148980
ttacaacgga ctctggagaa accattatgg tgcgcaacga acagcttacc aataataaag 149040
tgttgcaggg aatcgtgcag gtattgggtc tagacttcaa ctgccattac aaaacacagg 149100
aagagcgagc aaagctgaga tacggctgca ttgttgcgtg cgttgatcaa gatctggatg 149160
ggtgtggaaa aatccttgga ctgctgctgg cctactttca cctgttttgg cctcagctta 149220
ttatccatgg tttcgtaaaa cgactgctta ccccgctgat acgtgtgtat gaaaagggta 149280
agaccatgcc cgtggaattt tactatgaac aagagtttga tgcctgggca aaaaagcaga 149340
ccagcttagc caaccatacc gtaaaatatt acaagggatt ggcggcgcat gacacccatg 149400
aagtaaaaag catgttcaaa cattttgaca acatggtgta cacgtttacc ctggatgact 149460
cagcaaagga gttgtttcat atttattttg gcggggagtc ggagttgcga aaaagagagc 149520
tttgcaccgg cgtggtgccg ctcaccgaaa cccagacgca gtccattcat agtgtccgac 149580
gaattccttg cagcctgcat ctgcaagtag ataccaaggc ttacaagctg gatgccatcg 149640
agcggcagat tcccaacttc ttagacggga tgacgcgggc gcggcgcaaa attttagccg 149700
ggggggtgaa atgcttcgcc tccaacaacc gtgaacgaaa ggtttttcag ttcgggggct 149760
acgttgcaga tcacatgttt tatcaccatg gcgacatgtc gttaaacaca agtattataa 149820
aagccgccca gtattaccca ggctcctccc acctctatcc ggtattcata ggcataggaa 149880
gttttggctc caggcacctg ggaggaaagg atgcaggatc cccaagatac atcagtgtgc 149940
agcttgcgtc tgaatttatt aaaacaatgt tccccgcgga ggactcatgg cttctcccct 150000
acgtctttga ggacggccag cgggcggaac cagagtacta cgtgcctgtg ttgccgcttg 150060
ctattatgga gtacggcgcc aacccatcgg agggctggaa gtacaccact tgggcccggc 150120
aactggaaga cattttggcc ttggtgaggg cctacgtcga caaagacaac ccaaaacacg 150180
agctactgca ctatgcaata aaacataaga ttactatact cccgctgcgg ccctccaatt 150240
acaatttcaa gggccatttg aagcggtttg gccaatacta ctacagctac ggcacgtacg 150300
tcatctcaga gcagcgaaat ataattacta ttacggagct tcctctgcgt gttcctacgg 150360
ttgcatacat cgaaagtata aaaaaatcga gtaaccgcat gacatttatt gaagaaatca 150420
tcgactacag tagttcagaa actattgaaa ttctggtgaa attaaagcca aatagtctta 150480
accgtatcgt ggaagaattt aaggagactg aagagcaaga ttccatagaa aatttttctgc 150540
gcctgcgcaa ttgtttacat tcacatctaa actttgtaaa acctaaaggt ggcattatcg 150600
agtttaacac gtattatgaa attttgtatg cgtggctacc ttacaggcgt gagctttacc 150660
aaaagcgtct tatgcgtgag cacgcggtgc ttaagctgcg cattatcatg gaaactgcta 150720
ttgtacgcta catcaatgag tctgcagagc taaatctttc ccattatgag gatgaaaagg 150780
aggcaagccg cattctaagc gagcatggat ttcccccgct gaaccacacg ctgatcattt 150840
cccctgagtt tgcctctata gaggaactca atcaaaaagc actgcagggc tgttatacct 150900
atatactatc tttgcaggct cgagaattgc ttatcgcagc caaaactcgt cgggtggaaa 150960
aaataaaaaa aatgcaagct cgtcttgata aggttgagca gcttttgcaa gagtctccct 151020
ttcccggcgc cagcgtatgg ctggaggaaa ttgatgcggt ggaaaaggct attataaaag 151080
gaagaaatac tcagtggaaa tttcattaaa cgctaccggt tttatgatgt ccaataggtg 151140
ttaagcaatc agttcatcaa cattttttc aagaatttga aaagtttgga taatgttctg 151200
aatacttttt tctaaaagag ttatcaaatc ttcttgtgag gccttatgaa taattgttaa 151260
taccatttct tgcttatggg gaacacactg ataccccaca aagctaatat caggaatcat 151320
ttcataaata tatgttttta gcagatttcc gatggtatgg gtttcatctt ttatcgtgat 151380
aatggccttt gtttttttcct catccatgga aaacagcaca agttccggct gcggctcttc 151440
aaagttttca taaatttttt gaatgctttg gattcggcca ataatgatcc ggcaggcgtt 151500
ttttaaatac gtgcgaacgg cctggttgat atgtggcagc ggcaccgctg gaaagcaaag 151560
ccccaggcgg tggtgacgcg ggtctgaggt catagagctt tgcttgtaac cgctaagcgc 151620
catatattct tttttatccg ttgggtactg ttcaatgtca aggtgggaaa aatgtgtttt 151680
aacggcaaga ttaaaggcgg catgctttcg tcctatgccc tttttaatat agatatcctc 151740
tataatcaac gattttccgg gttgtaggaa gccaatctca aaggtaggat taaaaatcgg 151800
gtatttaagc ttagggcctg ccacctggat gagatcgcgg ctatagatgg ttttaacctc 151860
acagctattg tttaaactcc gcagagcaaa taccagtgtc tcgtttttcg cataaatcgg 151920
aatgaaatta atgcggtttc taataaattg ttccgtcata aacaggtccg tggaatcctc 151980
gatcttatac ccaccgggct taatatctag catataattg ggaatttcat cttgcaagac 152040
ccgcgacagg ccgtggaccg cggctctgct aatgccctta aagtccataa caacattgac 152100
cgggacgagg ggcaactgct cctcgagctg aaatagtttt ttggccgcat ttttaataaa 152160
gaggttggaa aagtctatca aaaacggttt gatttccacg ttttggaaaa ttttttccat 152220
ttgtattata aatatatcta tatatattca aattatggta gtttatgact tgctcgtttc 152280
tttaagtaag gaatccatag atgtgctacg gtttgtagag gcaaaccttg cggcgtttaa 152340
ccagcagtat atttttttca atatccaaag aaaaaactcg atcacgacac cccttctcat 152400
tacgccgcag caggaaaaaa tttcgcaaat tgttgagttt ttaatggatg aatataataa 152460
gaacaataga aggccctccg ggccgccgcg tgagcagccc atgcacccat tattgccgta 152520
tcaacaatcc tcggacgaac agcccatgat gccgtatcaa cagcccccgg ggaatgatga 152580
tcagccatat gagcaaatat accataaaaa acacgcgtcg cagcaagtaa atactgaact 152640
gaacgattat tatcaacata ttcttgcatt aggcgatgaa gacaaaggta tggacagcat 152700
gttaaaactt ccagaaaagg caaaaaggga tagcgatgat gaggacgaca tgttttctat 152760
aaaaaactaa cgacgtaaca attaaacaaa aataaaaatc attataaaat gaatcttgaa 152820
tacgtccaag ttgttcaaaa atttaatcaa gtactcctag aacttaccaa aaaagtatgt 152880
accgttgtgg gcgggagcaa acccacctat tggtatcacc acattagaag ggtttgctca 152940
gaatgtccat ccatgccgat gagtatgata ggtccgtatc tgaatgtcta taaagcccaa 153000
attctaacaa gggacaagaa tttttttatg aatttcgatc ccgcgcataa tgagtacacc 153060
tttatcattc aaaaactaaa agaagcagcc cgaaatatgc cggaagacga attagaacag 153120
tactgggtaa aacttttatt tttacttaaa agctacataa aatgtaagcc ctttattaat 153180
taaagaattg atgcataact aataaatggc cggtcgtgtt aaaataaaac agaaagagct 153240
catagactct actgtaaaaa acaaaaatgt gatgaatctg ttccatgaaa ttataggctc 153300
aaaaggcaat attaatttta gcgttgtctg gcccaagttt aaaaaaatca aacagagcgt 153360
ttatgactac atttccactc tttctgtgct ggaaaaagca aacgttatgc aaaactttga 153420
agctgataag aaactgttgg aactttttgt acaaaagctg tgggctgcct atgaaggcta 153480
tttcaaatat cccgagattg aaaaatatga ggtggaaggc caggtaaatt tcaatctcgt 153540
acctcagtgc gtcctcgaaa agtttagcca gttgtatagg ataagaatca attcagagct 153600
tgtcacactc atcctaaaca gctgtgcctt tatgagtaaa tataacgatt atattctcaa 153660
aaaagatccc tacatactaa ccataacccc cggcctatgc ttttccccca ttcccaactt 153720
cgaggaccta aattttaaac atctttacaa cagtgataaa aattctcagc atgacaaaga 153780
gtttatcatg tttatattat ataagcttta tacggctgcc ctaggagtgt acaatgccat 153840
ctcgattcca gacatcgacg tagaagacct tgaaaatatc atcctatcct cggtgagcca 153900
gattaaaaaa caaattccgc gctgcaaaga cgccttcaac aaaattgaat cttcggtaca 153960
cctgttgcgc aaaaatttta acacatatta cagtgactat gtgggctcag gctacaaccc 154020
aaccatcatt atggaacagt acattaaaga catatcacag gattccaaga acatatcacc 154080
acgcatttcc taccagttta gaaccatcat caagtattac cgcgacatga ttgccaccag 154140
gcatcaaacg atggaccccc aggtattaaa cctcgtaaag cacgtcgaaa agaaattaga 154200
tatgcttgat agagaaaaaa attagtatat atagttatgg tgaatctttt tcctgttttt 154260
accttaattg tgattattac aattttaatt acgactcgag aactatccac cacgatgctt 154320
attgtttctc ttgtaacaga ttatattatt attaatacac agtatacgga acagcagcat 154380

-continued gaaaacaata catttttcat gccgcaaaaa aattctttta acgaatctta taataaagac 154440
aaaaaatcta atatacatat tccctaccag tggctggcgc ctgaactgaa ggaagctgag 154500
agcaagtact ggtggggcaa ttatgatcct catagcgagc ccgttctcgc tggcgcatct 154560
tgaatatctt catacgtggc acgtcaccat caaaaacatt gcccaacagc acgggcttga 154620
tataaaggtg gccattgtgg tctcaacatc gcatttaaat aatttttgc caatttccgg 154680
ggcgcttaac atcgaatgta taaccttccc cagttgcggc atcaaggaga tagacctcct 154740
atgggcgcgc attaaactat ttcaacatta ctgcgccatc ggtgcccgtc ttttatggct 154800
ggtaagtgct gacatcaggc cccctgtttc agcgtggcca gccatcgccg acagtctaaa 154860
aaagggagca gatgcggtcg ttattcccta cccctcccga tggaacaatc ttatacctac 154920
cgtcatcaaa gaaatagttg tccaccaaaa aaaatgcctt gtggcggtgg atgcacgcca 154980
ccttgataca gatacccaga ttgtaggggc cgggatgggc tgcatcgtcc taaccctaaa 155040
ggcccttatg gtgcgcctaa gtattggcaa acagcccgtt aagatactgt ggcccgacct 155100
tcacggcact gccgagggca ttcctctgga gggggtggag gttggctggt ttttaaacgc 155160
ttatgcgcat aaattaaata tacgctgcct aggggctgat catattgcgc agcacttaac 155220
ttaattcttt atttaaaaag tccacgcatc cagtggcggc ctacattaag ggcctacgca 155280
cataaatata cactggctag aagtacgcct tcatttaaac cattgaatta tttatataat 155340
ggctgcaaac attattgcaa caagagccgt gccaaagatg gccagcaaaa aagagcatca 155400
atactgtctg ctagactccc aggaaaagcg tcatgggcat tatccctttt catttgaatt 155460
aaagccttat gggcaaacag gcgcaaatat cataggagta cagggctcac ttacccatgt 155520
tatcaaaatg acagtatttc catttatgat tccttttcct ttacaaaaaa ctcatataga 155580
tgattttatt ggtggacgca tttatttatt ttttaaggaa ctggacatgc aagcagtttc 155640
tgatgtaaat ggaatgcaat accacttcga gttcaaggtt gttcctgtaa gccccaacca 155700
agtagagctt cttcctgtga ataataaata taaatttaca tatgctatac cggtagtgca 155760
ataccttacc ccaatctttt atgatctttc gggaccgcta gatttcccat tagatactct 155820
ttcggtccat gtggatatcc tctccaatca tatacagctt cctatccaaa accataacct 155880
aacaacgggt gatcgtgttt ttatttctgg atataaacac ctgcaaacga ttgaattatg 155940
taaaaataac aagattttta tcaaaaatat accgccgctt tcatccgaaa aaataaaact 156000
atatatacta aaaaatcgaa tcagaattcc gctatacttt aaatctttaa aaacgtctaa 156060
gtaataacat ttttatagtc tactcctagt tccgaaatag gctgaatttc tttttaagt 156120
cctttaaacc aaggatgtga tacaagactc ttaaaggaaa gccgcttatt ttcattaatt 156180
gttaaacatt ccgtgataaa ctgttttccc gtctctgaaa tgttctcggg aatataattt 156240
tcccgtttca ggatatcatt taaataaaaa ttttctgcac gaaatctaaa aagattaacc 156300
gcgaccatac ctatcgtcca cacggttaaa ggaagctggt agtaataacc ataataataa 156360
aattctggac acacgtattc ccatgttcca aacatattat attggggacg ggtttcgtct 156420
aatctaacag cgcttccaaa gtcaatgacc ttaatgatct tttgatttat gtctataata 156480
aggttctcat ccttaatatc cccatggata aagcccttct cataaatgtt ttgtataata 156540
agaataagct ggaatattat ttttttggct tcggtttcct caagtttttt aaagtaatga 156600
taatgaagta gatcaacact atttggaata tattctatga ttagtatatg atacatagca 156660
ttttcggtat attcgataag cttaataaca ccgggagtat cttgcagggc tttcaacacg 156720
atgacttcat ttcctggaat ttcttttta gaaacgtact taaatataat gggttgccct 156780
acttgatgac ccaaaaagac gttatttctg ccaccctcaa acatgggtct cgtcgcaatg 156840
aaatacatgt gctgcgttgt ggagatcctt tccacctttg ctgtaggata aaacgcatat 156900
tgtgcctggg gatttttaa catttttta agctgttgtt ccggcctgga catgttttat 156960
tagctttata tataaagggt tagaaggttt aatttcaata tatgccttaa tgatgggatt 157020
atattcgtaa aaggtatagc ctaatcctac gtctttgttt ttttggtaaa aaaactgttt 157080
gccctcgtag gatatgctat aggcttttac ttcggctttt acaagcggtt ggcagggatt 157140
gggcaaacgt aaatcgcgtt caaagttttc atgaaaaagc aaagcatttg tgggctgaca 157200
catcagacag ccgctttcgc cattgaaggc acattcaatg gccgcccttt ttagtaaatc 157260
gcggaaagca gaattaagat ggctcttttc aagccccctt tcgtgaaaac gctcatcaat 157320
cgttttttgt tcctgactgc cttcgggaat actataaaac attttttgat tagccaccgc 157380
gatgtacaaa aaaggctgta cggttttctc ctcgggcggt agcgcatcgt ggctaccaat 157440
gcgtataatg cgcgccttca cttgatcctc tcgggcctta tcccagtacg gctctaggat 157500
atgaacctgc cgcccgtatt tgagatccaa tccctcagct cctgttttag agacgagtaa 157560
aattttaata acctctccgt gtatattcag cggcgaattc caaagctgct ggatcatgtc 157620
gcgctcttta gataaaattt tccctgtaat aagcgtaaat cgtgttattt tggaggacag 157680
gactaacgta tgggtcggcc catcttccgc aaagttttc accataagat ctttcccatc 157740
cttatgaagg aggatggtgt tgtgcccttc ttccaatact tttaggggct gaaggcactg 157800
gtagccctct atttctaaaa agcgggccac gacgtgaagg cccaattcca caaactgtga 157860
gtaaatgagc acagggcccg gagacgtttt aatattttt agcatgcgta ctattttggg 157920
actagaattt tctgtgaagg cctctttggg cagctgctga acagcctctg ataattttc 157980 atcctccttt actgttagca tttcggacgc gaagatgctg atcatacggg aacgcacata 158040
gtaggaggag cctgactctt gctccgatcc tggcaggcag agggcggcgg catttatttt 158100
ttcatacatt cctgagctgg cgtgcttttc cgcgttttca acgtctcggg ccagcagata 158160
ttgcctatac tgctcgggtg acatttcaac cttttctata ataagaggaa gctctgtggg 158220
gaatagcttg ttgagctcat tctggtttcc agcgtagctt atcataccca ctaggcggtt 158280
tagtagtttg tccgcgttta aagggctatt cgttgtttta ttgacataag cggtgtagaa 158340
tctttcatag tgaagaggta ataagattcg cccgcttagc atattaaaac agggcaccat 158400
ttcaaagggg tccttcgaac acggggtgcc tgttaaaaac agaatacgaa tatttttagc 158460
ttgcataata ttattgtaca gctggcgggc atttgtttta tcattggcgc tattgataat 158520
tcctctaaag aggttgtgtg cctcgtcaac gatgagcagg catccattta gggaccctcc 158580
cgcctttatg atctgctgcc ccatgttgta agcgtctagg gacacaaacc tgaagcgccg 158640
cgagattttt tgtagctctt tggagtgatc cgtcgtttcc ggatataaaa gtttaataag 158700
ctttaacaaa gactgttgga agtttgagtg caacgacttg ggtgcgatca gaatcgggtt 158760
gtaaatatgt gaaagtgaga tggcaagcga caggctcaaa atggttttcc ccatgcccat 158820
ctggtgatag atgaggaggc cccgtgtgtt ttccccctgg cctatcccaa atttaggatc 158880
cgaaaaggcg gtgtaaatta aaaactggta gtatttcagg gctcgtgcaa agcgggcagt 158940
gagtgaggtg tctttgcttt cctgaagctc tttatatttt tcatatacct cttttaggta 159000
tgcttctatt tggacgggga aggaggtgtt gttgtgcacg caagacatga ctcgttataa 159060
ggatcccata ttaaaacttc attagaagaa tagggctgct gatagctagc gctgcactta 159120
aaaatggggt agcccttttt cttgtaaatc cggtgcctgt cgtagacctg gctagaaagc 159180
gggcttagtg tatctttaat gtccacaacg atgcgtacct tttttcatc cgatccctgc 159240
cgggtaatac gtcccaagat ttgctccatg ttgtttctgc ggggcgttgc catgatgatc 159300
gatgtcatat gcttgaagga aatgcctcta cgcccgtagc cataggtcag caagataatg 159360
gaagcgctgt gtgcctgaga aagagcggta tttgaaaccc cgccgcatag gagcgccacc 159420
tccggaacga taatttgaac atctttgaat tctttggaaa gcgcctgata aaaaatttct 159480
aaaagtttgc gaaattccac gaaaatgatg atgccatacg gctcatcggt cccccatttg 159540
tgaggctcag cggtatgcag ggagtaaagc cgctttgcct catttacgac aagttgtata 159600
cgcgaaggat cttgaagtag tttatcaatg gtggcaatgg ccgatacctt ttcattaata 159660
tacacagggc taacgaagtc aggatgtccc tgatattcga tttccctcac gtacccggaa 159720
aaggttgtgg tgggacttac agtcctctgg ggctgtccta gatggtgaat aataatcttg 159780
tccataccat cgggccggtc caggggtgta gcggacagtc ctaatatccg actaagttgt 159840
attttccaaa aaattttgta attctccggc gagtgtaatt catgtgcctc atctaacacg 159900
actagaccaa agggctcaaa gaactgctca ggcttcttgc gcagggtatt aatgattccc 159960
acgatgacgt cgtactcttt gctcgtcatg tcctttttct tgcacgctgc attattgtaa 160020
gcagctacac gtaggtgggg caggagcaat gttagctcgt cgatccactg tatttgaatc 160080
gccttggtgg gcacgatgac cagggtaggg tacaaaagtt tttgaataat gctgatcgca 160140
atacgcgttt tccccaaacc ggtatttaga tgtaggtaaa agcgcccata gggggacagg 160200
agctttttat gaatcttatc gaccatttct tgctggtagt taaatagtgg aaattctgtt 160260
tcaacgcatg ggagggcccg cagcgacacg ggcgcgtcg tgtaaaccat gttaaacatt 160320
tcaaactgct tttgcagcaa tatgggaaaa taaatgtatt cccctgcag cgtgaaggca 160380
gtttcctgtc ttatggctat gtgctttggc tgcccgggta atgcccgcgc cgtaacggtg 160440
agcgccttaa gaacgcgccc gaaatcatgt tgtaatttac tttgtagctt cttataattt 160500
attcctattc cagcaaagga tataatggcc tccattctca cgctggacgg gttatatgca 160560
gaggttccaa aattcttacc agaggcgtta cgagagggct gtgctggcaa gaatcctcta 160620
agcttttata ttcaacaaat tttaaattta atgggatgtg acggtaacga gtaccatgtt 160680
ctttttacca gcagctccga ggaagcaaat actcatatga tcatggccgc cgtgcgtcgc 160740
catttgctgc ggacgcagca aaggcctcat gtcattatcg gagcagccga gcccccctagc 160800
gtcaccgaat gtgtgaaggc attggcgcag gaaaaacgct gcgtatacac catcatcccc 160860
ctaaaaaatt ttgaaataga tcctgttgcg gtatacgatg ccatacaaag caatacctgc 160920
ttagcgtgca tttcaggcac taatgctgtt gtcaaaacgt tcaacaaact ccaggacatc 160980
agcaacgtgt taaaaggtat tcccctgcac tcagaagtga gtgatcttgt ttatcaagga 161040
tgtattcaac aaaatccgcc cgctgatagt ttttcaataa atagtctcta cggcttcctg 161100
ggagtcggtg ttttgggaat gaagaaaaag gtcatgcaag gattggggcc gctcattttt 161160
ggaggagggc tgagaggcgg aagccctaat atacccggaa ttcatgccat gtataaaacg 161220
ctaacccagc aaaggccttc tatgaaaaaa aataaataca atacatacgc tgttcatgaa 161280
aactttaaaa aacatcagca tgtatatcta cccatagggg gcgtgtctgc agaggacacg 161340
tctgcagaaa acatatctac aaaagacatg cctgttgaag gcccgaaggg actcccgggc 161400
tatattttat ttagcgttgg ccgtcgcgcc gaggagctac aaaaaaaaat tttcactaaa 161460
tttaatataa aggttggccg tgttgttgac ttacaagaga tactgtttcg tatcaaaata 161520
ccccaaaaat actgggagac attattgttc atccaattaa gagataattt gaccaaagag 161580
gacataaaaa gagttatggt tgttttgatg catttagata ccatcactcc tcgtggctct 161640
cttcctcctc cgagccactc ttcttctttt tcttaatcgt ttttgtttgt tctataataa 161700
gggaaaagaa ctccgtggga tcttgttccc cgtacaggtt atctgcgacc ataaggatgc 161760
ttagaatggt aaacaggtga gaatacataa gggtttgcgt tttaagaaaa ccctgacgtt 161820
gaatcataat tgaaaacacc ttgcaaagcc gactcatcag ttgttctgta atggcgttaa 161880
gcattttctg gaatttttct tggttttcgg gtgtgatttt atattcatgt agaaagtgtt 161940
tcacacctga ggagaagaat ctttcctcct tcgagagccc atctttgatg atgggaagtt 162000
ccttgatcag ggcaaaccat tcctcctctt gggcttgcgg attctgaaga tactgatggc 162060
agatatggtt tagaatggtg cacacgtagc taataagctc tgagctgatt ctttggttgg 162120
ttttcaaatg ttggcgaaag tagtttttca ccgaagtgca tgtaataaac gtcttcattt 162180
tcttataata tacaacagta tgttgagtct ttaatttaaa attacaagga gttttctagg 162240
tctttatgcg tataggtgtt tctttgtcgt aaattttcaa tagccgacat tgtttgtgaa 162300
gcagtgttct gagtagtgac tgtcgtgtaa ggctcagccg gatgagcagg agcactcgcg 162360
gccgcaggtg cggccgccgg cccgccagtt gccatgacta gtctgtccgt aactgggttg 162420
tccgtaactg gtttgtttgt tgctggtctg tttgttgccg gtctgcccgt gactggcttg 162480
cctacacttg ctgtagtcgc tccagctggt ttagaggtac ctggttgtgg agtgacttct 162540
acccactgct gatcttgata aggatttata aactgtatat cttcctcctc aatagcagca 162600
gctttttct ttcttgaaga gaatagatag attagaacga tgataatgat gactaagacc 162660
acgatagcaa tgagaatagt atacatatgt gtggagaaga agcttggtgt agtgactggt 162720
gacaaacact caccataatg ccgcggataa accggttgaa aaaattcaga atccatttaa 162780
gatactatta taaataatat ataaaaatgt tgtggcgcaa tgaaattaca gaatttatgg 162840
accaactttc caagtattct caagaaatct taaaaacgtt taagcaattg cgtcctagtg 162900
aatataaaca atacaatgaa tttttaacac aagttacacc gttgctgcaa aaaacccctg 162960
aaaaaattcc agagttggtt gaccatatat tcaattacct agacaacgtt gaaaaaattt 163020
gtgagctcct cgtgaatgct agctcaatta ttattagttc aaaaatacga gaacaagtaa 163080
aacacggaat gagcttcagc tataaagccg acctcgactc cttggcggac attctctctc 163140
aaaaacagta cgtgcttatg catctttcaa aaaatattgc ggccgagtat tttaatacgt 163200
gtttaaacca agggaaatcc aagttagatc tcaaagctgc ctctgtattt tatagtagtc 163260
gttcccgaac ggcaagctca gcagaactct atagaaaaat gctatacgcc tatggttcac 163320
cgcaggaaat taattattat actgaaaaag cccgaaataa gacgttggat gtggaggaga 163380
gcgacagcat ggccatcatc gaacgaacgg cccgacacaa cctttccctt atgcacccgc 163440
tagaagccat ggggcttacc tttggggcaa ccaacacgga cgccgacccg gaggatctga 163500
aggacaaaac ggtgataaat ttaacgctcc cgcaggcaac agaaagcatc acctaccatc 163560
ttaaatccct aatgcagcta aaaaaagtaa gtacggcttc aggactaaat acaaacattt 163620
tgaaagcatt tgataatatt atttccaccc ctgtgaaaaa aaataaaatg gcctccaagt 163680
tggcgcccgg gatggatgtc gtgttcacta gcgataacgg aaaaacattt tttactaaaa 163740
acattttaag caaaaacatg ctagcggggc ccaaagagcg ggtgtttgca tataataatc 163800
tcattagtaa tttaaataac tcctgtttca tacaaaatca caacgatttt ttaagacagc 163860
aggactcttg gcccttctat gacgcgcaca attttaccaa caagttttta atgcagccta 163920
tttttcggg gcagacccgt cctcggcttc agggagccat ggaggcggcg catgtggaaa 163980
cgcatctcac ggcattttta caaagtattc agccctctag gccacaagat ccctctgttt 164040
tggcttcccc caagttatct gctctaatct tgaactaaaa acagcctttc ttggacttaa 164100
atgatggtct accagttttt gaaataactt agagaactat gaagattttc atgaaattta 164160
aattagagat ttgcaaaggt tacttgcggt catttctgt tgaattaaat aattattcga 164220
atagtataat gtctgaagat attcgtcgtg gtcctggcag accgccaaag aaaagggttg 164280
ttcccaactt tgagcgcaag ggcattctgg aaaaaccagt tcggccacaa agccgtctcg 164340
agttttccta tgataacccg ctgatattta aaaatctttt tatttacttt aaaaacctta 164400
aaagtaaaaa tattttggtg cgatgtaccc ccaccgagat taccttttt tcacgtgacc 164460
agtcgcaggc aagctttgtt attgccacca tcgacggaaa aaacgtgaac cattattacg 164520
ccagtgatgt cttttggcta ggcatcaaca gagagctcgt tgaaaaaatg tttaacagca 164580
ttgatcgctc ttttttaaaa attaccatcg ttcaccgcta tgacaagcct gaaaccctgt 164640
tttttatctt tacggatttt gacattgaca aggagtgcac gtatcagatt acggtctcgg 164700
agcccgagct cgatatggac cttatcgaaa tggaaaaaag catcagtgaa gaaagactca 164760
agaactatcc tctgcgctgg gagtttacct ccaagcagct caagaaaaca tttagcgact 164820
tatcaaacta caccgagctc gtgaccattg aaaaactcgg cggcgatacg ccgctgcacc 164880
tgtatttcca aaagtttaac tccatctcat accacgagat gtataaatct tccaacaaga 164940
tcaacctgac ctcgaccatt cctaagtcgc aggtgttcca gataaatgtt aaaattgctc 165000
acatcaagtc gctggcctcg gctatggtca ccgacaagat ccgcattctg tgcgaagaaa 165060
atgggaacct aatctttcaa tcggaaatgg atgcccttat gttaaatacg attaccttga 165120
acaccacgat atagttcggt aacattagat gttctaatat ttagcatcta aataatacgc 165180
tgtagtccgg tcagggttgc gtcacagttt tcccattttt ttgcctcgtc ggcggtggcc 165240
accgttgccc tatcatttac gcccggtaag acaaagctaa aggcgttcag cggggcttgg 165300
caatgcccgc ccagcgtgaa ggagctcgga ggattttgcg catcccgaaa tcccttagcc 165360
atgttgttta acacttcggt tacgtcaatc gagtgaaggg atcccttggg atccgtgaat 165420
gtaaagacgc agtttctaaa gcgcatgtat gcgatggacg attcatcggg ggttttgaag 165480
gtaacagtgt tccccttgct gtacttaaag ggggaccatc cggtaaaatt ataccaaatg 165540
aaagcaataa taattaaaat aaccaacaca atagttatag acaacacaaa gtctgtagtg 165600
ccgcccatta ttaaataaaa atattttaga ccgccggctt aaaatttact tattgctcat 165660
agcttaagtc tattttattc atagcttaag tttattgctc atggcttaag tctattgctt 165720
atagcttaag tctattttat tcatagctta agtctattgt tcatggctta agtttgttgc 165780
tcatagctta actccattac tgatagctta ctgatcatga cttaaataaa aatattttgc 165840
ccgcttaaaa attgtttagg tttgaaaaaa taagagatgg agggggcaac ttatcgtcat 165900
tgtgtttacc cccactggaa gacatcaaac ggtaaataat tataagaatc aaaatgatta 165960
atataagggt taaaaaagga tgattcatca cattaattaa aaacgtattt ataacgctgt 166020
tgcagttgaa attttggtat aggtcggaaa tattgcccga gcctccgtat tctgcaatgt 166080
tctgacatat ggtgagtccg gaggggcact gcttgttggt caaaatattt ctttgctccg 166140
ttgttttata ggcattttta tttccattac acggagcaaa cgcacattca ggccataggg 166200
tgccggagtt cacacaggca caatactggc tatacgcata ctcatccttt gagcacaatc 166260
cctgtttatc gcatatgctc ccaataatat tgtcatcctc cgccgtttgt tgatttgtat 166320
gcgagcgtaa aatagcggcc caggccttgg gctccttttt ttgcagctcg gaaatcgaag 166380
ggcctgtaca gctaaagtcg acccaaatat cattgcattt cgtggaaact ggcatgcaag 166440
acataattga aataattaat aagtatatat catggcaaca aatttttttta ttcaacctat 166500
caccgaagaa gctgaagcat actacccacc ttccgtgata acgaataaac ggaaggacct 166560
gggggtagac gtatactgtt gctccgacct agtgcttcaa cctggactaa atattgttcg 166620
cctgcatatt aaagtagcat gcgaacacat gggcaaaaaa tgcggtttta aaatcatggc 166680
gagaagcagt atgtgcaccc atgaacggct gctcatcctt gcaaacggaa ttggtttaat 166740
agacccgggt tatgtgggcg agctcatgct caagatcatt aatcttggcg acaccccggt 166800
ccaaatatgg gccaaagaat gtttggtgca gttggtggcc caaggtgacc atgtgcctga 166860
ccatatcaac atcctaaaaa gaaaccaaat atttccgctg tttgcgccta ccccaagagg 166920
cgagggtaga tttgggagca cgggcgaggc cgggattatg agaacttaat tttattttt 166980
ttcttaacat aatgggaggc tctacaagca aaaattcctt taaaaatacg accaacatta 167040
tcagcaattc cattttcaat cagatgcaaa gttgtatttc catgttggat ggcaaaaatt 167100
acataggcgt attcggtgat ggaaatattt taaaccacgt tttccaggat ttaaacttat 167160
cattaaacac aagttgcgtg caaaagcacg taaacgagga aaatttcatt acaaatcttt 167220
cgaaccaaat tactcaaaat ttaaaagacc aagaagttgc gttaacccaa tggatggacg 167280
caggaactca cgatcagaaa acggatatag aagaaaatat aaaggtaaac ttaacaacca 167340
cacttattca aaactgcgtt tcatccctgt cgggtatgaa cgtgctggtg gtgaagggga 167400
atggcaacat tgttgaaaac gcaactcaga agcagtcgca gcaaatcatc tctaactgct 167460
tgcaggggag caagcaggcc atagacacca caaccggcat cactaacacg gtaaatcagt 167520
actcacacta cacctcaaaa aactttttg acttcattgc agacgcaatt tcggctgttt 167580
ttaaaaacat catggtcgcg gctgtagtta tcgttctaat catcgtaggg tttatagccg 167640
tcttttactt tttgcattca cggcaccgcc atgaggagga agaagaagct gaaccactca 167700
taagcaacaa ggtattaaaa aatgctgccg tttcgtaata atttaattaa aagtaaaaaa 167760
aaaggtattg ttatagtgat ggcagatttt aattctccaa tccagtattt gaaagaagat 167820
tcgagggacc ggacctctat aggttctcta gaatacgatg aaaatgccga cacgatgata 167880
ccgagcttcg cagcaggctt ggaagagttt gaacccattc ccgactatga ccctaccaca 167940
tcaacttccc tgtattcaca attgacccac aacatggaaa aaatcgcaga ggaagaggat 168000
agtaattttc tacacgatac tagggagttt acttcactgg tccccgatga ggcagacaat 168060
aaaccggaag atgacgaaga aagcggtgca aaacctaaaa agaaaaaaca tttgtttcca 168120
aaattaagct cgcataaatc gaagtaaaaa ttgaagcgaa aaaaagtaga aaaaaaatgt 168180
ttggagcttt tgtaagccac cgtttgtggt cagatagtgg ttgtacgacc acctgcatca 168240
caaacagcat tgctaattat gtagccttcg gcgaacaaat tggatttccc tttaaatcag 168300
ctcaggtatt tattgccggc cctagaaagg ctgtgataaa tattcaggaa gatgataaag 168360
ttgagctttt aaagatgatt gttaagcaca atctttgggt tgttgctcat ggaacctact 168420
tagatgtgcc ctggtcccgt aagagtgcgt ttgttacaca ttttatacaa caagaactac 168480
ttatatgcaa ggaagtcggt attaaagggt tagttttaca cctaggcgct gtggagcctg 168540
aacttattat ggaaggacta aaaaaaatta agccggttga gggggttgtc atttacctgg 168600
aaaccccgca taacaaacat catacatata aatacagtac aattgagcag atcaaagaat 168660
tgtttttacg gatacgaaat accaggttga aacagattgg tttatgcatt gatacggctc 168720
acatctggtc ttccggtgtc aacatctcca gctataatga cgcggggcaa tggctgcgct 168780
cgctggaaaa cattcattcc gtgatcccac caagccacat tatgttccac ctaaatgatg 168840
ccgccacaga atgcggaagc ggtatagacc gacatgcaag tctttttgaa ggaatgattt 168900
ggaaatcata tagccataaa ataaagcaaa gcggtttata ttgtttttgtt gaatacgtta 168960
cgcgacacca gtgtccggct atattggaga gaaacctcgg gtcttccatg caattacaaa 169020
ccgctttaac cgcagaattt actacattaa aatcgttatt aaaataagga tgagttttag 169080
cgaatgtccc ttagttatta gtgcatgcaa aaaatttcta caaaagcgta ttacaataga 169140
gaatgaagca cttataaatg ccttaataac cgctttagcg cagaccagca cgttgaatga 169200
tctttgttta ttacctattc aaacctattt gcttagttat aaaaatgctt ttgagtggat 169260
acacttcgta tgtattgcaa tcaccactat tttggataat aagtataact ggaaggactg 169320
tacggtagat attaattata tttttctcca tgtaacctat atttacaata ttaaaaccaa 169380
ggaataccta gactactgtt cttaaacttt attttttcta tatttacgcc aaagagaata 169440
tttaaagttt ttttgaaaaa aataatatat gtagataaaa ttcagttaca tgatatatgt 169500
gtaaacatgt gtggtaaaca acatatggtt atgctttata agataaatgc gcataatata 169560
tgtaaacaaa atatggttat gtgttaaatg catataaatg tattttaacg tatatcttgt 169620
gataatggat atatgcattt attaaaagag gctgtattta ttataaatct tgctaaggat 169680
gccattgtca acatatatcc catgttggac aaattgcgtt gcgatccagt tcttttttttt 169740
tgattttgtt taatgctatc ctttttgaag ggatggttgt ccaccatatt tattcgatgt 169800
tcaatgaata ggtctgcttt ttcgtaaggc agtgaaggtc gttccaagac tccttgaacg 169860
atggacgtgt tttcttggat ccacttaaaa agcacgtggc attcaaaaac aggacagtga 169920
ttggatcctt ggatatgctt tggacagcca atgcttgaag agatgtagtc ccttttcttt 169980
aggacaagct tctccacgct ggggcaacag agatcgttca agttctggac ggtcgcattt 170040
ggaatgttga aacttcgtat ccattcaccc tcgggtcctc ccttatgaag aaggagtatt 170100
tgctcatggt ccttagtaat cttaaccaaa tgttggaaga tcattttttt acctgcttta 170160
aaggcctgaa gggtgtcagt tggcaaagct attgaattcg ggagtgggct ttcatcaagc 170220
gtgaaatggt gaatgtgacg cgactggaaa gaaaacgacc gttgatttat tttttcaaag 170280
attgggtcga ttccgccatg aaagaacagc tgcaagattt tagaaggcgt atttttttcc 170340
caataaaaaa tgaccacttc tcgtgggatt aaaatcgtct gtgtcccatt ttcattatat 170400
aattggccca taaagccatc aacgtcaatc aacaccaaaa gcatggtata gagagctttt 170460
agaaccggag ttcgttaaaa aaatacaaag ttcgtttaaa acgtgtaatg ttactaaaaa 170520
aatgtaatgt ttaaatgata atgataccac atgcattaat gaaaaaaact tttaaatttt 170580
tgttttaata tttgcatgaa aatggaaaca tttttagtct gtttatttca caatgcagat 170640
ggtttacatc aacagattca ggaaattttg tatttattgc ggatgcatat ttacgaaaca 170700
aatctttact taaagcagga actatcacgg cttatatatc caaataggca actttctttt 170760
gtgttactta tgccccttc ccttctaaga aactgggatg acattgaata tttaacggac 170820
gttgtagatg ataagcagac tctacattac gcggcaaatt tgctgacaaa ctacgttcta 170880
catctatcca tgtttcaaaa gctgacaaaa ccatacttcc ttttagcggt caagcgggtc 170940
agcgaaaaac tcaacaaaaa gcagcgacat tcattttacg aggtattggt aacctccgaa 171000
accttgaata attatgaaaa cctatctaaa aacattttaa atacgttgat gtttgccgtg 171060
cgctacgtat ttaaacctac gccgaactat tcagaaattc tcgcagagtt ggaaaaaaaa 171120
aataaaattc accatattat ttttaatatg gtaattacgg attttgcgca aatccgtgaa 171180
caacaaatgg ataaacatct gtgtgaaaca aataatgagc ttcgtcagga atgtaaagaa 171240
actatttttg atttaaaggt ggtaggaaat gtttagccaa taaactcatg cccgcatttt 171300
ttacaggtac aaaatatcgt ggatggctca tcgagggcgc gtgtttgtac ttctctgtag 171360
gtacacatac gctgcttgca gttgggacac ttataaagtt gtgacgtctt ttcggcgacc 171420
ttttgctgcg aacgtagagt aatttctgtc ttctccttta aggcggcaga ggggcaaagc 171480
tcggcgaacg tcatgctacc aattgcctcc ggttttagct cgccagaaat tagcttatta 171540
agggcatcgt tatcctgttg ttggtgactt tttttttcgc agttaataat atgattgatc 171600
gtcccacaac gggttgaata ttcttctaaa aaggtttttt cttgttgctg gtacgtataa 171660
tgataacacg aggcctcgat tttttgcgcg tattcggtgc ataaatcagt atgttcctta 171720
aaaaacatat gtttttgaag cgttctaaaa aacatcattt ggatgatatc acgcatttcc 171780
aaaataatat agggttctag tcttttggaa tctttcataa ctagatcggt ggtaatattc 171840
ttagtcatac aatttattaa aaatggttta atatattgta aatatttttt aggcgtgtca 171900
gcctgtaaaa aacattcttg ttcaatctta tttgtaagga tagtattttg caaatactta 171960
tttagcaaaa atacgataga atcgcgggct atatgcattt tcatataatt tttttttaaa 172020
atttaataca aaaaaaagaa gtatagactc ttcttctagt ccggttagtt cgttggttgc 172080
ctcaacatgg agactcagaa gttgatttcc atggttaagg aagccttaga aaaatatcaa 172140
taccctctta ctgctaaaaa tattaaagta gtgatacaaa aagagcacaa tgtcgtctta 172200
cctacaggat ctataaatag catactgtac agtaactcag aactttttga gaagattgat 172260
aagacaaata ccatttatcc cccgctttgg atacggaaaa actaattgta accagtagta 172320
catttaagga tagtttaagc agtaaatgta gaataacaca gttaagcaat aaataacaag 172380
tatataggaa tatataggaa tatatagaaa tatatagaaa tagctaagct taatactaat 172440
tcagcttttt ttttaactaa aacctgaata gatgcgaagt agcggacata tacatactaa 172500
aataagccat acatttactt tcttcttgaa catgaaacct tttttcttc tgttgttggt 172560
atataaacaa taggactgtt tgctgaggtt gtatgatctt ctacaactgc tgtctcagga 172620
tgacgatgtt tttttaaact aaaagtgtag gatggaatga gtggaatata gttatggctc 172680
gacttatcct gtttcgtaca ggaatatttt ttacaaatag aacgcaacaa gcatatgaat 172740
aaaaacagaa atgatataca ggagcataaa atagatatga acactaaggg gtagcagctt 172800
ttataacgtt ccgtattttt cttagctatc aattgattta ccgtaatatt tatctcggga 172860
aactttgttc tacaatattt tgtttggtat tccagaaact catgtcctgg cttattcccg 172920
cagcttaaaa aatgatacaa aaatgtgtta ttgttactaa aattaattct tcttaagaaa 172980
aactgcggaa gacgctttag gtacgtctgt tcctgtttta gtaggaagta gtataaggga 173040
caatttcttt ttccacacat tagattattg taatataggt aggttggggt gttggagcga 173100
ataagttttc tgagtatgtt ataatctatg acttgtaaat cgttatacct taggtccaaa 173160
aacttgagtt ctttaccaaa gccacctgca atttcagaaa tatttttcat cccgcagcgg 173220
ataatacgga tgtcctgaaa cgtctttaaa atacttgtat tgtagtgaat acttatgtta 173280
ttttttgta aataatctat gtcatgacaa gtgcatgaaa tgccagcagc attgcttggt 173340
atagtattat atgcaggaag aactatacta ctattgagaa tagtcacatt gtacttatac 173400
catgtattat tttctgatat aaagtatttg caggtgacct gtggtttaat cctacctgtt 173460
aagccacttc ctaaaaaaac aaaaaatatg aaaaccctta gcatcctgta tatactatta 173520
aaaatttata aaattttctg tttaaatttc atttagacaa aaaaataata tatatacatc 173580
agcaagaaat tatatacaga ttatataatt ttctgatttt tttttgccac aataagcatc 173640
attatatgca ttaaaatctc aatactaaac actaaaatct aaattctaag cattaaattc 173700
taagcattaa attctatgca ctaaactgta agcactaaaa tctaagtaac taaaatcaac 173760
actaaatgta tgcaacctaa aatgtaaagc attactcatc atcctcctct tcttcatcct 173820
catcatcata ggttaagata tatgtgtcat cctccatttc ttcacattca tcttcataag 173880
catcactggg tattggtgga acattggatg cagcattttt aaaatattct atgtcttctg 173940
gtgaacactc atctaatgat tttttgacag tccttttaac ttccatggga tatgattcca 174000
aatcctcttt atataagagt ttacggtagc ttttagctgc atccacattt gctggagaat 174060
ctggatttgg ctcattgagc agtgaaatta cactaagaag aatggtatca atcttttgag 174120
ccggagacca agtcattccc tgttcttcag cattgtctcc gtgtaagata gagatacata 174180
gttttccatc agagtaaata ttaggatgcc acatttcaga ggtgaatgtt aatctgggtg 174240
gtgcatatgg gtattctgga ggaaaggcga tttttgcctt gaataagcct ccctcataaa 174300
aagtgtcagg tgggcccctt aagatcacat cccattcagt catatccttc tcattcaccg 174360
aaattttgaa attctcagag ggattctcta tcaggtgtct gtactctgct attaaaaacc 174420
tggaaaccat ggttatttaa tattaattaa attccctggt ttattcctcc ttaaaagtag 174480
atgaacctct tttgtttttt attgggttca tttttactaa atttatgaac tggaaaaaac 174540
tttaacggca taattatcag atctagtaac atagatgaca ccgcgcgcga taatttatcc 174600
tagtttgcgc gctatatttt gttttctatc gcgtattaaa tgtataattg cgggactcta 174660
atcataaaaa cccatctcat aaataacgtc atgcattaca tgttaattat tacatgctta 174720
acgtaattca acagaaatta tatgataatc atcgcaagac cggcaacagg attcaatctt 174780
aagaaacttt attgccaaat gtttgaacga tcggggaaat tcgagctcgg tagcaattcc 174840
cgaggctgta gccgacgatg gtgcgccagg agagttgttg atttactact tgtacagctc 174900
gtccatgccg ccggtggagt ggcggccctc ggcgcgttcg tactgttcca cgatggtgta 174960
gtcctcgttg tgggaggtga tgtccaactt gatgttgacg ttgtaggcgc cgggcagctg 175020
cacgggcttc ttggccttgt aggtggtctt gacctcagcg tcgtagtggc cgccgtcctt 175080
cagcttcagc ctctgcttga tctcgccctt cagggcgccg tcctcggggt acatccgctc 175140
ggaggaggcc tcccagccca tggtcttctt ctgcattacg gggccgtcgg aggggaagtt 175200
ggtgccgcgc agcttcacct tgtagatgaa ctcgccgtcc tggagggagg agtcctgggt 175260
cacggtcacc acgccgccgt cctcgaagtt catcacgcgc tcccacttga agccctcggg 175320
gaaggacagc ttcaagtagt cggggatgtc ggcggggtgc ttcacgtagg ccttggagcc 175380
gtacatgaac tgaggggaca ggatgtccca ggcgaagggc agggggccac ccttggtcac 175440
cttcagcttg gcggtctggg tgccctcgta ggggcggccc tcgccctcgc cctcgatctc 175500
gaactcgtgg ccgttcacgg agccctccat gtgcaccttg aagcgcatga actccttgat 175560
gatggccatg ttatcctcct cgcccttgct caccatataa tgttataaaa ataatttatt 175620
gtttttatta aatatggcgg tttatgcgaa ggatcttgat aataacaaag agttaaacca 175680
aaaattaatt aacgatcagc ttaaaattat tgacacgctc ttgctagcag aaaaaaaaaa 175740 cttttggtg tatgaattgc ctgcccttt tgacttttct ccggctaaaa gattattata 175800
ttcgaatgtt tgtccaatat ggacaacttt gtcaccagat gttacatttg atttggttgt 175860
tagtggctga agcttggcac aatcaaaaat aagcccatta acactaagat atagaggagt 175920
gggttgatct attttctcat agtttaatat tccatctttc cacgtaatag cttgataatt 175980
atccgcagca atgagttgaa attttataaa tagtacaggg gttttagttg tcgttataca 176040
tttaaagggt gttttataaa aataaaaata ataattgtta aaagtatgat aataatcgcc 176100
aaaataattt catacatttt ttataagaat tatacatagt atggtattta aaatattagc 176160
taaatttaaa aaaacttcat gatttttaaa acagggaaaa aggggattag gttgaataaa 176220
aaaggtaagc acttgtctat atattttttt tacaatgttg ccttgagtcg catttttaac 176280
tggctgggga gtatcagagt ggaatatcac tgtagtaggt ctataaggtc ttgttaaaat 176340
atgatcggtc attgttttcg tactagtgtc atttagggtc gacctgatag ctcgatataa 176400
agttataggg gataacctat caaatacagt cttatctgtg ctgaaatgta tatcgtcttc 176460
tttatcacta ataatattag gaatggctgt cattaaataa ttactacttg ttgttgtggg 176520
tgaaatagtt gtactggtat tattggaaat ggctgtcatt aaataattac tacttgttgt 176580
tgtgggtgaa atagttgtac tagtattatt agaaatggct gtcgttaaat aattactacc 176640
tattacaagt aaactaatgc taactacatt tttaacctca ataaacctaa aaagccatac 176700
taaataccta aacaacatcc tgttataata tgagcagaaa aaaaaataag tataattagg 176760
gaattattct tattcgctta ctattaagaa taattcagaa tcttatttag ttagaaacta 176820
tcataaagtg aataggactc atcgtcggat gaagattccg tttcagagat agtttctttt 176880
tcttcctcag aataatctgt tcctacaata gaatcggtgt catcctcaga aagagaagta 176940
tttaaatatg gactatctat agcaatatcc tcttctatct cgcaatcctc ctcctccatt 177000
tccatagtgt gtaggagaat atttttatca tcatgctcac ttcttttttt gttgaaagat 177060
gaaccgtcct caatacggtt catgttaagt tccttcatct tatgtataat ttccgtaatc 177120
cgtgatgttt ttgacatgta agatggtttt aaggttatat ccacaataac aggagaatct 177180
ctatcatttt catttgataa actttgatct ttgatttctt cgtctaaaat tcttgtcttt 177240
ttttgggtac tagatgaaat agaggaattc atattctgaa acgatatatc aaggggagct 177300
ggacgctttt ttccaattaa accgtttttc gagatactat gattagatga atgatcttta 177360
gccaagctgt ccttggatat actatagtta gatattttac ctttaaataa tattcttcta 177420
tacaagttat tcttaggtaa agaattagta tggattccta tatttttatc tgaaggagtg 177480
tccatatcgg agaacgtcct cttacgaata ttttgaccac gagccatttc atccactata 177540
ggcagtattt tggctggcta tggttctttg ttgtgacaat tctatgagat ttgattgcaa 177600
atcaattttt agttttaaat atattggtac ctaggacaaa gaaagtatat atagccaata 177660
attattccac taaattgatt tccagactga tgggtatgga gccatgttgt ctctgcagac 177720
gatcgcaaaa atggccgtag caacaaacac ctactccaag tatcactatc caatactgaa 177780
ggtctttggg ctgtggtgga aaaacaatac gctaaatggc cctattaaaa tatgtaacca 177840
ttgcaacaac ataatggtag gagaatatcc tatgtgttac aatcatggaa tgagtctgga 177900
tatagctttg attcgggcag taaaggagcg taatatatcc ttagtccagc ttttcaccga 177960
atggggggga aatattgact atggggcact ttgtgctaac actccatcta tgcaaagatt 178020
atgtaaaagt ttgggagcca aaccaccaaa gggccgaatg tatatggatg ctcttataca 178080
tctttcagat accttgaatg ataatgatct gattaggggg tatgagattt ttgatgataa 178140
tagcgtgttg gattgtgtca atctcatacg actcaaaata atgcttacct tgaaggcccg 178200
tatacctctc atggaacaac tagaccaaat tgccttaaaa caacttctgc agcgatactg 178260
gtatgccatg gctgtacaac acaacttaac aatcgctatc cactattttg ataatcatat 178320
tcctaatata aagccattta gtctgcgctg tgctttgtat tttaatgatc cctttaaaat 178380
ccatgatgct tgcagaactg taaatatgga tcctaatgag atgatgaaca ttgcttgtca 178440
acaggattta aactttcaaa gcatttacta ttgttatctt ttaggggctg atattaatca 178500
ggctatgcta atgtctttaa agtatggtca tctttctaat atgtggtttt gcatagattt 178560
gggggcggat gcctttaaag aggcaggggc gcttgctgag aaaaaaataa aagagtgtta 178620
caacacatat taggtcttaa tatctttaag cgagagttga ttcccccctg taaagatcct 178680
gatccttatc aaatccaaat tctgttaaaa aactacattc taaaaaatgt ctcaactgtt 178740
tttacatatt attgccagta gccattgttt atatcagaaa ataacccatt tgtttatctt 178800
tttttgtggg gcaaccatta agacccgacg caaaaaaaga ttaatctttt atcagatacc 178860
taaaacgttc tataagggag tctatgagat ggatcatatt ttgatggtca tagtaagaag 178920
caagcttttt ggcgaaaaca acggagttaa agaatttaac ccgctcatgt ttggatagga 178980
cttttaacag cgagccaaaa cagtatttaa aaatttggca atagtttttt tgggatgcaa 179040
taaacaaaca cttgatcagt gcccgcttca ctttctgatc agacatgttt gccgcataac 179100
aggccttttt aaacttagta atataattat gttccgcaag caccattaac aagggaacga 179160
tgggaagctg cttttcttgg tgaaatttac gtaaatattc gatggccacc gcttggacga 179220
ctgtgtaatt tactaagtta gaaatgatag ctttcatggt tgtaaaaata tacataggat 179280
tttctttttc tgtatacagt ttgaaaagct tatgattacg tgaaatgatg gccattttta 179340
atacaagatg gtatagtgta tctttaggta aaaatgcctt gcaagccgcg atgatgtcga 179400
tgttgtctcc atgaacagcg atagaaacta atgtttccaa tctaaatgtt tttatctgca 179460
ttaatagaag aatgcagtca atgttattat acttaataat actgtaatac accgaatcaa 179520
tgaccgtcat ctgagaatca agctgactta ttagtaaatt taacgttttt ttggaggcat 179580
gacctttgat cgcggcacta agtgcacaca gtatagcaaa attgttaaat acattttgat 179640
ttaggagaag gagtaatatt ttccttcggt tatagtacgc agcatctgtg atgattattg 179700
gccgataaat gttaaaatgt gttaacagct ttttaaaaaa acggaagtaa tttttttgga 179760
tcgctgtttg catcatcgaa ataatgagat aatcagggta tataatgggt aggtcacatg 179820
ctacctctaa caaagaatag tcgcccaatc taaaggctgt gttgaaaagc gtactatcat 179880
catacgtatc gagtacccct gctgttacaa accaagcgat aagatgaatg tgccgttcct 179940
tgcaagctat cgcaaatagg gagtttccta tggaatgtcg aataatgtac tccctatttt 180000
tttccaaaat gtttggaaaa ttgtatagcg ttgcggcata cagtagacac tccattctgg 180060
cgttataatt tttactttta catatgaata ggtggaagaa ctcgaataat tcttgagaac 180120
ttgttaaatg cataatatgg tgatattttg gtgtcgttaa atggtatgag aaaatgcatt 180180
ctaatacatc ttttcggtta tgctttagcg cctgagctaa ggcatattca ggctcgaccc 180240
ataggactag tgtttctata attgagatat tcgcctgctt tgccagggca tactttaaga 180300
cgctccggtt agaaaaaatg ttgttatgaa gatggataac cgtatccatt tttacgatgg 180360
gaccattcca gtatagtcct aaatgctgta gcagatcttt tgttagttgt gaagcgttct 180420
cgggtgtcat ataaatatgt tgcagggctt ttttctgtaa ggagaacatt tcgtcgtaat 180480
cgtacaaaaa aaattaaaat ttgggcatgg atgattcaaa cataacaaaa tcaagatttt 180540
ataacagttt gcattaacct atacatatat gcaagtaaat gagatattat ctatcataac 180600
gaatcaaggg atatttgtat atatcaggag tttctgaaat aaagatatga agattatcat 180660
agtagtatcc atcaatcaca atgcaacttc ctttaaggca taatttagta aactcagcac 180720
tcccatcttc tggatgcttt acaactaaca ttaaaaactc ctcagtcata ttatctgtaa 180780
taaaataaga tcctcctgga gccatttgta gcatgtctct tattcctaca aaatcttttt 180840
tgggatggta aaaactcagc agtttcaaac tcttttttag ttttttttcc tggtatttaa 180900
gccatttgtt ataaaacagt tttcttatga aaatgcattt gaaaatattg ggaatgttta 180960
accatgcttc ttccgagcac atctccagat acttactttc tttgtttccc atgtctaatt 181020
tattgctcac taagttagta atgaatctat tttaataatc tactttacta atctatctta 181080
ataacctatc ttataatcta tcttaataac ctaattataa cctatttata attggctaat 181140
gctgccggca tttcatgcct atctaaacaa ctcctactaa gcaatctact attacatata 181200
tagattcact ttttatattt gtaaatcatg agaattataa aatcattact catttttatt 181260
gtaaattagt gggtatttgt aaaaatcttc aaacgtttta agatagtttt ctagagagaa 181320
gtaatctttg ccatcaatat ataatgcttt tcctttaaac tccagttttg ctatgtttag 181380
tgagccgttt ctagatcttt ttgggcaata aatagatttt cattggttgc atcgtccgta 181440
agcagaaagg taccactagg cacgttaaaa aacatacgtt ctatttcatg gtcggatttt 181500
tgagaataga aaaaatctaa ttttttaatc cgcgttaact ctttttttatc aatctttcca 181560
gactgtttta tatatacttt attgcaaatc ttacaatcct ctatggcttc attatactta 181620
ttttgcttat cctctattga catgtccgta tttgataggt aacttccgtt aaggcggttc 181680
cccatggttt tagatagatt tttaattcag ttgtatactt ttattatgag gctaaaatat 181740
agaagtttga tcctaaaaaa ataaaaagat tttgtacatt tatttatggt ttatagcggt 181800
atagaggccg ataaaaggta tccgggtagt ctcctatgat atcgtcaatt ttggtataat 181860
aacagttgtt atggtagtat tgtccaaacc gagtatgtat gcgccggtga agcgtccgcc 181920
cgctaatggt acagttccag gttaagacaa tcatatcaca cccaaaaaga gaggaaacag 181980
cataggtgcc caaaggttca ttatataaca tacgccgcat atattttagt tttttttctc 182040
catggtaata atcacaggtt ttcatgtcct gcttaatagg atgattcccc atgtatgata 182100
atatataata aatttagttt ttagcttttt caaaaaattg ggcgctcgaa actaaatttt 182160
ccttatcaca gcgtttggag aaagcgtatt taaagatata tcttcttcta acaagactgc 182220
aaaaaaaatc ttacccctta tttttataat gttcatcata gcgtttgaag atatcagaag 182280
gtgccaggtt ttataaaaat atcctttagg atttataacg atacaagggt ctataaaata 182340
tatgcgggta taatcttata aaatcatcga ttttttcata atattctccg tttatacaat 182400
aaagatcata acagatattg atgcgtagat gcattattcg cgtgttcgtt gggcagctaa 182460
aggatatcac aacgtagttt tttttaagaa aagacgaaac tacataagtc cctaagggtt 182520
cattgaatag taaacgccat atttgtttta aattttgttg ttcaccatag tagtattcgc 182580
actttttcaa gtctttttta ataagcctat tccccatgta tgcttataaa taaaaattta 182640
gaaatgtgct atattatttg ttgatgaatc atgaacacgt cttatatgtt gatatgttac 182700
tttaaaaaca tttgtatttt caacagacgc gttctattct tattaagaat gatgccgtct 182760
ttattttaaa ccttggttta aaatttaaag aagtatttat aaactataat catgggaact 182820
ttttcagtaa ctgcctctgc aaaaagtgac gatgctgttt gtaagtattt agaagaacca 182880
atagatgaaa attacagaaa catattaaga aatgagcatg ttaaaaaaaa tttaaatgag 182940
gctctgaatc gacatattac tacctataat ccagtagttg attggtgtaa taactattca 183000
acattttcat ctcaggattt cgatgaatat aaaatttata tacatagcga tcttatggat 183060
ggacgacctc gtccaaaaaa aacatggtgt gtcatcatgt aatgtttgtt agttttatat 183120
aaacgcaaaa atattcttct aggagatgtt gatatactac ctattgaatt caatatatta 183180
aagtacattt ctggctattc ccattacggt attattatta ctatttttaa gagctagatg 183240
tggatttaag taataataac attctcccgt tcctcctaga gacacctcat caaattccca 183300
tcctatgcaa cctttatgtt gtaaacataa tgattgacag cattcatctt cttttgacca 183360
agtcgtccaa atcctaccaa gatctatacg tgtttttcca aatggagatt gaagatcagc 183420
agtagtggca ttaaacctat aaaaaccagg tgcataatca catgaacgga tcgtaggatc 183480
taatttaata tcttttatat cttgttttac tgcttctaga caacttttat cagtacatgt 183540
tccacgtaca cagtggtgtc ctttatcctt acaatccgta tctgtcttac attttttttt 183600
cggcggttta tgtttcagat ggtaaaaacc cagtattaaa ataatcacaa gaataattcc 183660
tataagtact tgaacaacag gataaaacat tttaatatta aatatatttt ttaattaaat 183720
gaatagattt aatccaagta gtattaaaat tttttagaaa tagtgttcta caaataatga 183780
aatgaatggt ccaaaaaaaa taaggtgtac aataatgtaa tatattgtta ggctaagtaa 183840
atttaatatt ttaaagtatt tggaaaaata ttttttaaca tatgatgtct aggaatattt 183900
tttagacatt taaaaccata tagttacttt atttattaca ctgaacttga aaagacttat 183960
tacctaaaat attaatagat gaagtaatat tgtgtaattg agtccataac atgggtggga 184020
aacaaaaatc tcgtaatatg aaaaataaac atcctaaaaa gagtgcaatt gttataagtt 184080
tatgtaactt tattttaaag taagaatata aaaatatgag tacaagagga atagggggcca 184140
ttactaacat tggctccaac atcctgttgt ctacaaaaaa aaatattttt tttagcaaaa 184200
aaaaatccat ggaaggatat taatacacat aattatttga catcacatta gtgtacttac 184260
caaatagtaa tatacaacca tcctaatatt cacctttatg aaatgatccc aacctatacg 184320
gtaaaatagt ataggtttta ataaagaaaa aagatattct gtggttttta tttttgtata 184380
gtgtgtgaat acaaaataaa atcccaaatt ttaacctttc tttttttttct atacaggatg 184440
ttagaaatta gtattggcaa cgctgctagg cgacctgcag cggctccggg ttcttacccc 184500
tcagcagcgg gcagttgcct tctttcgagc caatactaag gagctagagg acttcttatg 184560
ctcagatggg cagtctgagg aggtactgtc tggccccctt cttaaccgtc tactagaacc 184620
ctcaggccct cttgatattt taaccggata tcacctattt cgtcagaatc ccaaggcagg 184680
tcagttgcgc ggccttgagg tcaagatgct tgaacggtta tacgatgcta atatttacaa 184740
tatactgtct cggctgcggc ctgaaaaagt tcgcaacaag gctattgagc tatactgggt 184800
tttccgagct atccatattt gtcatgctcc tttagtttta gatattgtac gatatgagga 184860
accggacttt gctgaactgg cctttatttg tgctgcttac tttggtgaac ctcaggtaat 184920
gtatttgctc tacaaatata tgcctctgac ccgcgcagtt cttacggatg ccatccggat 184980
aagtcttgag agcaacaacc aggtagggat ttgctatgct tacttgatgg gaggcagcct 185040
caagggacta gtctccgccc cactgcgtaa acgtctgcgc gccaaactac gctcgcagcg 185100
caaaaagaag gacgttcttt caccccacga cttcttactg ctgctccagt agcttttttt 185160
gccgcaggag caccgcggat aggagctcct ccacgctcgc gatccggcgc tggaagcgga 185220
accgatcgac cgccacctgc tcccagggac ccttgcgctc gatgtcgtcg gcttcccaca 185280
cctcgacggc tgtggcaaaa tggacatgct tcgcgtcgtt cgtccgtttt ttgcgccgcc 185340
tccccattat tcttcctgta agattagtgt ttaataccta taataacata attttaagat 185400
ttaatatacc aaaacttaaa ctatttttgt atagtaacta ttagcatgtc tacacatgat 185460
tgttctctaa aagagaaacc ggttgatatg aacgatatat ctgagaaatc agttgtcgtg 185520
gataatgcac ccgagaaacc agctggagcg aatcatatac ctgagaagtc ggcccgcgaa 185580
atgacatcat cagaatggat tgctgaatat tggaaaggta taaaacgtgg aaatgacgtg 185640
ccatgttgtt gtccaagaaa aatgaccagt gcagacaaaa agttttcagt atttggtaag 185700
ggatccctaa tgcgctccat ccagaagaat aattaaaaaa aatatttttt ttagcaagtt 185760
tttaaactat ttaaataaat gtggtaaaaa aattcacata ataattaaag tgaacgtgtt 185820
agaattaata ttttttttata atcggatata atatccatta aatcaataaa tgatagtgtt 185880
gctaccacac taaacaataa caaacagaaa cgcacgatac ctttcctcat gatttataat 185940
agcgtgttat ctaaagattt ttttgaaaaa aatattaaat tttagttgat tattttttttc 186000 agttacaaca ttgctttaga aaaaatacct aattactaca tagcaaataa agcgagcgca 186060
ttgttacaaa caacattttt tttgcgcctg gatactccta tatatgagaa ctataatacg 186120
gtatattaat cctattacca acattgtcaa taatagtatg taggcaatga catactttaa 186180
ataccaaata tccatggtta tttctaaaaa tcttgaaaaa acgttaaatt ttagatcggt 186240
cacctacgac agtaatacta attttaataa ttgatgactg aaatcataat ataatgccgt 186300
gcgaaaaata attatttttc ggttaaagat accattacat aaaaaatatg ccatctactc 186360
tacaagtgct tgctaaaaag gtattggcct taggggagca taaagaaaat gaacatatat 186420
ctagagaata ttattatcat atattaaagt gttgcggttt atggtggcat gaagctccga 186480
ttatactttg ttatgatggg agtgagcaaa tgatgataaa gactccaatc tttgaagaag 186540
gcatattact taatactgca ttaatgaaag ctgtacagga gaataattat gaattaataa 186600
agttgtttac tgaatgggga gcaaacatca attatggatt aatttccatt aataccgagc 186660
atgcccggga tctatgtcga aaattaggag ctaaagaaat gcttgaagga aatgaattta 186720
tacaaattat attcaaaaca ttagatgata ccaccagtag taatataatt ttatgtcatg 186780
aattattcac caacaatcct cttttagaga atgtaaatat gggggaaatg aggatgataa 186840
tttattggag gatgaaaaat ttaacgaacc tattattaaa taatgactct attagtgaaa 186900
tattaactaa attctggtat ggtatagcag taaaatataa tcttaaggat gcgatccaat 186960
atttttacca gagattcatg gacttcaacg agtggcgagt aacatgtgct ctttctttta 187020
ataatgtgaa tgatcttcat aagatgtata taacagagaa ggttcatatg aataatgacg 187080
aaatgatgaa tctagcctgc agcattcaag acagaaattt atcaaccatt tactattgtt 187140
ttctattggg gggctaacat caatcaagca atgttaacct cagtattaaa ttataatatt 187200
tttaacttat tcttttgtat agacttaggg gctgatgcct ttgaagaggg taagaccctg 187260
gcgaaacaaa aggggtataa tgaaatagtg gaaatcttat cattagatat catttatagt 187320
ccaaatactg acttctcatc aaaaatagaa cctgaacata ttagttcttt gttaaaaaac 187380
ttttatccaa aaaatctgtt cgcttttgat cgttgcaacc ccggtttata ttattcttag 187440
aggaccgcta caaaaattat ttttttctt gatcaaagct ccaaaataat tattagatta 187500
aagtcgccta tagcagcagc ccactccaaa aaaagtattt tatagtacaa aaaacacgaa 187560
aaatagtttg cggccggcgg caaactattt gttgttgtct aaaacttaat gttttttttaa 187620
tatttttaaa tgcaaccatg gattgttgga ctatcaggga gaagaactat agctacatca 187680
tattgtcaat actggtaata ctattaatat ggtatcttat acttaactat tgtcgatcga 187740
aaaaaaatgc agttacaaac aacatgccgc caccatacac ggtgtcaagt agctgttctc 187800
aataataggg ttgattgacg ctcttcgtaa taatatgttg attgacgcat cataaaatgc 187860
tgtggttgat taatatgttg attgtcgcct actttattat ataagtaatg atttttgtat 187920
aaaatacggg tttgtgaggg ctttattttt tcttattaga acaaagcatg caatttaagg 187980
cctacagcaa gagtaattta acacctacaa cagtaatttt aaggtcagta ataatgttta 188040
attaaggcct gaccactaaa acttaaacga ttttgtaaaa aaaaatgtct actccacttt 188100
ctctacagac tcttgttaaa aaagtgctgg ccacacagca catatctaaa gaacactact 188160
ttattttgaa atattgtggt ttatggtggc atgaagcgcc gattacgatt tgcattgatg 188220
aggatagcca aatattgata aaatcggcaa gcttcaaaga aggcttatct ttagatatcg 188280
cattaatgaa agtcgtgcaa gaaaataacc atgatttaat agagttgttt accaagtggg 188340
gtgcagatat caactctagc ttagttactg ttaatacgga gtatacccgg aacctttgtc 188400
agaaattagg cgcaaaggaa gctttgaatg aaagggatat tttacaaata ttttataaaa 188460
cacgtcatct taaaactagc agtaatatta ttttatataa tgaattgttt tctaataatc 188520
tccttttcca aaatatagag agattgagtt taatagttta taggggcttg aaaaacttat 188580
caatcaactt tatattggat gatatttcat ttagcgaaat gttaactaga tactggtata 188640
gtatggcgat attatataac cttactgaag ccatccaata tttttatcaa cgatataggc 188700
atttaaaaga ttggcggctt atatgtgggc tttcttttaa caatttgtct gaccttcatg 188760
aagtatataa cttagagaag acggatatag acattgatga aatgatgaag ttgacctgta 188820
gtacgtatga tggtaattat tcgactattt attattgttt tatgttgggg gctgacatca 188880
atcgggcaat gttaacctcg gtaataaact ttcatattgg taacttgttc ctttgtatag 188940
atttaggagc tgatgctttc gaagacagca tggaactagc aaaacaaaag aataataata 189000
tattagtaga aatattatca tttaaaaatt attatagttc aaatacctct cttttatcaa 189060
taaaaacgac agatccggaa aaaattaatg ccttattaga tgaagaaaag tatgagtcaa 189120
aaaatatgtt aatgtatgaa gaattatctc attgatacaa aattattttt tataacagaa 189180
ctctctgatg gtgacaaatc tccgatagga atatatgacg taacataatt atttttttcg 189240
cccagaaaaa aattataaat gttattattg ccagcacttt tatcaactat acgtacaaaa 189300
aggtgttgac caaaaaaata atttttttc ttgatcaaag tatgtaaacg cccgcttaca 189360
gcaaggatct taagtgagag ccattaaatt ttattgatag ctgcttgcca ccagtagaat 189420
acggccaaac cacctaacag gaaatacaag gcggcccttc ggccaataag gtggataaaa 189480
atcacgcata agacggttgt aacatagcac tttagtgcga atatcaggaa tgccaatagc 189540
atgtagataa ggcaccaaac atcgcagcta tacatggcta aagatcaacc agaaaaggtt 189600
taaattttaa cgccggccca aaacttaaac ttttttgat atttttaagt gcagccatgg 189660
attggtccgg ccataggatg acctatgcct acgtggcatt ctcattgatg gcaatagcaa 189720
taatatggta tattctactt atctattgcc gatcgaaaaa aaatgttgtt acaagcggta 189780
atacgctcgc tttagcgcca atatcgcata tgtgaaaaat gttcgccgaa aaaaacatta 189840
aaatttagaa ccgccgcggc atctcagggg cggcaacatt tttttttata tggatattgt 189900
cacacaccac ctcatctatg acgcaatata ttactgctaa tatcaggttc cccaatagta 189960
tgtagagaaa ccacacaaga tagatattca tggcgatttt tgacgaaaaa acattaagtt 190020
ttagcttctt tgacgcctgt gtactaataa tgtttaacgc ctgtagtata ataattgata 190080
cctacagcag taattgatac ctacggcgat aatgtctctc tggccgcccc aaaaaaaagt 190140
atttacggta gggtttatta ccggcggcgt aacaccagtt atggtcaatt ttgtctggcc 190200
cgccgcccag ccgcaaaaaa aaatcaatta caaccgcaaa aaaaaatatt tccggccgcg 190260
gcgtttcaaa aaataatctt tgcgaaataa ttccgcatct tgtgaaatga acgcctacag 190320
taataatttt aatctttgac acctacagca gtagtaataa ttttaatctt taacgcctgc 190380
agcagtacta atattttaat ctttaacgcc tacagcagta gtaataattt taatgtttaa 190440
cgcctacagc agtagtaat 190459

<210> SEQ ID NO 3
<211> LENGTH: 534
<212> TYPE: DNA
<213> ORGANISM: African swine fever virus

<400> SEQUENCE: 3
atgtatgaaa ttattttggc gattattatc atacttttaa caattattat tttttatttt 60
tataaaacac cctttaaatg tataacgaca actaaaaccc ctgtactatt tataaaattt 120
caactcattg ctgcggataa ttatcaagct attacgtgga aagatggaat attaaactat 180
gagaaaatag atcaacccac tcctctatat cttagtgtta atgggcttat ttttgattgt 240
gccaagcttc agccactaac aaccaaatca aatgtaacat ctggtgacaa agttgtccat 300
attggacaaa cattcgaata taataatctt ttaatgtgga aagttaatga tcagggcttt 360
ttaaatatta gtgttactgg taccaaattt aacttaatag ccattaccgg caagctagga 420
ttttatacgg atccccttc gcatttgata attatgccgt taaagttttt tccagttcat 480
aaatttagta aaaatgaacc caataaaaaa caaaagaggt tcatctactt ttaa 534

<210> SEQ ID NO 4
<211> LENGTH: 177
<212> TYPE: PRT
<213> ORGANISM: African swine fever virus

<400> SEQUENCE: 4

Met Tyr Glu Ile Ile Leu Ala Ile Ile Ile Ile Leu Leu Thr Ile Ile
1 5 10 15

Ile Phe Tyr Phe Tyr Lys Thr Pro Phe Lys Cys Ile Thr Thr Thr Lys
20 25 30

Thr Pro Val Leu Phe Ile Lys Phe Gln Leu Ile Ala Ala Asp Asn Tyr
35 40 45

Gln Ala Ile Thr Trp Lys Asp Gly Ile Leu Asn Tyr Glu Lys Ile Asp
50 55 60

Gln Pro Thr Pro Leu Tyr Leu Ser Val Asn Gly Leu Ile Phe Asp Cys
65 70 75 80

Ala Lys Leu Gln Pro Leu Thr Thr Lys Ser Asn Val Thr Ser Gly Asp
85 90 95

Lys Val Val His Ile Gly Gln Thr Phe Glu Tyr Asn Asn Leu Leu Met
100 105 110

Trp Lys Val Asn Asp Gln Gly Phe Leu Asn Ile Ser Val Thr Gly Thr
115 120 125

Lys Phe Asn Leu Ile Ala Ile Thr Gly Lys Leu Gly Phe Tyr Thr Asp
130 135 140

-continued

```
Pro Pro Ser His Leu Ile Ile Met Pro Leu Lys Phe Phe Pro Val His
145                 150                 155                 160

Lys Phe Ser Lys Asn Glu Pro Asn Lys Lys Gln Lys Arg Phe Ile Tyr
                165                 170                 175

Phe


<210> SEQ ID NO 5
<211> LENGTH: 333
<212> TYPE: DNA
<213> ORGANISM: Artificial Sequence
<220> FEATURE:
<223> OTHER INFORMATION: Chemically Synthesized

<400> SEQUENCE: 5

atgtatgaaa ttattttggc gattattatc atacttttaa caattattat tttttatttt     60

tataaaacac cctttaaatg tataacgaca actaaaaccc ctgtactatt tataaaattt    120

caactcattg ctgcggataa ttatcaagct attacgtgga aagatggaat attaaactat    180

gagaaaatag atcaacccac tcctctatat cttagtgtta atgggcttat ttttgattgt    240

gccaagcttc agccactaac aaccaaatca aatgtaacat ctggtgacaa agttgtccat    300

attggacaaa cattcgaata taataatctt tta                                 333


<210> SEQ ID NO 6
<211> LENGTH: 111
<212> TYPE: PRT
<213> ORGANISM: Artificial Sequence
<220> FEATURE:
<223> OTHER INFORMATION: Chemically Synthesized

<400> SEQUENCE: 6

Met Tyr Glu Ile Ile Leu Ala Ile Ile Ile Ile Leu Leu Thr Ile Ile
1               5                   10                  15

Ile Phe Tyr Phe Tyr Lys Thr Pro Phe Lys Cys Ile Thr Thr Thr Lys
            20                  25                  30

Thr Pro Val Leu Phe Ile Lys Phe Gln Leu Ile Ala Ala Asp Asn Tyr
        35                  40                  45

Gln Ala Ile Thr Trp Lys Asp Gly Ile Leu Asn Tyr Glu Lys Ile Asp
    50                  55                  60

Gln Pro Thr Pro Leu Tyr Leu Ser Val Asn Gly Leu Ile Phe Asp Cys
65                  70                  75                  80

Ala Lys Leu Gln Pro Leu Thr Thr Lys Ser Asn Val Thr Ser Gly Asp
                85                  90                  95

Lys Val Val His Ile Gly Gln Thr Phe Glu Tyr Asn Asn Leu Leu
            100                 105                 110
```